US010612096B2

(12) United States Patent
Rava et al.

(10) Patent No.: US 10,612,096 B2
(45) Date of Patent: *Apr. 7, 2020

(54) METHODS FOR DETERMINING FRACTION OF FETAL NUCLEIC ACIDS IN MATERNAL SAMPLES

(71) Applicant: VERINATA HEALTH, INC., Redwood City, CA (US)

(72) Inventors: Richard P. Rava, Redwood City, CA (US); Yue-Jen Chuu, Cupertino, CA (US); Manjula Chinnappa, Foster City, CA (US); David A. Comstock, San Francisco, CA (US); Gabrielle Heilek, Mountain View, CA (US); Michael Hunkapiller, San Carlos, CA (US)

(73) Assignee: VERINATA HEALTH, INC., Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/299,335

(22) Filed: Oct. 20, 2016

(65) Prior Publication Data

US 2017/0037474 A1    Feb. 9, 2017

Related U.S. Application Data

(63) Continuation of application No. 13/461,582, filed on May 1, 2012, now Pat. No. 9,493,828, which is a continuation of application No. 12/958,347, filed on Dec. 1, 2010, now abandoned.

(60) Provisional application No. 61/407,017, filed on Oct. 26, 2010, provisional application No. 61/455,849, filed on Oct. 26, 2010, provisional application No. 61/360,837, filed on Jul. 1, 2010, provisional application No. 61/296,358, filed on Jan. 19, 2010.

(51) Int. Cl.
| | | |
|---|---|---|
| *C12Q 1/6883* | (2018.01) | |
| *C12Q 1/6827* | (2018.01) | |
| *C12Q 1/6886* | (2018.01) | |
| *G16B 30/00* | (2019.01) | |
| *C12Q 1/6869* | (2018.01) | |

(52) U.S. Cl.
CPC ......... *C12Q 1/6883* (2013.01); *C12Q 1/6827* (2013.01); *C12Q 1/6869* (2013.01); *C12Q 1/6886* (2013.01); *G16B 30/00* (2019.02); *C12Q 2537/143* (2013.01); *C12Q 2600/106* (2013.01); *C12Q 2600/156* (2013.01); *C12Q 2600/16* (2013.01)

(58) Field of Classification Search
None
See application file for complete search history.

(56) References Cited

U.S. PATENT DOCUMENTS

| | | |
|---|---|---|
| 5,994,057 A | 11/1999 | Mansfield |
| 6,258,540 B1 | 7/2001 | Lo et al. |
| 6,440,706 B1 | 8/2002 | Vogelstein et al. |
| 6,555,315 B1 | 4/2003 | Short |
| 7,252,946 B2 | 8/2007 | Szasz |
| 7,332,277 B2 | 2/2008 | Dhallan |
| 7,645,576 B2 | 1/2010 | Lo et al. |
| 7,888,017 B2 | 2/2011 | Quake et al. |
| 8,008,018 B2 | 8/2011 | Quake et al. |
| 8,137,912 B2 | 3/2012 | Kapur et al. |
| 8,195,415 B2 | 6/2012 | Fan et al. |
| 8,318,430 B2 | 11/2012 | Chuu et al. |
| 8,532,936 B2 | 9/2013 | Rava |
| 2002/0142324 A1 | 10/2002 | Wang et al. |
| 2003/0044388 A1 | 3/2003 | Lo et al. |
| 2003/0064368 A1 | 4/2003 | Sakai et al. |
| 2003/0194704 A1 | 10/2003 | Penn et al. |
| 2004/0137470 A1 | 7/2004 | Dhallan |
| 2004/0209299 A1 | 10/2004 | Pinter et al. |
| 2005/0221341 A1 | 10/2005 | Shimkets et al. |
| 2006/0046258 A1 | 3/2006 | Lapidus et al. |
| 2006/0121452 A1 | 6/2006 | Dhallan |
| 2006/0134599 A1 | 6/2006 | Toner et al. |
| 2006/0257895 A1 | 11/2006 | Pinkel et al. |
| 2006/0286558 A1 | 12/2006 | Novoradovskaya et al. |
| 2007/0134658 A1 | 6/2007 | Bohmer et al. |
| 2007/0207466 A1 | 9/2007 | Cantor et al. |
| 2008/0020390 A1 | 1/2008 | Mitchell et al. |
| 2008/0050739 A1 | 2/2008 | Stoughton et al. |
| 2008/0064098 A1 | 3/2008 | Allickson |
| 2008/0070792 A1 | 3/2008 | Stoughton et al. |
| 2008/0138809 A1 | 6/2008 | Kapur et al. |

(Continued)

FOREIGN PATENT DOCUMENTS

| | | |
|---|---|---|
| EP | 2334812 | 6/2011 |
| EP | 2496717 | 9/2012 |

(Continued)

OTHER PUBLICATIONS

Pakstis et al. Candidate SNPs for a universal individual identification panel. 2007. Hum Genet, vol. 121, pp. 305-317.*
"Combined Search and Examination Report in GB Patent Application No. 1118396.9", dated Mar. 16, 2012.
"Combined Search and Examination Report in GB Patent Application No. 1118398.5", dated Mar. 16, 2012.
"European Search Report in EP Patent Application No. 10825822.9", dated Feb. 22, 2012, 4 pages.
"European Search Report in EP Patent Application No. 10830938.6", dated Feb. 22, 2012, 4 pages.

(Continued)

*Primary Examiner* — Channing S Mahatan
(74) *Attorney, Agent, or Firm* — Illumina, Inc.; Brent C. Moore

(57) ABSTRACT

The invention provides compositions and methods for determining the fraction of fetal nucleic acids in a maternal sample comprising a mixture of fetal and maternal nucleic acids. The fraction of fetal nucleic acids can be used in determining the presence or absence of fetal aneuploidy.

18 Claims, 7 Drawing Sheets

Specification includes a Sequence Listing.

(56) References Cited

U.S. PATENT DOCUMENTS

| | | |
|---|---|---|
| 2008/0193927 A1 | 8/2008 | Mann et al. |
| 2008/0220422 A1 | 9/2008 | Shoemaker et al. |
| 2008/0299562 A1 | 12/2008 | Oeth et al. |
| 2009/0029377 A1 | 1/2009 | Lo et al. |
| 2009/0087847 A1 | 4/2009 | Lo et al. |
| 2009/0098547 A1 | 4/2009 | Ghosh |
| 2009/0117542 A1 | 5/2009 | Maybruck et al. |
| 2009/0215042 A1 | 8/2009 | Sella-Tavor et al. |
| 2009/0270601 A1 | 10/2009 | Benner et al. |
| 2009/0291443 A1* | 11/2009 | Stoughton ............ C12Q 1/6883 435/6.11 |
| 2009/0299645 A1 | 12/2009 | Colby et al. |
| 2009/0307181 A1 | 12/2009 | Colby et al. |
| 2009/0317817 A1 | 12/2009 | Oeth et al. |
| 2009/0317818 A1 | 12/2009 | Ehrich et al. |
| 2010/0068711 A1 | 3/2010 | Umansky et al. |
| 2010/0093835 A1 | 4/2010 | McSwiggen et al. |
| 2010/0112575 A1 | 5/2010 | Fan et al. |
| 2010/0112590 A1 | 5/2010 | Lo et al. |
| 2010/0138165 A1 | 6/2010 | Fan et al. |
| 2010/0167954 A1 | 7/2010 | Earnshaw et al. |
| 2010/0184043 A1 | 7/2010 | Mitchell et al. |
| 2010/0184075 A1 | 7/2010 | Cantor et al. |
| 2010/0216151 A1 | 8/2010 | Lapidus et al. |
| 2010/0216153 A1 | 8/2010 | Lapidus et al. |
| 2010/0285537 A1 | 11/2010 | Zimmerman |
| 2011/0105353 A1 | 5/2011 | Lo et al. |
| 2011/0118145 A1 | 5/2011 | Akmaev et al. |
| 2011/0177517 A1 | 7/2011 | Rava et al. |
| 2011/0201507 A1 | 8/2011 | Rava et al. |
| 2011/0224087 A1 | 9/2011 | Quake et al. |
| 2011/0230358 A1 | 9/2011 | Rava |
| 2011/0245085 A1 | 10/2011 | Rava et al. |
| 2011/0312503 A1 | 12/2011 | Chuu et al. |
| 2011/0319272 A1* | 12/2011 | Fan ...................... C12Q 1/6883 506/2 |
| 2012/0010085 A1 | 1/2012 | Rava et al. |
| 2012/0034603 A1 | 2/2012 | Oliphant et al. |
| 2012/0034685 A1 | 2/2012 | Sparks et al. |
| 2012/0040859 A1 | 2/2012 | Sparks et al. |
| 2012/0094849 A1 | 4/2012 | Rava et al. |
| 2012/0100548 A1 | 4/2012 | Rava et al. |
| 2012/0149582 A1 | 6/2012 | Rava et al. |
| 2012/0149583 A1 | 6/2012 | Rava et al. |
| 2012/0184449 A1 | 7/2012 | Hixson et al. |
| 2012/0214678 A1 | 8/2012 | Rava et al. |
| 2012/0214680 A1 | 8/2012 | Oeth et al. |
| 2012/0237928 A1 | 9/2012 | Rava et al. |
| 2012/0238738 A1 | 9/2012 | Hendrickson |
| 2013/0029852 A1 | 1/2013 | Rava et al. |
| 2013/0034546 A1 | 2/2013 | Rava et al. |
| 2013/0096011 A1 | 4/2013 | Rava et al. |
| 2014/0038830 A1 | 2/2014 | Srinivasan et al. |
| 2014/0199691 A1 | 7/2014 | Chuu et al. |

FOREIGN PATENT DOCUMENTS

| | | |
|---|---|---|
| EP | 1981995 | 7/2013 |
| GB | 2479471 | 10/2011 |
| GB | 2479476 | 10/2011 |
| GB | 2479080 | 1/2012 |
| GB | 2485635 | 11/2012 |
| GB | 2485644 | 11/2012 |
| GB | 2485645 | 11/2012 |
| WO | 1996019586 | 6/1996 |
| WO | 1998014275 | 4/1998 |
| WO | 199839474 A1 | 9/1998 |
| WO | 1998044151 | 10/1998 |
| WO | 2000018957 | 4/2000 |
| WO | 2003004677 | 1/2003 |
| WO | 2006010610 | 2/2006 |
| WO | 2006028152 | 3/2006 |
| WO | 2006028153 | 3/2006 |
| WO | 2007100911 | 9/2007 |
| WO | 2007/147073 | 12/2007 |
| WO | 2007147074 | 12/2007 |
| WO | 2007147079 | 12/2007 |
| WO | 2009013492 | 1/2009 |
| WO | 2009013496 | 1/2009 |
| WO | 2009114543 | 9/2009 |
| WO | 2010033578 | 3/2010 |
| WO | 2011051283 | 5/2011 |
| WO | 2011057094 | 5/2011 |
| WO | 2012019187 | 2/2012 |
| WO | 2012019193 | 2/2012 |
| WO | 2012019198 | 2/2012 |
| WO | 2012019200 | 2/2012 |

OTHER PUBLICATIONS

"Examination Report in EP Patent Application No. 10825822.9", dated Mar. 19, 2012, 5.
"Examination Report in EP Patent Application No. 10830938.6", dated Oct. 18, 2012.
"Examination Report in EP Patent Application No. 10830938.6", dated Mar. 16, 2012.
"Examination Report in EP Patent Application No. 10830938.6", dated Apr. 10, 2013.
"Examination Report in EP Patent Application No. 10830939.4", dated Oct. 17, 2012.
"Examination Report in EP Patent Application No. 10830939.4", dated Mar. 16, 2012.
"Examination Report in EP Patent Application No. 11744148.5", dated Nov. 20, 2012.
"Examination Report in EP Patent Application No. 11744148.5", dated Apr. 10, 2013.
"Examination Report in GB Patent Application No. 1106394.8", dated Jun. 24, 2011.
"Examination Report in GB Patent Application No. 1107268.3", dated Nov. 15, 2011.
"Examination Report in GB Patent Application No. 1107268.3", dated Jul. 15, 2011.
"Examination Report in GB Patent Application No. 1108794.7", dated Jul. 15, 2011.
"Examination Report in GB Patent Application No. 1108795.4", dated Dec. 16, 2011.
"Examination Report in GB Patent Application No. 1108795.4", dated Mar. 9, 2012.
"Examination Report in GB Patent Application No. 1108795.4", dated Jul. 15, 2011.
"Examination Report in GB Patent Application No. 1114713.9", dated Dec. 7, 2011.
"Extended European Search Report in EP Patent Application No. 11175845.4", dated Nov. 17, 2011.
"Final Office Action in U.S. Appl. No. 12/958,353", dated Sep. 10, 2013.
"International Search Report in PCT Application No. PCT/US2010/058606", dated Feb. 28, 2011.
"International Search Report in PCT Application No. PCT/US2010/058609", dated Apr. 4, 2011.
"International Search Report in PCT Application No. PCT/US2010/058612", dated May 19, 2011.
"International Search Report in PCT Application No. PCT/US2010/058614", dated Mar. 1, 2011.
"International Search Report in PCT Application No. PCT/US2011/021729", dated Apr. 11, 2011.
"Notice of Allowance in U.S. Appl. No. 12/696,509", dated Mar. 1, 2012.
"Notice of Allowance in U.S. Appl. No. 13/452,083", dated Jul. 12, 2012.
"Office Action for U.S. Appl. No. 13/482,964", dated Feb. 4, 2014.
"Office Action in U.S. Appl. No. 12/958,352", dated Oct. 10, 2012.
"Office Action in U.S. Appl. No. 12/958,353", dated Dec. 20, 2012.
"Office Action in U.S. Appl. No. 12/958,356", dated Jan. 11, 2013.
"Office Action in U.S. Appl. No. 13/323,683", dated Jun. 28, 2012.
"Office Action in U.S. Appl. No. 13/333,832", dated May 23, 2012.
"Office Action in U.S. Appl. No. 13/364,809", dated Aug. 10, 2012.

(56) References Cited

OTHER PUBLICATIONS

"Office Action in U.S. Appl. No. 13/365,134", dated Aug. 15, 2012.
"Office Action in U.S. Appl. No. 13/368,035", dated Mar. 13, 2012.
"Search Report relating to claims 16-23, in part 24-31 in GB Patent Application No. 1114713.9", dated Apr. 17, 2012.
"Search Report relating to claims 8-11, in part 12-15 in GB Patent Application No. 1114713.9", dated Apr. 17, 2012.
Amaral, et al., "Application of massive parallel sequencing to whole genome SNP discovery in the porcine genome", BMC Genomics, Biomed Central Ltd, London, UK, vol. 10, No. 1, Aug. 12, 2009, 374.
Bentley, et al., "Accurate whole human genome sequencing using reversible terminator chemistry", Nature, vol. 456, Nov. 6, 2008, 53-59.
Beroukhim, et al., "The landscape of somatic copy-number alteration across human cancers", Nature, vol. 463, Feb. 2010, 899-905.
Bianchi, et al., "Genome-Wide Fetal Aneuploidy Detection by Maternal Plasma DNA Sequencing", Obstetrics and Gynecology, vol. 119, No. 5, May 5, 2012, 890-901.
Borsting, "Multiplex PCR, amplicon size and hybridization efficiency on the NanoChip electronic microarray", Int J. Legal Med. vol. 118, 2004, 75-82.
Botezatu, et al., "Genetic Analysis of DNA excreted in urine: a new approach for detecting specific genomic DNA sequences from cells dying in an organism", Clin Chem. 46(8 Pt1), Aug. 2000, 1078-84.
Buck, et al., "Design Strategies and Performance of Custom DNA Sequencing Primers", Biotechniques vol. 27, 1999, 528-536.
Butler, et al., "Short tandem repeat typing technologies used in human identity testing", Biotechniques 43(4), Oct. 2007, ii-v.
Butler, et al., "The Development of reduced size STR amplicons as tools for analysis of degraded DNA", J. Forensic Sci 48(5), 2003, 1054-64.
Chan, et al., "Size Distributions of maternal and fetal DNA in Maternal Plasma", Clin. Chem 50(1), Jan. 2004, 88-92.
Chen, et al., "Microsatellite alterations in plasma DNA of small cell lung cancer patients", Nat Med. 2(9), 1996, 1033-5.
Chiang, et al., "High-resolution mapping of copy-number alterations with massively parallel sequencing", Nature Methods, vol. 6, No. 1 (2009), published online: doi:10.1038/nmeth.1276, Jan. 2009, 99-103.
Chiu, et al., "Maternal Plasma DNA Analysis with Massively Parallel Sequencing by Ligation for Noninvasive Prenatal Diagnosis of Trisomy 21", Clinical Chemistry 56:3, 2010, 459-463.
Chiu, et al., "Non-invasive prenatal assessment of trisomy 21 by multiplexed maternal plasma DNA sequencing: large scale validity study", BMJ 342, Jan. 11, 2011, c7401.
Chiu, et al., "Non-invasive prenatal diagnosis by single molecule counting technologies", Trends Genet. 25 (7), Jul. 1, 2009, 324-331 pp.
Chiu, et al., "Noninvasive prenatal diagnosis of fetal chromosomal aneuploidy by massively parallel genomic sequencing of DNA in maternal plasma", PNAS, vol. 105, No. 51, Dec. 23, 2008, pp. 20458-20463.
Chu, et al., "Statistical model for whole genome sequencing and its application to minimally invasive of fetal genetic disease", Bioinformatics 25(10), May 15, 2009, 1244-1250.
Chuu et al., "U.S. Appl. No. 13/012,222", Jan. 24, 2010.
Clarke, et al., "Effects of chemotherapy and hormonal therapy for early breast cancer on recurrence and 15-year survival: an overview of randomised trials", Lancet vol. 365, 2005, 1687-1717.
Clarke, et al., "Effects of radiotherapy and of differences in the extent of surgery for early breast cancer on local recurrence and 15-year survival: an overview of the randomised trials", Lancet vol. 366, 2005, 2087-2106.
Coble, et al., "Characterization of New MiniSTR Loci to Aid Analysis of Degraded DNA", J Forensic Sci, 50(1), Jan. 2005, 43-53.
Deng, et al., "Enumeration and microfluidic chip separation of circulating fetal cells early in pregnancy from maternal blood", American Journal of Obstetrics & Gynecology, vol. 199, Issue 6, Dec. 2008, S134.
Dhallan, et al., "A non-invasive test for prenatal diagnosis based on fetal DNA present in maternal blood: a preliminary study", Lancet 369(9560), Feb. 10, 2007, 474-481.
Ding, et al., "MS analysis of single-nucleotide differences in circulating nucleic acids: Application to noninvasive prenatal diagnosis", Proceedings of National Academy of Sciences 101(29), 2004, pp. 10762-10767.
Dixon, et al., "Analysis of artificially degraded DNA using STRs and SNPs- results of a collaborative European (EDNAP) exercise", Forensic Sci Int 164(1), Dec. 1, 2006, 33-44.
Ehrich, "Noninvasive detection of fetal trisomy 21 by sequencing of DNA in maternal blood: a study in a clinical setting", Am J Obstet Gynecol, 204(3), Mar. 2011, 205.el-11.
Fan, et al., "Analysis of the size distributions of fetal and maternal cell-free DNA by paired-end sequencing", Clin. Chem 56(8), Aug. 1, 2010, 1279-1286.
Fan, et al., "Detection of aneuploidy with digital polymerase chain reaction", Anal Chem. 79(19), Oct. 1, 2007, 7576-7579.
Fan, et al., "In principle method for noninvasive determination of the fetal genome", Nature Precedings: Nature Precedings 10.1038/npre, Dec. 8, 2010, 5373.1.
Fan, et al., "Microfluidic digital PCR enables rapid prenatal diagnosis of fetal aneuploidy", Am J Obstet Gynecol 200(5), May 2009, 543.e1-7.
Fan, et al., "Microfluidic digital PCR enables rapid prenatal diagnosis of fetal aneuploidy", American Journal of Obstetrics & Gynecology, May 2009, 543e1-543-e7.
Fan, et al., "Noninvasive diagnosis of fetal aneuploidy by shotgun sequencing DNA from maternal blood", Proceedings of the National Academy of Sciences, vol. 105, No. 42, also available at: http://www.pnas.org/cgi/doi/10.1073/pnas.0808319105, Oct. 21, 2008, 16266-71.
Fan, et al., "Sensitivity of noninvasive prenatal detection of fetal aneuploidy from maternal plasma using shotgun sequencing is limited only by counting statistics", PLoS One 5(5), May 3, 2010, e10439.
Fan, et al., "U.S. Appl. No. 13/452,083", Apr. 20, 2012.
Fan, et al., "Whole-genome molecular haplotyping of single cells", Nature Biotechnology, Advanced Online Publication, Dec. 19, 2010, 9 pages.
Frohling, et al., "Chromosomal Abnormalities in Cancer", New England Journal of Medicine, vol. 359, 2008, 722-734.
Ghanta, et al., "Non-Invasive Prenatal Detection of Trisomy 21 Using Tandem Single Nucleotide Polymorphisms", PLos One, vol. 5, Issue 10, e13184, Oct. 2010, 10 pages.
Goossens, et al., "Simultaneous Mutation and Copy Number Variation (CNV) Detection by Multiplex PCR—Based GS-FLX Sequencing", Human Mutation, vol. 30, Issue 3, Dec. 2008, 472-476.
Grubweiser, et al., "A new "miniSTR-multiplex" displaying reduced amplicon lengths for the analysis of degrade DNA", Int J. Legal Med 120(2), 2006, 115-20.
Hanson, et al., "Whole genome amplification strategy for forensic genetic analysis using single or few cell equivalents of genomic DNA", Anal Biochem. 346(2), Nov. 15, 2005, 246-57.
Harris, et al., "Single-Molecule DNA Sequencing of a Viral Genome", Science 320, Apr. 4, 2008, 106-109 and Suppl. Materials 1-25.
Harrison, et al., "Polymer-stimulated ligation: enhanced ligation of oligo-and polynucleotides by T4 RNA ligase in polymer solutions", Nucleic Acids Research vol. 12 No. 21 1984, 1984, 8235-51.
Hayashi, et al., "Regulation of inter-and intramolecular ligation with T4 DNA ligase in the presence of polyethylene glycol", Nucleic Acids Res. 14(19), Oct. 10, 1986, 7617-31.
Hill, et al., "Characterization of 26 new miniSTR Loci", Poster #44—17th International Symposium on Human Identification, Nashville, TN, Oct. 10-12, 2006, 1.
Hoffman, et al., "The genome-enabled electronic medical record", Journal of Biomedical Informatics 10 (2007) published online, Mar. 15, 2006, 44-46.

(56) References Cited

OTHER PUBLICATIONS

Huang, "Isolation of cell-free DNA from maternal plasma using manual and automated systems", Methods Mol Biol. 444, 2008, 203-8.
Hung, "Detection of circulating fetal nucleic acids: a review of methods and applications", J Clin Pathol 62(4), 2009, 308-13.
Illumina, "Preparing Samples for ChIp sequencing of DNA", E-pub at grcf.jhmi.edu/hts/protocols/11257047_ChIP_Sample_Prep.pdf., 2007, 15.
International, "The International HapMap Consortium Project", Nature 426:789-96, 2003.
Jama, et al., "Quantification of cell-free fetal DNA Levels on maternal plasma by STR analysis", 2010 ACMG Annual Clinical Genetics Meeting, 2010, 2 pages.
Jorgez, et al., "Improving Enrichment of circulating fetal DNA for genetic testing: size fractionation followed by whole gene amplification", Fetal Diagnosis and Therapy, Karger Basel, CH, vol. 25, No. 3, 2009, pp. 314-319.
Ju, et al., "Four-Color DNA Sequencing by Synthesis Using Cleavable Florescent Nucleotide Reversible Terminators", PNAS vol. 103, No. 52, 2006, 19635-19640.
Kidd, et al., "Developing a SNP panel for forensic identification of individuals", Forensic Science International 164 ( 2006), 2006, 20-32.
Kim, et al., "rSW-seq: algorithm for detection of copy number alterations in deep sequencing data", BMC Bioinformatics, vol. 11, Aug. 18, 2010, 432.
Koide, et al., "Fragmentation of cell-free fetal DNA in plasma and urine of pregnant women", Prenat Diagn. Jul. 2005;25(7), www.interscience.wiley.com, Mar. 14, 2005, 604-7.
Kozarewa, et al., "Amplification-free Illumina sequencing-library preparation facilitates improved mapping and assembly of GC-biased genomes", Nat. Methods, 6(4), Apr. 2009, 291-295.
Lazinski, et al., "Modified Protocol for Illumina Paired-End Library Construction", http://genomics.med.tufts.edu/documents/htseq_protocol_for_illumina_paired.pdf, Feb. 27, 2009, 10.
Lee, et al., "Improving the efficiency of genomic loci capture using oligonucleotide arrays for high throughput resequencing", BMC Genomics, Biomed Central Ltd, London, UK, vol. 10, No. 646, Dec. 31, 2009, 1-12.
Leon, et al., "Free DNA in the Serum of Cancer Patients and the Effect of Therapy", Cancer Research 37, Mar. 1977, 646-650.
Levy, et al., "The Diploid Genome Sequence of an Individual Human", PLoS Biology, vol. 5, Issue 10, Oct. 2007, 2113-2144.
Li, et al., "Detection of paternally inherited fetal point mutations for beta-thalassemia using size-fractionated cell-free DNA in maternal plasma", J. Amer. Med. Assoc., vol. 293, Feb. 16, 2005, 843-849.
Li, et al., "Size Separation of Circulatory DNA in Maternal Plasma Permits Ready Detection of Fetal DNA Polymorphisms", Clin. Chem., vol. 50, No. 6, 2004, 1002-1011.
Li, et al., "SNP detection for massively parallel whole-genome resequencing", Genome Research, vol. 19, No. 6, Jun. 1, 2009, 1124-1132.
Liao, et al., "Targeted Massively parallel sequencing of maternal plasma DNA permits efficient and unbiased detection of fetal alleles", Clinical Chemistry 57:1, 2011, 92-101.
Liu, et al., "Feasibility study of using fetal DNA in maternal plasma for non-invasive prenatal diagnosis", Acta Obstet Gynecol Scand. 86(5), 2007, 535-41.
Lo, et al., "Digital PCR for the molecular detection of fetal chromosomal aneuploidy", Proc Natl Acad Sci USA. 104(32), Aug. 7, 2007, 13116-13121.
Lo, et al., "Increased fetal DNA concentrations in the plasma of pregnant women carrying fetuses with trisomy 21", Clinical Chemistry 45:10, 1999, 1747-51.
Lo, et al., "Maternal Plasma DNA Sequencing Reveals the Genome-Wide Genetic and Mutational Profile of the Fetus", Sci Transl Med. 2(61):, Dec. 8, 2010, 61ra91.
Lo, et al., "Noninvasive prenatal detection of fetal chromosomal aneuploidies by maternal plasma nucleic acid analysis: a review of the current state of the art", BJOG, vol. 116, 2009, 152-157.
Lo, et al., "Noninvasive prenatal diagnosis of fetal chromosomal aneuploidies by maternal plasma nucleic acid analysis", Clin Chem. 54(3), Jan. 2008, 461-466.
Lo, et al., "Prenatal diagnosis of fetal RhD Status by molecular analysis of maternal plasma", The New England Journal of Medicine, vol. 339, Dec. 10, 1998, 1734-1738.
Lo, et al., "Presence of fetal DNA in maternal plasma and serum", Lancet. 350(9076), Aug. 16, 1997, 485-487.
Lo, et al., "Quantitative analysis of fetal DNA in maternal plasma and serum: implications for noninvasive prenatal diagnosis", Am J Hum Genet 62(4), Apr. 1998, 768-775.
Lo, et al., "Rapid Clearance of fetal DNA from Maternal Plasma", Am J Hum Genet. 64(1), 1999, 218-24.
Lun, et al., "Microfluidics digital PCR Reveals a Higher than expected fraction of fetal DNA in maternal plasma", Clinical Chemistry, vol. 54, No. 10, Oct. 1, 2008, 1664-1672.
Lun, et al., "Noninvasive prenatal diagnosis of monogenic diseases by digital size selection and relative mutation dosage on DNA in maternal plasma", Proceedings of National Academy of Sciences 105(50), 2008, pp. 19920-19925.
McKernan, et al., "Sequence and structural variation in a human genome uncovered by short-read, massively parallel ligation sequencing using two-base encoding", Genome Res. 19(9), Sep. 2009, 1527-41.
Metzker, M.L., "Applications of Next-Generation Sequencing: Sequencing technologies-the next generation", Nature Reviews Genetics, Nature Publishing Group, GB, vol. 11(1), Jan. 1, 2010, 31-46.
Meyerson, et al., "Advances in understanding cancer genomes through second-generation sequencing", Nature Reviews Genetics, vol. 11, 2010, 685-696.
Mullighan, et al., "Genome-wide profiling of genetic alterations in acute lymphoblastic leukemia: recent insights and future directions.", Leukemia vol. 23, Feb. 26, 2009, 1209-1218.
Nakamoto, "Detection of Microsatellite alterations in Plasma DNA of Malignant Mucosal Melanoma Using Whole Genome Amplification", Bull Tokyo Dent Coll. May 2008; 49(2), May 2008, 77-87.
Nicklas, "A real-time multiplex SNP melting assay to discriminate individuals", J. Forensic Sci. 53(6), Nov. 2008, 1316-24.
Opliphant, et al., "U.S. Appl. No. 61/371,605" Aug. 6, 2010.
Pakstis, et al., "Candidate SNPs for a universal individual identification panel", Hum Genet. 121(3-4), May 2007, 305-17.
Pakstis, et al., "Candidate SNPs for a universal individual identification panel", Hum Genet. 127(3), Mar. 2010, 315-24.
Pandey, et al., "Chapter 3 Applied Biosystems Solid Systems: Ligation-Based Sequencing", Next Generation Genome Sequencing: Towards Personalized Medicine 2008. Edited by Michael Janitz., 2008, 14.
Park, et al., "A single-tube protocol for next gen library construction increases complexity and simplifies parallel sample handling", Cancer Research 71(8): Suppl. 1, Abstract No. 4851, Apr. 15, 2011.
Pathak, et al., "Circulating Cell-Free DNA in Plasma/Serum of Lung Cancer Patients as a Potential Screening and Prognostic Tool", Clin Chem. 52(10):, Oct. 2006, 1833-42.
Pertl, et al., "Detection of male and female fetal DNA in maternal plasma by multiplex fluorescent polymerase chain reaction amplification of short tandem repeats", Hum Genet. 106(1), Jan. 2000, 45-9.
Peters, D. et al., "Noninvasive Prenatal Diagnosis of a Fetal Microdeletion Syndrome", New England Journal of Medicine 365;19, Correspondence, Nov. 10, 2011, 1847-1848.
Pheiffer, et al., "Polymer-stimulated ligation: enhanced blunt—or cohesive-end ligation of DNA or deoxyribooligonucleotides by T4 DNA ligase in polymer solutions", Nucleic Acids Res.11(22), Nov. 25, 1983, 7853-71.
Pui, et al., "Acute lymphoblastic leukaemia", Lancet vol. 371, 2008, 1030-1043.
Pushkarev, et al., "Single-molecule sequencing of an individual human genome", Nat Biotechnol. 27(9):, Sep. 2009, 847-50.
Quail, et al., "A large genome center's improvements to the Illumina sequencing system", Nature Methods, 5, 2008, 1005-1010.

(56) References Cited

OTHER PUBLICATIONS

Quake, et al., "U.S. Appl. No. 12/958,356", Dec. 1, 2010.
Quake, et al., "U.S. Appl. No. 13/365,240", Feb. 2, 2012.
Rava, et al., "U.S. Appl. No. 12/958,347", Dec. 1, 2010.
Rava, et al., "U.S. Appl. No. 12/958,352", Dec. 1, 2010.
Rava, et al., "U.S. Appl. No. 12/958,353", Dec. 1, 2010.
Rava, et al., "U.S. Appl. No. 13/009,718", Jan. 19, 2010.
Rava, et al., "U.S. Appl. No. 13/087,842", Apr. 15, 2011.
Rava, et al., "U.S. Appl. No. 13/191,366", Jul. 26, 2011.
Rava, et al., "U.S. Appl. No. 13/333,832", Dec. 21, 2011.
Rava, et al., "U.S. Appl. No. 13/364,809", Feb. 2, 2012.
Rava, et al., "U.S. Appl. No. 13/365,134", Feb. 2, 2012.
Rava, et al., "U.S. Appl. No. 13/400,028", Feb. 17, 2012.
Rava, et al., "U.S. Appl. No. 13/461,582", May 1, 2012.
Schwarzenbach, et al., "Cell-free Tumor DNA in Blood Plasma as a Marker for Circulating Tumor Cells in Prostate Cancer", Clin Cancer Res. 15(3):, Feb. 1, 2009, 1032-8.
Schwarzenbach, et al., "Comparative evaluation of cell-free tumor DNA in blood and disseminated tumor cells in bone marrow of patients with primary breast cancer", Breast Cancer Res. 11(5), 2009, R71.
Sehnert, et al., "Optimal Detection of Fetal Chromosomal Abnormalities by Massively Parallel DNA Sequencing of Cell-Free Fetal DNA from Maternal Blood", Clinical Chemistry, Jul. 2011, vol. 57 No. 7, E-pub on Apr. 25, 2011 as doi:10.1373/clinchem.2011.165910., Apr. 25, 2011, 1042-1049.
Shendure, et al., "Accurate Multiplex Polony Sequencing of an Evolved Bacterial Genome", Science 309, Sep. 9, 2005, 1728-1732.
Stoughton et al., "U.S. Appl. No. 13/433,232", Mar. 28, 2012.
Su, et al., "Human Urine Contains Small, 150 to 250 Nucleotide-Sized, Soluble DNA Derived from the Circulation and May be useful in the Detection of Colorectal Cancer", J Mol Diagn. 6(2), May 2004, 101-7.
Teixeira, et al., "Multiple numerical chromosome aberrations in cancer: what are their causes and what are their consequences?", Seminars in Cancer Biology, vol. 15, Issue 1, Feb. 2005, 3-12.
Thorstenson, et al., "An Automated Hydrodynamic Process for Controlled, Unbiased DNA Shearing", Genome Research 8, 1998, 848-855.
Tong, et al., "Noninvasive Prenatal Detection of Fetal Trisomy 18 by Epigenetic Allelic Ratio Analysis in Maternal Plasma: Theoretical and Empirical Considerations", Clinical Chemistry 52:12, 2006, 2194-2202.
Tong, et al., "Noninvasive prenatal detection of trisomy 21 by an epigenetic-genetic chromosome-dosage approach", Clin Chem. 56(1), Jan. 2010, 90-8.
Turner, et al., "Methods for Genomic Partitioning", Annual Review of Genomics and Human Genetics, vol. 10, No. 1, Sep. 1, 2009, 263-284.
Vallone, et al., "Demonstration of rapid multiplex PCR amplification involving 16 genetic loci", Forensic Sci Int Genet. 3(1), Dec. 2008, 42-5.
Voelkerding, et al., "Digital Fetal Aneuploidy Diagnosis by Next-Generation Sequencing", Clin Chem. 56(3), Mar. 2010, 336-8.
Voelkerding, et al., "Next-Generation Sequencing: From Basic Research to Diagnostics", Clinical Chemistry 55:4, 2009, 641-658.
Vogelstein, et al., "Digital PCR", PNAS USA, vol. 96, Aug. 3, 1999, 9236-9241.
Wright, et al., "The use of cell-free fetal nucleic acids in maternal blood for non-invasive prenatal diagnosis", Hum Reprod Update. 15(1), Jan. 1, 2009, 139-151.
Yamazawa, et al., "Monozygotic female twins for Silver-Russell syndrome and hypomethylation of H19-DMR", J. Human Genetics, vol. 53, 2008, 950-955.
Zimmerman, et al., "Macromolecular crowding allows blunt-end ligation by DNA ligases from rat liver or *Escherichia coli*", Proc Natl Acas Sci USA. 80(19), Oct. 1983, 5852-6.
NCBI: NCBI assay ID ss3206919 for rr560681, Sep. 5, 2001.
European Search Report for EP18160303.6, dated Jun. 19, 2018, 12 pages.
Bauer, M. , et al., "A prospective analysis of cell-free fetal DNA concentrationin maternal plasma as an indicator for adverse pregnancyoutcome", Prenatal Diagnosis, Jul. 11, 2006, 831-836.
Shendure , et al., "Next-generation DNA sequencing", Nature Biotechnology 26(10), 2008, 1135-1145.

\* cited by examiner

| Amplified Loci: Locus Designation | Chromosome Location | Alleles Included in Identifiler Allelic Ladder | Dye Label | Control DNA 9947A |
|---|---|---|---|---|
| D8S1179 | 8 | 8, 9 10, 11, 12, 13, 14, 15, 16, 17, 18, 19 | 6-FAM | 13a |
| D21S11 | 21q11.2-q21 | 24, 24.2, 25, 26, 27, 28, 28.2, 29, 29.2, 30, 30.2, 31, 31.2, 32, 32.2, 33, 33.2, 34, 34.2, 35, 35.2, 36, 37, 38 | | 30b |
| D7S820 | 7q11.21-22 | 6, 7, 8, 9, 10, 11, 12, 13, 14, 15 | | 10, 11 |
| CSF1PO | 5q33.3-34 | 6, 7, 8, 9, 10, 11, 12, 13, 14, 15 | | 10, 12 |
| D3S1358 | 3p | 12, 13, 14, 15, 16, 17, 18, 19 | VIC | 14, 15 |
| TH01 | 11p15.5 | 4, 5, 6, 7, 8, 9, 9.3, 10, 11, 13.3 | | 8, 9.3 |
| D13S317 | 13q22-31 | 8, 9, 10, 11, 12, 13, 14, 15 | | 11c |
| D16S539 | 16q24-qter | 5, 8, 9, 10, 11, 12, 13, 14, 15 | | 11, 12 |
| D2S1338 | 2q35-37.1 | 15, 16, 17, 18, 19, 20, 21, 22, 23, 24, 25, 26, 27, 28 | | 19, 23 |
| D19S433 | 19q12-13.1 | 9, 10, 11, 12, 12.2, 13, 13.2, 14, 14.2, 15, 15.2, 16, 16.2, 17, 17.2 | NED | 14, 15 |
| vWA | 12p12-pter | 11, 12, 13, 14, 15, 16, 17, 18, 19, 20, 21, 22, 23, 24 | | 17, 18 |
| TPOX | 2p23-2per | 6, 7, 8, 9, 10, 11, 12, 13 | | 8d |
| D18S51 | 18q21.3 | 7, 9, 10, 10.2, 11, 12, 13, 13.2, 14, 14.2, 15, 16, 17, 18, 19, 20, 21, 22, 23, 24, 25, 26, 27 | | 15, 19 |
| Amelogenin | X: p22.1-22.3<br>Y: p11.2 | X, Y | PET | X |
| D5S818 | 5q21-31 | 7, 8, 9, 10, 11, 12, 13, 14, 15, 16 | | 11e |
| FGA | 4q28 | 17, 18, 19, 20, 21, 22, 23, 24, 25, 26, 26.2, 27, 28, 29, 30, 30.2, 31.2, 32.2, 33.2, 42.2, 43.2, 44.2, 45.2, 46.2, 47.2, 48.2, 50.2, 51.2 | | 23, 24 |

FIGURE 4

| Amplified Loci: Locus Designation | Chromosome Location | Alleles Included in Identifiler Allelic Ladder | Dye Label | Control DNA 9947A |
|---|---|---|---|---|
| D8S1179 | 8 | 8, 9 10, 11, 12, 13, 14, 15, 16, 17, 18, 19 | 6-FAM | 13a |
| D21S11 | 21q11.2-q21 | 24, 24.2, 25, 26, 27, 28, 28.2, 29, 29.2, 30, 30.2, 31, 31.2, 32, 32.2, 33, 33.2, 34, 34.2, 35, 35.2, 36, 37, 38 | | 30b |
| D7S820 | 7q11.21-22 | 6, 7, 8, 9, 10, 11, 12, 13, 14, 15 | | 10, 11 |
| CSF1PO | 5q33.3-34 | 6, 7, 8, 9, 10, 11, 12, 13, 14, 15 | | 10, 12 |
| D3S1358 | 3p | 12, 13, 14, 15, 16, 17, 18, 19 | VIC | 14, 15 |
| TH01 | 11p15.5 | 4, 5, 6, 7, 8, 9, 9.3, 10, 11, 13.3 | | 8, 9.3 |
| D13S317 | 13q22-31 | 8, 9, 10, 11, 12, 13, 14, 15 | | 11c |
| D16S539 | 16q24-qter | 5, 8, 9, 10, 11, 12,13, 14, 15 | | 11, 12 |
| D2S1338 | 2q35-37.1 | 15, 16, 17, 18, 19, 20, 21, 22, 23, 24, 25, 26, 27, 28 | | 19, 23 |
| D19S433 | 19q12-13.1 | 9, 10, 11, 12, 12.2, 13, 13.2, 14, 14.2, 15, 15.2, 16, 16.2, 17, 17.2 | NED | 14, 15 |
| vWA | 12p12-pter | 11,12, 13, 14, 15, 16, 17, 18, 19, 20, 21, 22, 23, 24 | | 17, 18 |
| TPOX | 2p23-2per | 6, 7, 8, 9, 10, 11, 12, 13 | | 8d |
| D18S51 | 18q21.3 | 7, 9, 10, 10.2, 11, 12, 13, 13.2, 14, 14.2, 15, 16, 17, 18, 19, 20, 21, 22, 23, 24, 25, 26, 27 | | 15, 19 |
| Amelogenin | X: p22.1-22.3 Y: p11.2 | X, Y | PET | X |
| D5S818 | 5q21-31 | 7, 8, 9, 10, 11, 12, 13, 14, 15, 16 | | 11e |
| FGA | 4q28 | 17, 18, 19, 20, 21, 22, 23, 24, 25, 26, 26.2, 27, 28, 29, 30, 30.2, 31.2, 32.2, 33.2, 42.2, 43.2, 44.2, 45.2, 46.2, 47.2, 48.2, 50.2, 51.2 | | 23, 24 |

FIGURE 5

METHODS FOR DETERMINING FRACTION OF FETAL NUCLEIC ACIDS IN MATERNAL SAMPLES

CROSS-REFERENCE

This application is a Continuation of U.S. application Ser. No. 13/461,582, filed on Aug. 23, 2012, which is a Continuation of U.S. application Ser. No. 12/958,347, filed on Dec. 1, 2010, which claims priority to U.S. Provisional Application Ser. No. 61/296,358 entitled "Methods for Determining Fraction of Fetal Nucleic Acids in Maternal Samples", filed on Jan. 19, 2010; U.S. Provisional Application Ser. No. 61/360,837 entitled "Methods for Determining Fraction of Fetal Nucleic Acids in Maternal Samples", filed on Jul. 1, 2010; U.S. Provisional Application Ser. No. 61/407,017 entitled "Method for Determining Copy Number Variations", filed on Oct. 26, 2010; and U.S. Provisional Application Ser. No. 61/455,849 entitled "Simultaneous determination of Aneuploidy and Fetal Fraction", filed on Oct. 26, 2010; each of which is incorporated herein by reference in its entirety.

SEQUENCE LISTING

The instant application contains a Sequence Listing which has been submitted in ASCII format via EFS-Web and is hereby incorporated by reference in its entirety. Said ASCII copy, created on Apr. 30, 2012, is named Seq_List_0117_301US.txt and is 238,613 bytes in size.

FIELD OF THE INVENTION

The present invention relates to methods and compositions for detecting fetal nucleic acids in a maternal sample and determining the fraction of cell-free fetal nucleic acid circulating in a maternal sample.

BACKGROUND OF THE INVENTION

Invasive prenatal tests are potentially harmful to the mother and to the fetus. Therefore, there is a need for the development of noninvasive prenatal tests. Maternal blood can contain fetal cells (see e.g., U.S. Patent Application Publication No. 20080070792) and cell-free fetal DNA (see e.g., Huang et al. (2008), *Methods in Molecular Biology*, 444:203-208). While circulating fetal cells present an attractive target for non invasive prenatal diagnostics, particularly for the diagnosis of fetal sex and chromosomal abnormalities by simple karyotyping, the scarcity of intact fetal cells in the maternal circulation (around one cell per ml of maternal blood), low efficiency of enrichment (Bianchi et al., Am J Hum Genet 61:822-829 [1997]) and difficulties with chromosomal analysis associated with abnormally dense nuclei in some cells (Babochkina et al., Haematologica 90:740-745 [2005]), have favored research on cell-free DNA.

The establishment of the concentrations of cell-free fetal DNA (cfDNA) in maternal plasma in healthy pregnant women has formed the platform on which fetal DNA abnormalities in pregnancy-associated disorders can be studied. The finding of a gradual increase in fetal DNA concentration in maternal serum as gestation progresses has been shown to precede complications associated with pre-term labor. A five-fold increase in fetal DNA concentration has also been found in the serum obtained from women affected by preeclampsia. Other pregnancy-related disorders that have been linked to an elevated concentration of cfDNA include hyperemesis gravidarum (severe morning sickness), invasive placentation (in which the placenta contacts the maternal bloodstream), intrauterine growth restriction, fetomaternal haemorrhage and polyhydramnios. (Wright C. F. and Burton H., Human Reproduction Update 15(1):139-151 [2009]).

Quantitative analysis of cell free DNA by real-time PCR strategies has also indicated that the concentrations of circulatory fetal DNA are increased in pregnancies with fetal aneuploidies, most notably trisomy 21 (Lo et al., Clin Chem 45:1747-1751 [1999]). However, the fraction of fetal DNA in maternal cell-free plasma DNA is usually determined by comparing the amount of fetal-specific locus (such as the SRY locus on chromosome Y in male pregnancies) to that of a locus on any autosome that is common to both the mother and the fetus by using quantitative real-time PCR (Dalillan et al., Lancet 369:474-481 [2007]; Li et al., Clin Chem 1002-1011 [2004]; Fan et al., Proc Natl Acad Sci 105:16266-16271 [2008]).

Thus, there is a need for additional methods that would enable the determination of the fraction of fetal nucleic acid in both male and female pregnancies.

The method of the invention fulfills the need in providing the means to determine fetal fraction that is independent of the gender of the fetus. The method can be applied for determining simultaneously the presence or absence of a chromosomal aneuploidy or other copy number variation, and may be used in conjunction with nay known methods that are used to determine aneuploidies in maternal sample.

SUMMARY OF THE INVENTION

The invention provides compositions and methods for determining the fraction of fetal nucleic acids in a maternal sample comprising a mixture of fetal and maternal nucleic acids. The fraction of fetal nucleic acids can be used in determining the presence or absence of fetal aneuploidy.

In one embodiment, the invention provides a method for determining the fraction of fetal nucleic acids in a maternal sample comprising a mixture of fetal and maternal genomic DNA, wherein the method comprises the steps of: (a) amplifying a plurality of polymorphic target nucleic acids in the mixture of fetal and maternal genomic DNA; (b) performing massively parallel sequencing of at least a portion of the amplified product obtained in (a), wherein sequencing comprises providing a plurality of sequence tags; and (c) based on the sequencing, determining the fraction. The plurality of polymorphic nucleic acids are located on a plurality of different chromosomes. In one embodiment, the plurality of polymorphic nucleic acids can be located on chromosomes 1-22. In another embodiment, the plurality of polymorphic nucleic acids can be located on different autosomes other than chromosomes 13, 18 and 21. The maternal sample is selected from blood, plasma, serum, urine and saliva. Preferably, the maternal sample is a plasma sample.

In one embodiment, the invention provides a method for determining the fraction of fetal nucleic acids in a maternal sample comprising a mixture of fetal and maternal genomic DNA, wherein the method comprises the steps of: (a) amplifying a plurality of polymorphic target nucleic acids in the mixture of fetal and maternal genomic DNA; (b) performing massively parallel sequencing of at least a portion of the amplified product obtained in (a), wherein sequencing comprises an amplification and provides a plurality of sequence tags; and (c) based on the sequencing, determining the fraction. The maternal sample is selected from blood, plasma, serum, urine and saliva. Preferably, the maternal sample is a plasma sample.

In another embodiment, the invention provides a method for determining the fraction of fetal nucleic acids in a maternal sample comprising a mixture of fetal and maternal genomic DNA, wherein the method comprises the steps of: (a) amplifying a plurality of polymorphic target nucleic acids in the mixture of fetal and maternal genomic DNA; (b) performing massively parallel sequencing of at least a portion of the amplified product obtained in (a), wherein sequencing comprises providing a plurality of sequence tags; and (c) based on the sequencing, determining the fraction. The plurality of polymorphic target nucleic acids comprises at least one single nucleotide polymorphism (SNP). Alternatively, the plurality of polymorphic target nucleic acids comprises at least one short tandem repeat (STR). The plurality of polymorphic nucleic acids are located on a plurality of different chromosomes. For example, the plurality of polymorphic nucleic acids can be located on a plurality of different chromosomes other than chromosomes 13, 18, 21, X or Y. The maternal sample is selected from blood, plasma, serum, urine and saliva. Preferably, the maternal sample is a plasma sample.

In another embodiment, the invention provides a method for determining the fraction of fetal nucleic acids in a maternal sample comprising a mixture of fetal and maternal genomic DNA, wherein the method comprises the steps of: (a) amplifying a plurality of polymorphic target nucleic acids in the mixture of fetal and maternal genomic DNA; (b) performing massively parallel sequencing of at least a portion of the amplified product obtained in (a), wherein sequencing comprises providing a plurality of sequence tags; and (c) based on the sequencing, determining the fraction. The plurality of polymorphic target nucleic acids comprises at least one single nucleotide polymorphism (SNP). Alternatively, the plurality of polymorphic target nucleic acids comprises at least one short tandem repeat (STR). The plurality of polymorphic nucleic acids are located on a plurality of different chromosomes. In one embodiment, the plurality of polymorphic nucleic acids can be located on chromosomes 1-22. For example, the plurality of polymorphic nucleic acids can be located on a plurality of different chromosomes other than chromosomes 13, 18, 21, X or Y. The massively parallel sequencing is sequencing-by-synthesis with reversible dye terminators. Alternatively, the massively parallel sequencing is sequencing-by-ligation or single molecule sequencing. The maternal sample is selected from blood, plasma, serum, urine and saliva. Preferably, the maternal sample is a plasma sample.

In another embodiment, the invention provides a method for determining the fraction of fetal nucleic acids in a maternal sample comprising a mixture of fetal and maternal genomic DNA, wherein the method comprises the steps of: (a) amplifying a plurality of polymorphic target nucleic acids in the mixture of fetal and maternal genomic DNA; (b) performing massively parallel sequencing of at least a portion of the amplified product obtained in (a), wherein sequencing comprises an amplification and provides a plurality of sequence tags; and (c) based on the sequencing, determining the fraction. The plurality of polymorphic target nucleic acids comprises at least one single nucleotide polymorphism (SNP). Alternatively, the plurality of polymorphic target nucleic acids comprises at least one short tandem repeat (STR). The plurality of polymorphic nucleic acids are located on a plurality of different chromosomes. In one embodiment, the plurality of polymorphic nucleic acids can be located on chromosomes 1-22 For example, the plurality of polymorphic nucleic acids can be located on a plurality of different chromosomes other than chromosomes 13, 18, 21, X or Y. The maternal sample is selected from blood, plasma, serum, urine and saliva. Preferably, the maternal sample is a plasma sample.

In another embodiment, the invention provides a method for determining the fraction of fetal nucleic acids in a maternal sample comprising a mixture of fetal and maternal genomic DNA, wherein the method comprises the steps of: (a) amplifying a plurality of polymorphic target nucleic acids in the mixture of fetal and maternal genomic DNA; (b) performing massively parallel sequencing of at least a portion of the amplified product obtained in (a), wherein sequencing comprises an amplification and provides a plurality of sequence tags; and (c) based on the sequencing, determining the fraction. The plurality of polymorphic target nucleic acids comprises at least one single nucleotide polymorphism (SNP). Alternatively, the plurality of polymorphic target nucleic acids comprises at least one short tandem repeat (STR). The plurality of polymorphic nucleic acids are located on a plurality of different chromosomes. In one embodiment, the plurality of polymorphic nucleic acids can be located on chromosomes 1-22. For example, the plurality of polymorphic nucleic acids can be located on a plurality of different chromosomes other than chromosomes 13, 18, 21, X or Y. The massively parallel sequencing is sequencing-by-synthesis with reversible dye terminators. Alternatively, the massively parallel sequencing is sequencing-by-ligation or single molecule sequencing. The maternal sample is selected from blood, plasma, serum, urine and saliva. Preferably, the maternal sample is a plasma sample.

In one embodiment, the invention provides a method for determining the fraction of fetal nucleic acids in a maternal sample comprising a mixture of fetal and maternal genomic DNA e.g. cell-free DNA, wherein the method comprises the steps of: (a) amplifying a plurality of polymorphic target nucleic acids in the mixture of fetal and maternal genomic DNA; (b) performing massively parallel sequencing of at least a portion of the amplified product obtained in (a), wherein sequencing comprises providing a plurality of sequence tags; and (c) based on the sequencing, determining the fraction. The plurality of polymorphic nucleic acids are located on a plurality of different chromosomes. In one embodiment, the plurality of polymorphic nucleic acids can be located on chromosomes 1-22. For example, the plurality of polymorphic nucleic acids can be located on a plurality of different chromosomes other than chromosomes 13, 18, 21, X or Y. The maternal sample is selected from blood, plasma, serum, urine and saliva. Preferably, the maternal sample is a plasma sample.

In one embodiment, the invention provides a method for determining the fraction of fetal nucleic acids in a maternal sample comprising a mixture of fetal and maternal genomic DNA e.g. cell-free DNA, wherein the method comprises the steps of: (a) amplifying a plurality of polymorphic target nucleic acids in the mixture of fetal and maternal genomic DNA; (b) performing massively parallel sequencing of at least a portion of the amplified product obtained in (a), wherein sequencing comprises an amplification and provides a plurality of sequence tags; and (c) based on the sequencing, determining the fraction. The plurality of polymorphic nucleic acids are located on a plurality of different chromosomes. In one embodiment, the plurality of polymorphic nucleic acids can be located on chromosomes 1-22. For example, the plurality of polymorphic nucleic acids can be located on a plurality of different chromosomes other than chromosomes 13, 18, 21, X or Y. The maternal sample is selected from blood, plasma, serum, urine and saliva. Preferably, the maternal sample is a plasma sample.

In another embodiment, the invention provides a method for determining the fraction of fetal nucleic acids in a maternal sample comprising a mixture of fetal and maternal genomic DNA e.g. cell-free DNA, wherein the method comprises the steps of: (a) amplifying a plurality of polymorphic target nucleic acids in the mixture of fetal and maternal genomic DNA; (b) performing massively parallel sequencing of at least a portion of the amplified product obtained in (a), wherein sequencing comprises providing a plurality of sequence tags; and (c) based on the sequencing, determining the fraction. The plurality of polymorphic target nucleic acids comprises at least one single nucleotide polymorphism (SNP). Alternatively, the plurality of polymorphic target nucleic acids comprises at least one short tandem repeat (STR). The plurality of polymorphic nucleic acids are located on a plurality of different chromosomes. In one embodiment, the plurality of polymorphic nucleic acids can be located on chromosomes 1-22. For example, the plurality of polymorphic nucleic acids can be located on a plurality of different chromosomes other than chromosomes 13, 18, 21, X or Y. The maternal sample is selected from blood, plasma, serum, urine and saliva. Preferably, the maternal sample is a plasma sample.

In another embodiment, the invention provides a method for determining the fraction of fetal nucleic acids in a maternal sample comprising a mixture of fetal and maternal genomic DNA e.g. cell-free DNA, wherein the method comprises the steps of: (a) amplifying a plurality of polymorphic target nucleic acids in the mixture of fetal and maternal genomic DNA; (b) performing massively parallel sequencing of at least a portion of the amplified product obtained in (a), wherein sequencing comprises providing a plurality of sequence tags; and (c) based on the sequencing, determining the fraction. The plurality of polymorphic target nucleic acids comprises at least one single nucleotide polymorphism (SNP). Alternatively, the plurality of polymorphic target nucleic acids comprises at least one short tandem repeat (STR). The plurality of polymorphic nucleic acids are located on a plurality of different chromosomes. In one embodiment, the plurality of polymorphic nucleic acids can be located on chromosomes 1-22. For example, the plurality of polymorphic nucleic acids can be located on a plurality of different chromosomes other than chromosomes 13, 18, 21, X or Y. The massively parallel sequencing is sequencing-by-synthesis with reversible dye terminators. Alternatively, the massively parallel sequencing is sequencing-by-ligation or single molecule sequencing. The maternal sample is selected from blood, plasma, serum, urine and saliva. Preferably, the maternal sample is a plasma sample.

In another embodiment, the invention provides a method for determining the fraction of fetal nucleic acids in a maternal sample comprising a mixture of fetal and maternal genomic DNA e.g. cell-free DNA, wherein the method comprises the steps of: (a) amplifying a plurality of polymorphic target nucleic acids in the mixture of fetal and maternal genomic DNA; (b) performing massively parallel sequencing of at least a portion of the amplified product obtained in (a), wherein sequencing comprises an amplification and provides a plurality of sequence tags; and (c) based on the sequencing, determining the fraction. The plurality of polymorphic target nucleic acids comprises at least one single nucleotide polymorphism (SNP). Alternatively, the plurality of polymorphic target nucleic acids comprises at least one short tandem repeat (STR). The plurality of polymorphic nucleic acids are located on a plurality of different chromosomes. In one embodiment, the plurality of polymorphic nucleic acids can be located on chromosomes 1-22. For example, the plurality of polymorphic nucleic acids can be located on a plurality of different chromosomes other than chromosomes 13, 18, 21, X or Y. The maternal sample is selected from blood, plasma, serum, urine and saliva. Preferably, the maternal sample is a plasma sample.

In another embodiment, the invention provides a method for determining the fraction of fetal nucleic acids in a maternal sample comprising a mixture of fetal and maternal genomic DNA e.g. cell-free DNA, wherein the method comprises the steps of: (a) amplifying a plurality of polymorphic target nucleic acids in the mixture of fetal and maternal genomic DNA; (b) performing massively parallel sequencing of at least a portion of the amplified product obtained in (a), wherein sequencing comprises an amplification and provides a plurality of sequence tags; and (c) based on the sequencing, determining the fraction. The plurality of polymorphic target nucleic acids comprises at least one single nucleotide polymorphism (SNP). Alternatively, the plurality of polymorphic target nucleic acids comprises at least one short tandem repeat (STR). The plurality of polymorphic nucleic acids are located on a plurality of different chromosomes. In one embodiment, the plurality of polymorphic nucleic acids can be located on chromosomes 1-22. For example, the plurality of polymorphic nucleic acids can be located on a plurality of different chromosomes other than chromosomes 13, 18, 21, X or Y. The massively parallel sequencing is sequencing-by-synthesis with reversible dye terminators. Alternatively, the massively parallel sequencing is sequencing-by-ligation or single molecule sequencing. The maternal sample is selected from blood, plasma, serum, urine and saliva. Preferably, the maternal sample is a plasma sample.

In one embodiment, the invention provides a method for determining the fraction of fetal nucleic acids in a maternal sample comprising a mixture of fetal and maternal genomic DNA, wherein the method comprises the steps of: (a) amplifying a plurality of polymorphic target nucleic acids in the mixture of fetal and maternal genomic DNA; (b) performing massively parallel sequencing of at least a portion of the amplified product obtained in (a), wherein sequencing comprises providing a plurality of sequence tags; and (c) based on the sequencing, determining the fraction, wherein determining the fraction comprises determining the number of fetal and maternal sequence tags mapped to a reference genome comprising of at least one polymorphic nucleic acid. The plurality of polymorphic nucleic acids are located on a plurality of different chromosomes. In one embodiment, the plurality of polymorphic nucleic acids can be located on chromosomes 1-22. For example, the plurality of polymorphic nucleic acids can be located on a plurality of different chromosomes other than chromosomes 13, 18, 21, X or Y. The maternal sample is selected from blood, plasma, serum, urine and saliva. Preferably, the maternal sample is a plasma sample.

In one embodiment, the invention provides a method for determining the fraction of fetal nucleic acids in a maternal sample comprising a mixture of fetal and maternal genomic DNA, wherein the method comprises the steps of: (a) amplifying a plurality of polymorphic target nucleic acids in the mixture of fetal and maternal genomic DNA; (b) performing massively parallel sequencing of at least a portion of the amplified product obtained in (a), wherein sequencing comprises an amplification and provides a plurality of sequence tags; and (c) based on the sequencing, determining the fraction, wherein determining the fraction comprises determining the number of fetal and maternal sequence tags mapped to a reference genome comprising of at least one polymorphic nucleic acid. The plurality of polymorphic nucleic acids are located on a plurality of different chromosomes. In one embodiment, the plurality of polymorphic nucleic acids can be located on chromosomes 1-22. For example, the plurality of polymorphic nucleic acids can be located on a plurality of different chromosomes other than chromosomes 13, 18, 21, X or Y. The maternal sample is selected from blood, plasma, serum, urine and saliva. Preferably, the maternal sample is a plasma sample.

In another embodiment, the invention provides a method for determining the fraction of fetal nucleic acids in a maternal sample comprising a mixture of fetal and maternal genomic DNA, wherein the method comprises the steps of: (a) amplifying a plurality of polymorphic target nucleic acids in the mixture of fetal and maternal genomic DNA; (b) performing massively parallel sequencing of at least a portion of the amplified product obtained in (a), wherein sequencing comprises providing a plurality of sequence tags; and (c) based on the sequencing, determining the fraction, wherein determining the fraction comprises determining the number of fetal and maternal sequence tags mapped to a reference genome comprising of at least one polymorphic nucleic acid. The plurality of polymorphic target nucleic acids comprises at least one single nucleotide polymorphism (SNP). Alternatively, the plurality of polymorphic target nucleic acids comprises at least one short tandem repeat (STR). The plurality of polymorphic nucleic acids are located on a plurality of different chromosomes. In one embodiment, the plurality of polymorphic nucleic acids can be located on chromosomes 1-22. For example, the plurality of polymorphic nucleic acids can be located on a plurality of different chromosomes other than chromosomes 13, 18, 21, X or Y. The maternal sample is selected from blood, plasma, serum, urine and saliva. Preferably, the maternal sample is a plasma sample.

In another embodiment, the invention provides a method for determining the fraction of fetal nucleic acids in a maternal sample comprising a mixture of fetal and maternal genomic DNA, wherein the method comprises the steps of: (a) amplifying a plurality of polymorphic target nucleic acids in the mixture of fetal and maternal genomic DNA; (b) performing massively parallel sequencing of at least a portion of the amplified product obtained in (a), wherein sequencing comprises providing a plurality of sequence tags; and (c) based on the sequencing, determining the fraction, wherein determining the fraction comprises determining the number of fetal and maternal sequence tags mapped to a reference genome comprising of at least one polymorphic nucleic acid. The plurality of polymorphic target nucleic acids comprises at least one single nucleotide polymorphism (SNP). Alternatively, the plurality of polymorphic target nucleic acids comprises at least one short tandem repeat (STR). The plurality of polymorphic nucleic acids are located on a plurality of different chromosomes. In one embodiment, the plurality of polymorphic nucleic acids can be located on chromosomes 1-22. For example, the plurality of polymorphic nucleic acids can be located on a plurality of different chromosomes other than chromosomes 13, 18, 21, X or Y. The massively parallel sequencing is sequencing-by-synthesis with reversible dye terminators. Alternatively, the massively parallel sequencing is sequencing-by-ligation or single molecule sequencing. The maternal sample is selected from blood, plasma, serum, urine and saliva. Preferably, the maternal sample is a plasma sample.

In another embodiment, the invention provides a method for determining the fraction of fetal nucleic acids in a maternal sample comprising a mixture of fetal and maternal genomic DNA, wherein the method comprises the steps of: (a) amplifying a plurality of polymorphic target nucleic acids in the mixture of fetal and maternal genomic DNA; (b) performing massively parallel sequencing of at least a portion of the amplified product obtained in (a), wherein sequencing comprises an amplification and provides a plurality of sequence tags; and (c) based on the sequencing, determining the fraction, wherein determining the fraction comprises determining the number of fetal and maternal sequence tags mapped to a reference genome comprising of at least one polymorphic nucleic acid. The plurality of polymorphic target nucleic acids comprises at least one single nucleotide polymorphism (SNP). Alternatively, the plurality of polymorphic target nucleic acids comprises at least one short tandem repeat (STR). The plurality of polymorphic nucleic acids are located on a plurality of different chromosomes. In one embodiment, the plurality of polymorphic nucleic acids can be located on chromosomes 1-22. For example, the plurality of polymorphic nucleic acids can be located on a plurality of different chromosomes other than chromosomes 13, 18, 21, X or Y. The maternal sample is selected from blood, plasma, serum, urine and saliva. Preferably, the maternal sample is a plasma sample.

In another embodiment, the invention provides a method for determining the fraction of fetal nucleic acids in a maternal sample comprising a mixture of fetal and maternal genomic DNA, wherein the method comprises the steps of: (a) amplifying a plurality of polymorphic target nucleic acids in the mixture of fetal and maternal genomic DNA; (b) performing massively parallel sequencing of at least a portion of the amplified product obtained in (a), wherein sequencing comprises an amplification and provides a plurality of sequence tags; and (c) based on the sequencing, determining the fraction, wherein determining the fraction comprises determining the number of fetal and maternal sequence tags mapped to a reference genome comprising of at least one polymorphic nucleic acid. The plurality of polymorphic target nucleic acids comprises at least one single nucleotide polymorphism (SNP). Alternatively, the plurality of polymorphic target nucleic acids comprises at least one short tandem repeat (STR). The plurality of polymorphic nucleic acids are located on a plurality of different chromosomes. In one embodiment, the plurality of polymorphic nucleic acids can be located on chromosomes 1-22. For example, the plurality of polymorphic nucleic acids can be located on a plurality of different chromosomes other than chromosomes 13, 18, 21, X or Y. The massively parallel sequencing is sequencing-by-synthesis with reversible dye terminators. Alternatively, the massively parallel sequencing is sequencing-by-ligation or single molecule sequencing. The maternal sample is selected from blood, plasma, serum, urine and saliva. Preferably, the maternal sample is a plasma sample.

In one embodiment, the invention provides a method for determining the fraction of fetal nucleic acids in a maternal sample comprising a mixture of fetal and maternal genomic DNA e.g. cell-free DNA, wherein the method comprises the steps of: (a) amplifying a plurality of polymorphic target nucleic acids in the mixture of fetal and maternal genomic DNA; (b) performing massively parallel sequencing of at least a portion of the amplified product obtained in (a), wherein sequencing comprises providing a plurality of sequence tags; and (c) based on the sequencing, determining the fraction, wherein determining the fraction comprises determining the number of fetal and maternal sequence tags mapped to a reference genome comprising of at least one polymorphic nucleic acid. The plurality of polymorphic nucleic acids are located on a plurality of different chromosomes. In one embodiment, the plurality of polymorphic nucleic acids can be located on chromosomes 1-22. For example, the plurality of polymorphic nucleic acids can be located on a plurality of different chromosomes other than chromosomes 13, 18, 21, X or Y. The maternal sample is selected from blood, plasma, serum, urine and saliva. Preferably, the maternal sample is a plasma sample.

In one embodiment, the invention provides a method for determining the fraction of fetal nucleic acids in a maternal sample comprising a mixture of fetal and maternal genomic DNA e.g. cell-free DNA, wherein the method comprises the steps of: (a) amplifying a plurality of polymorphic target nucleic acids in the mixture of fetal and maternal genomic DNA; (b) performing massively parallel sequencing of at least a portion of the amplified product obtained in (a), wherein sequencing comprises an amplification and provides a plurality of sequence tags; and (c) based on the sequencing, determining the fraction, wherein determining the fraction comprises determining the number of fetal and maternal sequence tags mapped to a reference genome comprising of at least one polymorphic nucleic acid. The plurality of polymorphic nucleic acids are located on a plurality of different chromosomes. In one embodiment, the plurality of polymorphic nucleic acids can be located on chromosomes 1-22. For example, the plurality of polymorphic nucleic acids can be located on a plurality of different chromosomes other than chromosomes 13, 18, 21, X or Y. The maternal sample is selected from blood, plasma, serum, urine and saliva. Preferably, the maternal sample is a plasma sample.

In another embodiment, the invention provides a method for determining the fraction of fetal nucleic acids in a maternal sample comprising a mixture of fetal and maternal genomic DNA e.g. cell-free DNA, wherein the method comprises the steps of: (a) amplifying a plurality of polymorphic target nucleic acids in the mixture of fetal and maternal genomic DNA; (b) performing massively parallel sequencing of at least a portion of the amplified product obtained in (a), wherein sequencing comprises providing a plurality of sequence tags; and (c) based on the sequencing, determining the fraction, wherein determining the fraction comprises determining the number of fetal and maternal sequence tags mapped to a reference genome comprising of at least one polymorphic nucleic acid. The plurality of polymorphic target nucleic acids comprises at least one single nucleotide polymorphism (SNP). Alternatively, the plurality of polymorphic target nucleic acids comprises at least one short tandem repeat (STR). The plurality of polymorphic nucleic acids are located on a plurality of different chromosomes. In one embodiment, the plurality of polymorphic nucleic acids can be located on chromosomes 1-22. For example, the plurality of polymorphic nucleic acids can be located on a plurality of different chromosomes other than chromosomes 13, 18, 21, X or Y. The maternal sample is selected from blood, plasma, serum, urine and saliva. Preferably, the maternal sample is a plasma sample.

In another embodiment, the invention provides a method for determining the fraction of fetal nucleic acids in a maternal sample comprising a mixture of fetal and maternal genomic DNA e.g. cell-free DNA, wherein the method comprises the steps of: (a) amplifying a plurality of polymorphic target nucleic acids in the mixture of fetal and maternal genomic DNA; (b) performing massively parallel sequencing of at least a portion of the amplified product obtained in (a), wherein sequencing comprises providing a plurality of sequence tags; and (c) based on the sequencing, determining the fraction, wherein determining the fraction comprises determining the number of fetal and maternal sequence tags mapped to a reference genome comprising of at least one polymorphic nucleic acid. The plurality of polymorphic target nucleic acids comprises at least one single nucleotide polymorphism (SNP). Alternatively, the plurality of polymorphic target nucleic acids comprises at least one short tandem repeat (STR). The massively parallel sequencing is sequencing-by-synthesis with reversible dye terminators. Alternatively, the massively parallel sequencing is sequencing-by-ligation or single molecule sequencing. The plurality of polymorphic nucleic acids are located on a plurality of different chromosomes. In one embodiment, the plurality of polymorphic nucleic acids can be located on chromosomes 1-22. For example, the plurality of polymorphic nucleic acids can be located on a plurality of different chromosomes other than chromosomes 13, 18, 21, X or Y. The maternal sample is selected from blood, plasma, serum, urine and saliva. Preferably, the maternal sample is a plasma sample.

In another embodiment, the invention provides a method for determining the fraction of fetal nucleic acids in a maternal sample comprising a mixture of fetal and maternal genomic DNA e.g. cell-free DNA, wherein the method comprises the steps of: (a) amplifying a plurality of polymorphic target nucleic acids in the mixture of fetal and maternal genomic DNA; (b) performing massively parallel sequencing of at least a portion of the amplified product obtained in (a), wherein sequencing comprises an amplification and provides a plurality of sequence tags; and (c) based on the sequencing, determining the fraction, wherein determining the fraction comprises determining the number of fetal and maternal sequence tags mapped to a reference genome comprising of at least one polymorphic nucleic acid. The plurality of polymorphic target nucleic acids comprises at least one single nucleotide polymorphism (SNP). Alternatively, the plurality of polymorphic target nucleic acids comprises at least one short tandem repeat (STR). The plurality of polymorphic nucleic acids are located on a plurality of different chromosomes. In one embodiment, the plurality of polymorphic nucleic acids can be located on chromosomes 1-22. For example, the plurality of polymorphic nucleic acids can be located on a plurality of different chromosomes other than chromosomes 13, 18, 21, X or Y. The maternal sample is selected from blood, plasma, serum, urine and saliva. Preferably, the maternal sample is a plasma sample.

In another embodiment, the invention provides a method for determining the fraction of fetal nucleic acids in a maternal sample comprising a mixture of fetal and maternal genomic DNA e.g. cell-free DNA, wherein the method comprises the steps of: (a) amplifying a plurality of polymorphic target nucleic acids in the mixture of fetal and maternal genomic DNA; (b) performing massively parallel sequencing of at least a portion of the amplified product obtained in (a), wherein sequencing comprises an amplification and provides a plurality of sequence tags; and (c) based on the sequencing, determining the fraction, wherein determining the fraction comprises determining the number of fetal and maternal sequence tags mapped to a reference genome comprising of at least one polymorphic nucleic acid. The plurality of polymorphic target nucleic acids comprises at least one single nucleotide polymorphism (SNP). Alternatively, the plurality of polymorphic target nucleic acids comprises at least one short tandem repeat (STR). The massively parallel sequencing is sequencing-by-synthesis with reversible dye terminators. Alternatively, the massively parallel sequencing is sequencing-by-ligation or single molecule sequencing. The maternal sample is selected from blood, plasma, serum, urine and saliva. Preferably, the maternal sample is a plasma sample.

In another embodiment, the invention provides a method for determining the fraction of fetal nucleic acids in a maternal sample comprising a mixture of fetal and maternal genomic DNA e.g. cell-free DNA, wherein the method comprises the steps of: (a) amplifying a plurality of polymorphic target nucleic acids in the mixture of fetal and maternal genomic DNA; (b) performing massively parallel sequencing of at least a portion of the amplified product obtained in (a), wherein sequencing comprises providing a plurality of sequence tags; and (c) based on the sequencing, determining the fraction. The plurality of polymorphic target nucleic acids comprises at least one single nucleotide polymorphism (SNP). Alternatively, the plurality of polymorphic target nucleic acids comprises at least one short tandem repeat (STR). In some embodiments, the at least one SNP is a single SNP selected from rs560681 (SEQ ID NOS 1 & 2), rs1109037 (SEQ ID NOS 3 & 4), rs9866013 (SEQ ID NOS 5 & 6), rs13182883 (SEQ ID NOS 7 & 8), rs13218440 (SEQ ID NOS 9 & 10), rs7041158 (SEQ ID NOS 11 & 12), rs740598 (SEQ ID NOS 13 & 14), rs10773760 (SEQ ID NOS 15 & 16), rs4530059 (SEQ ID NOS 17 & 18), rs7205345 (SEQ ID NOS 19 & 20), rs8078417 (SEQ ID NOS 21 & 22), rs576261 (SEQ ID NOS 23 & 24), rs2567608 (SEQ ID NOS 25 & 26), rs430046 (SEQ ID NOS 27 & 28), rs9951171 (SEQ ID NOS 29 & 30), rs338882 (SEQ ID NOS 31 & 32), rs10776839 (SEQ ID NOS 33 & 34), rs9905977 (SEQ ID NOS 35 & 36), rs1277284 (SEQ ID NOS 37 & 38), rs258684 (SEQ ID NOS 39 & 40), rs1347696 (SEQ ID NOS 41 & 42), rs508485 (SEQ ID NOS 43 & 44), rs9788670 (SEQ ID NOS 45 & 46), rs8137254 (SEQ ID NOS 47 & 48), rs3143 (SEQ ID NOS 49 & 50), rs2182957 (SEQ ID NOS 51 & 52), rs3739005 (SEQ ID NOS 53 & 54), and rs530022 (SEQ ID NOS 55 & 56). In other embodiments, the at least one SNP is a tandem SNP selected from tandem SNP pairs rs7277033-rs2110153 (SEQ ID NOS 312 & 313); rs2822654-rs1882882 (SEQ ID NOS 314 & 315); rs368657-rs376635 (SEQ ID NOS 316 & 317); rs2822731-rs2822732 (SEQ ID NOS 318 & 319); rs1475881-rs7275487 (SEQ ID NOS 320 & 321); rs1735976-rs2827016 (SEQ ID NOS 322 & 323); rs447340-rs2824097 (SEQ ID NOS 324 & 325); rs418989-rs13047336 (SEQ ID NOS 326 & 327); rs987980-rs987981 (SEQ ID NOS 328 & 329); rs4143392-rs4143391 (SEQ ID NOS 330 & 331); rs1691324-rs13050434 (SEQ ID NOS 332 & 333); rs11909758-rs9980111 (SEQ ID NOS 334 & 335); rs2826842-rs232414 (SEQ ID NOS 336 & 337); rs1980969-rs1980970 (SEQ ID NOS 338 & 339); rs9978999-rs9979175 (SEQ ID NOS 340 & 341); rs1034346-rs12481852 (SEQ ID NOS 342 & 343); rs7509629-rs2828358 (SEQ ID NOS 344 & 345); rs4817013-rs7277036 (SEQ ID NOS 346 & 347); rs9981121-rs2829696 (SEQ ID NOS 348 & 349); rs455921-rs2898102 (SEQ ID NOS 350 & 351); rs2898102-rs458848 (SEQ ID NOS 352 & 353); rs961301-rs2830208 (SEQ ID NOS 354 & 355); rs2174536-rs458076 (SEQ ID NOS 356 & 357); rs11088023-rs11088024 (SEQ ID NOS 358 & 359); rs1011734-rs1011733 (SEQ ID NOS 360 & 361); rs2831244-rs9789838 (SEQ ID NOS 362 & 363); rs8132769-rs2831440 (SEQ ID NOS 364 & 365); rs8134080-rs2831524 (SEQ ID NOS 366 & 367); rs4817219-rs4817220 (SEQ ID NOS 368 & 369); rs2250911-rs2250997 (SEQ ID NOS 370 & 371); rs2831899-rs2831900 (SEQ ID NOS 372 & 373); rs2831902-rs2831903 (SEQ ID NOS 374 & 375); rs11088086-rs2251447 (SEQ ID NOS 376 & 377); rs2832040-rs11088088 (SEQ ID NOS 378 & 379); rs2832141-rs2246777 (SEQ ID NOS 380 & 381); rs2832959 rs9980934 (SEQ ID NOS 382 & 383); rs2833734-rs2833735 (SEQ ID NOS 384 & 385); rs933121-rs933122 (SEQ ID NOS 386 & 387); rs2834140-rs12626953 (SEQ ID NOS 388 & 389); rs2834485-rs3453 (SEQ ID NOS 390 & 391); rs9974986-rs2834703 (SEQ ID NOS 392 & 393); rs2776266-rs2835001 (SEQ ID NOS 394 & 395); rs1984014-rs1984015 (SEQ ID NOS 396 & 397); rs7281674-rs2835316 (SEQ ID NOS 398 & 399); rs13047304-rs13047322 (SEQ ID NOS 400 & 401); rs2835545-rs4816551 (SEQ ID NOS 402 & 403); rs2835735-rs2835736 (SEQ ID NOS 404 & 405); rs13047608-rs2835826 (SEQ ID NOS 406 & 407); rs2836550-rs2212596 (SEQ ID NOS 408 & 409); rs2836606-rs2836661 (SEQ ID NOS 410 & 411); rs465612-rs8131220 (SEQ ID NOS 412 & 413); rs9980072-rs8130031 (SEQ ID NOS 414 & 415); rs418359-rs2836926 (SEQ ID NOS 416 & 417); rs7278447-rs7278858 (SEQ ID NOS 418 & 419); rs385787-rs367001 (SEQ ID NOS 420 & 421); rs367001-rs386095 (SEQ ID NOS 422 & 423); rs2837296-rs2837297 (SEQ ID NOS 424 & 425); and rs2837381-rs4816672 (SEQ ID NOS 426 & 427). The at least one STR is selected from CSF1PO, FGA, TH01, vWA, D3S1358, D5S818, D7S820, D8S1179, D13S317, D16S539, D18S51, D21S11, D2S1338, Penta D, Penta E, D22S1045, D20S1082, D20S482, D18S853, D17S1301, D17S974, D14S1434, D12ATA63, D11S4463, D10S1435, D10S1248, D9S2157, D9S1122, D8S1115, D6S1017, D6S474, D5S2500, D4S2408, D4S2364, D3S4529, D3S3053, D2S1776, D2S441, D1S1677, D1S1627, and D1GATA113. The maternal sample is selected from blood, plasma, serum, urine and saliva. Preferably, the maternal sample is a plasma sample.

In another embodiment, the invention provides a method for determining the fraction of fetal nucleic acids in a maternal sample comprising a mixture of fetal and maternal genomic DNA e.g. cell-free DNA, wherein the method comprises the steps of: (a) amplifying a plurality of polymorphic target nucleic acids in the mixture of fetal and maternal genomic DNA; (b) performing massively parallel sequencing of at least a portion of the amplified product obtained in (a), wherein sequencing comprises providing a plurality of sequence tags; and (c) based on the sequencing, determining the fraction. The plurality of polymorphic target nucleic acids comprises at least one single nucleotide polymorphism (SNP). Alternatively, the plurality of polymorphic target nucleic acids comprises at least one short tandem repeat (STR). In some embodiments, the at least one SNP is a single SNP selected from rs560681 (SEQ ID NOS 1 & 2), rs1109037 (SEQ ID NOS 3 & 4), rs9866013 (SEQ ID NOS 5 & 6), rs13182883 (SEQ ID NOS 7 & 8), rs13218440 (SEQ ID NOS 9 & 10), rs7041158 (SEQ ID NOS 11 & 12), rs740598 (SEQ ID NOS 13 & 14), rs10773760 (SEQ ID NOS 15 & 16), rs4530059 (SEQ ID NOS 17 & 18), rs7205345 (SEQ ID NOS 19 & 20), rs8078417 (SEQ ID NOS 21 & 22), rs576261 (SEQ ID NOS 23 & 24), rs2567608 (SEQ ID NOS 25 & 26), rs430046 (SEQ ID NOS 27 & 28), rs9951171 (SEQ ID NOS 29 & 30), rs338882 (SEQ ID NOS 31 & 32), rs10776839 (SEQ ID NOS 33 &

34), rs9905977 (SEQ ID NOS 35 & 36), rs1277284 (SEQ ID NOS 37 & 38), rs258684 (SEQ ID NOS 39 & 40), rs1347696 (SEQ ID NOS 41 & 42), rs508485 (SEQ ID NOS 43 & 44), rs9788670 (SEQ ID NOS 45 & 46), rs8137254 (SEQ ID NOS 47 & 48), rs3143 (SEQ ID NOS 49 & 50), rs2182957 (SEQ ID NOS 51 & 52), rs3739005 (SEQ ID NOS 53 & 54), and rs530022 (SEQ ID NOS 55 & 56). In other embodiments, the at least one SNP is a tandem SNP selected from tandem SNP pairs rs7277033-rs2110153 (SEQ ID NOS 312 & 313); rs2822654-rs1882882 (SEQ ID NOS 314 & 315); rs368657-rs376635 (SEQ ID NOS 316 & 317); rs2822731-rs2822732 (SEQ ID NOS 318 & 319); rs1475881-rs7275487 (SEQ ID NOS 320 & 321); rs1735976-rs2827016 (SEQ ID NOS 322 & 323); rs447340-rs2824097 (SEQ ID NOS 324 & 325); rs418989-rs13047336 (SEQ ID NOS 326 & 327); rs987980-rs987981 (SEQ ID NOS 328 & 329); rs4143392-rs4143391 (SEQ ID NOS 330 & 331); rs1691324-rs13050434 (SEQ ID NOS 332 & 333); rs11909758-rs9980111 (SEQ ID NOS 334 & 335); rs2826842-rs232414 (SEQ ID NOS 336 & 337); rs1980969-rs1980970 (SEQ ID NOS 338 & 339); rs9978999-rs9979175 (SEQ ID NOS 340 & 341); rs1034346-rs12481852 (SEQ ID NOS 342 & 343); rs7509629-rs2828358 (SEQ ID NOS 344 & 345); rs4817013-rs7277036 (SEQ ID NOS 346 & 347); rs9981121-rs2829696 (SEQ ID NOS 348 & 349); rs455921-rs2898102 (SEQ ID NOS 350 & 351); rs2898102-rs458848 (SEQ ID NOS 352 & 353); rs961301-rs2830208 (SEQ ID NOS 354 & 355); rs2174536-rs458076 (SEQ ID NOS 356 & 357); rs11088023-rs11088024 (SEQ ID NOS 358 & 359); rs1011734-rs1011733 (SEQ ID NOS 360 & 361); rs2831244-rs9789838 (SEQ ID NOS 362 & 363); rs8132769-rs2831440 (SEQ ID NOS 364 & 365); rs8134080-rs2831524 (SEQ ID NOS 366 & 367); rs4817219-rs4817220 (SEQ ID NOS 368 & 369); rs2250911-rs2250997 (SEQ ID NOS 370 & 371); rs2831899-rs2831900 (SEQ ID NOS 372 & 373); rs2831902-rs2831903 (SEQ ID NOS 374 & 375); rs11088086-rs2251447 (SEQ ID NOS 376 & 377); rs2832040-rs11088088 (SEQ ID NOS 378 & 379); rs2832141-rs2246777 (SEQ ID NOS 380 & 381); rs2832959-rs9980934 (SEQ ID NOS 382 & 383); rs2833734-rs2833735 (SEQ ID NOS 384 & 385); rs933121-rs933122 (SEQ ID NOS 386 & 387); rs2834140-rs12626953 (SEQ ID NOS 388 & 389); rs2834485-rs3453 (SEQ ID NOS 390 & 391); rs9974986-rs2834703 (SEQ ID NOS 392 & 393); rs2776266-rs2835001 (SEQ ID NOS 394 & 395); rs1984014-rs1984015 (SEQ ID NOS 396 & 397); rs7281674-rs2835316 (SEQ ID NOS 398 & 399); rs13047304-rs13047322 (SEQ ID NOS 400 & 401); rs2835545-rs4816551 (SEQ ID NOS 402 & 403); rs2835735-rs2835736 (SEQ ID NOS 404 & 405); rs13047608-rs2835826 (SEQ ID NOS 406 & 407); rs2836550-rs2212596 (SEQ ID NOS 408 & 409); rs2836660-rs2836661 (SEQ ID NOS 410 & 411); rs465612-rs8131220 (SEQ ID NOS 412 & 413); rs9980072-rs8130031 (SEQ ID NOS 414 & 415); rs418359-rs2836926 (SEQ ID NOS 416 & 417); rs7278447-rs7278858 (SEQ ID NOS 418 & 419); rs385787-rs367001 (SEQ ID NOS 420 & 421); rs367001-rs386095 (SEQ ID NOS 422 & 423); rs2837296-rs2837297 (SEQ ID NOS 424 & 425); and rs2837381-rs4816672 (SEQ ID NOS 426 & 427). The at least one STR is selected from CSF1PO, FGA, TH01, vWA, D3S1358, D5S818, D7S820, D8S1179, D13S317, D16S539, D18S51, D21S11, D2S1338, Penta D, Penta E, D22S1045, D20S1082, D20S482, D18S853, D17S1301, D17S974, D14S1434, D12ATA63, D11S4463, D10S1435, D10S1248, D9S2157, D9S1122, D8S1115, D6S1017, D6S474, D5S2500, D4S2408, D4S2364, D3S4529, D3S3053, D2S1776, D2S441, D1S1677, D1S1627, and D1GATA113. The massively parallel sequencing is sequencing-by-synthesis with reversible dye terminators. Alternatively, the massively parallel sequencing is sequencing-by-ligation or single molecule sequencing. The maternal sample is selected from blood, plasma, serum, urine and saliva. Preferably, the maternal sample is a plasma sample.

In another embodiment, the invention provides a method for determining the fraction of fetal nucleic acids in a maternal sample comprising a mixture of fetal and maternal genomic DNA e.g. cell-free DNA, wherein the method comprises the steps of: (a) amplifying a plurality of polymorphic target nucleic acids in the mixture of fetal and maternal genomic DNA; (b) performing massively parallel sequencing of at least a portion of the amplified product obtained in (a), wherein sequencing comprises an amplification and provides a plurality of sequence tags; and (c) based on the sequencing, determining the fraction. The plurality of polymorphic target nucleic acids comprises at least one single nucleotide polymorphism (SNP). Alternatively, the plurality of polymorphic target nucleic acids comprises at least one short tandem repeat (STR). In some embodiments, the at least one SNP is a single SNP selected from rs560681 (SEQ ID NOS 1 & 2), rs1109037 (SEQ ID NOS 3 & 4), rs9866013 (SEQ ID NOS 5 & 6), rs13182883 (SEQ ID NOS 7 & 8), rs13218440 (SEQ ID NOS 9 & 10), rs7041158 (SEQ ID NOS 11 & 12), rs740598 (SEQ ID NOS 13 & 14), rs10773760 (SEQ ID NOS 15 & 16), rs4530059 (SEQ ID NOS 17 & 18), rs7205345 (SEQ ID NOS 19 & 20), rs8078417 (SEQ ID NOS 21 & 22), rs576261 (SEQ ID NOS 23 & 24), rs2567608 (SEQ ID NOS 25 & 26), rs430046 (SEQ ID NOS 27 & 28), rs9951171 (SEQ ID NOS 29 & 30), rs338882 (SEQ ID NOS 31 & 32), rs10776839 (SEQ ID NOS 33 & 34), rs9905977 (SEQ ID NOS 35 & 36), rs1277284 (SEQ ID NOS 37 & 38), rs258684 (SEQ ID NOS 39 & 40), rs1347696 (SEQ ID NOS 41 & 42), rs508485 (SEQ ID NOS 43 & 44), rs9788670 (SEQ ID NOS 45 & 46), rs8137254 (SEQ ID NOS 47 & 48), rs3143 (SEQ ID NOS 49 & 50), rs2182957 (SEQ ID NOS 51 & 52), rs3739005 (SEQ ID NOS 53 & 54), and rs530022 (SEQ ID NOS 55 & 56). In other embodiments, the at least one SNP is a tandem SNP selected from tandem SNP pairs rs7277033-rs2110153 (SEQ ID NOS 312 & 313); rs2822654-rs1882882 (SEQ ID NOS 314 & 315); rs368657-rs376635 (SEQ ID NOS 316 & 317); rs2822731-rs2822732 (SEQ ID NOS 318 & 319); rs1475881-rs7275487 (SEQ ID NOS 320 & 321); rs1735976-rs2827016 (SEQ ID NOS 322 & 323); rs447340-rs2824097 (SEQ ID NOS 324 & 325); rs418989-rs13047336 (SEQ ID NOS 326 & 327); rs987980-rs987981 (SEQ ID NOS 328 & 329); rs4143392-rs4143391 (SEQ ID NOS 330 & 331); rs1691324-rs13050434 (SEQ ID NOS 332 & 333); rs11909758-rs9980111 (SEQ ID NOS 334 & 335); rs2826842-rs232414 (SEQ ID NOS 336 & 337); rs1980969-rs1980970 (SEQ ID NOS 338 & 339); rs9978999-rs9979175 (SEQ ID NOS 340 & 341); rs1034346-rs12481852 (SEQ ID NOS 342 & 343); rs7509629-rs2828358 (SEQ ID NOS 344 & 345); rs4817013-rs7277036 (SEQ ID NOS 346 & 347); rs9981121-rs2829696 (SEQ ID NOS 348 & 349); rs455921-rs2898102 (SEQ ID NOS 350 & 351); rs2898102-rs458848 (SEQ ID NOS 352 & 353); rs961301-rs2830208 (SEQ ID NOS 354 & 355); rs2174536-rs458076 (SEQ ID NOS 356 & 357); rs11088023-rs11088024 (SEQ ID NOS 358 & 359); rs1011734-rs1011733 (SEQ ID NOS 360 & 361); rs2831244-rs9789838 (SEQ ID NOS 362 & 363);

rs8132769-rs2831440 (SEQ ID NOS 364 & 365); rs8134080-rs2831524 (SEQ ID NOS 366 & 367); rs4817219-rs4817220 (SEQ ID NOS 368 & 369); rs2250911-rs2250997 (SEQ ID NOS 370 & 371); rs2831899-rs2831900 (SEQ ID NOS 372 & 373); rs2831902-rs2831903 (SEQ ID NOS 374 & 375); rs11088086-rs2251447 (SEQ ID NOS 376 & 377); rs2832040-rs11088088 (SEQ ID NOS 378 & 379); rs2832141-rs2246777 (SEQ ID NOS 380 & 381); rs2832959-rs9980934 (SEQ ID NOS 382 & 383); rs2833734-rs2833735 (SEQ ID NOS 384 & 385); rs933121-rs933122 (SEQ ID NOS 386 & 387); rs2834140-rs12626953 (SEQ ID NOS 388 & 389); rs2834485-rs3453 (SEQ ID NOS 390 & 391); rs9974986-rs2834703 (SEQ ID NOS 392 & 393); rs2776266-rs2835001 (SEQ ID NOS 394 & 395); rs1984014-rs1984015 (SEQ ID NOS 396 & 397); rs7281674-rs2835316 (SEQ ID NOS 398 & 399); rs13047304-rs13047322 (SEQ ID NOS 400 & 401); rs2835545-rs4816551 (SEQ ID NOS 402 & 403); rs2835735-rs2835736 (SEQ ID NOS 404 & 405); rs13047608-rs2835826 (SEQ ID NOS 406 & 407); rs2836550-rs2212596 (SEQ ID NOS 408 & 409); rs2836660-rs2836661 (SEQ ID NOS 410 & 411); rs465612-rs8131220 (SEQ ID NOS 412& 413); rs9980072-rs8130031 (SEQ ID NOS 414 & 415); rs418359-rs2836926 (SEQ ID NOS 416 & 417); rs7278447-rs7278858 (SEQ ID NOS 418 & 419); rs385787-rs367001 (SEQ ID NOS 420 & 421); rs367001-rs386095 (SEQ ID NOS 422 & 423); rs2837296-rs2837297 (SEQ ID NOS 424 & 425); and rs2837381-rs4816672 (SEQ ID NOS 426 & 427). The at least one STR is selected from CSF1PO, FGA, TH01, vWA, D3S1358, D5S818, D7S820, D8S1179, D13S317, D16S539, D18S51, D21S11, D2S1338, Penta D, Penta E, D22S1045, D20S1082, D20S482, D18S853, D17S1301, D17S974, D14S1434, D12ATA63, D11S4463, D10S1435, D10S1248, D9S2157, D9S1122, D8S1115, D6S1017, D6S474, D5S2500, D4S2408, D4S2364, D3S4529, D3S3053, D2S1776, D2S441, D1S1677, D1S1627, and D1GATA113. The maternal sample is selected from blood, plasma, serum, urine and saliva. Preferably, the maternal sample is a plasma sample.

In another embodiment, the invention provides a method for determining the fraction of fetal nucleic acids in a maternal sample comprising a mixture of fetal and maternal genomic DNA e.g. cell-free DNA, wherein the method comprises the steps of: (a) amplifying a plurality of polymorphic target nucleic acids in the mixture of fetal and maternal genomic DNA; (b) performing massively parallel sequencing of at least a portion of the amplified product obtained in (a), wherein sequencing comprises an amplification and provides a plurality of sequence tags; and (c) based on the sequencing, determining the fraction. The plurality of polymorphic target nucleic acids comprises at least one single nucleotide polymorphism (SNP). Alternatively, the plurality of polymorphic target nucleic acids comprises at least one short tandem repeat (STR). In some embodiments, the at least one SNP is a single SNP selected from rs560681 (SEQ ID NOS 1 & 2), rs1109037 (SEQ ID NOS 3 & 4), rs9866013 (SEQ ID NOS 5 & 6), rs13182883 (SEQ ID NOS 7 & 8), rs13218440 (SEQ ID NOS 9 & 10), rs7041158 (SEQ ID NOS 11 & 12), rs740598 (SEQ ID NOS 13 & 14), rs10773760 (SEQ ID NOS 15 & 16), rs4530059 (SEQ ID NOS 17 & 18), rs7205345 (SEQ ID NOS 19 & 20), rs8078417 (SEQ ID NOS 21 & 22), rs576261 (SEQ ID NOS 23 & 24), rs2567608 (SEQ ID NOS 25 & 26), rs430046 (SEQ ID NOS 27 & 28), rs9951171 (SEQ ID NOS 29 & 30), rs338882 (SEQ ID NOS 31 & 32), rs10776839 (SEQ ID NOS 33 & 34), rs9905977 (SEQ ID NOS 35 & 36), rs1277284 (SEQ ID NOS 37 & 38), rs258684 (SEQ ID NOS 39 & 40), rs1347696 (SEQ ID NOS 41 & 42), rs508485 (SEQ ID NOS 43 & 44), rs9788670 (SEQ ID NOS 45 & 46), rs8137254 (SEQ ID NOS 47 & 48), rs3143 (SEQ ID NOS 49 & 50), rs2182957 (SEQ ID NOS 51 & 52), rs3739005 (SEQ ID NOS 53 & 54), and rs530022 (SEQ ID NOS 55 & 56). In other embodiments, the at least one SNP is a tandem SNP selected from tandem SNP pairs rs7277033-rs2110153 (SEQ ID NOS 312 & 313); rs2822654-rs1882882 (SEQ ID NOS 314 & 315); rs368657-rs376635 (SEQ ID NOS 316 & 317); rs2822731-rs2822732 (SEQ ID NOS 318 & 319); rs1475881-rs7275487 (SEQ ID NOS 320 & 321); rs1735976-rs2827016 (SEQ ID NOS 322 & 323); rs447340-rs2824097 (SEQ ID NOS 324 & 325); rs418989-rs13047336 (SEQ ID NOS 326 & 327); rs987980-rs987981 (SEQ ID NOS 328 & 329); rs4143392-rs4143391 (SEQ ID NOS 330 & 331); rs1691324-rs13050434 (SEQ ID NOS 332 & 333); rs11909758-rs9980111 (SEQ ID NOS 334 & 335); rs2826842-rs232414 (SEQ ID NOS 336 & 337); rs1980969-rs1980970 (SEQ ID NOS 338 & 339); rs9978999-rs9979175 (SEQ ID NOS 340 & 341); rs1034346-rs12481852 (SEQ ID NOS 342 & 343); rs7509629-rs2828358 (SEQ ID NOS 344 & 345); rs4817013-rs7277036 (SEQ ID NOS 346 & 347); rs9981121-rs2829696 (SEQ ID NOS 348 & 349); rs455921-rs2898102 (SEQ ID NOS 350 & 351); rs2898102-rs458848 (SEQ ID NOS 352 & 353); rs961301-rs2830208 (SEQ ID NOS 354 & 355); rs2174536-rs458076 (SEQ ID NOS 356 & 357); rs11088023-rs11088024 (SEQ ID NOS 358 & 359); rs1011734-rs1011733 (SEQ ID NOS 360 & 361); rs2831244-rs9789838 (SEQ ID NOS 362 & 363); rs8132769-rs2831440 (SEQ ID NOS 364 & 365); rs8134080-rs2831524 (SEQ ID NOS 366 & 367); rs4817219-rs4817220 (SEQ ID NOS 368 & 369); rs2250911-rs2250997 (SEQ ID NOS 370 & 371); rs2831899-rs2831900 (SEQ ID NOS 372 & 373); rs2831902-rs2831903 (SEQ ID NOS 374 & 375); rs11088086-rs2251447 (SEQ ID NOS 376 & 377); rs2832040-rs11088088 (SEQ ID NOS 378 & 379); rs2832141-rs2246777 (SEQ ID NOS 380 & 381); rs2832959-rs9980934 (SEQ ID NOS 382 & 383); rs2833734-rs2833735 (SEQ ID NOS 384 & 385); rs933121-rs933122 (SEQ ID NOS 386 & 387); rs2834140-rs12626953 (SEQ ID NOS 388 & 389); rs2834485-rs3453 (SEQ ID NOS 390 & 391); rs9974986-rs2834703 (SEQ ID NOS 392 & 393); rs2776266-rs2835001 (SEQ ID NOS 394 & 395); rs1984014-rs1984015 (SEQ ID NOS 396 & 397); rs7281674-rs2835316 (SEQ ID NOS 398 & 399); rs13047304-rs13047322 (SEQ ID NOS 400 & 401); rs2835545-rs4816551 (SEQ ID NOS 402 & 403); rs2835735-rs2835736 (SEQ ID NOS 404 & 405); rs13047608-rs2835826 (SEQ ID NOS 406 & 407); rs2836550-rs2212596 (SEQ ID NOS 408 & 409); rs2836660-rs2836661 (SEQ ID NOS 410 & 411); rs465612-rs8131220 (SEQ ID NOS 412& 413); rs9980072-rs8130031 (SEQ ID NOS 414 & 415); rs418359-rs2836926 (SEQ ID NOS 416 & 417); rs7278447-rs7278858 (SEQ ID NOS 418 & 419); rs385787-rs367001 (SEQ ID NOS 420 & 421); rs367001-rs386095 (SEQ ID NOS 422 & 423); rs2837296-rs2837297 (SEQ ID NOS 424 & 425); and rs2837381-rs4816672 (SEQ ID NOS 426 & 427). The at least one STR is selected from CSF1PO, FGA, TH01, vWA, D3S1358, D5S818, D7S820, D8S1179, D13S317, D16S539, D18S51, D21S11, D2S1338, Penta D, Penta E, D22S1045, D20S1082, D20S482, D18S853, D17S1301, D17S974, D14S1434, D12ATA63, D11S4463, D10S1435, D10S1248, D9S2157, D9S1122, D8S1115, D6S1017, D6S474, D5S2500, D4S2408, D4S2364, D3S4529, D3S3053, D2S1776, D2S441, D1S1677, D1S1627, and D1GATA113. The massively parallel sequencing is sequencing-by-synthesis with reversible dye terminators. Alternatively, the massively parallel sequencing is sequencing-by-ligation or single molecule sequencing. The maternal sample is selected from blood, plasma, serum, urine and saliva. Preferably, the maternal sample is a plasma sample.

In one embodiment, the invention provides a method for determining the fraction of fetal nucleic acids in a maternal sample comprising a mixture of fetal and maternal genomic DNA, wherein the method comprises the steps of: (a) amplifying a plurality of polymorphic target nucleic acids in the mixture of fetal and maternal genomic DNA; (b) performing massively parallel sequencing of at least a portion of the amplified product obtained in (a), wherein sequencing comprises providing a plurality of sequence tags; and (c) based on the sequencing, determining the fraction, wherein determining the fraction comprises determining the number of fetal and maternal sequence tags mapped to a reference genome comprising of at least one polymorphic nucleic acid. The maternal sample is selected from blood, plasma, serum, urine and saliva. Preferably, the maternal sample is a plasma sample.

In another embodiment, the invention provides a method for determining the fraction of fetal nucleic acids in a maternal sample comprising a mixture of fetal and maternal genomic DNA, wherein the method comprises the steps of: (a) amplifying a plurality of polymorphic target nucleic acids in the mixture of fetal and maternal genomic DNA; (b) performing massively parallel sequencing of at least a portion of the amplified product obtained in (a), wherein sequencing comprises providing a plurality of sequence tags; and (c) based on the sequencing, determining the fraction, wherein determining the fraction comprises determining the number of fetal and maternal sequence tags mapped to a reference genome comprising of at least one polymorphic nucleic acid. The plurality of polymorphic target nucleic acids comprises at least one single nucleotide polymorphism (SNP). Alternatively, the plurality of polymorphic target nucleic acids comprises at least one short tandem repeat (STR). In some embodiments, the at least one SNP is a single SNP selected from rs560681 (SEQ ID NOS 1 & 2), rs1109037 (SEQ ID NOS 3 & 4), rs9866013 (SEQ ID NOS 5 & 6), rs13182883 (SEQ ID NOS 7 & 8), rs13218440 (SEQ ID NOS 9 & 10), rs7041158 (SEQ ID NOS 11 & 12), rs740598 (SEQ ID NOS 13 & 14), rs10773760 (SEQ ID NOS 15 & 16), rs4530059 (SEQ ID NOS 17 & 18), rs7205345 (SEQ ID NOS 19 & 20), rs8078417 (SEQ ID NOS 21 & 22), rs576261 (SEQ ID NOS 23 & 24), rs2567608 (SEQ ID NOS 25 & 26), rs430046 (SEQ ID NOS 27 & 28), rs9951171 (SEQ ID NOS 29 & 30), rs338882 (SEQ ID NOS 31 & 32), rs10776839 (SEQ ID NOS 33 & 34), rs9905977 (SEQ ID NOS 35 & 36), rs1277284 (SEQ ID NOS 37 & 38), rs258684 (SEQ ID NOS 39 & 40), rs1347696 (SEQ ID NOS 41 & 42), rs508485 (SEQ ID NOS 43 & 44), rs9788670 (SEQ ID NOS 45 & 46), rs8137254 (SEQ ID NOS 47 & 48), rs3143 (SEQ ID NOS 49 & 50), rs2182957 (SEQ ID NOS 51 & 52), rs3739005 (SEQ ID NOS 53 & 54), and rs530022 (SEQ ID NOS 55 & 56). In other embodiments, the at least one SNP is a tandem SNP selected from tandem SNP pairs rs7277033-rs2110153 (SEQ ID NOS 312 & 313); rs2822654-rs1882882 (SEQ ID NOS 314 & 315); rs368657-rs376635 (SEQ ID NOS 316 & 317); rs2822731-rs2822732 (SEQ ID NOS 318 & 319); rs1475881-rs7275487 (SEQ ID NOS 320 & 321); rs1735976-rs2827016 (SEQ ID NOS 322 & 323); rs447340-rs2824097 (SEQ ID NOS 324 & 325); rs418989-rs13047336 (SEQ ID NOS 326 & 327); rs987980-rs987981 (SEQ ID NOS 328 & 329); rs4143392-rs4143391 (SEQ ID NOS 330 & 331); rs1691324-rs13050434 (SEQ ID NOS 332 & 333); rs11909758-rs9980111 (SEQ ID NOS 334 & 335); rs2826842-rs232414 (SEQ ID NOS 336 & 337); rs1980969-rs1980970 (SEQ ID NOS 338 & 339); rs9978999-rs9979175 (SEQ ID NOS 340 & 341); rs1034346-rs12481852 (SEQ ID NOS 342 & 343); rs7509629-rs2828358 (SEQ ID NOS 344 & 345); rs4817013-rs7277036 (SEQ ID NOS 346 & 347); rs9981121-rs2829696 (SEQ ID NOS 348 & 349); rs455921-rs2898102 (SEQ ID NOS 350 & 351); rs2898102-rs458848 (SEQ ID NOS 352 & 353); rs961301-rs2830208 (SEQ ID NOS 354 & 355); rs2174536-rs458076 (SEQ ID NOS 356 & 357); rs11088023-rs11088024 (SEQ ID NOS 358 & 359); rs1011734-rs1011733 (SEQ ID NOS 360 & 361); rs2831244-rs9789838 (SEQ ID NOS 362 & 363); rs8132769-rs2831440 (SEQ ID NOS 364 & 365); rs8134080-rs2831524 (SEQ ID NOS 366 & 367); rs4817219-rs4817220 (SEQ ID NOS 368 & 369); rs2250911-rs2250997 (SEQ ID NOS 370 & 371); rs2831899-rs2831900 (SEQ ID NOS 372 & 373); rs2831902-rs2831903 (SEQ ID NOS 374 & 375); rs11088086-rs2251447 (SEQ ID NOS 376 & 377); rs2832040-rs11088088 (SEQ ID NOS 378 & 379); rs2832141-rs2246777 (SEQ ID NOS 380 & 381); rs2832959-rs9980934 (SEQ ID NOS 382 & 383); rs2833734-rs2833735 (SEQ ID NOS 384 & 385); rs933121-rs933122 (SEQ ID NOS 386 & 387); rs2834140-rs12626953 (SEQ ID NOS 388 & 389); rs2834485-rs3453 (SEQ ID NOS 390 & 391); rs9974986-rs2834703 (SEQ ID NOS 392 & 393); rs2776266-rs2835001 (SEQ ID NOS 394 & 395); rs1984014-rs1984015 (SEQ ID NOS 396 & 397); rs7281674-rs2835316 (SEQ ID NOS 398 & 399); rs13047304-rs13047322 (SEQ ID NOS 400 & 401); rs2835545-rs4816551 (SEQ ID NOS 402 & 403); rs2835735-rs2835736 (SEQ ID NOS 404 & 405); rs13047608-rs2835826 (SEQ ID NOS 406 & 407); rs2836550-rs2212596 (SEQ ID NOS 408 & 409); rs2836660-rs2836661 (SEQ ID NOS 410 & 411); rs465612-rs8131220 (SEQ ID NOS 412 & 413); rs9980072-rs8130031 (SEQ ID NOS 414 & 415); rs418359-rs2836926 (SEQ ID NOS 416 & 417); rs7278447-rs7278858 (SEQ ID NOS 418 & 419); rs385787-rs367001 (SEQ ID NOS 420 & 421); rs367001-rs386095 (SEQ ID NOS 422 & 423); rs2837296-rs2837297 (SEQ ID NOS 424 & 425); and rs2837381-rs4816672 (SEQ ID NOS 426 & 427). The at least one STR is selected from CSF1PO, FGA, TH01, vWA, D3S1358, D5S818, D7S820, D8S1179, D13S317, D16S539, D18S51, D21S11, D2S1338, Penta D, Penta E, D22S1045, D20S1082, D20S482, D18S853, D17S1301, D17S974, D14S1434, D12ATA63, D11S4463, D10S1435, D10S1248, D9S2157, D9S1122, D8S1115, D6S1017, D6S474, D5S2500, D4S2408, D4S2364, D3S4529, D3S3053, D2S1776, D2S441, D1S1677, D1S1627, and D1GATA113. The maternal sample is selected from blood, plasma, serum, urine and saliva. Preferably, the maternal sample is a plasma sample.

In another embodiment, the invention provides a method for determining the fraction of fetal nucleic acids in a maternal sample comprising a mixture of fetal and maternal genomic DNA, wherein the method comprises the steps of: (a) amplifying a plurality of polymorphic target nucleic acids in the mixture of fetal and maternal genomic DNA; (b) performing massively parallel sequencing of at least a portion of the amplified product obtained in (a), wherein sequencing comprises providing a plurality of sequence tags; and (c) based on the sequencing, determining the fraction, wherein determining the fraction comprises determining the number of fetal and maternal sequence tags mapped to a reference genome comprising of at least one polymorphic nucleic acid. The plurality of polymorphic target nucleic acids comprises at least one single nucleotide polymorphism (SNP). Alternatively, the plurality of polymorphic target nucleic acids comprises at least one short tandem repeat (STR). In some embodiments, the at least one SNP is a single SNP selected from rs560681 (SEQ ID NOS 1 & 2), rs1109037 (SEQ ID NOS 3 & 4), rs9866013 (SEQ ID NOS 5 & 6), rs13182883 (SEQ ID NOS 7 & 8), rs13218440 (SEQ ID NOS 9 & 10), rs7041158 (SEQ ID NOS 11 & 12), rs740598 (SEQ ID NOS 13 & 14), rs10773760 (SEQ ID NOS 15 & 16), rs4530059 (SEQ ID NOS 17 & 18), rs7205345 (SEQ ID NOS 19 & 20), rs8078417 (SEQ ID NOS 21 & 22), rs576261 (SEQ ID NOS 23 & 24), rs2567608 (SEQ ID NOS 25 & 26), rs430046 (SEQ ID NOS 27 & 28), rs9951171 (SEQ ID NOS 29 & 30), rs338882 (SEQ ID NOS 31 & 32), rs10776839 (SEQ ID NOS 33 & 34), rs9905977 (SEQ ID NOS 35 & 36), rs1277284 (SEQ ID NOS 37 & 38), rs258684 (SEQ ID NOS 39 & 40), rs1347696 (SEQ ID NOS 41 & 42), rs508485 (SEQ ID NOS 43 & 44), rs9788670 (SEQ ID NOS 45 & 46), rs8137254 (SEQ ID NOS 47 & 48), rs3143 (SEQ ID NOS 49 & 50), rs2182957 (SEQ ID NOS 51 & 52), rs3739005 (SEQ ID NOS 53 & 54), and rs530022 (SEQ ID NOS 55 & 56). In other embodiments, the at least one SNP is a tandem SNP selected from tandem SNP pairs rs7277033-rs2110153 (SEQ ID NOS 312 & 313); rs2822654-rs1882882 (SEQ ID NOS 314 & 315); rs368657-rs376635 (SEQ ID NOS 316 & 317); rs2822731-rs2822732 (SEQ ID NOS 318 & 319); rs1475881-rs7275487 (SEQ ID NOS 320 & 321); rs1735976-rs2827016 (SEQ ID NOS 322 & 323); rs447340-rs2824097 (SEQ ID NOS 324 & 325); rs418989-rs13047336 (SEQ ID NOS 326 & 327); rs987980-rs987981 (SEQ ID NOS 328 & 329); rs4143392-rs4143391 (SEQ ID NOS 330 & 331); rs1691324-rs13050434 (SEQ ID NOS 332 & 333); rs11909758-rs9980111 (SEQ ID NOS 334 & 335); rs2826842-rs232414 (SEQ ID NOS 336 & 337); rs1980969-rs1980970 (SEQ ID NOS 338 & 339); rs9978999-rs9979175 (SEQ ID NOS 340 & 341); rs1034346-rs12481852 (SEQ ID NOS 342 & 343); rs7509629-rs2828358 (SEQ ID NOS 344 & 345); rs4817013-rs7277036 (SEQ ID NOS 346 & 347); rs9981121-rs2829696 (SEQ ID NOS 348 & 349); rs455921-rs2898102 (SEQ ID NOS 350 & 351); rs2898102-rs458848 (SEQ ID NOS 352 & 353); rs961301-rs2830208 (SEQ ID NOS 354 & 355); rs2174536-rs458076 (SEQ ID NOS 356 & 357); rs11088023-rs11088024 (SEQ ID NOS 358 & 359); rs1011734-rs1011733 (SEQ ID NOS 360 & 361); rs2831244-rs9789838 (SEQ ID NOS 362 & 363); rs8132769-rs2831440 (SEQ ID NOS 364 & 365); rs8134080-rs2831524 (SEQ ID NOS 366 & 367); rs4817219-rs4817220 (SEQ ID NOS 368 & 369); rs2250911-rs2250997 (SEQ ID NOS 370 & 371); rs2831899-rs2831900 (SEQ ID NOS 372 & 373); rs2831902-rs2831903 (SEQ ID NOS 374 & 375); rs11088086-rs2251447 (SEQ ID NOS 376 & 377); rs2832040-rs11088088 (SEQ ID NOS 378 & 379); rs2832141-rs2246777 (SEQ ID NOS 380 & 381); rs2832959-rs9980934 (SEQ ID NOS 382 & 383); rs2833734-rs2833735 (SEQ ID NOS 384 & 385); rs933121-rs933122 (SEQ ID NOS 386 & 387); rs2834140-rs12626953 (SEQ ID NOS 388 & 389); rs2834485-rs3453 (SEQ ID NOS 390 & 391); rs9974986-rs2834703 (SEQ ID NOS 392 & 393); rs2776266-rs2835001 (SEQ ID NOS 394 & 395); rs1984014-rs1984015 (SEQ ID NOS 396 & 397); rs7281674-rs2835316 (SEQ ID NOS 398 & 399); rs13047304-rs13047322 (SEQ ID NOS 400 & 401); rs2835545-rs4816551 (SEQ ID NOS 402 & 403); rs2835735-rs2835736 (SEQ ID NOS 404 & 405); rs13047608-rs2835826 (SEQ ID NOS 406 & 407); rs2836550-rs2212596 (SEQ ID NOS 408 & 409); rs2836660-rs2836661 (SEQ ID NOS 410 & 411); rs465612-rs8131220 (SEQ ID NOS 412 & 413); rs9980072-rs8130031 (SEQ ID NOS 414 & 415); rs418359-rs2836926 (SEQ ID NOS 416 & 417); rs7278447-rs7278858 (SEQ ID NOS 418 & 419); rs385787-rs367001 (SEQ ID NOS 420 & 421); rs367001-rs386095 (SEQ ID NOS 422 & 423); rs2837296-rs2837297 (SEQ ID NOS 424 & 425); and rs2837381-rs4816672 (SEQ ID NOS 426 & 427). The at least one STR is selected from CSF1PO, FGA, TH01, vWA, D3S1358, D5S818, D7S820, D8S1179, D13S317, D16S539, D18S51, D21S11, D2S1338, Penta D, Penta E, D22S1045, D20S1082, D20S482, D18S853, D17S1301, D17S974, D14S1434, D12ATA63, D11S4463, D10S1435, D10S1248, D9S2157, D9S1122, D8S1115, D6S1017, D6S474, D5S2500, D4S2408, D4S2364, D3S4529, D3 S3053, D2S1776, D2S441, D1S1677, D1S1627, and D1GATA113. The massively parallel sequencing is sequencing-by-synthesis with reversible dye terminators. Alternatively, the massively parallel sequencing is sequencing-by-ligation or single molecule sequencing. The maternal sample is selected from blood, plasma, serum, urine and saliva. Preferably, the maternal sample is a plasma sample.

In another embodiment, the invention provides a method for determining the fraction of fetal nucleic acids in a maternal sample comprising a mixture of fetal and maternal genomic DNA, wherein the method comprises the steps of: (a) amplifying a plurality of polymorphic target nucleic acids in the mixture of fetal and maternal genomic DNA; (b) performing massively parallel sequencing of at least a portion of the amplified product obtained in (a), wherein sequencing comprises an amplification and provides a plurality of sequence tags; and (c) based on the sequencing, determining the fraction, wherein determining the fraction comprises determining the number of fetal and maternal sequence tags mapped to a reference genome comprising of at least one polymorphic nucleic acid. The plurality of polymorphic target nucleic acids comprises at least one single nucleotide polymorphism (SNP). Alternatively, the plurality of polymorphic target nucleic acids comprises at least one short tandem repeat (STR). In some embodiments, the at least one SNP is a single SNP selected from rs560681 (SEQ ID NOS 1 & 2), rs1109037 (SEQ ID NOS 3 & 4), rs9866013 (SEQ ID NOS 5 & 6), rs13182883 (SEQ ID NOS 7 & 8), rs13218440 (SEQ ID NOS 9 & 10), rs7041158 (SEQ ID NOS 11 & 12), rs740598 (SEQ ID NOS 13 & 14), rs10773760 (SEQ ID NOS 15 & 16), rs4530059 (SEQ ID NOS 17 & 18), rs7205345 (SEQ ID NOS 19 & 20), rs8078417 (SEQ ID NOS 21 & 22), rs576261 (SEQ ID NOS 23 & 24), rs2567608 (SEQ ID NOS 25 & 26), rs430046 (SEQ ID NOS 27 & 28), rs9951171 (SEQ ID NOS 29 & 30), rs338882 (SEQ ID NOS 31 & 32), rs10776839 (SEQ ID NOS 33 & 34), rs9905977 (SEQ ID NOS 35 & 36), rs1277284 (SEQ ID NOS 37 & 38), rs258684 (SEQ ID NOS 39 & 40), rs1347696 (SEQ ID NOS 41 & 42), rs508485 (SEQ ID NOS 43 & 44), rs9788670 (SEQ ID NOS 45 & 46), rs8137254 (SEQ ID NOS 47 & 48), rs3143 (SEQ ID NOS 49 & 50), rs2182957 (SEQ ID NOS 51 & 52), rs3739005 (SEQ ID NOS 53 & 54), and rs530022 (SEQ ID NOS 55 &

56). In other embodiments, the at least one SNP is a tandem SNP selected from tandem SNP pairs rs7277033-rs2110153 (SEQ ID NOS 312 & 313); rs2822654-rs1882882 (SEQ ID NOS 314 & 315); rs368657-rs376635 (SEQ ID NOS 316 & 317); rs2822731-rs2822732 (SEQ ID NOS 318 & 319); rs1475881-rs7275487 (SEQ ID NOS 320 & 321); rs1735976-rs2827016 (SEQ ID NOS 322 & 323); rs447340-rs2824097 (SEQ ID NOS 324 & 325); rs418989-rs13047336 (SEQ ID NOS 326 & 327); rs987980-rs987981 (SEQ ID NOS 328 & 329); rs4143392-rs4143391 (SEQ ID NOS 330 & 331); rs1691324-rs13050434 (SEQ ID NOS 332 & 333); rs11909758-rs9980111 (SEQ ID NOS 334 & 335); rs2826842-rs232414 (SEQ ID NOS 336 & 337); rs1980969-rs1980970 (SEQ ID NOS 338 & 339); rs9978999-rs9979175 (SEQ ID NOS 340 & 341); rs1034346-rs12481852 (SEQ ID NOS 342 & 343); rs7509629-rs2828358 (SEQ ID NOS 344 & 345); rs4817013-rs7277036 (SEQ ID NOS 346 & 347); rs9981121-rs2829696 (SEQ ID NOS 348 & 349); rs455921-rs2898102 (SEQ ID NOS 350 & 351); rs2898102-rs458848 (SEQ ID NOS 352 & 353); rs961301-rs2830208 (SEQ ID NOS 354 & 355); rs2174536-rs458076 (SEQ ID NOS 356 & 357); rs11088023-rs11088024 (SEQ ID NOS 358 & 359); rs1011734-rs1011733 (SEQ ID NOS 360 & 361); rs2831244-rs9789838 (SEQ ID NOS 362 & 363); rs8132769-rs2831440 (SEQ ID NOS 364 & 365); rs8134080-rs2831524 (SEQ ID NOS 366 & 367); rs4817219-rs4817220 (SEQ ID NOS 368 & 369); rs2250911-rs2250997 (SEQ ID NOS 370 & 371); rs2831899-rs2831900 (SEQ ID NOS 372 & 373); rs2831902-rs2831903 (SEQ ID NOS 374 & 375); rs11088086-rs2251447 (SEQ ID NOS 376 & 377); rs2832040-rs11088088 (SEQ ID NOS 378 & 379); rs2832141-rs2246777 (SEQ ID NOS 380 & 381); rs2832959-rs9980934 (SEQ ID NOS 382 & 383); rs2833734-rs2833735 (SEQ ID NOS 384 & 385); rs933121-rs933122 (SEQ ID NOS 386 & 387); rs2834140-rs12626953 (SEQ ID NOS 388 & 389); rs2834485-rs3453 (SEQ ID NOS 390 & 391); rs9974986-rs2834703 (SEQ ID NOS 392 & 393); rs2776266-rs2835001 (SEQ ID NOS 394 & 395); rs1984014-rs1984015 (SEQ ID NOS 396 & 397); rs7281674-rs2835316 (SEQ ID NOS 398 & 399); rs13047304-rs13047322 (SEQ ID NOS 400 & 401); rs2835545-rs4816551 (SEQ ID NOS 402 & 403); rs2835735-rs2835736 (SEQ ID NOS 404 & 405); rs13047608-rs2835826 (SEQ ID NOS 406 & 407); rs2836550-rs2212596 (SEQ ID NOS 408 & 409); rs2836660-rs2836661 (SEQ ID NOS 410 & 411); rs465612-rs8131220 (SEQ ID NOS 412 & 413); rs9980072-rs8130031 (SEQ ID NOS 414 & 415); rs418359-rs2836926 (SEQ ID NOS 416 & 417); rs7278447-rs7278858 (SEQ ID NOS 418 & 419); rs385787-rs367001 (SEQ ID NOS 420 & 421); rs367001-rs386095 (SEQ ID NOS 422 & 423); rs2837296-rs2837297 (SEQ ID NOS 424 & 425); and rs2837381-rs4816672 (SEQ ID NOS 426 & 427). The at least one STR is selected from CSF1PO, FGA, TH01, vWA, D3S1358, D5S818, D7S820, D8S1179, D13S317, D16S539, D18S51, D21S11, D2S1338, Penta D, Penta E, D22S1045, D20S1082, D20S482, D18S853, D17S1301, D17S974, D14S1434, D12ATA63, D11S4463, D10S1435, D10S1248, D9S2157, D9S1122, D8S1115, D6S1017, D6S474, D5S2500, D4S2408, D4S2364, D3S4529, D3S3053, D2S1776, D2S441, D1S1677, D1S1627, and D1GATA113. The maternal sample is selected from blood, plasma, serum, urine and saliva. Preferably, the maternal sample is a plasma sample.

In another embodiment, the invention provides a method for determining the fraction of fetal nucleic acids in a maternal sample comprising a mixture of fetal and maternal genomic DNA, wherein the method comprises the steps of: (a) amplifying a plurality of polymorphic target nucleic acids in the mixture of fetal and maternal genomic DNA; (b) performing massively parallel sequencing of at least a portion of the amplified product obtained in (a), wherein sequencing comprises an amplification and provides a plurality of sequence tags; and (c) based on the sequencing, determining the fraction, wherein determining the fraction comprises determining the number of fetal and maternal sequence tags mapped to a reference genome comprising of at least one polymorphic nucleic acid. The plurality of polymorphic target nucleic acids comprises at least one single nucleotide polymorphism (SNP). Alternatively, the plurality of polymorphic target nucleic acids comprises at least one short tandem repeat (STR). In some embodiments, the at least one SNP is a single SNP selected from rs560681 (SEQ ID NOS 1 & 2), rs1109037 (SEQ ID NOS 3 & 4), rs9866013 (SEQ ID NOS 5 & 6), rs13182883 (SEQ ID NOS 7 & 8), rs13218440 (SEQ ID NOS 9 & 10), rs7041158 (SEQ ID NOS 11 & 12), rs740598 (SEQ ID NOS 13 & 14), rs10773760 (SEQ ID NOS 15 & 16), rs4530059 (SEQ ID NOS 17 & 18), rs7205345 (SEQ ID NOS 19 & 20), rs8078417 (SEQ ID NOS 21 & 22), rs576261 (SEQ ID NOS 23 & 24), rs2567608 (SEQ ID NOS 25 & 26), rs430046 (SEQ ID NOS 27 & 28), rs9951171 (SEQ ID NOS 29 & 30), rs338882 (SEQ ID NOS 31 & 32), rs10776839 (SEQ ID NOS 33 & 34), rs9905977 (SEQ ID NOS 35 & 36), rs1277284 (SEQ ID NOS 37 & 38), rs258684 (SEQ ID NOS 39 & 40), rs1347696 (SEQ ID NOS 41 & 42), rs508485 (SEQ ID NOS 43 & 44), rs9788670 (SEQ ID NOS 45 & 46), rs8137254 (SEQ ID NOS 47 & 48), rs3143 (SEQ ID NOS 49 & 50), rs2182957 (SEQ ID NOS 51 & 52), rs3739005 (SEQ ID NOS 53 & 54), and rs530022 (SEQ ID NOS 55 & 56). In other embodiments, the at least one SNP is a tandem SNP selected from tandem SNP pairs rs7277033-rs2110153 (SEQ ID NOS 312 & 313); rs2822654-rs1882882 (SEQ ID NOS 314 & 315); rs368657-rs376635 (SEQ ID NOS 316 & 317); rs2822731-rs2822732 (SEQ ID NOS 318 & 319); rs1475881-rs7275487 (SEQ ID NOS 320 & 321); rs1735976-rs2827016 (SEQ ID NOS 322 & 323); rs447340-rs2824097 (SEQ ID NOS 324 & 325); rs418989-rs13047336 (SEQ ID NOS 326 & 327); rs987980-rs987981 (SEQ ID NOS 328 & 329); rs4143392-rs4143391 (SEQ ID NOS 330 & 331); rs1691324-rs13050434 (SEQ ID NOS 332 & 333); rs11909758-rs9980111 (SEQ ID NOS 334 & 335); rs2826842-rs232414 (SEQ ID NOS 336 & 337); rs1980969-rs1980970 (SEQ ID NOS 338 & 339); rs9978999-rs9979175 (SEQ ID NOS 340 & 341); rs1034346-rs12481852 (SEQ ID NOS 342 & 343); rs7509629-rs2828358 (SEQ ID NOS 344 & 345); rs4817013-rs7277036 (SEQ ID NOS 346 & 347); rs9981121-rs2829696 (SEQ ID NOS 348 & 349); rs455921-rs2898102 (SEQ ID NOS 350 & 351); rs2898102-rs458848 (SEQ ID NOS 352 & 353); rs961301-rs2830208 (SEQ ID NOS 354 & 355); rs2174536-rs458076 (SEQ ID NOS 356 & 357); rs11088023-rs11088024 (SEQ ID NOS 358 & 359); rs1011734-rs1011733 (SEQ ID NOS 360 & 361); rs2831244-rs9789838 (SEQ ID NOS 362 & 363); rs8132769-rs2831440 (SEQ ID NOS 364 & 365); rs8134080-rs2831524 (SEQ ID NOS 366 & 367); rs4817219-rs4817220 (SEQ ID NOS 368 & 369); rs2250911-rs2250997 (SEQ ID NOS 370 & 371); rs2831899-rs2831900 (SEQ ID NOS 372 & 373); rs2831902-rs2831903 (SEQ ID NOS 374 & 375);

rs11088086-rs2251447 (SEQ ID NOS 376 & 377); rs2832040-rs11088088 (SEQ ID NOS 378 & 379); rs2832141-rs2246777 (SEQ ID NOS 380 & 381); rs2832959-rs9980934 (SEQ ID NOS 382 & 383); rs2833734-rs2833735 (SEQ ID NOS 384 & 385); rs933121-rs933122 (SEQ ID NOS 386 & 387); rs2834140-rs12626953 (SEQ ID NOS 388 & 389); rs2834485-rs3453 (SEQ ID NOS 390 & 391); rs9974986-rs2834703 (SEQ ID NOS 392 & 393); rs2776266-rs2835001 (SEQ ID NOS 394 & 395); rs1984014-rs1984015 (SEQ ID NOS 396 & 397); rs7281674-rs2835316 (SEQ ID NOS 398 & 399); rs13047304-rs13047322 (SEQ ID NOS 400 & 401); rs2835545-rs4816551 (SEQ ID NOS 402 & 403); rs2835735-rs2835736 (SEQ ID NOS 404 & 405); rs13047608-rs2835826 (SEQ ID NOS 406 & 407); rs2836550-rs2212596 (SEQ ID NOS 408 & 409); rs2836660-rs2836661 (SEQ ID NOS 410 & 411); rs465612-rs8131220 (SEQ ID NOS 412 & 413); rs9980072-rs8130031 (SEQ ID NOS 414 & 415); rs418359-rs2836926 (SEQ ID NOS 416 & 417); rs7278447-rs7278858 (SEQ ID NOS 418 & 419); rs385787-rs367001 (SEQ ID NOS 420 & 421); rs367001-rs386095 (SEQ ID NOS 422 & 423); rs2837296-rs2837297 (SEQ ID NOS 424 & 425); and rs2837381-rs4816672 (SEQ ID NOS 426 & 427). The at least one STR is selected from CSF1PO, FGA, TH01, vWA, D3S1358, D5S818, D7S820, D8S1179, D13S317, D16S539, D18S51, D21S11, D2S1338, Penta D, Penta E, D22S1045, D20S1082, D20S482, D18S853, D17S1301, D17S974, D14S1434, D12ATA63, D11S4463, D10S1435, D10S1248, D9S2157, D9S1122, D8S1115, D6S1017, D6S474, D5S2500, D4S2408, D4S2364, D3S4529, D3 S3053, D2S1776, D2S441, D1S1677, D1S1627, and D1GATA113. The massively parallel sequencing is sequencing-by-synthesis with reversible dye terminators. Alternatively, the massively parallel sequencing is sequencing-by-ligation or single molecule sequencing. The maternal sample is selected from blood, plasma, serum, urine and saliva. Preferably, the maternal sample is a plasma sample.

In one embodiment, the invention provides a method for determining the fraction of fetal nucleic acids in a maternal sample comprising a mixture of fetal and maternal genomic DNA e.g. cell-free DNA, wherein the method comprises the steps of: (a) amplifying a plurality of polymorphic target nucleic acids in the mixture of fetal and maternal genomic DNA; (b) performing massively parallel sequencing of at least a portion of the amplified product obtained in (a), wherein sequencing comprises providing a plurality of sequence tags; and (c) based on the sequencing, determining the fraction, wherein determining the fraction comprises determining the number of fetal and maternal sequence tags mapped to a reference genome comprising of at least one polymorphic nucleic acid. The maternal sample is selected from blood, plasma, serum, urine and saliva. Preferably, the maternal sample is a plasma sample.

In one embodiment, the invention provides a method for determining the fraction of fetal nucleic acids in a maternal sample comprising a mixture of fetal and maternal genomic DNA e.g. cell-free DNA, wherein the method comprises the steps of: (a) amplifying a plurality of polymorphic target nucleic acids in the mixture of fetal and maternal genomic DNA; (b) performing massively parallel sequencing of at least a portion of the amplified product obtained in (a), wherein sequencing comprises an amplification and provides a plurality of sequence tags; and (c) based on the sequencing, determining the fraction, wherein determining the fraction comprises determining the number of fetal and maternal sequence tags mapped to a reference genome comprising of at least one polymorphic nucleic acid. The maternal sample is selected from blood, plasma, serum, urine and saliva. Preferably, the maternal sample is a plasma sample.

In another embodiment, the invention provides a method for determining the fraction of fetal nucleic acids in a maternal sample comprising a mixture of fetal and maternal genomic DNA e.g. cell-free DNA, wherein the method comprises the steps of: (a) amplifying a plurality of polymorphic target nucleic acids in the mixture of fetal and maternal genomic DNA; (b) performing massively parallel sequencing of at least a portion of the amplified product obtained in (a), wherein sequencing comprises providing a plurality of sequence tags; and (c) based on the sequencing, determining the fraction, wherein determining the fraction comprises determining the number of fetal and maternal sequence tags mapped to a reference genome comprising of at least one polymorphic nucleic acid. The plurality of polymorphic target nucleic acids comprises at least one single nucleotide polymorphism (SNP). Alternatively, the plurality of polymorphic target nucleic acids comprises at least one short tandem repeat (STR). In some embodiments, the at least one SNP is a single SNP selected from rs560681 (SEQ ID NOS 1 & 2), rs1109037 (SEQ ID NOS 3 & 4), rs9866013 (SEQ ID NOS 5 & 6), rs13182883 (SEQ ID NOS 7 & 8), rs13218440 (SEQ ID NOS 9 & 10), rs7041158 (SEQ ID NOS 11 & 12), rs740598 (SEQ ID NOS 13 & 14), rs10773760 (SEQ ID NOS 15 & 16), rs4530059 (SEQ ID NOS 17 & 18), rs7205345 (SEQ ID NOS 19 & 20), rs8078417 (SEQ ID NOS 21 & 22), rs576261 (SEQ ID NOS 23 & 24), rs2567608 (SEQ ID NOS 25 & 26), rs430046 (SEQ ID NOS 27 & 28), rs9951171 (SEQ ID NOS 29 & 30), rs338882 (SEQ ID NOS 31 & 32), rs10776839 (SEQ ID NOS 33 & 34), rs9905977 (SEQ ID NOS 35 & 36), rs1277284 (SEQ ID NOS 37 & 38), rs258684 (SEQ ID NOS 39 & 40), rs1347696 (SEQ ID NOS 41 & 42), rs508485 (SEQ ID NOS 43 & 44), rs9788670 (SEQ ID NOS 45 & 46), rs8137254 (SEQ ID NOS 47 & 48), rs3143 (SEQ ID NOS 49 & 50), rs2182957 (SEQ ID NOS 51 & 52), rs3739005 (SEQ ID NOS 53 & 54), and rs530022 (SEQ ID NOS 55 & 56). In other embodiments, the at least one SNP is a tandem SNP selected from tandem SNP pairs rs7277033-rs2110153 (SEQ ID NOS 312 & 313); rs2822654-rs1882882 (SEQ ID NOS 314 & 315); rs368657-rs376635 (SEQ ID NOS 316 & 317); rs2822731-rs2822732 (SEQ ID NOS 318 & 319); rs1475881-rs7275487 (SEQ ID NOS 320 & 321); rs1735976-rs2827016 (SEQ ID NOS 322 & 323); rs447340-rs2824097 (SEQ ID NOS 324 & 325); rs418989-rs13047336 (SEQ ID NOS 326 & 327); rs987980-rs987981 (SEQ ID NOS 328 & 329); rs4143392-rs4143391 (SEQ ID NOS 330 & 331); rs1691324-rs13050434 (SEQ ID NOS 332 & 333); rs11909758-rs9980111 (SEQ ID NOS 334 & 335); rs2826842-rs232414 (SEQ ID NOS 336 & 337); rs1980969-rs1980970 (SEQ ID NOS 338 & 339); rs9978999-rs9979175 (SEQ ID NOS 340 & 341); rs1034346-rs12481852 (SEQ ID NOS 342 & 343); rs7509629-rs2828358 (SEQ ID NOS 344 & 345); rs4817013-rs7277036 (SEQ ID NOS 346 & 347); rs9981121-rs2829696 (SEQ ID NOS 348 & 349); rs455921-rs2898102 (SEQ ID NOS 350 & 351); rs2898102-rs458848 (SEQ ID NOS 352 & 353); rs961301-rs2830208 (SEQ ID NOS 354 & 355); rs2174536-rs458076 (SEQ ID NOS 356 & 357); rs11088023-rs11088024 (SEQ ID NOS 358 & 359); rs1011734-rs1011733 (SEQ ID NOS 360 & 361); rs2831244-rs9789838 (SEQ ID NOS 362 & 363); rs8132769-rs2831440 (SEQ ID NOS 364 & 365); rs8134080-rs2831524 (SEQ ID NOS 366 & 367);

rs4817219-rs4817220 (SEQ ID NOS 368 & 369); rs2250911-rs2250997 (SEQ ID NOS 370 & 371); rs2831899-rs2831900 (SEQ ID NOS 372 & 373); rs2831902-rs2831903 (SEQ ID NOS 374 & 375); rs11088086-rs2251447 (SEQ ID NOS 376 & 377); rs2832040-rs11088088 (SEQ ID NOS 378 & 379); rs2832141-rs2246777 (SEQ ID NOS 380 & 381); rs2832959-rs9980934 (SEQ ID NOS 382 & 383); rs2833734-rs2833735 (SEQ ID NOS 384 & 385); rs933121-rs933122 (SEQ ID NOS 386 & 387); rs2834140-rs12626953 (SEQ ID NOS 388 & 389); rs2834485-rs3453 (SEQ ID NOS 390 & 391); rs9974986-rs2834703 (SEQ ID NOS 392 & 393); rs2776266-rs2835001 (SEQ ID NOS 394 & 395); rs1984014-rs1984015 (SEQ ID NOS 396 & 397); rs7281674-rs2835316 (SEQ ID NOS 398 & 399); rs13047304-rs13047322 (SEQ ID NOS 400 & 401); rs2835545-rs4816551 (SEQ ID NOS 402 & 403); rs2835735-rs2835736 (SEQ ID NOS 404 & 405); rs13047608-rs2835826 (SEQ ID NOS 406 & 407); rs2836550-rs2212596 (SEQ ID NOS 408 & 409); rs2836660-rs2836661 (SEQ ID NOS 410 & 411); rs465612-rs8131220 (SEQ ID NOS 412 & 413); rs9980072-rs8130031 (SEQ ID NOS 414 & 415); rs418359-rs2836926 (SEQ ID NOS 416 & 417); rs7278447-rs7278858 (SEQ ID NOS 418 & 419); rs385787-rs367001 (SEQ ID NOS 420 & 421); rs367001-rs386095 (SEQ ID NOS 422 & 423); rs2837296-rs2837297 (SEQ ID NOS 424 & 425); and rs2837381-rs4816672 (SEQ ID NOS 426 & 427). The at least one STR is selected from CSF1PO, FGA, TH01, vWA, D3S1358, D5S818, D7S820, D8S1179, D13S317, D16S539, D18S51, D21S11, D2S1338, Penta D, Penta E, D22S1045, D20S1082, D20S482, D18S853, D17S1301, D17S974, D14S1434, D12ATA63, D11S4463, D10S1435, D10S1248, D9S2157, D9S1122, D8S1115, D6S1017, D6S474, D5S2500, D4S2408, D4S2364, D3S4529, D3S3053, D2S1776, D2S441, D1S1677, D1S1627, and D1GATA113. The maternal sample is selected from blood, plasma, serum, urine and saliva. Preferably, the maternal sample is a plasma sample.

In another embodiment, the invention provides a method for determining the fraction of fetal nucleic acids in a maternal sample comprising a mixture of fetal and maternal genomic DNA e.g. cell-free DNA, wherein the method comprises the steps of: (a) amplifying a plurality of polymorphic target nucleic acids in the mixture of fetal and maternal genomic DNA; (b) performing massively parallel sequencing of at least a portion of the amplified product obtained in (a), wherein sequencing comprises providing a plurality of sequence tags; and (c) based on the sequencing, determining the fraction, wherein determining the fraction comprises determining the number of fetal and maternal sequence tags mapped to a reference genome comprising of at least one polymorphic nucleic acid. The plurality of polymorphic target nucleic acids comprises at least one single nucleotide polymorphism (SNP). Alternatively, the plurality of polymorphic target nucleic acids comprises at least one short tandem repeat (STR). In some embodiments, the at least one SNP is a single SNP selected from rs560681 (SEQ ID NOS 1 & 2), rs1109037 (SEQ ID NOS 3 & 4), rs9866013 (SEQ ID NOS 5 & 6), rs13182883 (SEQ ID NOS 7 & 8), rs13218440 (SEQ ID NOS 9 & 10), rs7041158 (SEQ ID NOS 11 & 12), rs740598 (SEQ ID NOS 13 & 14), rs10773760 (SEQ ID NOS 15 & 16), rs4530059 (SEQ ID NOS 17 & 18), rs7205345 (SEQ ID NOS 19 & 20), rs8078417 (SEQ ID NOS 21 & 22), rs576261 (SEQ ID NOS 23 & 24), rs2567608 (SEQ ID NOS 25 & 26), rs430046 (SEQ ID NOS 27 & 28), rs9951171 (SEQ ID NOS 29 & 30), rs338882 (SEQ ID NOS 31 & 32), rs10776839 (SEQ ID NOS 33 & 34), rs9905977 (SEQ ID NOS 35 & 36), rs1277284 (SEQ ID NOS 37 & 38), rs258684 (SEQ ID NOS 39 & 40), rs1347696 (SEQ ID NOS 41 & 42), rs508485 (SEQ ID NOS 43 & 44), rs9788670 (SEQ ID NOS 45 & 46), rs8137254 (SEQ ID NOS 47 & 48), rs3143 (SEQ ID NOS 49 & 50), rs2182957 (SEQ ID NOS 51 & 52), rs3739005 (SEQ ID NOS 53 & 54), and rs530022 (SEQ ID NOS 55 & 56). In other embodiments, the at least one SNP is a tandem SNP selected from tandem SNP pairs rs7277033-rs2110153 (SEQ ID NOS 312 & 313); rs2822654-rs1882882 (SEQ ID NOS 314 & 315); rs368657-rs376635 (SEQ ID NOS 316 & 317); rs2822731-rs2822732 (SEQ ID NOS 318 & 319); rs1475881-rs7275487 (SEQ ID NOS 320 & 321); rs1735976-rs2827016 (SEQ ID NOS 322 & 323); rs447340-rs2824097 (SEQ ID NOS 324 & 325); rs418989-rs13047336 (SEQ ID NOS 326 & 327); rs987980-rs987981 (SEQ ID NOS 328 & 329); rs4143392-rs4143391 (SEQ ID NOS 330 & 331); rs1691324-rs13050434 (SEQ ID NOS 332 & 333); rs11909758-rs9980111 (SEQ ID NOS 334 & 335); rs2826842-rs232414 (SEQ ID NOS 336 & 337); rs1980969-rs1980970 (SEQ ID NOS 338 & 339); rs9978999-rs9979175 (SEQ ID NOS 340 & 341); rs1034346-rs12481852 (SEQ ID NOS 342 & 343); rs7509629-rs2828358 (SEQ ID NOS 344 & 345); rs4817013-rs7277036 (SEQ ID NOS 346 & 347); rs9981121-rs2829696 (SEQ ID NOS 348 & 349); rs455921-rs2898102 (SEQ ID NOS 350 & 351); rs2898102-rs458848 (SEQ ID NOS 352 & 353); rs961301-rs2830208 (SEQ ID NOS 354 & 355); rs2174536-rs458076 (SEQ ID NOS 356 & 357); rs11088023-rs11088024 (SEQ ID NOS 358 & 359); rs1011734-rs1011733 (SEQ ID NOS 360 & 361); rs2831244-rs9789838 (SEQ ID NOS 362 & 363); rs8132769-rs2831440 (SEQ ID NOS 364 & 365); rs8134080-rs2831524 (SEQ ID NOS 366 & 367); rs4817219-rs4817220 (SEQ ID NOS 368 & 369); rs2250911-rs2250997 (SEQ ID NOS 370 & 371); rs2831899-rs2831900 (SEQ ID NOS 372 & 373); rs2831902-rs2831903 (SEQ ID NOS 374 & 375); rs11088086-rs2251447 (SEQ ID NOS 376 & 377); rs2832040-rs11088088 (SEQ ID NOS 378 & 379); rs2832141-rs2246777 (SEQ ID NOS 380 & 381); rs2832959-rs9980934 (SEQ ID NOS 382 & 383); rs2833734-rs2833735 (SEQ ID NOS 384 & 385); rs933121-rs933122 (SEQ ID NOS 386 & 387); rs2834140-rs12626953 (SEQ ID NOS 388 & 389); rs2834485-rs3453 (SEQ ID NOS 390 & 391); rs9974986-rs2834703 (SEQ ID NOS 392 & 393); rs2776266-rs2835001 (SEQ ID NOS 394 & 395); rs1984014-rs1984015 (SEQ ID NOS 396 & 397); rs7281674-rs2835316 (SEQ ID NOS 398 & 399); rs13047304-rs13047322 (SEQ ID NOS 400 & 401); rs2835545-rs4816551 (SEQ ID NOS 402 & 403); rs2835735-rs2835736 (SEQ ID NOS 404 & 405); rs13047608-rs2835826 (SEQ ID NOS 406 & 407); rs2836550-rs2212596 (SEQ ID NOS 408 & 409); rs2836660-rs2836661 (SEQ ID NOS 410 & 411); rs465612-rs8131220 (SEQ ID NOS 412 & 413); rs9980072-rs8130031 (SEQ ID NOS 414 & 415); rs418359-rs2836926 (SEQ ID NOS 416 & 417); rs7278447-rs7278858 (SEQ ID NOS 418 & 419); rs385787-rs367001 (SEQ ID NOS 420 & 421); rs367001-rs386095 (SEQ ID NOS 422 & 423); rs2837296-rs2837297 (SEQ ID NOS 424 & 425); and rs2837381-rs4816672 (SEQ ID NOS 426 & 427). The at least one STR is selected from CSF1PO, FGA, TH01, vWA, D3S1358, D5S818, D7S820, D8S1179, D13S317, D16S539, D18S51, D21S11, D2S1338, Penta D, Penta E, D22S1045, D20S1082, D20S482, D18S853, D17S1301, D17S974, D14S1434, D12ATA63, D11S4463, D10S1435, D10S1248, D9S2157, D9S1122, D8S1115, D6S1017, D6S474, D5S2500, D4S2408, D4S2364, D3S4529, D3S3053, D2S1776, D2S441, D1S1677, D1S1627, and D1GATA113. The massively parallel sequencing is sequencing-by-synthesis with reversible dye terminators. Alternatively, the massively parallel sequencing is sequencing-by-ligation or single molecule sequencing. The maternal sample is selected from blood, plasma, serum, urine and saliva. Preferably, the maternal sample is a plasma sample.

In another embodiment, the invention provides a method for determining the fraction of fetal nucleic acids in a maternal sample comprising a mixture of fetal and maternal genomic DNA e.g. cell-free DNA, wherein the method comprises the steps of: (a) amplifying a plurality of polymorphic target nucleic acids in the mixture of fetal and maternal genomic DNA; (b) performing massively parallel sequencing of at least a portion of the amplified product obtained in (a), wherein sequencing comprises an amplification and provides a plurality of sequence tags; and (c) based on the sequencing, determining the fraction, wherein determining the fraction comprises determining the number of fetal and maternal sequence tags mapped to a reference genome comprising of at least one polymorphic nucleic acid. The plurality of polymorphic target nucleic acids comprises at least one single nucleotide polymorphism (SNP). Alternatively, the plurality of polymorphic target nucleic acids comprises at least one short tandem repeat (STR). In some embodiments, the at least one SNP is a single SNP selected from rs560681 (SEQ ID NOS 1 & 2), rs1109037 (SEQ ID NOS 3 & 4), rs9866013 (SEQ ID NOS 5 & 6), rs13182883 (SEQ ID NOS 7 & 8), rs13218440 (SEQ ID NOS 9 & 10), rs7041158 (SEQ ID NOS 11 & 12), rs740598 (SEQ ID NOS 13 & 14), rs10773760 (SEQ ID NOS 15 & 16), rs4530059 (SEQ ID NOS 17 & 18), rs7205345 (SEQ ID NOS 19 & 20), rs8078417 (SEQ ID NOS 21 & 22), rs576261 (SEQ ID NOS 23 & 24), rs2567608 (SEQ ID NOS 25 & 26), rs430046 (SEQ ID NOS 27 & 28), rs9951171 (SEQ ID NOS 29 & 30), rs338882 (SEQ ID NOS 31 & 32), rs10776839 (SEQ ID NOS 33 & 34), rs9905977 (SEQ ID NOS 35 & 36), rs1277284 (SEQ ID NOS 37 & 38), rs258684 (SEQ ID NOS 39 & 40), rs1347696 (SEQ ID NOS 41 & 42), rs508485 (SEQ ID NOS 43 & 44), rs9788670 (SEQ ID NOS 45 & 46), rs8137254 (SEQ ID NOS 47 & 48), rs3143 (SEQ ID NOS 49 & 50), rs2182957 (SEQ ID NOS 51 & 52), rs3739005 (SEQ ID NOS 53 & 54), and rs530022 (SEQ ID NOS 55 & 56). In other embodiments, the at least one SNP is a tandem SNP selected from tandem SNP pairs rs7277033-rs2110153 (SEQ ID NOS 312 & 313); rs2822654-rs1882882 (SEQ ID NOS 314 & 315); rs368657-rs376635 (SEQ ID NOS 316 & 317); rs2822731-rs2822732 (SEQ ID NOS 318 & 319); rs1475881-rs7275487 (SEQ ID NOS 320 & 321); rs1735976-rs2827016 (SEQ ID NOS 322 & 323); rs447340-rs2824097 (SEQ ID NOS 324 & 325); rs418989-rs13047336 (SEQ ID NOS 326 & 327); rs987980-rs987981 (SEQ ID NOS 328 & 329); rs4143392-rs4143391 (SEQ ID NOS 330 & 331); rs1691324-rs13050434 (SEQ ID NOS 332 & 333); rs11909758-rs9980111 (SEQ ID NOS 334 & 335); rs2826842-rs232414 (SEQ ID NOS 336 & 337); rs1980969-rs1980970 (SEQ ID NOS 338 & 339); rs9978999-rs9979175 (SEQ ID NOS 340 & 341); rs1034346-rs12481852 (SEQ ID NOS 342 & 343); rs7509629-rs2828358 (SEQ ID NOS 344 & 345); rs4817013-rs7277036 (SEQ ID NOS 346 & 347); rs9981121-rs2829696 (SEQ ID NOS 348 & 349); rs455921-rs2898102 (SEQ ID NOS 350 & 351); rs2898102-rs458848 (SEQ ID NOS 352 & 353); rs961301-rs2830208 (SEQ ID NOS 354 & 355); rs2174536-rs458076 (SEQ ID NOS 356 & 357); rs11088023-rs11088024 (SEQ ID NOS 358 & 359); rs1011734-rs1011733 (SEQ ID NOS 360 & 361); rs2831244-rs9789838 (SEQ ID NOS 362 & 363); rs8132769-rs2831440 (SEQ ID NOS 364 & 365); rs8134080-rs2831524 (SEQ ID NOS 366 & 367); rs4817219-rs4817220 (SEQ ID NOS 368 & 369); rs2250911-rs2250997 (SEQ ID NOS 370 & 371); rs2831899-rs2831900 (SEQ ID NOS 372 & 373); rs2831902-rs2831903 (SEQ ID NOS 374 & 375); rs11088086-rs2251447 (SEQ ID NOS 376 & 377); rs2832040-rs11088088 (SEQ ID NOS 378 & 379); rs2832141-rs2246777 (SEQ ID NOS 380 & 381); rs2832959-rs9980934 (SEQ ID NOS 382 & 383); rs2833734-rs2833735 (SEQ ID NOS 384 & 385); rs933121-rs933122 (SEQ ID NOS 386 & 387); rs2834140-rs12626953 (SEQ ID NOS 388 & 389); rs2834485-rs3453 (SEQ ID NOS 390 & 391); rs9974986-rs2834703 (SEQ ID NOS 392 & 393); rs2776266-rs2835001 (SEQ ID NOS 394 & 395); rs1984014-rs1984015 (SEQ ID NOS 396 & 397); rs7281674-rs2835316 (SEQ ID NOS 398 & 399); rs13047304-rs13047322 (SEQ ID NOS 400 & 401); rs2835545-rs4816551 (SEQ ID NOS 402 & 403); rs2835735-rs2835736 (SEQ ID NOS 404 & 405); rs13047608-rs2835826 (SEQ ID NOS 406 & 407); rs2836550-rs2212596 (SEQ ID NOS 408 & 409); rs2836660-rs2836661 (SEQ ID NOS 410 & 411); rs465612-rs8131220 (SEQ ID NOS 412 & 413); rs9980072-rs8130031 (SEQ ID NOS 414 & 415); rs418359-rs2836926 (SEQ ID NOS 416 & 417); rs7278447-rs7278858 (SEQ ID NOS 418 & 419); rs385787-rs367001 (SEQ ID NOS 420 & 421); rs367001-rs386095 (SEQ ID NOS 422 & 423); rs2837296-rs2837297 (SEQ ID NOS 424 & 425); and rs2837381-rs4816672 (SEQ ID NOS 426 & 427). The at least one STR is selected from CSF1PO, FGA, TH01, vWA, D3S1358, D5S818, D7S820, D8S1179, D13S317, D16S539, D18S51, D21S11, D2S1338, Penta D, Penta E, D22S1045, D20S1082, D20S482, D18S853, D17S1301, D17S974, D14S1434, D12ATA63, D11S4463, D10S1435, D10S1248, D9S2157, D9S1122, D8S1115, D6S1017, D6S474, D5S2500, D4S2408, D4S2364, D3S4529, D3S3053, D2S1776, D2S441, D1S1677, D1S1627, and D1GATA113. The maternal sample is selected from blood, plasma, serum, urine and saliva. Preferably, the maternal sample is a plasma sample.

In another embodiment, the invention provides a method for determining the fraction of fetal nucleic acids in a maternal sample comprising a mixture of fetal and maternal genomic DNA e.g. cell-free DNA, wherein the method comprises the steps of: (a) amplifying a plurality of polymorphic target nucleic acids in the mixture of fetal and maternal genomic DNA; (b) performing massively parallel sequencing of at least a portion of the amplified product obtained in (a), wherein sequencing comprises an amplification and provides a plurality of sequence tags; and (c) based on the sequencing, determining the fraction, wherein determining the fraction comprises determining the number of fetal and maternal sequence tags mapped to a reference genome comprising of at least one polymorphic nucleic acid. The plurality of polymorphic target nucleic acids comprises at least one single nucleotide polymorphism (SNP). Alternatively, the plurality of polymorphic target nucleic acids comprises at least one short tandem repeat (STR). In some embodiments, the at least one SNP is a single SNP selected from rs560681 (SEQ ID NOS 1 & 2), rs1109037 (SEQ ID NOS 3 & 4), rs9866013 (SEQ ID NOS 5 & 6), rs13182883 (SEQ ID NOS 7 & 8), rs13218440 (SEQ ID NOS 9 & 10), rs7041158 (SEQ ID NOS 11 & 12), rs740598 (SEQ ID NOS 13 & 14), rs10773760 (SEQ ID NOS 15 & 16), rs4530059 (SEQ ID NOS 17 & 18), rs7205345 (SEQ ID NOS 19 & 20), rs8078417 (SEQ ID NOS 21 & 22), rs576261 (SEQ ID NOS 23 & 24), rs2567608 (SEQ ID NOS 25 & 26), rs430046 (SEQ ID NOS 27 & 28), rs9951171 (SEQ ID NOS 29 & 30), rs338882 (SEQ ID NOS 31 & 32), rs10776839 (SEQ ID NOS 33 & 34), rs9905977 (SEQ ID NOS 35 & 36), rs1277284 (SEQ ID NOS 37 & 38), rs258684 (SEQ ID NOS 39 & 40), rs1347696 (SEQ ID NOS 41 & 42), rs508485 (SEQ ID NOS 43 & 44), rs9788670 (SEQ ID NOS 45 & 46), rs8137254 (SEQ ID NOS 47 & 48), rs3143 (SEQ ID NOS 49 & 50), rs2182957 (SEQ ID NOS 51 & 52), rs3739005 (SEQ ID NOS 53 & 54), and rs530022 (SEQ ID NOS 55 & 56). In other embodiments, the at least one SNP is a tandem SNP selected from tandem SNP pairs rs7277033-rs2110153 (SEQ ID NOS 312 & 313); rs2822654-rs1882882 (SEQ ID NOS 314 & 315); rs368657-rs376635 (SEQ ID NOS 316 & 317); rs2822731-rs2822732 (SEQ ID NOS 318 & 319); rs1475881-rs7275487 (SEQ ID NOS 320 & 321); rs1735976-rs2827016 (SEQ ID NOS 322 & 323); rs447340-rs2824097 (SEQ ID NOS 324 & 325); rs418989-rs13047336 (SEQ ID NOS 326 & 327); rs987980-rs987981 (SEQ ID NOS 328 & 329); rs4143392-rs4143391 (SEQ ID NOS 330 & 331); rs1691324-rs13050434 (SEQ ID NOS 332 & 333); rs11909758-rs9980111 (SEQ ID NOS 334 & 335); rs2826842-rs232414 (SEQ ID NOS 336 & 337); rs1980969-rs1980970 (SEQ ID NOS 338 & 339); rs9978999-rs9979175 (SEQ ID NOS 340 & 341); rs1034346-rs12481852 (SEQ ID NOS 342 & 343); rs7509629-rs2828358 (SEQ ID NOS 344 & 345); rs4817013-rs7277036 (SEQ ID NOS 346 & 347); rs9981121-rs2829696 (SEQ ID NOS 348 & 349); rs455921-rs2898102 (SEQ ID NOS 350 & 351); rs2898102-rs458848 (SEQ ID NOS 352 & 353); rs961301-rs2830208 (SEQ ID NOS 354 & 355); rs2174536-rs458076 (SEQ ID NOS 356 & 357); rs11088023-rs11088024 (SEQ ID NOS 358 & 359); rs1011734-rs1011733 (SEQ ID NOS 360 & 361); rs2831244-rs9789838 (SEQ ID NOS 362 & 363); rs8132769-rs2831440 (SEQ ID NOS 364 & 365); rs8134080-rs2831524 (SEQ ID NOS 366 & 367); rs4817219-rs4817220 (SEQ ID NOS 368 & 369); rs2250911-rs2250997 (SEQ ID NOS 370 & 371); rs2831899-rs2831900 (SEQ ID NOS 372 & 373); rs2831902-rs2831903 (SEQ ID NOS 374 & 375); rs11088086-rs2251447 (SEQ ID NOS 376 & 377); rs2832040-rs11088088 (SEQ ID NOS 378 & 379); rs2832141-rs2246777 (SEQ ID NOS 380 & 381); rs2832959-rs9980934 (SEQ ID NOS 382 & 383); rs2833734-rs2833735 (SEQ ID NOS 384 & 385); rs933121-rs933122 (SEQ ID NOS 386 & 387); rs2834140-rs12626953 (SEQ ID NOS 388 & 389); rs2834485-rs3453 (SEQ ID NOS 390 & 391); rs9974986-rs2834703 (SEQ ID NOS 392 & 393); rs2776266-rs2835001 (SEQ ID NOS 394 & 395); rs1984014-rs1984015 (SEQ ID NOS 396 & 397); rs7281674-rs2835316 (SEQ ID NOS 398 & 399); rs13047304-rs13047322 (SEQ ID NOS 400 & 401); rs2835545-rs4816551 (SEQ ID NOS 402 & 403); rs2835735-rs2835736 (SEQ ID NOS 404 & 405); rs13047608-rs2835826 (SEQ ID NOS 406 & 407); rs2836550-rs2212596 (SEQ ID NOS 408 & 409); rs2836660-rs2836661 (SEQ ID NOS 410 & 411); rs465612-rs8131220 (SEQ ID NOS 412 & 413); rs9980072-rs8130031 (SEQ ID NOS 414 & 415); rs418359-rs2836926 (SEQ ID NOS 416 & 417); rs7278447-rs7278858 (SEQ ID NOS 418 & 419); rs385787-rs367001 (SEQ ID NOS 420 & 421); rs367001-rs386095 (SEQ ID NOS 422 & 423); rs2837296-rs2837297 (SEQ ID NOS 424 & 425); and rs2837381-rs4816672 (SEQ ID NOS 426 & 427). The at least one STR is selected from CSF1PO, FGA, TH01, vWA, D3S1358, D5S818, D7S820, D8S1179, D13S317, D16S539, D18S51, D21S11, D2S1338, Penta D, Penta E, D2S51045, D20S1082, D20S482, D18S853, D17S1301, D17S974, D14S1434, D12ATA63, D11S4463, D10S1435, D10S1248, D9S2157, D9S1122, D8S1115, D6S1017, D6S474, D5S2500, D4S2408, D4S2364, D3S4529, D3S3053, D2S1776, D2S441, D1S1677, D1S1627, and D1GATA113. The massively parallel sequencing is sequencing-by-synthesis with reversible dye terminators. Alternatively, the massively parallel sequencing is sequencing-by-ligation or single molecule sequencing. The maternal sample is selected from blood, plasma, serum, urine and saliva. Preferably, the maternal sample is a plasma sample.

In another embodiment, the invention provides a method for determining the fraction of fetal nucleic acids in a maternal plasma sample comprising a mixture of fetal and maternal genomic DNA, wherein the method comprises the steps of: (a) amplifying a plurality of polymorphic nucleic acids in said mixture of fetal and maternal nucleic acids, wherein each of said at least one polymorphic nucleic acid comprises an STR; (b) determining the amount of fetal and maternal STR alleles at least one polymorphic nucleic acid; and (c) determining said fraction using said amount of fetal and maternal STR alleles. The plurality of polymorphic nucleic acids are located on a plurality of different chromosomes. In one embodiment, the plurality of polymorphic nucleic acids can be located on chromosomes 1-22. For example, the plurality of polymorphic nucleic acids can be located on a plurality of different chromosomes other than chromosomes 13, 18, 21, X or Y. The method is a fetal gender-independent method.

In another embodiment, the invention provides a method for determining the fraction of fetal nucleic acids in a maternal plasma sample comprising a mixture of fetal and maternal genomic DNA, wherein the method comprises the steps of: (a) amplifying a plurality of polymorphic nucleic acids in said mixture of fetal and maternal nucleic acids, wherein each of said at least one polymorphic nucleic acid comprises an STR; (b) determining the amount of fetal and maternal STR alleles at least one polymorphic nucleic acid; and (c) determining said fraction using said amount of fetal and maternal STR alleles. The plurality of polymorphic nucleic acids are located on a plurality of different chromosomes. In one embodiment, the plurality of polymorphic nucleic acids can be located on chromosomes 1-22. For example, the plurality of polymorphic nucleic acids are located on a plurality of different chromosomes other than chromosomes 13, 18, 21, X or Y. The method further comprises preamplifying the mixture of fetal and maternal nucleic acids. The method is a fetal gender-independent method.

In another embodiment, the invention provides a method for determining the fraction of fetal nucleic acids in a maternal plasma sample comprising a mixture of fetal and maternal genomic DNA, wherein the method comprises the steps of: (a) amplifying a plurality of polymorphic nucleic acids in said mixture of fetal and maternal nucleic acids, wherein each of said at least one polymorphic nucleic acid comprises an STR; (b) determining the amount of fetal and maternal STR alleles at least one polymorphic nucleic acid; and (c) determining said fraction using said amount of fetal and maternal STR alleles. The plurality of polymorphic nucleic acids are located on a plurality of different chromosomes. In one embodiment, the plurality of polymorphic nucleic acids can be located on chromosomes 1-22. For example, the plurality of polymorphic nucleic acids can be located on a plurality of different chromosomes other than chromosomes 13, 18, 21, X or Y. The method further comprises resolving the size of the STRs using capillary electrophoresis. The method is a fetal gender-independent method.

In another embodiment, the invention provides a method for determining the fraction of fetal nucleic acids in a maternal plasma sample comprising a mixture of fetal and maternal genomic DNA, wherein the method comprises the steps of: (a) amplifying a plurality of polymorphic nucleic acids in said mixture of fetal and maternal nucleic acids, wherein each of said at least one polymorphic nucleic acid comprises an STR; (b) determining the amount of fetal and maternal STR alleles at least one polymorphic nucleic acid; and (c) determining said fraction using said amount of fetal and maternal STR alleles. The plurality of polymorphic nucleic acids are located on a plurality of different chromosomes. In one embodiment, the plurality of polymorphic nucleic acids can be located on chromosomes 1-22. For example, the plurality of polymorphic nucleic acids can be located on a plurality of different chromosomes other than chromosomes 13, 18, 21, X or Y. The method further comprises preamplifying the mixture of fetal and maternal nucleic acids, and resolving the size of the STRs using capillary electrophoresis. The method is a fetal gender-independent method.

In another embodiment, the invention provides a method for determining the fraction of fetal nucleic acids in a maternal plasma sample comprising a mixture of fetal and maternal genomic DNA, wherein the method comprises the steps of: (a) amplifying a plurality of polymorphic nucleic acids in said mixture of fetal and maternal nucleic acids, wherein each of said at least one polymorphic nucleic acid comprises an STR; (b) determining the amount of fetal and maternal STR alleles at least one polymorphic nucleic acid; and (c) determining said fraction using said amount of fetal and maternal STR alleles. The plurality of polymorphic nucleic acids can be located on a plurality of different chromosomes. For example, the plurality of polymorphic nucleic acids are located on a plurality of different chromosomes other than chromosomes 13, 18, 21, X or Y. The at least one STR is selected from CSF1PO, FGA, TH01, vWA, D3S1358, D5S818, D7S820, D8S1179, D13S317, D16S539, D18S51, D2S1338, PentaD, PentaE, D22S1045, D20S1082, D20S482, D18S853, D17S1301, D17S974, D14S1434, D12ATA63, D11S4463, D10S1435, D10S1248, D9S2157, D9S1122, D8S1115, D6S1017, D6S474, D5S2500, D4S2408, D4S2364, D3S4529, D3S3053, D2S1776, D2S441, D1S1677, D1S1627, and D1GATA113. Optionally, the at least one STR can be the panel of STRs comprising CSF1PO, D13S317, D16S539, D18S51, D21S11, D2S1338, D7S820 and FGA. The method is a fetal gender-independent method.

In another embodiment, the invention provides a method for determining the fraction of fetal nucleic acids in a maternal plasma sample comprising a mixture of fetal and maternal genomic DNA, wherein the method comprises the steps of: (a) amplifying a plurality of polymorphic nucleic acids in said mixture of fetal and maternal nucleic acids, wherein each of said at least one polymorphic nucleic acid comprises an STR; (b) determining the amount of fetal and maternal STR alleles at least one polymorphic nucleic acid; and (c) determining said fraction using said amount of fetal and maternal STR alleles. The plurality of polymorphic nucleic acids are located on a plurality of different chromosomes. In one embodiment, the plurality of polymorphic nucleic acids can be located on chromosomes 1-22. For example, the plurality of polymorphic nucleic acids can be located on a plurality of different chromosomes other than chromosomes 13, 18, 21, X or Y. The method further comprises preamplifying the mixture of fetal and maternal nucleic acids. The at least one STR is selected from CSF1PO, FGA, TH01, vWA, D3S1358, D5S818, D7S820, D8S1179, D13S317, D16S539, D18S51, D2S1338, PentaD, PentaE, D22S1045, D20S1082, D20S482, D18S853, D17S1301, D17S974, D14S1434, D12ATA63, D11S4463, D10S1435, D10S1248, D9S2157, D9S1122, D8S1115, D6S1017, D6S474, D5S2500, D4S2408, D4S2364, D3S4529, D3S3053, D2S1776, D2S441, D1S1677, D1S1627, and D1GATA113. Optionally, the at least one STR can be the panel of STRs comprising CSF1PO, D13S317, D16S539, D18S51, D21S11, D2S1338, D7S820 and FGA. The method is a fetal gender-independent method.

In another embodiment, the invention provides a method for determining the fraction of fetal nucleic acids in a maternal plasma sample comprising a mixture of fetal and maternal genomic DNA, wherein the method comprises the steps of: (a) amplifying a plurality of polymorphic nucleic acids in said mixture of fetal and maternal nucleic acids, wherein each of said at least one polymorphic nucleic acid comprises an STR; (b) determining the amount of fetal and maternal STR alleles at least one polymorphic nucleic acid; and (c) determining said fraction using said amount of fetal and maternal STR alleles. The plurality of polymorphic nucleic acids are located on a plurality of different chromosomes. In one embodiment, the plurality of polymorphic nucleic acids can be located on chromosomes 1-22. For example, the plurality of polymorphic nucleic acids are located on a plurality of different chromosomes other than chromosomes 13, 18, 21, X or Y. The method further comprises resolving the size of the STRs using capillary electrophoresis. The at least one STR is selected from CSF1PO, FGA, TH01, vWA, D3S1358, D5S818, D7S820, D8S1179, D13S317, D16S539, D18S51, D2S1338, Penta D, Penta E, D22S1045, D20S1082, D20S482, D18S853, D17S1301, D17S974, D14S1434, D12ATA63, D11S4463, D10S1435, D10S1248, D9S2157, D9S1122, D8S1115, D6S1017, D6S474, D5S2500, D4S2408, D4S2364, D3S4529, D3S3053, D2S1776, D2S441, D1S1677, D1S1627, and D1GATA113. Optionally, the at least one STR can be the panel of STRs comprising CSF1PO, D13S317, D16S539, D18S51, D21S11, D2S1338, D7S820 and FGA.

In another embodiment, the invention provides a method for determining the fraction of fetal nucleic acids in a maternal plasma sample comprising a mixture of fetal and maternal genomic DNA, wherein the method comprises the steps of: (a) amplifying a plurality of polymorphic nucleic acids in said mixture of fetal and maternal nucleic acids, wherein each of said at least one polymorphic nucleic acid comprises an STR; (b) determining the amount of fetal and maternal STR alleles at least one polymorphic nucleic acid; and (c) determining said fraction using said amount of fetal and maternal STR alleles. The plurality of polymorphic nucleic acids are located on a plurality of different chromosomes. In one embodiment, the plurality of polymorphic nucleic acids can be located on chromosomes 1-22. For example, the plurality of polymorphic nucleic acids can be located on a plurality of different chromosomes other than chromosomes 13, 18, 21, X or Y. The method further comprises preamplifying the mixture of fetal and maternal nucleic acids, and resolving the size of the STRs using capillary electrophoresis. The at least one STR is selected from CSF1PO, FGA, TH01, vWA, D3S1358, D5S818, D7S820, D8S1179, D13S317, D16S539, D18S51, D2S1338, PentaD, PentaE, D22S1045, D20S1082, D20S482, D18S853, D17S1301, D17S974, D14S1434, D12ATA63, D11S4463, D10S1435, D10S1248, D9S2157, D9S1122, D8S1115, D6S1017, D6S474, D5S2500, D4S2408, D4S2364, D3S4529, D3S3053, D2S1776, D2S441, D1S1677, D1S1627, and D1GATA113. Optionally, the at least one STR can be the panel of STRs comprising CSF1PO, D13S317, D16S539, D18S51, D21S11, D2S1338, D7S820 and FGA.

In another embodiment, the invention provides a composition for determining the fraction of fetal cfDNA in a maternal sample, e.g. a plasma sample, wherein the composition comprises at least one set of primers for amplifying at least one polymorphic nucleic acid in said mixture. The set of primers does not amplify a sequence on the Y chromosome.

In another embodiment, the invention provides a composition for determining the fraction of fetal cfDNA in a maternal sample, e.g. a plasma sample, wherein the composition comprises at least one set of primers for amplifying at least one polymorphic nucleic acid in said mixture. The polymorphic nucleic acid comprises an STR, a SNP and/or a tandem SNP.

In another embodiment, the invention provides a composition for determining the fraction of fetal cfDNA in a maternal sample, e.g. a plasma sample, wherein the composition comprises at least one set of primers for amplifying at least one polymorphic nucleic acid in said mixture. The polymorphic nucleic acid comprises an STR selected from CSF1PO, FGA, TH01, vWA, D3S1358, D5S818, D7S820, D8S1179, D13S317, D16S539, D18S51, D2S1338, Penta D, Penta E, D22S1045, D20S1082, D20S482, D18S853, D17S1301, D17S974, D14S1434, D12ATA63, D11S4463, D10S1435, D10S1248, D9S2157, D9S1122, D8S1115, D6S1017, D6S474, D5S2500, D4S2408, D4S2364, D3S4529, D3S3053, D2S1776, D2S441, D1S1677, D1S1627, and D1GATA113; and/or a SNP selected from rs560681 (SEQ ID NOS 1 & 2), rs1109037 (SEQ ID NOS 3 & 4), rs9866013 (SEQ ID NOS 5 & 6), rs13182883 (SEQ ID NOS 7 & 8), rs13218440 (SEQ ID NOS 9 & 10), rs7041158 (SEQ ID NOS 11 & 12), rs740598 (SEQ ID NOS 13 & 14), rs10773760 (SEQ ID NOS 15 & 16), rs4530059 (SEQ ID NOS 17 & 18), rs7205345 (SEQ ID NOS 19 & 20), rs8078417 (SEQ ID NOS 21 & 22), rs576261 (SEQ ID NOS 23 & 24), rs2567608 (SEQ ID NOS 25 & 26), rs430046 (SEQ ID NOS 27 & 28), rs9951171 (SEQ ID NOS 29 & 30), rs338882 (SEQ ID NOS 31 & 32), rs10776839 (SEQ ID NOS 33 & 34), rs9905977 (SEQ ID NOS 35 & 36), rs1277284 (SEQ ID NOS 37 & 38), rs258684 (SEQ ID NOS 39 & 40), rs1347696 (SEQ ID NOS 41 & 42), rs508485 (SEQ ID NOS 43 & 44), rs9788670 (SEQ ID NOS 45 & 46), rs8137254 (SEQ ID NOS 47 & 48), rs3143 (SEQ ID NOS 49 & 50), rs2182957 (SEQ ID NOS 51 & 52), rs3739005 (SEQ ID NOS 53 & 54), rs530022 (SEQ ID NOS 55 & 56); and/or a tandem SNP rs7277033-rs2110153 (SEQ ID NOS 312 & 313); rs2822654-rs1882882 (SEQ ID NOS 314 & 315); rs368657-rs376635 (SEQ ID NOS 316 & 317); rs2822731-rs2822732 (SEQ ID NOS 318 & 319); rs1475881-rs7275487 (SEQ ID NOS 320 & 321); rs1735976-rs2827016 (SEQ ID NOS 322 & 323); rs447340-rs2824097 (SEQ ID NOS 324 & 325); rs418989-rs13047336 (SEQ ID NOS 326 & 327); rs987980-rs987981 (SEQ ID NOS 328 & 329); rs4143392-rs4143391 (SEQ ID NOS 330 & 331); rs1691324-rs13050434 (SEQ ID NOS 332 & 333); rs11909758-rs9980111 (SEQ ID NOS 334 & 335); rs2826842-rs232414 (SEQ ID NOS 336 & 337); rs1980969-rs1980970 (SEQ ID NOS 338 & 339); rs9978999-rs9979175 (SEQ ID NOS 340 & 341); rs1034346-rs12481852 (SEQ ID NOS 342 & 343); rs7509629-rs2828358 (SEQ ID NOS 344 & 345); rs4817013-rs7277036 (SEQ ID NOS 346 & 347); rs9981121-rs2829696 (SEQ ID NOS 348 & 349); rs455921-rs2898102 (SEQ ID NOS 350 & 351); rs2898102-rs458848 (SEQ ID NOS 352 & 353); rs961301-rs2830208 (SEQ ID NOS 354 & 355); rs2174536-rs458076 (SEQ ID NOS 356 & 357); rs11088023-rs11088024 (SEQ ID NOS 358 & 359); rs1011734-rs1011733 (SEQ ID NOS 360 & 361); rs2831244-rs9789838 (SEQ ID NOS 362 & 363); rs8132769-rs2831440 (SEQ ID NOS 364 & 365); rs8134080-rs2831524 (SEQ ID NOS 366 & 367); rs4817219-rs4817220 (SEQ ID NOS 368 & 369); rs2250911-rs2250997 (SEQ ID NOS 370 & 371); rs2831899-rs2831900 (SEQ ID NOS 372 & 373); rs2831902-rs2831903 (SEQ ID NOS 374 & 375); rs11088086-rs2251447 (SEQ ID NOS 376 & 377); rs2832040-rs11088088 (SEQ ID NOS 378 & 379); rs2832141-rs2246777 (SEQ ID NOS 380 & 381); rs2832959 rs9980934 (SEQ ID NOS 382 & 383); rs2833734-rs2833735 (SEQ ID NOS 384 & 385); rs933121-rs933122 (SEQ ID NOS 386 & 387); rs2834140-rs12626953 (SEQ ID NOS 388 & 389); rs2834485-rs3453 (SEQ ID NOS 390 & 391); rs9974986-rs2834703 (SEQ ID NOS 392 & 393); rs2776266-rs2835001 (SEQ ID NOS 394 & 395); rs1984014-rs1984015 (SEQ ID NOS 396 & 397); rs7281674-rs2835316 (SEQ ID NOS 398 & 399); rs13047304-rs13047322 (SEQ ID NOS 400 & 401); rs2835545-rs4816551 (SEQ ID NOS 402 & 403); rs2835735-rs2835736 (SEQ ID NOS 404 & 405); rs13047608-rs2835826 (SEQ ID NOS 406 & 407); rs2836550-rs2212596 (SEQ ID NOS 408 & 409); rs2836660-rs2836661 (SEQ ID NOS 410 & 411); rs465612-rs8131220 (SEQ ID NOS 412 & 413); rs9980072-rs8130031 (SEQ ID NOS 414 & 415); rs418359-rs2836926 (SEQ ID NOS 416 & 417); rs7278447-rs7278858 (SEQ ID NOS 418 & 419); rs385787-rs367001 (SEQ ID NOS 420 & 421); rs367001-rs386095 (SEQ ID NOS 422 & 423); rs2837296-rs2837297 (SEQ ID NOS 424 & 425); and rs2837381-rs4816672 (SEQ ID NOS 426 & 427).

In another embodiment, the invention provides a composition for determining the fraction of fetal cfDNA in a maternal sample by massively parallel sequencing the fetal and maternal cfDNA in the maternal sample, e.g. a plasma sample, wherein the composition comprises at least one set of primers for amplifying at least one polymorphic nucleic acid in said mixture.

In another embodiment, the invention provides a composition for determining the fraction of fetal cfDNA in a maternal sample, e.g. a plasma sample, wherein the composition comprises at least one set of primers for amplifying at least one polymorphic nucleic acid in said mixture. The polymorphic nucleic acid comprises an STR, a SNP and/or a tandem SNP.

In another embodiment, the invention provides a composition for determining the fraction of fetal cfDNA in a maternal sample by massively parallel sequencing the fetal and maternal cfDNA in the maternal sample, e.g. a plasma sample, wherein the composition comprises at least one set of primers for amplifying at least one polymorphic nucleic acid in said mixture. The polymorphic nucleic acid comprises an STR selected from CSF1PO, FGA, TH01, vWA, D3S1358, D5S818, D7S820, D8S1179, D13S317, D16S539, D18S51, D2S1338, Penta D, Penta E, D22S1045, D20S1082, D20S482, D18S853, D17S1301, D17S974, D14S1434, D12ATA63, D11S4463, D10S1435, D10S1248, D9S2157, D9S1122, D8S1115, D6S1017, D6S474, D5S2500, D4S2408, D4S2364, D3S4529, D3S3053, D2S1776, D2S441, D1S1677, D1S1627, and D1GATA113; a SNP selected from rs560681 (SEQ ID NOS 1 & 2), rs1109037 (SEQ ID NOS 3 & 4), rs9866013 (SEQ ID NOS 5 & 6), rs13182883 (SEQ ID NOS 7 & 8), rs13218440 (SEQ ID NOS 9 & 10), rs7041158 (SEQ ID NOS 11 & 12), rs740598 (SEQ ID NOS 13 & 14), rs10773760 (SEQ ID NOS 15 & 16), rs4530059 (SEQ ID NOS 17 & 18), rs7205345 (SEQ ID NOS 19 & 20), rs8078417 (SEQ ID NOS 21 & 22), rs576261 (SEQ ID NOS 23 & 24), rs2567608 (SEQ ID NOS 25 & 26), rs430046 (SEQ ID NOS 27 & 28), rs9951171 (SEQ ID NOS 29 & 30), rs338882 (SEQ ID NOS 31 & 32), rs10776839 (SEQ ID NOS 33 & 34), rs9905977 (SEQ ID NOS 35 & 36), rs1277284 (SEQ ID NOS 37 & 38), rs258684 (SEQ ID NOS 39 & 40), rs1347696 (SEQ ID NOS 41 & 42), rs508485 (SEQ ID NOS 43 & 44), rs9788670 (SEQ ID NOS 45 & 46), rs8137254 (SEQ ID NOS 47 & 48), rs3143 (SEQ ID NOS 49 & 50), rs2182957 (SEQ ID NOS 51 & 52), rs3739005 (SEQ ID NOS 53 & 54), and rs530022 (SEQ ID NOS 55 & 56); and/or a tandem SNP rs7277033-rs2110153 (SEQ ID NOS 312 & 313); rs2822654-rs1882882 (SEQ ID NOS 314 & 315); rs368657-rs376635 (SEQ ID NOS 316 & 317); rs2822731-rs2822732 (SEQ ID NOS 318 & 319); rs1475881-rs7275487 (SEQ ID NOS 320 & 321); rs1735976-rs2827016 (SEQ ID NOS 322 & 323); rs447340-rs2824097 (SEQ ID NOS 324 & 325); rs418989-rs13047336 (SEQ ID NOS 326 & 327); rs987980-rs987981 (SEQ ID NOS 328 & 329); rs4143392-rs4143391 (SEQ ID NOS 330 & 331); rs1691324-rs13050434 (SEQ ID NOS 332 & 333); rs11909758-rs9980111 (SEQ ID NOS 334 & 335); rs2826842-rs232414 (SEQ ID NOS 336 & 337); rs1980969-rs1980970 (SEQ ID NOS 338 & 339); rs9978999-rs9979175 (SEQ ID NOS 340 & 341); rs1034346-rs12481852 (SEQ ID NOS 342 & 343); rs7509629-rs2828358 (SEQ ID NOS 344 & 345); rs4817013-rs7277036 (SEQ ID NOS 346 & 347); rs9981121-rs2829696 (SEQ ID NOS 348 & 349); rs455921-rs2898102 (SEQ ID NOS 350 & 351); rs2898102-rs458848 (SEQ ID NOS 352 & 353); rs961301-rs2830208 (SEQ ID NOS 354 & 355); rs2174536-rs458076 (SEQ ID NOS 356 & 357); rs11088023-rs11088024 (SEQ ID NOS 358 & 359); rs1011734-rs1011733 (SEQ ID NOS 360 & 361); rs2831244-rs9789838 (SEQ ID NOS 362 & 363); rs8132769-rs2831440 (SEQ ID NOS 364 & 365); rs8134080-rs2831524 (SEQ ID NOS 366 & 367); rs4817219-rs4817220 (SEQ ID NOS 368 & 369); rs2250911-rs2250997 (SEQ ID NOS 370 & 371); rs2831899-rs2831900 (SEQ ID NOS 372 & 373); rs2831902-rs2831903 (SEQ ID NOS 374 & 375); rs11088086-rs2251447 (SEQ ID NOS 376 & 377); rs2832040-rs11088088 (SEQ ID NOS 378 & 379); rs2832141-rs2246777 (SEQ ID NOS 380 & 381); rs2832959-rs9980934 (SEQ ID NOS 382 & 383); rs2833734-rs2833735 (SEQ ID NOS 384 & 385); rs933121-rs933122 (SEQ ID NOS 386 & 387); rs2834140-rs12626953 (SEQ ID NOS 388 & 389); rs2834485-rs3453 (SEQ ID NOS 390 & 391); rs9974986-rs2834703 (SEQ ID NOS 392 & 393); rs2776266-rs2835001 (SEQ ID NOS 394 & 395); rs1984014-rs1984015 (SEQ ID NOS 396 & 397); rs7281674-rs2835316 (SEQ ID NOS 398 & 399); rs13047304-rs13047322 (SEQ ID NOS 400 & 401); rs2835545-rs4816551 (SEQ ID NOS 402 & 403); rs2835735-rs2835736 (SEQ ID NOS 404 & 405); rs13047608-rs2835826 (SEQ ID NOS 406 & 407); rs2836550-rs2212596 (SEQ ID NOS 408 & 409); rs2836660-rs2836661 (SEQ ID NOS 410 & 411); rs465612-rs8131220 (SEQ ID NOS 412 & 413); rs9980072-rs8130031 (SEQ ID NOS 414 & 415); rs418359-rs2836926 (SEQ ID NOS 416 & 417); rs7278447-rs7278858 (SEQ ID NOS 418 & 419); rs385787-rs367001 (SEQ ID NOS 420 & 421); rs367001-rs386095 (SEQ ID NOS 422 & 423); rs2837296-rs2837297 (SEQ ID NOS 424 & 425); and rs2837381-rs4816672 (SEQ ID NOS 426 & 427).

In another embodiment, the invention provides a composition for determining the fraction of fetal cfDNA in a maternal sample, e.g. a plasma sample, wherein the composition comprises at least one set of primers for amplifying at least one polymorphic nucleic acid in said mixture. The set of primers does not amplify a sequence on the Y chromosome.

In another embodiment, the invention provides a composition for determining the fraction of fetal cfDNA in a maternal sample, e.g. a plasma sample, wherein the composition comprises at least one set of primers for amplifying at least one polymorphic nucleic acid in the mixture. The set of primers does not amplify a sequence on the Y chromosome. The polymorphic nucleic acid comprises an STR, a SNP and/or a tandem SNP.

In another embodiment, the invention provides a composition for determining the fraction of fetal cfDNA in a maternal sample, e.g. a plasma sample, wherein the composition comprises at least one set of primers for amplifying at least one polymorphic nucleic acid in said mixture. The polymorphic nucleic acid comprises an STR selected from CSF1PO, FGA, TH01, vWA, D3S1358, D5S818, D7S820, D8S1179, D13S317, D16S539, D18S51, D2S1338, Penta D, Penta E, D22S1045, D20S1082, D20S482, D18S853, D17S1301, D17S974, D14S1434, D12ATA63, D11S4463, D10S1435, D10S1248, D9S2157, D9S1122, D8S1115, D6S1017, D6S474, D5S2500, D4S2408, D4S2364, D3S4529, D3S3053, D2S1776, D2S441, D1S1677, D1S1627, and D1GATA113; a SNP selected from rs560681 (SEQ ID NOS 1 & 2), rs1109037 (SEQ ID NOS 3 & 4), rs9866013 (SEQ ID NOS 5 & 6), rs13182883 (SEQ ID NOS 7 & 8), rs13218440 (SEQ ID NOS 9 & 10), rs7041158 (SEQ ID NOS 11 & 12), rs740598 (SEQ ID NOS 13 & 14), rs10773760 (SEQ ID NOS 15 & 16), rs4530059 (SEQ ID NOS 17 & 18), rs7205345 (SEQ ID NOS 19 & 20), rs8078417 (SEQ ID NOS 21 & 22), rs576261 (SEQ ID NOS 23 & 24), rs2567608 (SEQ ID NOS 25 & 26), rs430046 (SEQ ID NOS 27 & 28), rs9951171 (SEQ ID NOS 29 & 30), rs338882 (SEQ ID NOS 31 & 32), rs10776839 (SEQ ID NOS 33 & 34), rs9905977 (SEQ ID NOS 35 & 36), rs1277284 (SEQ ID NOS 37 & 38), rs258684 (SEQ ID NOS 39 & 40), rs1347696 (SEQ ID NOS 41 & 42), rs508485 (SEQ ID NOS 43 & 44), rs9788670 (SEQ ID NOS 45 & 46), rs8137254 (SEQ ID NOS 47 & 48), rs3143 (SEQ ID NOS 49 & 50), rs2182957 (SEQ ID NOS 51 & 52), rs3739005 (SEQ ID NOS 53 & 54), and rs530022 (SEQ ID NOS 55 & 56); and/or a tandem SNP rs7277033-rs2110153 (SEQ ID NOS 312 & 313); rs2822654-rs1882882 (SEQ ID NOS 314 & 315); rs368657-rs376635 (SEQ ID NOS 316 & 317); rs2822731-rs2822732 (SEQ ID NOS 318 & 319); rs1475881-rs7275487 (SEQ ID NOS 320 & 321); rs1735976-rs2827016 (SEQ ID NOS 322 & 323); rs447340-rs2824097 (SEQ ID NOS 324 & 325); rs418989-rs13047336 (SEQ ID NOS 326 & 327); rs987980-rs987981

(SEQ ID NOS 328 & 329); rs4143392-rs4143391 (SEQ ID NOS 330 & 331); rs1691324-rs13050434 (SEQ ID NOS 332 & 333); rs11909758-rs9980111 (SEQ ID NOS 334 & 335); rs2826842-rs232414 (SEQ ID NOS 336 & 337); rs1980969-rs1980970 (SEQ ID NOS 338 & 339); rs9978999-rs9979175 (SEQ ID NOS 340 & 341); rs1034346-rs12481852 (SEQ ID NOS 342 & 343); rs7509629-rs2828358 (SEQ ID NOS 344 & 345); rs4817013-rs7277036 (SEQ ID NOS 346 & 347); rs9981121-rs2829696 (SEQ ID NOS 348 & 349); rs455921-rs2898102 (SEQ ID NOS 350 & 351); rs2898102-rs458848 (SEQ ID NOS 352 & 353); rs961301-rs2830208 (SEQ ID NOS 354 & 355); rs2174536-rs458076 (SEQ ID NOS 356 & 357); rs11088023-rs11088024 (SEQ ID NOS 358 & 359); rs1011734-rs1011733 (SEQ ID NOS 360 & 361); rs2831244-rs9789838 (SEQ ID NOS 362 & 363); rs8132769-rs2831440 (SEQ ID NOS 364 & 365); rs8134080-rs2831524 (SEQ ID NOS 366 & 367); rs4817219-rs4817220 (SEQ ID NOS 368 & 369); rs2250911-rs2250997 (SEQ ID NOS 370 & 371); rs2831899-rs2831900 (SEQ ID NOS 372 & 373); rs2831902-rs2831903 (SEQ ID NOS 374 & 375); rs11088086-rs2251447 (SEQ ID NOS 376 & 377); rs2832040-rs11088088 (SEQ ID NOS 378 & 379); rs2832141-rs2246777 (SEQ ID NOS 380 & 381); rs2832959-rs9980934 (SEQ ID NOS 382 & 383); rs2833734-rs2833735 (SEQ ID NOS 384 & 385); rs933121-rs933122 (SEQ ID NOS 386 & 387); rs2834140-rs12626953 (SEQ ID NOS 388 & 389); rs2834485-rs3453 (SEQ ID NOS 390 & 391); rs9974986-rs2834703 (SEQ ID NOS 392 & 393); rs2776266-rs2835001 (SEQ ID NOS 394 & 395); rs1984014-rs1984015 (SEQ ID NOS 396 & 397); rs7281674-rs2835316 (SEQ ID NOS 398 & 399); rs13047304-rs13047322 (SEQ ID NOS 400 & 401); rs2835545-rs4816551 (SEQ ID NOS 402 & 403); rs2835735-rs2835736 (SEQ ID NOS 404 & 405); rs13047608-rs2835826 (SEQ ID NOS 406 & 407); rs2836550-rs2212596 (SEQ ID NOS 408 & 409); rs2836660-rs2836661 (SEQ ID NOS 410 & 411); rs465612-rs8131220 (SEQ ID NOS 412 & 413); rs9980072-rs8130031 (SEQ ID NOS 414 & 415); rs418359-rs2836926 (SEQ ID NOS 416 & 417); rs7278447-rs7278858 (SEQ ID NOS 418 & 419); rs385787-rs367001 (SEQ ID NOS 420 & 421); rs367001-rs386095 (SEQ ID NOS 422 & 423); rs2837296-rs2837297 (SEQ ID NOS 424 & 425); and rs2837381-rs4816672 (SEQ ID NOS 426 & 427).

In another embodiment, the invention provides a composition for determining the fraction of fetal cfDNA in a maternal sample by massively parallel sequencing the fetal and maternal cfDNA in the maternal sample, e.g. a plasma sample, wherein the composition comprises at least one set of primers for amplifying at least one polymorphic nucleic acid in said mixture.

In another embodiment, the invention provides a composition for determining the fraction of fetal cfDNA in a maternal sample, e.g. a plasma sample, wherein the composition comprises at least one set of primers for amplifying at least one polymorphic nucleic acid in said mixture. The set of primers does not amplify a sequence on the Y chromosome. The polymorphic nucleic acid comprises an STR, a SNP and/or a tandem SNP.

In another embodiment, the invention provides a composition for determining the fraction of fetal cfDNA in a maternal sample by massively parallel sequencing the fetal and maternal cfDNA in the maternal sample, e.g. a plasma sample, wherein the composition comprises at least one set of primers for amplifying at least one polymorphic nucleic acid in said mixture. The polymorphic nucleic acid comprises an STR selected from CSF1PO, FGA, TH01, vWA, D3S1358, D5S818, D7S820, D8S1179, D13S317, D16S539, D18S51, D2S1338, Penta D, Penta E, D22S, D20S1082, D20S482, D18S853, D17S1301, D17S974, D14S1434, D12ATA63, D11S4463, D10S1435, D10S1248, D9S2157, D9S1122, D8S1115, D6S1017, D6S474, D5S2500, D4S2408, D4S2364, D3S4529, D3S3053, D2S1776, D2S441, D1S1677, D1S1627, and D1GATA113; a SNP selected from rs560681 (SEQ ID NOS 1 & 2), rs1109037 (SEQ ID NOS 3 & 4), rs9866013 (SEQ ID NOS 5 & 6), rs13182883 (SEQ ID NOS 7 & 8), rs13218440 (SEQ ID NOS 9 & 10), rs7041158 (SEQ ID NOS 11 & 12), rs740598 (SEQ ID NOS 13 & 14), rs10773760 (SEQ ID NOS 15 & 16), rs4530059 (SEQ ID NOS 17 & 18), rs7205345 (SEQ ID NOS 19 & 20), rs8078417 (SEQ ID NOS 21 & 22), rs576261 (SEQ ID NOS 23 & 24), rs2567608 (SEQ ID NOS 25 & 26), rs430046 (SEQ ID NOS 27 & 28), rs9951171 (SEQ ID NOS 29 & 30), rs338882 (SEQ ID NOS 31 & 32), rs10776839 (SEQ ID NOS 33 & 34), rs9905977 (SEQ ID NOS 35 & 36), rs1277284 (SEQ ID NOS 37 & 38), rs258684 (SEQ ID NOS 39 & 40), rs1347696 (SEQ ID NOS 41 & 42), rs508485 (SEQ ID NOS 43 & 44), rs9788670 (SEQ ID NOS 45 & 46), rs8137254 (SEQ ID NOS 47 & 48), rs3143 (SEQ ID NOS 49 & 50), rs2182957 (SEQ ID NOS 51 & 52), rs3739005 (SEQ ID NOS 53 & 54), and rs530022 (SEQ ID NOS 55 & 56); and/or a tandem SNP rs7277033-rs2110153 (SEQ ID NOS 312 & 313); rs2822654-rs1882882 (SEQ ID NOS 314 & 315); rs368657-rs376635 (SEQ ID NOS 316 & 317); rs2822731-rs2822732 (SEQ ID NOS 318 & 319); rs1475881-rs7275487 (SEQ ID NOS 320 & 321); rs1735976-rs2827016 (SEQ ID NOS 322 & 323); rs447340-rs2824097 (SEQ ID NOS 324 & 325); rs418989-rs13047336 (SEQ ID NOS 326 & 327); rs987980-rs987981 (SEQ ID NOS 328 & 329); rs4143392-rs4143391 (SEQ ID NOS 330 & 331); rs1691324-rs13050434 (SEQ ID NOS 332 & 333); rs11909758-rs9980111 (SEQ ID NOS 334 & 335); rs2826842-rs232414 (SEQ ID NOS 336 & 337); rs1980969-rs1980970 (SEQ ID NOS 338 & 339); rs9978999-rs9979175 (SEQ ID NOS 340 & 341); rs1034346-rs12481852 (SEQ ID NOS 342 & 343); rs7509629-rs2828358 (SEQ ID NOS 344 & 345); rs4817013-rs7277036 (SEQ ID NOS 346 & 347); rs9981121-rs2829696 (SEQ ID NOS 348 & 349); rs455921-rs2898102 (SEQ ID NOS 350 & 351); rs2898102-rs458848 (SEQ ID NOS 352 & 353); rs961301-rs2830208 (SEQ ID NOS 354 & 355); rs2174536-rs458076 (SEQ ID NOS 356 & 357); rs11088023-rs11088024 (SEQ ID NOS 358 & 359); rs1011734-rs1011733 (SEQ ID NOS 360 & 361); rs2831244-rs9789838 (SEQ ID NOS 362 & 363); rs8132769-rs2831440 (SEQ ID NOS 364 & 365); rs8134080-rs2831524 (SEQ ID NOS 366 & 367); rs4817219-rs4817220 (SEQ ID NOS 368 & 369); rs2250911-rs2250997 (SEQ ID NOS 370 & 371); rs2831899-rs2831900 (SEQ ID NOS 372 & 373); rs2831902-rs2831903 (SEQ ID NOS 374 & 375); rs11088086-rs2251447 (SEQ ID NOS 376 & 377); rs2832040-rs11088088 (SEQ ID NOS 378 & 379); rs2832141-rs2246777 (SEQ ID NOS 380 & 381); rs2832959 rs9980934 (SEQ ID NOS 382 & 383); rs2833734-rs2833735 (SEQ ID NOS 384 & 385); rs933121-rs933122 (SEQ ID NOS 386 & 387); rs2834140-rs12626953 (SEQ ID NOS 388 & 389); rs2834485-rs3453 (SEQ ID NOS 390 & 391); rs9974986-rs2834703 (SEQ ID NOS 392 & 393); rs2776266-rs2835001 (SEQ ID NOS 394 & 395); rs1984014-rs1984015 (SEQ ID NOS 396 & 397);

rs7281674-rs2835316 (SEQ ID NOS 398 & 399); rs13047304-rs13047322 (SEQ ID NOS 400 & 401); rs2835545-rs4816551 (SEQ ID NOS 402 & 403); rs2835735-rs2835736 (SEQ ID NOS 404 & 405); rs13047608-rs2835826 (SEQ ID NOS 406 & 407); rs2836550-rs2212596 (SEQ ID NOS 408 & 409); rs2836660-rs2836661 (SEQ ID NOS 410 & 411); rs465612-rs8131220 (SEQ ID NOS 412 & 413); rs9980072-rs8130031 (SEQ ID NOS 414 & 415); rs418359-rs2836926 (SEQ ID NOS 416 & 417); rs7278447-rs7278858 (SEQ ID NOS 418 & 419); rs385787-rs367001 (SEQ ID NOS 420 & 421); rs367001-rs386095 (SEQ ID NOS 422 & 423); rs2837296-rs2837297 (SEQ ID NOS 424 & 425); and rs2837381-rs4816672 (SEQ ID NOS 426 & 427).

In another embodiment, the invention provides a kit that comprises the composition of the invention as described above and in the following.

INCORPORATION BY REFERENCE

All patents, patent applications, and other publications, including all sequences disclosed within these references, referred to herein are expressly incorporated by reference, to the same extent as if each individual publication, patent or patent application was specifically and individually indicated to be incorporated by reference. All documents cited are, in relevant part, incorporated herein by reference. However, the citation of any document is not to be construed as an admission that it is prior art with respect to the present invention.

BRIEF DESCRIPTION OF THE DRAWINGS

The novel features of the invention are set forth with particularity in the appended claims A better understanding of the features and advantages of the present invention will be obtained by reference to the following detailed description that sets forth illustrative embodiments, in which the principles of the invention are utilized, and the accompanying drawings of which:

FIG. 4 illustrates STR markers used in the AmpFlSTR® Identifiler® PCR Amplification Kit.

FIG. 5 illustrates STR markers used in the AmpFlSTR® MiniFiler® PCR Amplification Kit.

DETAILED DESCRIPTION OF THE INVENTION

Figure 1:
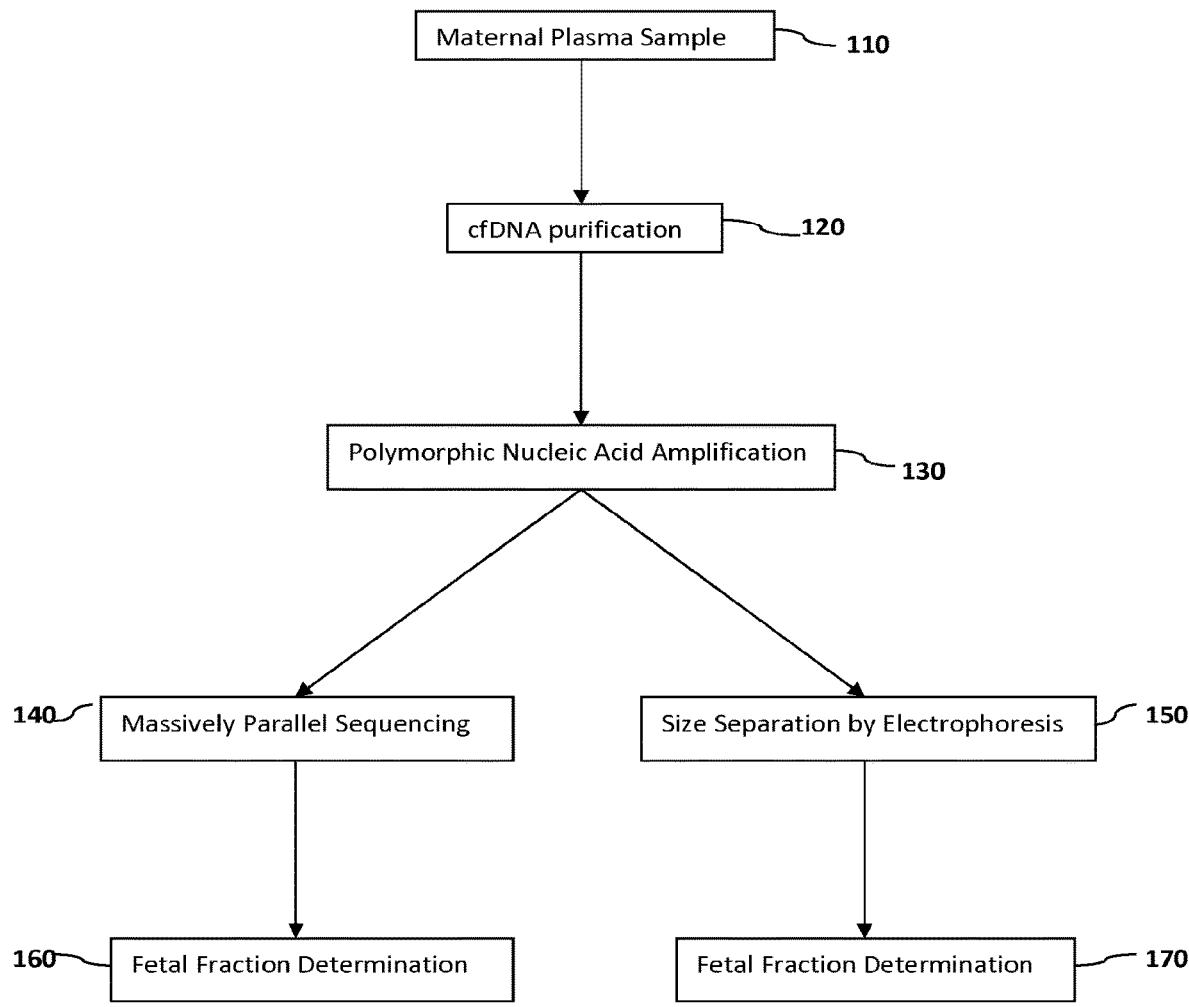
FIG. 1 is a flowchart of a method 100 for determining the fetal fraction in a maternal test sample comprising a mixture of fetal and maternal nucleic acids using massively parallel sequencing methods or size separation of polymorphic nucleic acid sequences.

The invention provides compositions and methods for determining the fraction of fetal nucleic acids in a maternal sample comprising a mixture of fetal and maternal nucleic acids. The fraction of fetal nucleic acids can be used in determining the presence or absence of fetal aneuploidy.

Unless otherwise indicated, the practice of the present invention involves conventional techniques commonly used in molecular biology, microbiology, protein purification, protein engineering, protein and DNA sequencing, and recombinant DNA fields, which are within the skill of the art. Such techniques are known to those of skill in the art and are described in numerous standard texts and reference works. All patents, patent applications, articles and publications mentioned herein are hereby expressly incorporated herein by reference in their entirety.

Numeric ranges are inclusive of the numbers defining the range. It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The headings provided herein are not limitations of the various aspects or embodiments of the invention which can be had by reference to the Specification as a whole. Accordingly, as indicated above, the terms defined immediately below are more fully defined by reference to the specification as a whole.

Unless defined otherwise herein, all technical and scientific terms used herein have the same meaning as commonly understood by one of ordinary skill in the art to which this invention belongs. Various scientific dictionaries that include the terms included herein are well known and available to those in the art. Although any methods and materials similar or equivalent to those described herein find use in the practice or testing of the present invention, some preferred methods and materials are described. Accordingly, the terms defined immediately below are more fully described by reference to the Specification as a whole. It is to be understood that this invention is not limited to the particular methodology, protocols, and reagents described, as these may vary, depending upon the context they are used by those of skill in the art.

Definitions

As used herein, the singular terms "a", "an," and "the" include the plural reference unless the context clearly indicates otherwise. Unless otherwise indicated, nucleic acids are written left to right in 5' to 3' orientation and amino acid sequences are written left to right in amino to carboxy orientation, respectively.

As used herein, the singular terms "a", "an," and "the" include the plural reference unless the context clearly indicates otherwise. Unless otherwise indicated, nucleic acids are written left to right in 5' to 3' orientation and amino acid sequences are written left to right in amino to carboxy orientation, respectively.

The term "portion" when used in reference to the amount of sequence information of fetal and maternal nucleic acid molecules in a biological sample herein refers to the amount of sequence information of fetal and maternal nucleic acid molecules in a biological sample that in sum amount to less than the sequence information of <1 human genome.

The terms "polynucleotide", "nucleic acid" and "nucleic acid molecules" are used interchangeably and refer to a covalently linked sequence of nucleotides (i.e., ribonucleotides for RNA and deoxyribonucleotides for DNA) in which the 3' position of the pentose of one nucleotide is joined by a phosphodiester group to the 5' position of the pentose of the next, include sequences of any form of nucleic acid, including, but not limited to RNA, DNA and cfDNA molecules. The term "polynucleotide" includes, without limitation, single- and double-stranded polynucleotide.

The term "copy number variation" herein refers to variation in the number of copies of a nucleic acid sequence that is 1 kb or larger present in a test sample in comparison with the copy number of the nucleic acid sequence present in a qualified sample. A "copy number variant" refers to the 1 kb or larger sequence of nucleic acid in which copy-number differences are found by comparison of a sequence of interest in test sample with that present in a qualified sample. Copy number variants/variations include deletions, including microdeletions, insertions, including microinsertions, duplications, multiplications, inversions, translocations and complex multi-site variants. CNV encompass chromosomal aneuploidies and partial aneuplodies.

As used herein, the term "fetal fraction" is used interchangeably with "fraction of fetal nucleic acid", which refers to the fraction of fetal nucleic acid in a sample comprising fetal and maternal nucleic acid. Similarly, the term "minor fraction" or "minor component" herein refers to the lesser fraction of the total genetic material that is present in a sample containing genetic material derived from separate sources e.g. individuals.

As used herein the term "allele" refers to one specific form of a genetic sequence (such as a gene) within a cell, a sample, an individual or within a population, the specific form differing from other forms of the same gene in the sequence of at least one, and frequently more than one, variant sites within the sequence of the gene. The sequences at these variant sites that differ between different alleles are termed "variants", "polymorphisms", or "mutations". In general, polymorphism is used to refer to variants that have a frequency of at least 1% in a population, while the term mutation is generally used for variants that occur at a frequency of less than 1% in a population. In diploid organisms such as humans, at each autosomal specific chromosomal location or "locus" an individual possesses two alleles, a first inherited from one parent and a second inherited from the other parent, for example one from the mother and one from the father. An individual is "heterozygous" at a locus if it has two different alleles at the locus. An individual is "homozygous" at a locus if it has two identical alleles at that locus.

The term "enrich" herein refers to the process of amplifying polymorphic target nucleic acids contained in a portion of a maternal sample, and combining the amplified product with the remainder of the maternal sample from which the portion was removed.

As used herein, the term "genotyping" refers to the determination of the genetic information an individual carries at one or more positions in the genome. For example, genotyping may comprise the determination of which allele or alleles an individual carries for a single SNP or the determination of which allele or alleles an individual carries for a plurality of SNPs. For example, a particular nucleotide in a genome may be a T in some individuals and a C in other individuals. Those individuals who have a T at the position have the T allele and those who have a C have the C allele.

In a diploid organism the individual will have two copies of the sequence containing the polymorphic position so the individual may have a T allele and a C allele or alternatively two copies of the T allele or two copies of the C allele. Those individuals who have two copies of the C allele are homozygous for the C allele, those individuals who have two copies of the T allele are homozygous for the T allele, and those individuals who have one copy of each allele are heterozygous. The alleles are often referred to as the A allele, often the major allele, and the B allele, often the minor allele. The genotypes may be AA (homozygous A), BB (homozygous B) or AB (heterozygous). Genotyping methods generally provide for identification of the sample as AA, BB or AB.

As used herein the term "chromosome" refers to the heredity-bearing gene carrier of a living cell which is derived from chromatin and which comprises DNA and protein components (especially histones). The conventional internationally recognized individual human genome chromosome numbering system is employed herein. The size of an individual chromosome can vary from one type to another with a given multi-chromosomal genome and from one genome to another. In the case of the human genome, the entire DNA mass of a given chromosome is usually greater than about 100,000,000 bp. For example, the size of the entire human genome is about $3 \times 10^9$ bp. The largest chromosome, chromosome no. 1, contains about $2.4 \times 10^8$ by while the smallest chromosome, chromosome no. 22, contains about $5.3 \times 10^7$ bp.

The term "aneuploidy" herein refers to the occurrence of one or more extra or missing chromosomes.

As used herein the term "chromosomal region" is a portion of a chromosome. The actual physical size or extent of any individual chromosomal region can vary greatly. The term "region" is not necessarily definitive of a particular one or more genes because a region need not take into specific account the particular coding segments (exons) of an individual gene.

As used herein the term "genetic marker" refers to a sequence of DNA that has a specific location on a chromosome that can be measured in a laboratory. The term "genetic marker" can also be used to refer to, e.g., a cDNA and/or an mRNA encoded by a genomic sequence, as well as to that genomic sequence. To be useful, a marker needs to have two or more alleles or variants. Markers can be either direct, that is, located within the gene or locus of interest (i.e., candidate gene), or indirect, that is closely linked with the gene or locus of interest (presumably due to a location which is proximate to, but not inside the gene or locus of interest). Moreover, markers can also include sequences which either do or do not modify the amino acid sequence of a gene.

As used herein, the term "maternal sample" refers to a biological sample obtained from a pregnant subject, and comprises a mixture of fetal and maternal nucleic acids. A "pregnant subject" is not limited to a human being, but may also include other organisms including but not limited to mammals, plants, bacteria or cells derived from any of the above.

The term "whole genome amplification" or "WGA" as used herein generally refers to a method for amplification of a limited DNA sample in a non-specific manner, in order to generate a new sample that is indistinguishable from the original but with a higher DNA concentration. The ideal whole genome amplification technique would amplify a sample up to a microgram level while maintaining the original sequence representation. The DNA of the sample may include an entire genome or a portion thereof. Degenerate oligonucleotide-primed PCR (DOP), primer extension PCR technique (PEP) including modified improved primer extension preamplification (mIPEP), and multiple displacement amplification (MDA), are examples of whole genome amplification methods.

The term "short tandem repeat" or "STR" as used herein refers to a class of polymorphisms that occurs when a pattern of two or more nucleotides are repeated and the repeated sequences are directly adjacent to each other. The pattern can range in length from 2 to 10 base pairs (bp) (for example (CATG)n in a genomic region) and is typically in the non-coding intron region. By examining several STR loci and counting how many repeats of a specific STR sequence there are at a given locus, it is possible to create a unique genetic profile of an individual.

The term "primer," as used herein refers to an isolated oligonucleotide which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer, use of the method, and the parameters used for primer design, as disclosed herein.

The term "primer pair" or "primer set" refers to a set of primers including a 5' "upstream primer" or "forward primer" that hybridizes with the complement of the 5' end of the DNA sequence to be amplified and a 3' "downstream primer" or "reverse primer" that hybridizes with the 3' end of the sequence to be amplified. As will be recognized by those of skill in the art, the terms "upstream" and "downstream" or "forward" and "reverse" are not intended to be limiting, but rather provide illustrative orientation in particular embodiments. A primer pair is said to be "unique" if it can be employed to specifically amplify a particular target nucleotide sequence in a given amplification mixture.

A "polymorphic marker" or "polymorphic site" is a locus at which nucleotide sequence divergence occurs. The locus may be as small as one base pair. Illustrative markers have at least two alleles, each occurring at frequency of greater than 1%, and more typically greater than 10% or 20% of a selected population. A polymorphic site may be as small as one base pair. Polymorphic markers include restriction fragment length polymorphism (RFLPs), variable number of tandem repeats (VNTR's), hypervariable regions, minisatellites, dinucleotide repeats, trinucleotide repeats, tetranucleotide repeats, simple sequence repeats, deletions, and insertion elements such as Alu. The first identified allelic form is arbitrarily designated as the reference form and other allelic forms are designated as alternative or variant alleles. The allelic form occurring most frequently in a selected population is sometimes referred to as the wild type form. Diploid organisms may be homozygous or heterozygous for allelic forms. A diallelic polymorphism has two forms. A triallelic polymorphism has three forms. A polymorphism between two nucleic acids can occur naturally, or be caused by exposure to or contact with chemicals, enzymes, or other agents, or exposure to agents that cause damage to nucleic acids, for example, ultraviolet radiation, mutagens or carcinogens. The terms "polymorphic locus" and "polymorphic site" are herein used interchangeably.

The terms "polymorphic target nucleic acid", "polymorphic sequence", "polymorphic target nucleic acid sequence" and "polymorphic nucleic acid" are used interchangeably herein to refer to a nucleic acid sequence e.g. a DNA sequence, that comprises one or more polymorphic sites e.g one SNP or a tandem SNP. Polymorphic sequences according to the present technology can be used to specifically differentiate between maternal and non-maternal alleles in the maternal sample comprising a mixture of fetal and maternal nucleic acids.

A "single nucleotide polymorphism" (SNP) occurs at a polymorphic site occupied by a single nucleotide, which is the site of variation between allelic sequences. The site is usually preceded by and followed by highly conserved sequences of the allele (e.g., sequences that vary in less than 1/100 or 1/1000 members of the populations). A SNP usually arises due to substitution of one nucleotide for another at the polymorphic site. A transition is the replacement of one purine by another purine or one pyrimidine by another pyrimidine. A transversion is the replacement of a purine by a pyrimidine or vice versa. SNPs can also arise from a deletion of a nucleotide or an insertion of a nucleotide relative to a reference allele. Single nucleotide polymorphisms (SNPs) are positions at which two alternative bases occur at appreciable frequency (>1%) in the human population, and are the most common type of human genetic variation.

As used herein, the term "short tandem repeat" or "STR" as used herein refers to a class of polymorphisms that occurs when a pattern of two or more nucleotides are repeated and the repeated sequences are directly adjacent to each other. The pattern can range in length from 2 to 10 base pairs (bp) (for example (CATG)n in a genomic region) and is typically in the non-coding intron region. By examining several STR loci and counting how many repeats of a specific STR sequence there are at a given locus, it is possible to create a unique genetic profile of an individual.

As used herein, the term "miniSTR" herein refers to tandem repeat of four or more base pairs that spans less than about 300 base pairs, less than about 250 base airs, less than about 200 base pairs, less than about 150 base pairs, less than about 100 base pairs, less than about 50 base pairs, or less than about 25 base pairs. "miniSTRs" are STRs that are amplifiable from cfDNA templates.

The term "tandem SNPs" herein refers to two or more SNPs that are present within a polymorphic target nucleic acid sequence.

The terms "plurality of polymorphic target nucleic acids", "polymorphic nucleic acids" and "polymorphic sequences" are used interchangeably herein and refer to a number of nucleic acid sequences each comprising at least one polymorphic site e.g. one SNP, such that at least 1, 2, 3, 4, 5, 6, 7, 8, 9, 10, 15, 20, 25, 30, or 40 or more different polymorphic sites are amplified from the polymorphic target nucleic acids to identify and/or quantify fetal alleles present in maternal samples comprising fetal and maternal nucleic acids.

As used herein, the term "substantially cell free" encompasses preparations of the desired sample from which components that are normally associated with it are removed. For example, a plasma sample is rendered essentially cell free by removing blood cells e.g. red cells, that are normally associated with it. In some embodiments, substantially free samples are processed to remove cells that would otherwise contribute to the desired genetic material that is to be tested for an abnormality As used herein the term "chromosome" refers to the heredity-bearing gene carrier of a living cell which is derived from chromatin and which comprises DNA and protein components (especially histones). The conventional internationally recognized individual human genome chromosome numbering system is employed herein. The size of an individual chromosome can vary from one type to another with a given multi-chromosomal genome and from one genome to another. In the case of the human genome, the entire DNA mass of a given chromosome is usually greater than about 100,000,000 bp. For example, the size of the entire human genome is about 3.times.10.sup.9 bp. The largest chromosome, chromosome no. 1, contains about 2.4.times.10.sup.8 by while the smallest chromosome, chromosome no. 22, contains about 5.3.times.10.sup.7 bp.

The term "oligonucleotide" is used to refer to a nucleic acid that is relatively short, generally shorter than 200 nucleotides, more particularly, shorter than 100 nucleotides, most particularly, shorter than 50 nucleotides. Typically, oligonucleotides are single-stranded DNA molecules.

The term "primer" refers to an oligonucleotide that is capable of hybridizing (also termed "annealing") with a nucleic acid and serving as an initiation site for nucleotide (RNA or DNA) polymerization under appropriate conditions (i.e., in the presence of four different nucleoside triphosphates and an agent for polymerization, such as DNA or RNA polymerase or reverse transcriptase) in an appropriate buffer and at a suitable temperature. The appropriate length of a primer depends on the intended use of the primer, but primers are typically at least 7 nucleotides long and, more typically range from 10 to 30 nucleotides, or even more typically from 15 to 30 nucleotides, in length. Other primers can be somewhat longer, e.g., 30 to 50 nucleotides long.

The term "allele call" as used herein, refers to successful characterization of an allele by a given analysis method. If the analysis provides successful characterization of both alleles of a gene locus of a DNA sample, it is said that two allele calls are made. If one allele is characterized while the other allele is not characterized, it is said that one allele call is made. If neither of the two alleles is successfully characterized, no allele calls are made.

The term "allele" as used herein, is any one of a number of viable DNA codings occupying a given locus (position) on a chromosome. Usually alleles are DNA (deoxyribonucleic acid) sequences that code for a gene, but sometimes the term is used to refer to a non-gene sequence. An individual's genotype for that gene is the set of alleles it happens to possess. In a diploid organism, one that has two copies of each chromosome, two alleles make up the individual's genotype.

The term "reaction mixture" as used herein refers to a mixture containing sufficient components to carry out an amplification reaction.

The term "sequence tag density" herein refers to the number of sequence reads that are mapped to a reference genome sequence e.g. the sequence tag density for chromosome 21 is the number of sequence reads generated by the sequencing method that are mapped to chromosome 21 of the reference genome. The term "sequence tag density ratio" herein refers to the ratio of the number of sequence tags that are mapped to a chromosome of the reference genome e.g. chromosome 21, to the length of the reference genome chromosome 21.

The terms "threshold value" and "qualified threshold value" herein refer to any number that is calculated using a qualifying data set and serves as a limit of diagnosis of a copy number variation e.g. an aneuploidy, in an organism. If a threshold is exceeded by results obtained from practicing the invention, a subject can be diagnosed with a copy number variation e.g. trisomy 21.

The term "read" refers to a DNA sequence of sufficient length (e.g., at least about 30 bp) that can be used to identify a larger sequence or region, e.g. that can be aligned and specifically assigned to a chromosome or genomic region or gene.

The term "sequence tag" is herein used interchangeably with the term "mapped sequence tag" to refer to a sequence read that has been specifically assigned i.e. mapped, to a larger sequence e.g. a reference genome, by alignment. Mapped sequence tags are uniquely mapped to a reference genome i.e. they are assigned to a single location to the reference genome. Tags that can be mapped to more than one location on a reference genome i.e. tags that do not map uniquely, are not included in the analysis.

The terms "aligned", "alignment", or "aligning" refer to one or more sequences that are identified as a match in terms of the order of their nucleic acid molecules to a known sequence from a reference genome. Such alignment can be done manually or by a computer algorithm, examples including the Efficient Local Alignment of Nucleotide Data (ELAND) computer program distributed as part of the Illumina Genomics Analysis pipeline. The matching of a sequence read in aligning can be a 100% sequence match or less than 100% (non-perfect match).

The term "reference genome" refers to any particular known genome sequence, whether partial or complete, of any organism or virus which may be used to reference identified sequences from a subject. For example, a reference genome used for human subjects as well as many other organisms is found at the National Center for Biotechnology Information on the world wide web at ncbi.nlm.nih.gov. A "genome" refers to the complete genetic information of an organism or virus, expressed in nucleic acid sequences.

The term "artificial target sequences genome" herein refers to a grouping of known sequences that encompass alleles of known polymorphic sites. For example, a "SNP reference genome" is an artificial target sequences genome comprising a grouping of sequences that encompass alleles of known SNPs.

The term "clinically-relevant sequence" herein refers to a nucleic acid sequence that is known or is suspected to be associated or implicated with a genetic or disease condition. Determining the absence or presence of a clinically-relevant sequence can be useful in determining a diagnosis or confirming a diagnosis of a medical condition, or providing a prognosis for the development of a disease.

The term "mixed sample" herein refers to a sample containing a mixture of nucleic acids, which are derived from different genomes.

The term "original maternal sample" herein refers to a biological sample obtained from a pregnant subject e.g. a woman, who serves as the source from which a portion is removed to amplify polymorphic target nucleic acids. The "original sample" can be any sample obtained from a pregnant subject, and the processed fractions thereof e.g. a purified cfDNA sample extracted from a maternal plasma sample. The term "original maternal sample" herein refers to a biological sample obtained from a pregnant subject e.g. a woman, who serves as the source from which a portion is removed to amplify polymorphic target nucleic acids. The "original sample" can be any sample obtained from a pregnant subject, and the processed fractions thereof e.g. a purified cfDNA sample extracted from a maternal plasma sample.

The term "biological fluid" herein refers to a liquid taken from a biological source and includes, for example, blood, serum, plasma, sputum, lavage fluid, cerebrospinal fluid, urine, semen, sweat, tears, saliva, and the like. As used herein, the terms "blood," "plasma" and "serum" expressly encompass fractions or processed portions thereof. Similarly, where a sample is taken from a biopsy, swab, smear, etc., the "sample" expressly encompasses a processed fraction or portion derived from the biopsy, swab, smear, etc.

The terms "maternal nucleic acids" and "fetal nucleic acids" herein refer to the nucleic acids of a pregnant female subject and the nucleic acids of the fetus being carried by the pregnant female, respectively.

The term "corresponding to" herein refers to a nucleic acid sequence e.g. a gene or a chromosome, that is present in the genome of different subjects, and which does not necessarily have the same sequence in all genomes, but serves to provide the identity rather than the genetic information of a sequence of interest e.g. a gene or chromosome.

The term "group of chromosomes" herein refers to two or more chromosomes.

The term "subject" herein refers to a human subject as well as a non-human subject such as a mammal, an invertebrate, a vertebrate, a fungus, a yeast, a bacteria, and a virus. Although the examples herein concern human cells and the language is primarily directed to human concerns, the concept of this invention is applicable to genomes from any plant or animal, and is useful in the fields of veterinary medicine, animal sciences, research laboratories and such.

DESCRIPTION

The methods described herein enable the determination of the fraction of the minor fetal nucleic acid component in a sample comprising a mixture of fetal and maternal nucleic acids. In particular, the method enables the determination of the fraction of cfDNA contributed by a fetus to the mixture of fetal and maternal cfDNA in a maternal sample e.g. a plasma sample. The difference between the maternal and fetal fraction is determined by the relative contribution of a polymorphic allele derived from the fetal genome to the contribution of the corresponding polymorphic allele derived from the maternal genome. Polymorphic sequences can be used in conjunction with clinically-relevant diagnostic tests as a positive control for the presence of cfDNA in order to highlight false-negative or false-positive results stemming from low levels of cfDNA below the identification limit. The methods described are independent of the gender of the fetus, and are useful across a range of gestational ages.

FIG. 1 provides a flow diagram of an embodiment of method of the invention 100 for determining the fraction of fetal nucleic acids in a maternal biological sample by massively parallel sequencing of PCR-amplified polymorphic target nucleic acids. In step 110 a maternal sample comprising a mixture of fetal and maternal nucleic acids is obtained from a subject. The sample is a maternal sample that is obtained from a pregnant female, for example a pregnant woman. Other maternal samples can be from mammals, for example, cow, horse, dog, or cat. If the subject is a human, the sample can be taken in the first or second trimester of pregnancy. Any maternal biological sample can be used a source of fetal and maternal nucleic acids which are contained in cells or that are "cell-free". In some embodiments, it is advantageous to obtain a maternal sample that comprises cell-free nucleic acids e.g. cfDNA. Preferably, the maternal biological sample is a biological fluid sample. A biological fluid includes, as non-limiting examples, blood, plasma, serum, sweat, tears, sputum, urine, sputum, ear flow, lymph, saliva, cerebrospinal fluid, ravages, bone marrow suspension, vaginal flow, transcervical lavage, brain fluid, ascites, milk, secretions of the respiratory, intestinal and genitourinary tracts, and leukophoresis samples. In some embodiments, the biological fluid sample is a sample that is easily obtainable by non-invasive procedures e.g. blood, plasma, serum, sweat, tears, sputum, urine, sputum, ear flow, and saliva. In some embodiments, the biological sample is a peripheral blood sample, or the plasma and/or the serum fractions thereof. In another embodiment, the sample is a mixture of two or more biological samples e.g. a biological sample can comprise two or more of a biological fluid samples. As used herein, the terms "blood," "plasma" and "serum" expressly encompass fractions or processed portions thereof. In some embodiments, the biological sample is processed to obtain a sample fraction e.g. plasma, that contains the mixture of fetal and maternal nucleic acids. A sample that can be used to determine the genotype of one or more fetal alleles can be any sample that contains fetal cells or fetal nucleic acid. For example, maternal serum or plasma sample comprising fetal and maternal cell-free nucleic acids (e.g., DNA or RNA) can be used to determine the genotypes of fetal alleles. In one embodiment, the sample can comprise a fetal cell, e.g., a fetal nucleated red blood cell or a trophoblast.

In step 120, the mixture of fetal and maternal nucleic acids is further processed from the sample fraction e.g. plasma, to obtain a sample comprising a purified mixture of fetal and maternal nucleic acids e.g. cfDNA. Cell-free nucleic acids, including cell-free DNA, can be obtained by various methods known in the art from biological samples including but not limited to plasma, serum and urine (Fan et al., Proc Natl Acad Sci 105:16266-16271 [2008]; Koide et al., Prenatal Diagnosis 25:604-607 [2005]; Chen et al., Nature Med. 2: 1033-1035 [1996]; Lo et al., Lancet 350: 485-487 [1997]. To separate cfDNA from cells, fractionation, centrifugation (e.g., density gradient centrifugation), DNA-specific precipitation, or high-throughput cell sorting and/or separation methods can be used. Examples of methods for processing fluid samples have been previously disclosed, e.g., U.S. Patent Application Nos. 20050282293, 20050224351, and 20050065735, which are herein incorporated by reference in their entireties. Commercially available kits for manual and automated separation of cfDNA are available (Roche Diagnostics, Indianapolis, Ind., Qiagen, Valencia, Calif., Macherey-Nagel, Duren, Del.). In some instances, it can be advantageous to fragment the nucleic acid molecules in the nucleic acid sample. Fragmentation can be random, or it can be specific, as achieved, for example, using restriction endonuclease digestion. Methods for random fragmentation are well known in the art, and include, for example, limited DNAse digestion, alkali treatment and physical shearing. In one embodiment, sample nucleic acids are obtained as cfDNA, which is not subjected to fragmentation. In other embodiments, the sample nucleic acids are obtained as genomic DNA, which is subjected to fragmentation into fragments of approximately 500 or more base pairs, and to which NGS methods can be readily applied.

In step 130, a portion of the purified mixture of fetal and maternal cfDNA is used for amplifying a plurality of polymorphic target nucleic acids each comprising a polymorphic site. In some embodiments, the target nucleic acids each comprise a SNP. In other embodiments, each of the target nucleic acids comprises a pair of tandem SNPs. In yet other embodiments, each the target nucleic acids comprises an STR. Polymorphic sites that are contained in the target nucleic acids include without limitation single nucleotide polymorphisms (SNPs), tandem SNPs, small-scale multi-base deletions or insertions, called IN-DELS (also called deletion insertion polymorphisms or DIPs), Multi-Nucleotide Polymorphisms (MNPs) Short Tandem Repeats (STRs), restriction fragment length polymorphism (RFLP), or a polymorphism comprising any other change of sequence in a chromosome. In some embodiments, the polymorphic sites that are encompassed by the method of the invention are located on autosomal chromosomes, thereby enabling the determination of fetal fraction independently of sex of the fetus. Polymorphisms associated with chromosomes other than chromosome 13, 18, 21 and Y can also be used in the methods described herein.

Polymorphisms can be indicative, informative, or both. Indicative polymorphisms indicate the presence of fetal cell-free DNA in a maternal sample. For example, the more there is of a particular genetic sequence, e.g. a SNP, the more a method will translate its presence into a particular color intensity, density of color, or some other property which is detectable and measurable and indicative of the presence, absence, and quantity of a particular fragment of DNA and/or particular polymorphism e.g. SNP of the embryo. Informative polymorphisms yield information about the fetus for example, the presence or absence of a disease, genetic abnormality, or any other biological information such as the stage of gestation or gender. With regard to the present invention, the methods are not conducted using all possible SNPs in a genome, but use those which are said to be "informative". "Informative SNPs" in this instance are those which identify differences in the sequence of the mother and the fetus. Any polymorphic site that can be encompassed by the reads generated by the sequencing methods described herein can be used to determine the fetal fraction.

In one embodiment, a portion of the mixture of fetal and maternal nucleic acids in the sample e.g. cfDNA, is used as template for amplifying target nucleic acids that comprise at least one SNP. In some embodiments, each target nucleic acid comprises a single i.e. one SNP. Target nucleic acid sequences comprising SNPs are available from publicly accessible databases including, but not limited to Human SNP Database at world wide web address wi.mit.edu, NCBI dbSNP Home Page at world wide web address ncbi.nlm.nih.gov, world wide web address lifesciences.perkinelmer.com, Applied Biosystems by Life Technologies™ (Carlsbad, Calif.) at world wide web address appliedbiosystems.com, Celera Human SNP database at world wide web address celera.com, the SNP Database of the Genome Analysis Group (GAN) at world wide web address gan.iarc.fr. In one embodiment, the SNPs chosen for enriching the fetal and maternal cfDNA are selected from the group of 92 individual identification SNPs (IISNPs) described by Pakstis et al. (Pakstis et al. Hum Genet 127: 315-324 [2010]), which have been shown to have a very small variation in frequency across populations ($F_{st}<0.06$), and to be highly informative around the world having an average heterozygosity ≥0.4. SNPs that are encompassed by the method of the invention include linked and unlinked SNPs. Other useful SNPs applicable or useful for the methods described herein are disclosed in U.S. Pat. Application Nos. 20080070792, 20090280492, 20080113358, 20080026390, 20080050739, 20080220422, and 20080138809, which are herein incorporated by reference in their entireties. Each target nucleic acid comprises at least one polymorphic site e.g. a single SNP, that differs from that present on another target nucleic acid to generate a panel of polymorphic sites e.g. SNPs, that contain a sufficient number of polymorphic sites of which at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 25, at least 30, at least 40 or more are informative. For example, a panel of SNPs can be configured to comprise at least one informative SNP. In one embodiment, the SNPs that are targeted for amplification are selected from rs560681 (SEQ ID NOS 1 & 2), rs1109037 (SEQ ID NOS 3 & 4), rs9866013 (SEQ ID NOS 5 & 6), rs13182883 (SEQ ID NOS 7 & 8), rs13218440 (SEQ ID NOS 9 & 10), rs7041158 (SEQ ID NOS 11 & 12), rs740598 (SEQ ID NOS 13 & 14), rs10773760 (SEQ ID NOS 15 & 16), rs4530059 (SEQ ID NOS 17 & 18), rs7205345 (SEQ ID NOS 19 & 20), rs8078417 (SEQ ID NOS 21 & 22), rs576261 (SEQ ID NOS 23 & 24), rs2567608 (SEQ ID NOS 25 & 26), rs430046 (SEQ ID NOS 27 & 28), rs9951171 (SEQ ID NOS 29 & 30), rs338882 (SEQ ID NOS 31 & 32), rs10776839 (SEQ ID NOS 33 & 34), rs9905977 (SEQ ID NOS 35 & 36), rs1277284 (SEQ ID NOS 37 & 38), rs258684 (SEQ ID NOS 39 & 40), rs1347696 (SEQ ID NOS 41 & 42), rs508485 (SEQ ID NOS 43 & 44), rs9788670 (SEQ ID NOS 45 & 46), rs8137254 (SEQ ID NOS 47 & 48), rs3143 (SEQ ID NOS 49 & 50), rs2182957 (SEQ ID NOS 51 & 52), rs3739005 (SEQ ID NOS 53 & 54), and rs530022 (SEQ ID NOS 55 & 56). In one embodiment, the panel of SNPs comprises at least 3, at least 5, at least 10, at least 13, at least 15, at least 20, at least 25, at least 30 or more SNPs. In one embodiment, the panel of SNPs comprises rs560681 (SEQ ID NOS 1 & 2), rs1109037 (SEQ ID NOS 3 & 4), rs9866013 (SEQ ID NOS 5 & 6), rs13182883 (SEQ ID NOS 7 & 8), rs13218440 (SEQ ID NOS 9 & 10), rs7041158 (SEQ ID NOS 11 & 12), rs740598 (SEQ ID NOS 13 & 14), rs10773760 (SEQ ID NOS 15 & 16), rs4530059 (SEQ ID NOS 17 & 18), rs7205345 (SEQ ID NOS 19 & 20), rs8078417 (SEQ ID NOS 21 & 22), rs576261 (SEQ ID NOS 23 & 24), and rs2567608 (SEQ ID NOS 25 & 26). The polymorphic nucleic acids comprising the SNPs can be amplified using exemplary primer pairs provided in Example 3, and disclosed as SEQ ID NOs:57-112.

In other embodiments, each target nucleic acid comprises two or more SNPs i.e. each target nucleic acid comprises tandem SNPs. Preferably, each target nucleic acid comprises two tandem SNPs. The tandem SNPs are analyzed as a single unit as short haplotypes, and are provided herein as sets of two SNPs. To identify suitable tandem SNP sequences, the International HapMap Consortium database can be searched (The International HapMap Project, Nature 426:789-796 [2003]). The database is available on the world wide web at hapmap.org. In one embodiment, tandem SNPs that are targeted for amplification are selected from the following sets of tandem pairs of SNPS rs7277033-rs2110153 (SEQ ID NOS 312 & 313); rs2822654-rs1882882 (SEQ ID NOS 314 & 315); rs368657-rs376635 (SEQ ID NOS 316 & 317); rs2822731-rs2822732 (SEQ ID NOS 318 & 319); rs1475881-rs7275487 (SEQ ID NOS 320 & 321); rs1735976-rs2827016 (SEQ ID NOS 322 & 323); rs447340-rs2824097 (SEQ ID NOS 324 & 325); rs418989-rs13047336 (SEQ ID NOS 326 & 327); rs987980-rs987981 (SEQ ID NOS 328 & 329); rs4143392-rs4143391 (SEQ ID NOS 330 & 331); rs1691324-rs13050434 (SEQ ID NOS 332 & 333); rs11909758-rs9980111 (SEQ ID NOS 334 & 335); rs2826842-rs232414 (SEQ ID NOS 336 & 337); rs1980969-rs1980970 (SEQ ID NOS 338 & 339); rs9978999-rs9979175 (SEQ ID NOS 340 & 341); rs1034346-rs12481852 (SEQ ID NOS 342 & 343); rs7509629-rs2828358 (SEQ ID NOS 344 & 345); rs4817013-rs7277036 (SEQ ID NOS 346 & 347); rs9981121-rs2829696 (SEQ ID NOS 348 & 349); rs455921-rs2898102 (SEQ ID NOS 350 & 351); rs2898102-rs458848 (SEQ ID NOS 352 & 353); rs961301-rs2830208 (SEQ ID NOS 354 & 355); rs2174536-rs458076 (SEQ ID NOS 356 & 357); rs11088023-rs11088024 (SEQ ID NOS 358 & 359); rs1011734-rs1011733 (SEQ ID NOS 360 & 361); rs2831244-rs9789838 (SEQ ID NOS 362 & 363); rs8132769-rs2831440 (SEQ ID NOS 364 & 365); rs8134080-rs2831524 (SEQ ID NOS 366 & 367); rs4817219-rs4817220 (SEQ ID NOS 368 & 369); rs2250911-rs2250997 (SEQ ID NOS 370 & 371); rs2831899-rs2831900 (SEQ ID NOS 372 & 373); rs2831902-rs2831903 (SEQ ID NOS 374 & 375); rs11088086-rs2251447 (SEQ ID NOS 376 & 377); rs2832040-rs11088088 (SEQ ID NOS 378 & 379); rs2832141-rs2246777 (SEQ ID NOS 380 & 381); rs2832959 rs9980934 (SEQ ID NOS 382 & 383); rs2833734-rs2833735 (SEQ ID NOS 384 & 385); rs933121-rs933122 (SEQ ID NOS 386 & 387); rs2834140-rs12626953 (SEQ ID NOS 388 & 389); rs2834485-rs3453 (SEQ ID NOS 390 & 391); rs9974986-rs2834703 (SEQ ID NOS 392 & 393); rs2776266-rs2835001 (SEQ ID NOS 394 & 395); rs1984014-rs1984015 (SEQ ID NOS 396 & 397); rs7281674-rs2835316 (SEQ ID NOS 398 & 399); rs13047304-rs13047322 (SEQ ID NOS 400 & 401); rs2835545-rs4816551 (SEQ ID NOS 402 & 403); rs2835735-rs2835736 (SEQ ID NOS 404 & 405); rs13047608-rs2835826 (SEQ ID NOS 406 & 407); rs2836550-rs2212596 (SEQ ID NOS 408 & 409); rs2836660-rs2836661 (SEQ ID NOS 410 & 411); rs465612-rs8131220 (SEQ ID NOS 412 & 413); rs9980072-rs8130031 (SEQ ID NOS 414 & 415); rs418359-rs2836926 (SEQ ID NOS 416 & 417); rs7278447-rs7278858 (SEQ ID NOS 418 & 419); rs385787-rs367001 (SEQ ID NOS 420 & 421); rs367001-rs386095 (SEQ ID NOS 422 & 423); rs2837296-rs2837297 (SEQ ID NOS 424 & 425); and rs2837381-rs4816672 (SEQ ID NOS 426 & 427). The polymorphic nucleic acids comprising the tandem SNPs can be amplified using primer pairs that amplify polymorphic sequences comprising the tandem SNPs. Examples of primer pairs that can be used to amplify the tandem SNPs disclosed herein are SEQ ID NOs:197-310 as provided in Example 8.

In one embodiment, a portion of the mixture of fetal and maternal nucleic acids in the sample e.g. cfDNA, is used as template for amplifying target nucleic acids that comprise at least one STR. In some embodiments, each target nucleic acid comprises a single i.e. one STR. STR loci are found on almost every chromosome in the genome and may be amplified using a variety of polymerase chain reaction (PCR) primers. Tetranucleotide repeats have been preferred among forensic scientists due to their fidelity in PCR amplification, although some tri- and pentanucleotide repeats are also in use. A comprehensive listing of references, facts and sequence information on STRs, published PCR primers, common multiplex systems, and related population data are compiled in STRBase, which may be accessed via the World Wide Web at ibm4.carb.nist.gov:8800/dnalhome.htm. Sequence information from GenBank® is available on the world wide web at ncbi.nlm.nih.gov/cgi-bin/genbank for commonly used STR loci is also accessible through STRBase. Commercial kits available for the analysis of STR loci generally provide all of the necessary reaction components and controls required for amplification. STR multiplex systems allow the simultaneous amplification of multiple nonoverlapping loci in a single reaction, substantially increasing throughput. With multicolor fluorescent detection, even overlapping loci can be multiplexed. The polymorphic nature of tandem repeated DNA sequences that are widespread throughout the human genome have made them important genetic markers for gene mapping studies, linkage analysis, and human identity testing. Because of the high polymorphism of STRs, most individuals will be heterozygous i.e. most people will possess two alleles (versions) of each—one inherited from each parent—with a different number of repeats. The PCR products comprising the STRs can be separated and detected using manual, semi-automated or automated methods. Semi-automated systems are gel-based and combine electrophoresis, detection and analysis into one unit. On a semiautomated system, gel assembly and sample loading are still manual processes; however, once samples are loaded onto the gel, electrophoresis, detection and analysis proceed automatically. Data collection occurs in "real time" as fluorescently labeled fragments migrate past the detector at a fixed point and can be viewed as they are collected. As the name implies, capillary electrophoresis is carried out in a microcapillary tube rather than between glass plates. Once samples, gel polymer and buffer are loaded onto the instrument, the capillary is filled with gel polymer and the sample is loaded automatically. Therefore, the non-maternally inherited fetal STR sequence will differ in the number of repeats from the maternal sequence. Amplification of these STR sequences can result in one or two major amplification products corresponding to the maternal alleles (and the maternally inherited fetal allele) and one minor product corresponding to the non-maternally inherited fetal allele. This technique was first reported in 2000 (Peril et al., Human Genetics 106:45-49 [2002]) and has subsequently been developed using simultaneous identification of multiple different STR regions using real-time PCR (Liu et al., Acta Obset Gyn Scand 86:535-541 [2007]). Various sized PCR amplicons have been used to discern the respective size distributions of circulating fetal and maternal DNA species, and have shown that the fetal DNA molecules in the plasma of pregnant women are generally shorter than maternal DNA molecules (Chan et al., Clin Chem 50:8892 [2004]). Size fractionation of circulating fetal DNA has confirmed that the average length of circulating fetal DNA fragments is <300 bp, while maternal DNA has been estimated to be between about 0.5 and 1 Kb (Li et al., Clin Chem, 50: 1002-1011 [2004]). The invention provides a method for determining the fraction of fetal nucleic acid in a maternal sample comprising determining the amount of copies of at least one fetal and one maternal allele at a polymorphic miniSTR site, which can be amplified to generate amplicons that are of lengths about the size of the circulating fetal DNA fragments e.g. less than about 250 base pairs. In one embodiment, the fetal fraction can be determined by a method that comprises sequencing at least a portion of amplified polymorphic target nucleic acids each comprising a miniSTR. Fetal and maternal alleles at an informative SIR site are discerned by their different lengths i.e. number of repeats, and the fetal fraction can be calculated as a percent ratio of the amount of fetal maternal alleles at that site. The method can use one or a combination of any number of informative miniSTRs to determine the fraction of fetal nucleic acid. For example, any one or a combination of any number of miniSTRs, for example the miniSTRs disclosed in Table 7 and FIGS. 4 and 5, can be used. In one embodiment, the fraction of fetal nucleic acid in a maternal sample is performed using a method that includes determining the number of copies of the maternal and fetal nucleic acid present in the maternal sample by amplifying at least one autosomal miniSTR chosen from CSFIPO, FGA, THOI, TPDX, vWA, D3S1358, D5S818, D7S820, D8S1I79, D13S317, D16S539, D18S51, D21S11, Penta D, Penta E, D2S1338, D1S1677, D2S441, D4S2364, D10S1248, D14S1434, D22S1045, D22S1045, D20S1082, D20S482, D18S853, D17S1301, D17S974, D14S1434, D12ATA63, D11S4463, D10S1435, D10S1248, D9S2157, D9S1122, D8S1115, D6S1017, D6S474, D5S2500, D5S2500, D4S2408, D4S2364, D3S4529, D3S3053, D2S1776, D2S441, D1S1677, D1S1627, and D1GATA113. In another embodiment, the at least one autosomal miniSTR is the group of miniSTRs CSF1PO, FGA, D13S317, D16S539, D18S51, D2S1338, D21S11, D2S1338 and D7S820. In one embodiment, the method comprises determining the number of copies of at least one fetal and at least one maternal allele at least at one polymorphic miniSTR that is amplified to generate amplicons that are less than about 300 bp, less than about 250 bp, less than about 200 bp, less than about 150 bp, less than about 100 bp, or less than about 50 bp. In another embodiment, the amplicons that are generated by amplifying the miniSTRs are less than about 300 bp. In another embodiment, the amplicons that are generated by amplifying the miniSTRs are less than about 250 bp. In another embodiment, the amplicons that are generated by amplifying the miniSTRs are less than about 200 bp. Amplification of the informative allele includes using miniSTR, primers, which allow for the amplification of reduced-size amplicons to detect STR alleles that are less than about 500 bp, less than about 450 bp, less than about 400 bp, less than about 350 bp, less than about 300 base pairs (bp), less than about 250 bp, less than about 200 bp, less than about 150 bp, less than about 100 bp, or less than about 50 bp. The reduced-size amplicons generated using the miniSTR primers are known as miniSTRs that are identified according to the marker name corresponding to the locus to which they have been mapped. In one embodiment, the miniSTR primers include mini STR primers that have permitted the maximum size reduction in amplicon size for all 13 CODIS STR loci in addition to the D2S1338, Penta D, and pentaE found in commercially available STR kits (Butler et al., J Forensic Sci 48:1054-1064 [2003]), miniSTR loci that are unlinked to the CODIS markers as described by Coble and Butler (Coble and Butler, J Forensic Sci 50:43-53 [2005]), and other minSTRs that have been characterized at NIST. Information regarding the miniSTRs characterized at NIST is accessible via the world wide web at cstl.nist.gov/biotech/strbase/newSTRs.htm. Any one pair or a combination of two or more pairs of miniSTR primers can be used to amplify at least one miniSTR.

In one embodiment, exemplary primer sets that can be used to amplify STRs in maternal cfDNA samples include the primer sets provided in Example 9 and disclosed as SEQ ID NOs:113-196.

Gender identification (sex-typing) in commonly performed in conjunction with STR typing using PCR products generated from the Amelogenin gene that occurs on both the X- and Y-chromosome. Amelogenin is not an STR locus, but it produces X and Y chromosome specific PCR products. A commonly used PCR primer set first published by Sullivan et al. (1993) (Sullivan et al., BioTechniques 15:637-641 [1993]) targets a 6 bp deletion that occurs on the X-chromosome, which enables amplicons generated from the X- and Y-chromosome to be distinguished from one another when electrophoretic separation is performed to separate STR alleles. Most commercial STR kits utilize the Sullivan et al. (1993) primers or minor modifications. Since females are X,X, only a single peak is observed when testing female DNA whereas males, which possess both X and Y chromosomes, exhibit two peaks with a standard Amelogenin test. In one embodiment, the method to determine the fraction of fetal nucleic acid in a maternal sample comprises coamplifying Ameleogenin with at least one miniSTR. In another embodiment, the method does not comprise coamplifying Amelogenin with miniSTR loci.

Amplification of the target nucleic acids in the mixture of fetal and maternal nucleic acid e.g. cfDNA, is accomplished any method that uses PCR or variations of the method including but not limited to digital PCR, real time PCR (RT-PCR), TaqMan PCR System (Applied Biosystems), SNPlex or GenPlex methods, asymmetric PCR, helicase-dependent amplification, hot-start PCR, qPCR, solid phase PCR, and touchdown PCR. Alternatively, replication of target nucleic acid sequences can be obtained by enzyme-independent methods e.g. chemical solid-phase synthesis using the phosphoramidites. Amplification of the target sequences is accomplished using primer pairs each capable of amplifying a target nucleic acid sequence comprising the polymorphic site e.g. SNP, in a multiplex PCR reaction. Multiplex PCR reactions include combining at least 2, at least three, at least 3, at least 5, at least 10, at least 15, at least 20, at least 25, at least 30, at least 40 or more sets of primers in the same reaction to quantify the amplified target nucleic acids comprising at least two, at least three, at least 5, at least 10, at least 15, at least 20, at least 25, at least 30, at least 40 or more polymorphic sites in the same sequencing reaction. Any panel of primer sets can be configured to amplify at least one informative polymorphic sequence.

In step 140 of method 100 (FIG. 1), a portion or all of the amplified polymorphic sequences are used to prepare a sequencing library for sequencing in a parallel fashion as described. In one embodiment, the library is prepared for sequencing-by-synthesis using Illumina's reversible terminator-based sequencing chemistry.

In step 140, sequence information that is needed for determining fetal fraction is obtained using any of the known DNA sequencing methods. In one embodiment, the method described herein employs next generation sequencing technology (NGS) in which clonally amplified DNA templates or single DNA molecules are sequenced in a massively parallel fashion within a flow cell (e.g. as described in Volkerding et al. Clin Chem 55:641-658 [2009]; Metzker M Nature Rev 11:31-46 [2010]). In addition to high-throughput sequence information, NGS provides digital quantitative information, in that each sequence read is a countable "sequence tag" representing an individual clonal DNA template or a single DNA molecule. This quantification allows NGS to expand the digital PCR concept of counting cell-free DNA molecules (Fan et al., Proc Natl Acad Sci USA 105:16266-16271 [2008]; Chiu et al., Proc Natl Acad Sci USA 2008; 105:20458-20463 [2008]). The sequencing technologies of NGS include pyrosequencing, sequencing-by-synthesis with reversible dye terminators, sequencing by oligonucleotide probe ligation and real time sequencing.

Some of the sequencing technologies are available commercially, such as the sequencing-by-hybridization platform from Affymetrix Inc. (Sunnyvale, Calif.) and the sequencing-by-synthesis platforms from 454 Life Sciences (Bradford, Conn.), Illumina/Solexa (Hayward, Calif.) and Helicos Biosciences (Cambridge, Mass.), and the sequencing-by-ligation platform from Applied Biosystems (Foster City, Calif.), as described below. In addition to the single molecule sequencing performed using sequencing-by-synthesis of Helicos Biosciences, other single molecule sequencing technologies are encompassed by the method of the invention and include the SMRT™ technology of Pacific Biosciences, the Ion Torrent™ technology, and nanopore sequencing being developed for example, by Oxford Nanopore Technologies.

While the automated Sanger method is considered as a 'first generation' technology, Sanger sequencing including the automated Sanger sequencing, can also be employed by the method of the invention. Additional sequencing methods that comprise the use of developing nucleic acid imaging technologies e.g. atomic force microscopy (AFM) or transmission electron microspcopy (TEM), are also encompassed by the method of the invention. Exemplary sequencing technologies are described below.

In one embodiment, the DNA sequencing technology that is used in the method of the invention is the Helicos True Single Molecule Sequencing (tSMS) (e.g. as described in Harris T. D. et al., Science 320:106-109 [2008]). In the tSMS technique, a DNA sample is cleaved into strands of approximately 100 to 200 nucleotides, and a polyA sequence is added to the 3' end of each DNA strand. Each strand is labeled by the addition of a fluorescently labeled adenosine nucleotide. The DNA strands are then hybridized to a flow cell, which contains millions of oligo-T capture sites that are immobilized to the flow cell surface. The templates can be at a density of about 100 million templates/cm$^2$. The flow cell is then loaded into an instrument, e.g., HeliScope™ sequencer, and a laser illuminates the surface of the flow cell, revealing the position of each template. A CCD camera can map the position of the templates on the flow cell surface. The template fluorescent label is then cleaved and washed away. The sequencing reaction begins by introducing a DNA polymerase and a fluorescently labeled nucleotide. The oligo-T nucleic acid selves as a primer. The polymerase incorporates the labeled nucleotides to the primer in a template directed manner. The polymerase and unincorporated nucleotides are removed. The templates that have directed incorporation of the fluorescently labeled nucleotide are discerned by imaging the flow cell surface. After imaging, a cleavage step removes the fluorescent label, and the process is repeated with other fluorescently labeled nucleotides until the desired read length is achieved. Sequence information is collected with each nucleotide addition step.

In one embodiment, the DNA sequencing technology that is used in the method of the invention is the 454 sequencing (Roche) (e.g. as described in Margulies, M. et al. Nature 437:376-380 [2005]). 454 sequencing involves two steps. In the first step, DNA is sheared into fragments of approximately 300-800 base pairs, and the fragments are blunt-ended. Oligonucleotide adaptors are then ligated to the ends of the fragments. The adaptors serve as primers for amplification and sequencing of the fragments. The fragments can be attached to DNA capture beads, e.g., streptavidin-coated beads using, e.g., Adaptor B, which contains 5'-biotin tag. The fragments attached to the beads are PCR amplified within droplets of an oil-water emulsion. The result is multiple copies of clonally amplified DNA fragments on each bead. In the second step, the beads are captured in wells (pico-liter sized). Pyrosequencing is performed on each DNA fragment in parallel. Addition of one or more nucleotides generates a light signal that is recorded by a CCD camera in a sequencing instrument. The signal strength is proportional to the number of nucleotides incorporated. Pyrosequencing makes use of pyrophosphate (PPi) which is released upon nucleotide addition. PPi is converted to ATP by ATP sulfulylase in the presence of adenosine 5' phosphosulfate. Luciferase uses ATP to convert luciferin to oxyluciferin, and this reaction generates light that is discerned and analyzed.

In one embodiment, the DNA sequencing technology that is used in the method of the invention is the SOLiD technology (Applied Biosystems). In SOLiD sequencing-by-ligation, genomic DNA is sheared into fragments, and adaptors are attached to the 5' and 3' ends of the fragments to generate a fragment library. Alternatively, internal adaptors can be introduced by ligating adaptors to the 5' and 3' ends of the fragments, circularizing the fragments, digesting the circularized fragment to generate an internal adaptor, and attaching adaptors to the 5' and 3' ends of the resulting fragments to generate a mate-paired library. Next, clonal bead populations are prepared in microreactors containing beads, primers, template, and PCR components. Following PCR, the templates are denatured and beads are enriched to separate the beads with extended templates. Templates on the selected beads are subjected to a 3' modification that permits bonding to a glass slide. The sequence can be determined by sequential hybridization and ligation of partially random oligonucleotides with a central determined base (or pair of bases) that is identified by a specific fluorophore. After a color is recorded, the ligated oligonucleotide is cleaved and removed and the process is then repeated.

In one embodiment, the DNA sequencing technology that is used in the method of the invention is the single molecule, real-time (SMRT™) sequencing technology of Pacific Biosciences. In SMRT sequencing, the continuous incorporation of dye-labeled nucleotides is imaged during DNA synthesis. Single DNA polymerase molecules are attached to the bottom surface of individual zero-mode wavelength identifiers (ZMW identifiers) that obtain sequence information while phospolinked nucleotides are being incorporated into the growing primer strand. A ZMW is a confinement structure which enables observation of incorporation of a single nucleotide by DNA polymerase against the background of fluorescent nucleotides that rapidly diffuse in an out of the ZMW (in microseconds). It takes several milliseconds to incorporate a nucleotide into a growing strand. During this time, the fluorescent label is excited and produces a fluorescent signal, and the fluorescent tag is cleaved off. Identification of the corresponding fluorescence of the dye indicates which base was incorporated. The process is repeated.

In one embodiment, the DNA sequencing technology that is used in the method of the invention is nanopore sequencing (e.g. as described in Soni GV and Meller A. Clin Chem 53: 1996-2001 [2007]). Nanopore sequencing DNA analysis techniques are being industrially developed by a number of companies, including Oxford Nanopore Technologies (Oxford, United Kingdom). Nanopore sequencing is a single-molecule sequencing technology whereby a single molecule of DNA is sequenced directly as it passes through a nanopore. A nanopore is a small hole, of the order of 1 nanometer in diameter. Immersion of a nanopore in a conducting fluid and application of a potential (voltage) across it results in a slight electrical current due to conduction of ions through the nanopore. The amount of current which flows is sensitive to the size and shape of the nanopore. As a DNA molecule passes through a nanopore, each nucleotide on the DNA molecule obstructs the nanopore to a different degree, changing the magnitude of the current through the nanopore in different degrees. Thus, this change in the current as the DNA molecule passes through the nanopore represents a reading of the DNA sequence.

In one embodiment, the DNA sequencing technology that is used in the method of the invention is the chemical-sensitive field effect transistor (chemFET) array (e.g., as described in U.S. Patent Application Publication No. 20090026082). In one example of the technique, DNA molecules can be placed into reaction chambers, and the template molecules can be hybridized to a sequencing primer bound to a polymerase. Incorporation of one or more triphosphates into a new nucleic acid strand at the 3' end of the sequencing primer can be discerned by a change in current by a chemFET. An array can have multiple chemFET sensors. In another example, single nucleic acids can be attached to beads, and the nucleic acids can be amplified on the bead, and the individual beads can be transferred to individual reaction chambers on a chemFET array, with each chamber having a chemFET sensor, and the nucleic acids can be sequenced.

In one embodiment, the DNA sequencing technology that is used in the method of the invention is the Halcyon Molecular's method that uses transmission electron microscopy (TEM). The method, termed Individual Molecule Placement Rapid Nano Transfer (IMPRNT), comprises utilizing single atom resolution transmission electron microscope imaging of high-molecular weight (150 kb or greater) DNA selectively labeled with heavy atom markers and arranging these molecules on ultra-thin films in ultra-dense (3 nm strand-to-strand) parallel arrays with consistent base-to-base spacing. The electron microscope is used to image the molecules on the films to determine the position of the heavy atom markers and to extract base sequence information from the DNA. The method is further described in PCT patent publication WO 2009/046445. The method allows for sequencing complete human genomes in less than ten minutes.

In one embodiment, the DNA sequencing technology is the Ion Torrent single molecule sequencing, which pairs semiconductor technology with a simple sequencing chemistry to directly translate chemically encoded information (A, C, G, T) into digital information (0, 1) on a semiconductor chip. In nature, when a nucleotide is incorporated into a strand of DNA by a polymerase, a hydrogen ion is released as a byproduct. Ion Torrent uses a high-density array of micro-machined wells to perform this biochemical process in a massively parallel way. Each well holds a different DNA molecule. Beneath the wells is an ion-sensitive layer and beneath that an ion sensor. When a nucleotide, for example a C, is added to a DNA template and is then incorporated into a strand of DNA, a hydrogen ion will be released. The charge from that ion will change the pH of the solution, which can be identified by Ion Torrent's ion sensor. The sequencer essentially the world's smallest solid-state pH meter calls the base, going directly from chemical information to digital information. The Ion personal Genome Machine (PGM™) sequencer then sequentially floods the chip with one nucleotide after another. If the next nucleotide that floods the chip is not a match. No voltage change will be recorded and no base will be called. If there are two identical bases on the DNA strand, the voltage will be double, and the chip will record two identical bases called. Direct identification allows recordation of nucleotide incorporation in seconds.

Other sequencing methods include digital PCR and sequencing by hybridization Digital polymerase chain reaction (digital PCR or dPCR) can be used to directly identify and quantify nucleic acids in a sample. Digital PCR can be performed in an emulsion. Individual nucleic acids are separated, e.g., in a microfluidic chamber device, and each nucleic can is individually amplified by PCR. Nucleic acids can be separated such there is an average of approximately 0.5 nucleic acids/well, or not more than one nucleic acid/well. Different probes can be used to distinguish fetal alleles and maternal alleles. Alleles can be enumerated to determine copy number. In sequencing by hybridization, the hybridization comprises contacting the plurality of polynucleotide sequences with a plurality of polynucleotide probes, wherein each of the plurality of polynucleotide probes can be optionally tethered to a substrate. The substrate might be flat surface comprising an array of known nucleotide sequences. The pattern of hybridization to the array can be used to determine the polynucleotide sequences present in the sample. In other embodiments, each probe is tethered to a bead, e.g., a magnetic bead or the like. Hybridization to the beads can be identified and used to identify the plurality of polynucleotide sequences within the sample.

In one embodiment, the method employs massively parallel sequencing of millions of DNA fragments using Illumina's sequencing-by-synthesis and reversible terminator-based sequencing chemistry (e.g. as described in Bentley et al., Nature 6:53-59 [2009]). Template DNA can be genomic DNA e.g. cfDNA. In some embodiments, genomic DNA from isolated cells is used as the template, and it is fragmented into lengths of several hundred base pairs. In other embodiments, cfDNA is used as the template, and fragmentation is not required as cfDNA exists as short fragments. For example fetal cfDNA circulates in the bloodstream as fragments of <300 bp, and maternal cfDNA has been estimated to circulate as fragments of between about 0.5 and 1 Kb (Li et al., Clin Chem, 50: 1002-1011 [2004]). Illumina's sequencing technology relies on the attachment of fragmented genomic DNA to a planar, optically transparent surface on which oligonucleotide anchors are bound. Template DNA is end-repaired to generate 5'-phospholylated blunt ends, and the polymerase activity of Klenow fragment is used to add a single A base to the 3 end of the blunt phospholylated DNA fragments. This addition prepares the DNA fragments for ligation to oligonucleotide adapters, which have an overhang of a single T base at their 3 end to increase ligation efficiency. The adapter oligonucleotides are complementary to the flow-cell anchors. Under limiting-dilution conditions, adapter-modified, single-stranded template DNA is added to the flow cell and immobilized by hybridization to the anchors. Attached DNA fragments are extended and bridge amplified to create an ultra-high density sequencing flow cell with hundreds of millions of clusters, each containing ~1,000 copies of the same template. The cluster amplified DNA molecules are sequenced using a robust four-color DNA sequencing-by-synthesis technology that employs reversible terminators with removable fluorescent dyes. High-sensitivity fluorescence identification is achieved using laser excitation and total internal reflection optics. Short sequence reads of about 20-40 bp e.g. 36 bp, are aligned against a repeat-masked reference genome and genetic differences are called using specially developed data analysis pipeline software. After completion of the first read, the templates can be regenerated in situ to enable a second read from the opposite end of the fragments. Thus, either single-end or paired end sequencing of the DNA fragments is used according to the method. Partial sequencing of DNA fragments present in the sample is performed, and sequence tags comprising reads of predetermined length e.g. 36 bp, that are mapped to a known reference genome are counted.

The length of the sequence read is associated with the particular sequencing technology. NGS methods provide sequence reads that vary in size from tens to hundreds of base pairs. In some embodiments of the method described herein, the sequence reads are about 20 bp, about 25 bp, about 30 bp, about 35 bp, about 40 bp, about 45 bp, about 50 bp, about 55 bp, about 60 bp, about 65 bp, about 70 bp, about 75 bp, about 80 bp, about 85 bp, about 90 bp, about 95 bp, about 100 bp, about 110 bp, about 120 bp, about 130, about 140 bp, about 150 bp, about 200 bp, about 250 bp, about 300 bp, about 350 bp, about 400 bp, about 450 bp, about 500 bp, about 550 bp or about 600 bp. It is expected that technological advances will enable single-end reads of greater than 500 bp enabling for reads of greater than about 1000 bp when paired end reads are generated. In one embodiment, the sequence reads are 36 bp. Other sequencing methods that can be employed by the method of the invention include the single molecule sequencing methods that can sequence nucleic acids molecules >5000 bp. The massive quantity of sequence output is transferred by an analysis pipeline that transforms primary imaging output from the sequencer into strings of bases. A package of integrated algorithms performs the core primary data transformation steps: image analysis, intensity scoring, base calling, and alignment.

In one embodiment, partial sequencing of amplified target polymorphic nucleic acids is performed, and sequence tags comprising reads of predetermined length e.g. 36 bp, that map to a known reference genome are counted. Only sequence reads that uniquely align to a reference genome are counted as sequence tags. In one embodiment, the reference genome is an artificial target sequences genome that comprises the sequences of the polymorphic target nucleic acids e.g. SNPs. In one embodiment, the reference genome is an artificial SNP reference genome. In another r embodiment, the reference genome is an artificial STR reference genome. In yet another embodiment, the reference genome is an artificial tandem-STR reference genome. Artificial reference genomes can be compiled using the sequences of the target polymorphic nucleic acids. Artificial reference genomes can comprise polymorphic target sequence each comprising one or more different types of polymorphic sequences. For example, an artificial reference genome can comprise polymorphic sequences comprising SNP alleles and/or STRs. In one embodiment, the reference genome is the human reference genome NCB136/hg18 sequence, which is available on the world wide web at genome.ucsc.edu/cgi-bin/hgGateway?org=Human&db=hg18&hgsid=166260105).

Other sources of public sequence information include GenBank, dbEST, dbSTS, EMBL (the European Molecular Biology Laboratory), and the DDBJ (the DNA Databank of Japan). In another embodiment, the reference genome comprises the human reference genome NCB136/hg18 sequence and an artificial target sequences genome, which includes the target polymorphic sequences e.g. a SNP genome. Mapping of the sequence tags is achieved by comparing the sequence of the mapped tag with the sequence of the reference genome to determine the chromosomal origin of the sequenced nucleic acid (e.g. cfDNA) molecule, and specific genetic sequence information is not needed. A number of computer algorithms are available for aligning sequences, including without limitation BLAST (Altschul et al., 1990), BLITZ (MPsrch) (Sturrock & Collins, 1993), FASTA (Person & Lipman, 1988), BOWTIE (Langmead et al., Genome Biology 10:R25.1-R25.10 [2009]), or ELAND (Illumina, Inc., San Diego, Calif., USA). In one embodiment, one end of the clonally expanded copies of the plasma cfDNA molecules is sequenced and processed by bioinformatic alignment analysis for the Illumina Genome Analyzer, which uses the Efficient Large-Scale Alignment of Nucleotide Databases (ELAND) software. In embodiments of the method that comprise determining the presence or absence of an aneuploidy and fetal fraction using NGS sequencing methods, analysis of sequencing information for the determination of aneuploidy may allow for a small degree of mismatch (0-2 mismatches per sequence tag) to account for minor polymorphisms that may exist between the reference genome and the genomes in the mixed sample. Analysis of sequencing information for the determination of fetal fraction may allow for a small degree of mismatch depending on the polymorphic sequence. For example, a small degree of mismatch may be allowed if the polymorphic sequence is an STR. In cases when the polymorphic sequence is a SNP, all sequence that match exactly to either of the two alleles at the SNP site are counted first and filtered from the remaining reads, for which a small degree of mismatch may be allowed. Quantification of the number of sequence reads aligning to each chromosome for determining chromosomal aneuploidies can be determined as described herein, or using alternative analyses that employ normalizing the median number of sequence tags for a chromosome of interest to the median number of tags for each of the other autosomes (Fan et al., Proc Natl Acad Sci 105:16266-16271 [2008]), or that compare the number of unique reads aligning to each chromosome to the total number of reads aligning to all chromosomes to derive a percent genomic representation for each chromosome. A "z score" is generated to represent the difference between the percent genomic representation of the chromosome of interest and the mean percent representation for the same chromosome between a euploid control group, divided by the standard deviation (Chiu et al., Clin Chem 56:459-463 [2010]). In another embodiment, the sequencing information can be determined as described in U.S. Provisional patent application 61/296,464 titled "Normalizing Biological Assays,", filed Jan. 19, 2010, which is herein incorporated by reference in its entirety.

Analysis of sequencing information for the determination of fetal fraction may allow for a small degree of mismatch depending on the polymorphic sequence. For example, a small degree of mismatch may be allowed if the polymorphic sequence is an STR. In cases when the polymorphic sequence is a SNP, all sequences that match exactly to either of the two alleles at the SNP site are counted first and filtered from the remaining reads, for which a small degree of mismatch may be allowed. The present method for determining fetal fraction by sequencing of nucleic acids can be used in combination with other methods.

In step 160, fetal fraction is determined based on the total number of tags that map to the first allele and the total number of tags that map to second allele at an informative polymorphic site e.g. a SNP, contained in a reference genome. For example, the reference genome is an artificial target sequence genome that encompasses the polymorphic sequences that comprise SNPs rs560681 (SEQ ID NOS 1 & 2), rs1109037 (SEQ ID NOS 3 & 4), rs9866013 (SEQ ID NOS 5 & 6), rs13182883 (SEQ ID NOS 7 & 8), rs13218440 (SEQ ID NOS 9 & 10), rs7041158 (SEQ ID NOS 11 & 12), rs740598 (SEQ ID NOS 13 & 14), rs10773760 (SEQ ID NOS 15 & 16), rs4530059 (SEQ ID NOS 17 & 18), rs7205345 (SEQ ID NOS 19 & 20), rs8078417 (SEQ ID NOS 21 & 22), rs576261 (SEQ ID NOS 23 & 24), rs2567608 (SEQ ID NOS 25 & 26), rs430046 (SEQ ID NOS 27 & 28), rs9951171 (SEQ ID NOS 29 & 30), rs338882 (SEQ ID NOS 31 & 32), rs10776839 (SEQ ID NOS 33 & 34), rs9905977 (SEQ ID NOS 35 & 36), rs1277284 (SEQ ID NOS 37 & 38), rs258684 (SEQ ID NOS 39 & 40), rs1347696 (SEQ ID NOS 41 & 42), rs508485 (SEQ ID NOS 43 & 44), rs9788670 (SEQ ID NOS 45 & 46), rs8137254 (SEQ ID NOS 47 & 48), rs3143 (SEQ ID NOS 49 & 50), rs2182957 (SEQ ID NOS 51 & 52), rs3739005 (SEQ ID NOS 53 & 54), and rs530022 (SEQ ID NOS 55 & 56). In one embodiment, the artificial reference genome includes the polymorphic target sequences of SEQ ID NOs:1-56 (see Example-3).

In another embodiment, the artificial genome is an artificial target sequence genome that encompasses polymorphic sequences that comprise tandem SNPs rs7277033-rs2110153 (SEQ ID NOS 312 & 313); rs2822654-rs1882882 (SEQ ID NOS 314 & 315); rs368657-rs376635 (SEQ ID NOS 316 & 317); rs2822731-rs2822732 (SEQ ID NOS 318 & 319); rs1475881-rs7275487 (SEQ ID NOS 320 & 321); rs1735976-rs2827016 (SEQ ID NOS 322 & 323); rs447340-rs2824097 (SEQ ID NOS 324 & 325); rs418989-rs13047336 (SEQ ID NOS 326 & 327); rs987980-rs987981 (SEQ ID NOS 328 & 329); rs4143392-rs4143391 (SEQ ID NOS 330 & 331); rs1691324-rs13050434 (SEQ ID NOS 332 & 333); rs11909758-rs9980111 (SEQ ID NOS 334 & 335); rs2826842-rs232414 (SEQ ID NOS 336 & 337); rs1980969-rs1980970 (SEQ ID NOS 338 & 339); rs9978999-rs9979175 (SEQ ID NOS 340 & 341); rs1034346-rs12481852 (SEQ ID NOS 342 & 343); rs7509629-rs2828358 (SEQ ID NOS 344 & 345); rs4817013-rs7277036 (SEQ ID NOS 346 & 347); rs9981121-rs2829696 (SEQ ID NOS 348 & 349); rs455921-rs2898102 (SEQ ID NOS 350 & 351); rs2898102-rs458848 (SEQ ID NOS 352 & 353); rs961301-rs2830208 (SEQ ID NOS 354 & 355); rs2174536-rs458076 (SEQ ID NOS 356 & 357); rs11088023-rs11088024 (SEQ ID NOS 358 & 359); rs1011734-rs1011733 (SEQ ID NOS 360 & 361); rs2831244-rs9789838 (SEQ ID NOS 362 & 363); rs8132769-rs2831440 (SEQ ID NOS 364 & 365); rs8134080-rs2831524 (SEQ ID NOS 366 & 367); rs4817219-rs4817220 (SEQ ID NOS 368 & 369); rs2250911-rs2250997 (SEQ ID NOS 370 & 371); rs2831899-rs2831900 (SEQ ID NOS 372 & 373); rs2831902-rs2831903 (SEQ ID NOS 374 & 375); rs11088086-rs2251447 (SEQ ID NOS 376 & 377); rs2832040-rs11088088 (SEQ ID NOS 378 & 379); rs2832141-rs2246777 (SEQ ID NOS 380 & 381); rs2832959-rs9980934 (SEQ ID NOS 382 & 383); rs2833734-rs2833735 (SEQ ID NOS 384 & 385); rs933121-rs933122 (SEQ ID NOS 386 & 387); rs2834140-rs12626953 (SEQ ID NOS 388 & 389); rs2834485-rs3453 (SEQ ID NOS 390 & 391); rs9974986-rs2834703 (SEQ ID NOS 392 & 393); rs2776266-rs2835001 (SEQ ID NOS 394 & 395); rs1984014-rs1984015 (SEQ ID NOS 396 & 397); rs7281674-rs2835316 (SEQ ID NOS 398 & 399); rs13047304-rs13047322 (SEQ ID NOS 400 & 401); rs2835545-rs4816551 (SEQ ID NOS 402 & 403); rs2835735-rs2835736 (SEQ ID NOS 404 & 405); rs13047608-rs2835826 (SEQ ID NOS 406 & 407); rs2836550-rs2212596 (SEQ ID NOS 408 & 409); rs2836660-rs2836661 (SEQ ID NOS 410 & 411); rs465612-rs8131220 (SEQ ID NOS 412 & 413); rs9980072-rs8130031 (SEQ ID NOS 414 & 415); rs418359-rs2836926 (SEQ ID NOS 416 & 417); rs7278447-rs7278858 (SEQ ID NOS 418 & 419); rs385787-rs367001 (SEQ ID NOS 420 & 421); rs367001-rs386095 (SEQ ID NOS 422 & 423); rs2837296-rs2837297 (SEQ ID NOS 424 & 425); and rs2837381-rs4816672 (SEQ ID NOS 426 & 427).

In another embodiment, the artificial target genome encompasses polymorphic sequences that comprise STRs selected from CSF1PO, FGA, TH01, TPOX, vWA, D3S1358, D5S818, D7S820, D8S1179, D13S317, D16S539, D18S51, D21S11, Penta D, Penta E, D2S1338, D1S1677, D2S441, D4S2364, D10S1248, D14S1434, D22S1045, D22S1045, D20S1082, D20S482, D18S853, D17S1301, D17S974, D14S1434, D12ATA63, D11S4463, D10S1435, D10S1248, D9S2157, D9S1122, D8S1115, D6S1017, D6S474, D5S2500, D5S2500, D4S2408, D4S2364, D3S4529, D3S3053, D2S1776, D2S441, D1S1677, D1S1627, and D1GATA113. The composition of the artificial target sequences genome will vary depending on the polymorphic sequences that are used for determining the fetal fraction. Accordingly, an artificial target sequences genome is not limited to the SNP, tandem SNP or STR sequences exemplified herein.

Figure 2:
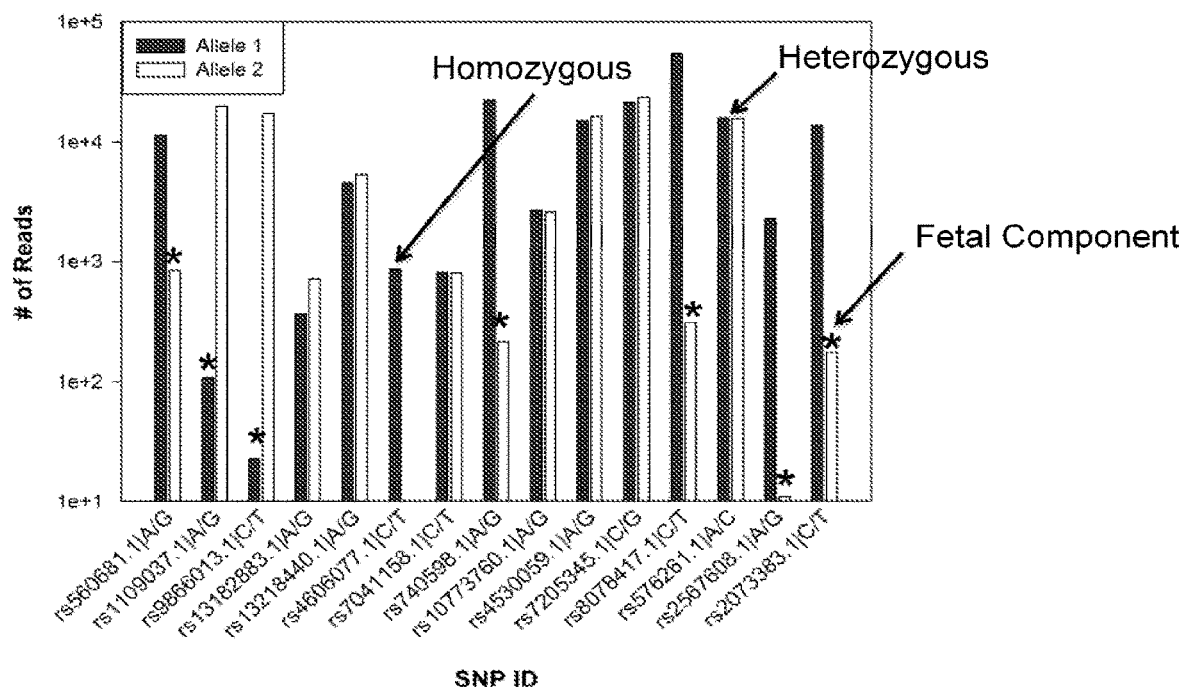
FIG. 2 is a bar diagram showing the identification of fetal and maternal polymorphic sequences (SNPs) used to determine fetal fraction in a test sample. The total number of sequence reads (Y-axis) mapped to the SNP sequences identified by rs numbers (X-axis), and the relative level of fetal nucleic acids (*) are shown.

The informative polymorphic site e.g. SNP, is identified by the difference in the allelic sequences and the amount of each of the possible alleles. Fetal cfDNA is present at a concentration that is <10% of the maternal cfDNA. Thus, the presence of a minor contribution of an allele to the mixture of fetal and maternal nucleic acids relative to the major contribution of the maternal allele can be assigned to the fetus. Alleles that are derived from the maternal genome are herein referred to as major alleles, and alleles that are derived from the fetal genome are herein referred to as minor alleles. Alleles that are represented by similar levels of mapped sequence tags represent maternal alleles. The results of an exemplary multiplex amplification of target nucleic acids comprising SNPs and derived from a maternal plasma sample is shown in FIG. 2. Informative SNPs are discerned from the single nucleotide change at a polymorphic site, and fetal alleles are discerned by their relative minor contribution to the mixture of fetal and maternal nucleic acids in the sample when compared to the major contribution to the mixture by the maternal nucleic acids. Accordingly, the relative abundance of fetal cfDNA in the maternal sample is determined as a parameter of the total number of unique sequence tags mapped to the target nucleic acid sequence on a reference genome for each of the two alleles of the predetermined polymorphic site. In one embodiment, the fraction of fetal nucleic acids in the mixture of fetal and maternal nucleic acids is calculated for each of the informative allele (allele$_x$) as follows:

$$\% \text{ fetal fraction allele}_x = ((\Sigma\text{Fetal sequence tags for allele}_x)/(\Sigma\text{Maternal sequence tags for allele}_x)) \times 100$$

and fetal fraction for the sample is calculated as the average of the fetal fraction of all of the informative alleles. Optionally, the fraction of fetal nucleic acids in the mixture of fetal and maternal nucleic acids is calculated for each of the informative allele (allele$_x$) as follows:

$$\% \text{ fetal fraction allele}_x = ((2\lambda\Sigma\text{Fetal sequence tags for allele}_x)/(\Sigma\text{Maternal sequence tags for allele}_x)) \times 100,$$

to compensate for the presence of 2 fetal alleles, one being masked by the maternal background.

The percent fetal fraction is calculated for at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 25, at least 30, at least 40 or more informative alleles. In one embodiment, the fetal fraction is the average fetal fraction determined for at least 3 informative alleles.

Figure 3:
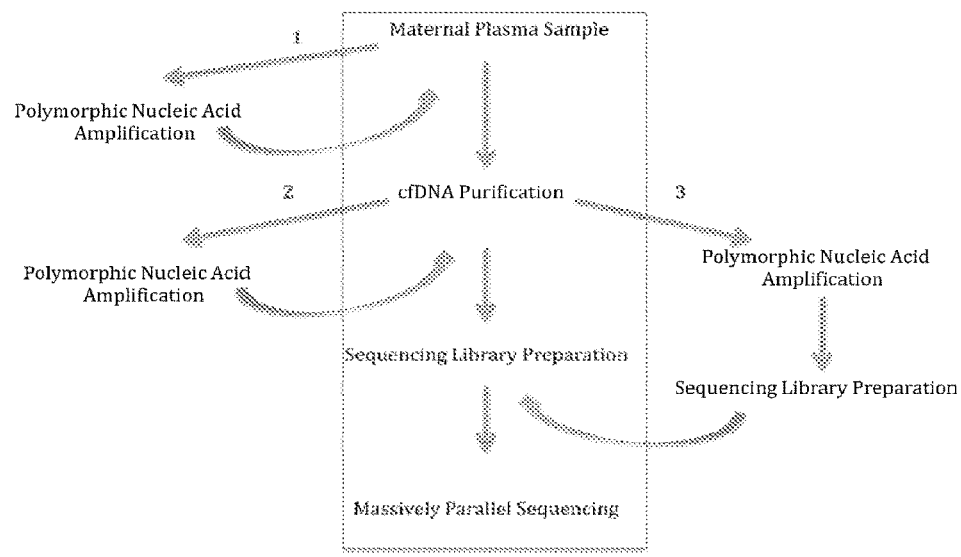
FIG. 3 is a flowchart outlining alternative embodiments of the method for determining fetal fraction by massively parallel sequencing shown in FIG. 1.

FIG. 3, shows a flowchart of alternate methods whereby fetal fraction can be determined from amplified target nucleic acids that have been combined with unamplified fetal and maternal cfDNA sample to allow for the simultaneous determination of fetal fraction and the presence or absence of fetal aneuploidy by enriching the maternal sample comprising fetal and maternal nucleic acids for polymorphic target nucleic acids. In one embodiment, the sample that is enriched is the plasma fraction of a blood sample (a). For example, a portion of an original maternal plasma sample is used for amplifying target nucleic acid sequences. Subsequently, some or all of the amplified product is combined with the remaining unamplified original plasma sample thereby enriching it (see Example 7). In another embodiment, the sample that is enriched is the sample of purified cfDNA that is extracted from plasma (b). For example, enrichment comprises amplifying the target nucleic acids that are contained in a portion of an original sample of purified mixture of fetal and maternal nucleic acids e.g. cfDNA that has been purified from a maternal plasma sample, and subsequently combining some or all of the amplified product with the remaining unamplified original purified sample (see Example 6). In yet another embodiment, the sample that is enriched is a sequencing library sample prepared from a purified mixture of fetal and maternal nucleic acids (c). For example, enrichment comprises amplifying the target nucleic acids that are contained in a portion of an original sample of purified mixture of fetal and maternal nucleic acids e.g. cfDNA that has been purified from a maternal plasma sample, preparing a first sequencing library of unamplified nucleic acid sequences, preparing a second sequencing library of amplified polymorphic target nucleic acids, and subsequently combining some or all of the second sequencing library with some or all of the first sequencing library (see Example 5). The amount of amplified product that is used to enrich the original sample is selected to obtain sufficient sequencing information for determining both the presence or absence of aneuploidy and the fetal fraction from the same sequencing run. At least about 3%, at least about 5%, at least about 7%, at least about 10%, at least about 15%, at least about 20%, at least about 25%, at least about 30% or more of the total number of sequence tags obtained from sequencing are mapped to determine the fetal fraction. Sequencing of the library generated following any one of the methods depicted in FIG. 3, provides sequence tags derived from the amplified target nucleic acids and tags derived from the original unamplified maternal sample. Fetal fraction is calculated from the number of tags mapped to an artificial reference genome, and the presence or absence of aneuploidy is determined from the number of tags that map to the subject genome e.g. human genome.

An alternative method for determining fetal fraction from amplified polymorphic target nucleic acids at step 130 of FIG. 1, uses size separation of amplified polymorphic target nucleic acids comprising STRs (step 150 of FIG. 1). As described above, the polymorphic character of a STR locus is due to variation in the number of tandemly repeated units between alleles. Because of the high polymorphism of the STRs most individuals will be heterozygous for STRs. Amplification of an STR will result in one or two PCR products in most samples. In samples obtained from pregnant women e.g. plasma samples, amplification of an STR will result in one or two major PCR products, which correspond to the one or two maternal alleles including one fetal maternally-inherited allele, and a third paternally-inherited fetal allele that is detected at an informative STR.

The STRs that are targeted for amplification are miniSTRs as described herein that are less than about 300 base pairs and that are amplified in a multiplex PCR reaction, which allows the simultaneous amplification of multiple loci in a single reaction. The primers are labeled with different fluorescent dyes each emitting fluorescence at a different wavelength e.g. 6FAM™, VIC™, NED™, and PET™, and the number of repeat units for each fluorescently tagged STR in the resulting PCR products is detected following their separation and accurate sizing that is achieved by slab or capillary electrophoresis. In one embodiment, capillary electrophoresis is used, and it can be performed in microfabricated channels or capillary arrays. Alternatively, methods utilizing mass spectrometry and microarray technology are used. Multiplex STR analysis can be performed to determine fetal fraction using commercially-available kits e.g. AmpFISTR® Identifiler® PCR Amplification Kit (FIG. 4) and AmpFISTR® MiniFiler® PCR Amplification Kit (FIG. 5) (Applied Biosystems, Foster City, Calif.). The AmpFISTR® MiniFiler® PCR Amplification Kit was designed to amplify as miniSTRs eight of the largest sized loci in the AmpFISTR® Identifiler® PCR Amplification Kit. Together with the gender-identification locus Amelogenin, the nine-locus multiplex enables simultaneous amplification of loci of cfDNA samples (see Example 10).

In one embodiment, multiplex STR analysis for determining fetal fraction is performed by amplifying polymorphic target nucleic acids present in a maternal plasma sample that each comprise a miniSTR selected from CSF1PO, FGA, TH01, vWA, D3S1358, D5S818, D7S820, D8S1179, D13S317, D16S539, D18S51, D2S1338, Penta D, Penta E, D22S1045, D20S1082, D20S482, D18S853, D17S1301, D17S974, D14S1434, D12ATA63, D11S4463, D10S1435, D10S1248, D9S2157, D9S1122, D8S1115, D6S1017, D6S474, D5S2500, D4S2408, D4S2364, D3S4529, D3S3053, D2S1776, D2S441, D1S1677, D1S1627, and D1GATA113. In another embodiment, multiplex STR analysis for determining fetal fraction is performed by amplifying polymorphic target nucleic acids present in a maternal plasma sample for the panel of miniSTRs: CSF1PO, D13S317, D16S539, D18S51, D21S11, D2S1338, D7S820 and FGA. The miniSTRs can be located on the same or on different chromosomes. The method is a fetal gender-independent method. Therefore, in some embodiments, the miniSTRs are located on chromosomes other than the Y chromosome. In other embodiments, the miniSTRs are located on chromosomes other than chromosomes 13, 18, 21 or X i.e. chromosomes that might be involved in an aneuploidy.

Samples of maternal plasma often contain less than 100 pg of cfDNA. The low copy number DNA samples can fall below the sensitivity limitations of STR analysis methods. The intractable samples can be made amenable by increasing the number of starting cfDNA available for subsequent STR analysis by a whole genome amplification strategy. In one embodiment, the mixture of fetal and maternal nucleic acids can be preamplified before alleles are detected or quantified. For example, template cell-free DNA can be amplified by PCR. The nucleic acid can be amplified for about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 cycles. Nucleic acid can be amplified for about 1-10 cycles, about 1-20 cycles, about 1-30 cycles, about 1-40 cycles, about 5-15 cycles, about 5-20 cycles, about 5-30 cycles, about 5-40 cycles, about 10-15 cycles, about 10-20 cycles, about 10-30 cycles, about 10-40 cycles, about 20-30 cycles, about 20-40 cycles, or about 30-40 cycles. The amount of template nucleic acid that can be amplified can be about 10-1000 pg, 25-1000 pg, 50-1000 pg, 100-1000, pg, 200-1000 pg, 300-1000 pg, 400-1000 pg, 500-1000 pg, 600-1000, pg, 700-1000 pg, or 800-1000 pg. Following preamplification, the nucleic acids can be diluted before alleles are detected or quantified. Preamplification can be used to increase the detection sensitivity of alleles in a sample, for example, a maternal sample (Example 11). In another embodiment, genotyping a polymorphism need not require a pre-amplification step. Any PCR-based amplification method can be used to pre-amplify the cfDNA. Amplification methods include but are not limited to whole genome amplification strategies including methods such as primer extension preamplification, degenerate oligonucleotide-primed PCR (DOP-PCR), low fragments from low quantities of DOP-PCR, improved primer extension preamplification PCR (IPEP PCR), and modified improved primer extension preamplification (mI-PEP). Thus, in one embodiment, the method that is used for determining the fetal fraction in a maternal sample e.g. plasma sample, comprises preamplifying the mixture of fetal and maternal nucleic acids present in the plasma cfDNA sample using a whole genome amplification method, amplifying a plurality of polymorphic nucleic acids in said mixture of fetal and maternal nucleic acids, wherein each of said at least one polymorphic nucleic acid comprises an STR; determining the amount of fetal and maternal STR alleles at least one polymorphic nucleic acid; and calculating the fetal fraction from the amount of fetal and maternal STR alleles. Following preamplification, multiplex STR analysis for determining fetal fraction is performed by amplifying polymorphic target nucleic acids present in a maternal plasma sample that each comprise a miniSTR selected from CSF1PO, FGA, TH01, vWA, D3S1358, D5S818, D7S820, D8S1179, D13S317, D16S539, D18S51, D2S1338, Penta D, Penta E, D22S1045, D20S1082, D20S482, D18S853, D17S1301, D17S974, D14S1434, D12ATA63, D11S4463, D10S1435, D10S1248, D9S2157, D9S1122, D8S1115, D6S1017, D6S474, D5S2500, D4S2408, D4S2364, D3S4529, D3S3053, D2S1776, D2S441, D1S1677, D1S1627, and D1GATA113. Alternatively, multiplex STR analysis for determining fetal fraction is performed by amplifying polymorphic target nucleic acids for the panel of miniSTRs: CSF1PO, D13S317, D16S539, D18S51, D2S11, D2S1338, D7S820 and FGA.

Applications

Methods described herein are applicable to diagnosis or prognosis of various disease conditions including, but not limited to, cancer, genetic disorders and infection. The fetal fraction of nucleic acid in a maternal sample can be used for determining a chromosomal abnormality. Examples of chromosomal abnormalities include, for example, aneuploidy, monosomy, trisomy, duplication, inversion, deletion, polyploidy, deletion of a part of a chromosome, addition, addition of a part of chromosome, insertion, a fragment of a chromosome, a region of a chromosome, chromosomal rearrangement, and translocation. For example, aneuploidy can refer to the occurrence of one or more extra or missing chromosomes in a sample.

Examples of fetal conditions that can be determined using the methods of the provided invention include, for example, Angleman syndrome (15q11.2-q13), cri-du-chat syndrome (5p-), DiGeorge syndrome and Velo-cardiofacial syndrome (22q11.2), Miller-Dieker syndrome (17 p13.3), Prader-Willi syndrome (15q11.2-q13), retinoblastoma (13q14), Smith-Magenis syndrome (17 p11.2), trisomy 13, trisomy 16, trisomy 18, trisomy 21 (Down's syndrome), triploidy, Williams syndrome (7q 11.23), and Wolf-Hirschhorn syndrome (4p-). Examples of sex chromosome abnormalities that can be detected by methods described herein include, but are not limited to, Kallman syndrome (Xp22.3), steroid sulfate deficiency (STS) (Xp22.3), X-linked ichthyosis (Xp22.3), Klinefelter syndrome (XXY), fragile X syndrome, Turner syndrome metafemales or trisomy X, and monosomy X.

In one embodiment, fetal fraction information can be used to set thresholds and estimate minimum sample size in aneuploidy detection. Such use is described in Example 7 below. Fetal fraction information can be used in conjunction with sequencing information. For example, nucleic acids from a cell-free sample, for example a maternal plasma or serum sample, can be used to enumerate sequences in a sample. Sequences can be enumerated using any of the sequencing techniques described above. Knowledge of fetal fraction can be used to set "cutoff" thresholds to call "aneuploidy," "normal," or "marginal/no call" (uncertain) states. Then, calculations can be performed to estimate the minimum number of sequences required to achieve adequate sensitivity (i.e. probability of correctly identifying an aneuploidy state).

The determination of fetal fraction according to the method of the invention can be practiced in combination with any method used to determine the presence of absence of fetal aneuploidy in a maternal plasma sample. In addition to the method described herein for the determination of aneuploidy, the determination of fetal fraction by massively parallel sequencing can be used in conjunction with other methods for determining fetal aneuploidy, for example, according to the methods described in U.S. U.S. Patent Application Publication Nos. US 2007/0202525A1; US2010/0112575A1, US 2009/0087847A1; US2009/0029377A1; US 2008/0220422A1; US2008/0138809A1, US2008/0153090A1, and U.S. Pat. No. 7,645,576. The methods can also be combined with assays for determining other prenatal conditions associated with the mother and/or the fetus. For example, the method can be used in conjunction with prenatal analyses, for example, as described in U.S. Patent Application Publication Nos. US2010/0112590A1, US2009/0162842A1, US2007/0207466A1, and US2001/0051341A1, all of which are incorporated by reference in their entirety.

The methods described can be applied to determine the fraction of any one population of nucleic acids in a mixture of nucleic acids contributed by different genomes. In addition to determining the fraction contributed to a sample by two individuals e.g. the different genomes are contributed by the fetus and the mother carrying the fetus, the methods can be used to determine the fraction of a genome in a mixture derived from two different cells of from one individual e.g. the genomes are contributed to the sample by aneuploid cancerous cells and normal euploid cells from the same subject.

Compositions and Kits

The present invention is also directed to compositions and kits or reagent systems useful for practicing the methods described herein.

The compositions of the invention can be included in kits for massively parallel sequencing mixtures of fetal and maternal nucleic acid molecules e.g. cfDNA, present in a maternal sample e.g. a plasma sample. The kits comprise a composition comprising at least one set of primers for amplifying at least one polymorphic target nucleic acid in said fetal and maternal nucleic acid molecules. Polymorphic target nucleic acids can comprise without limitation single nucleotide polymorphisms (SNPs), tandem SNPs, small-scale multi-base deletions or insertions, called IN-DELS (also called deletion insertion polymorphisms or DIPs), Multi-Nucleotide Polymorphisms (MNPs) Short Tandem Repeats (STRs), restriction fragment length polymorphism (RFLP), or a polymorphism comprising any other change of sequence in a chromosome. Sequencing methods utilizing the compositions of the invention are NGS methods of single nucleic acid molecules or clonally amplified nucleic acid molecules as described herein. The massively parallel sequencing methods of NGS include pyrosequencing, sequencing by synthesis with reversible dye terminators, real-time sequencing, or sequencing by oligonucleotide probe ligation.

In one embodiment, the compositions includes primers for amplifying polymorphic target nucleic acids that each comprise at least one SNP. In one embodiment, the at least one SNP is selected from SNPs rs560681 (SEQ ID NOS 1 & 2), rs1109037 (SEQ ID NOS 3 & 4), rs9866013 (SEQ ID NOS 5 & 6), rs13182883 (SEQ ID NOS 7 & 8), rs13218440 (SEQ ID NOS 9 & 10), rs7041158 (SEQ ID NOS 11 & 12), rs740598 (SEQ ID NOS 13 & 14), rs10773760 (SEQ ID NOS 15 & 16), rs4530059 (SEQ ID NOS 17 & 18), rs7205345 (SEQ ID NOS 19 & 20), rs8078417 (SEQ ID NOS 21 & 22), rs576261 (SEQ ID NOS 23 & 24), rs2567608 (SEQ ID NOS 25 & 26), rs430046 (SEQ ID NOS 27 & 28), rs9951171 (SEQ ID NOS 29 & 30), rs338882 (SEQ ID NOS 31 & 32), rs10776839 (SEQ ID NOS 33 & 34), rs9905977 (SEQ ID NOS 35 & 36), rs1277284 (SEQ ID NOS 37 & 38), rs258684 (SEQ ID NOS 39 & 40), rs1347696 (SEQ ID NOS 41 & 42), rs508485 (SEQ ID NOS 43 & 44), rs9788670 (SEQ ID NOS 45 & 46), rs8137254 (SEQ ID NOS 47 & 48), rs3143 (SEQ ID NOS 49 & 50), rs2182957 (SEQ ID NOS 51 & 52), rs3739005 (SEQ ID NOS 53 & 54), and rs530022 (SEQ ID NOS 55 & 56). Exemplary corresponding sets of primers for amplifying the SNPs are provided as SEQ ID NOs:57-112.

In another embodiment, the composition includes primers for amplifying polymorphic target nucleic acids that each comprise at least one tandem SNP. In one embodiment, the composition includes primers for amplifying tandem SNPs. In one embodiment, the composition includes primers for amplifying the tandem SNPs disclosed herein, and the composition comprises the corresponding exemplary primers of SEQ ID NOS:197-310.

In another embodiment, the composition includes primers for amplifying polymorphic target nucleic acids that each comprise at least one STR. Exemplary STRs include CSF1PO, FGA, TH01, TPOX, vWA, D3S1358, D5S818, D7S820, D8S1179, D13S317, D16S539, D18S51, D21S11, D2S1338, Penta D, Penta E, D22S1045, D20S1082, D20S482, D18S853, D17S1301, D17S974, D14S1434, D12ATA63, D11S4463, D10S1435, D10S1248, D9S2157, D9S1122, D8S1115, D6S1017, D6S474, D5S2500, D4S2408, D4S2364, D3S4529, D3S3053, D2S1776, D2S441, D1S1677, D1S1627 and D1GATA113, which can be amplified by the corresponding sets of primers of SEQ ID NOs:113-196.

Kits can contain a reagent combination including the elements required to conduct an assay according to the methods disclosed herein. The reagent system is presented in a commercially packaged form, as a composition or admixture where the compatibility of the reagents will allow, in a test device configuration, or more typically as a test kit, i.e., a packaged combination of one or more containers, devices, or the like holding the necessary reagents, and preferably including written instructions for the performance of assays. The kit of the present invention may be adapted for any configuration of assay and may include compositions for performing any of the various assay formats described herein. Kits for determining fetal fraction comprise compositions including primer sets for amplifying polymorphic nucleic acids present in a maternal sample as described and, where applicable, reagents for purifying cfDNA, are within the scope of the invention. In one embodiment, a kit designed to allow quantification of fetal and maternal polymorphic sequences e.g. STRs and/or SNPs and/or tandem SNPs, in a cfDNA plasma sample, includes at least one set of allele specific oligonucleotides specific for a selected SNP and/or region of tandem repeats. Preferably, the kit includes a plurality of primer sets to amplify a panel of polymorphic sequences. A kit can comprise other reagents and/or information for genotyping or quantifying alleles in a sample (e.g., buffers, nucleotides, instructions). The kits also include a plurality of containers of appropriate buffers and reagents.

The present invention is described in further detail in the following Examples which are not in any way intended to limit the scope of the invention as claimed. The attached Figures are meant to be considered as integral parts of the specification and description of the invention. The following examples are offered to illustrate, but not to limit the claimed invention.

EXPERIMENTAL

Example 1

Determination of Fetal Fraction Using Massively Parallel Sequencing

Sample Processing and cfDNA Extraction

Peripheral blood samples were collected from pregnant women in their first or second trimester of pregnancy and who were deemed at risk for fetal aneuploidy. Informed consent was obtained from each participant prior to the blood draw. Blood was collected before amniocentesis or chorionic villus sampling. Karyotype analysis was performed using the chorionic villus or amniocentesis samples to confirm fetal karyotype.

Peripheral blood drawn from each subject was collected in ACD tubes. One tube of blood sample (approximately 6-9 mL/tube) was transferred into one 15-mL low speed centrifuge tube. Blood was centrifuged at 2640 rpm, 4° C. for 10 mm using Beckman Allegra 6 R centrifuge and rotor model GA 3.8.

For cell-free plasma extraction, the upper plasma layer was transferred to a 15-ml high speed centrifuge tube and centrifuged at 16000×g, 4° C. for 10 mm using Beckman Coulter Avanti J-E centrifuge, and JA-14 rotor. The two centrifugation steps were performed within 72 h after blood collection. Cell-free plasma comprising cfDNA was stored at −80° C. and thawed only once before amplification of plasma cfDNA or for purification of cfDNA.

Purified cell-free DNA (cfDNA) was extracted from cell-free plasma using the QIAamp Blood DNA Mini kit (Qiagen) essentially according to the manufacturer's instruction. One milliliter of buffer AL and 100 μl of Protease solution were added to 1 ml of plasma. The mixture was incubated for 15 minutes at 56° C. One milliliter of 100% ethanol was added to the plasma digest. The resulting mixture was transferred to QIAamp mini columns that were assembled with Vac Valves and VacConnectors provided in the QIAvac 24 Plus column assembly (Qiagen). Vacuum was applied to the samples, and the cfDNA retained on the column filters was washed under vacuum with 750 µl of buffer AW1, followed by a second wash with 750 W of buffer AW24. The column was centrifuged at 14,000 RPM for 5 minutes to remove any residual buffer from the filter. The cfDNA was eluted with buffer AE by centrifugation at 14,000 RPM, and the concentration determined using Qubit™ Quantitation Platform (Invitrogen).

Example 2

Determination of Fetal Fraction Using Massively Parallel Sequencing

Preparation of Sequencing Libraries, Sequencing, and Analysis of Sequencing Data a. Preparation of Sequencing Libraries All sequencing libraries i.e. target, primary and enriched libraries, were prepared from approximately 2 ng of purified cfDNA that was extracted from maternal plasma. Library preparation was performed using reagents of the NEBNext™ DNA Sample Prep DNA Reagent Set 1 (Part No. E6000L; New England Biolabs, Ipswich, Mass.) for Illumina® as follows. Because cell-free plasma DNA is fragmented in nature, no further fragmentation by nebulization or sonication was done on the plasma DNA samples. The overhangs of approximately 2 ng purified cfDNA fragments contained in 40 µl were converted into phosphotylated blunt ends according to the NEBNext® End Repair Module by incubating in a 1.5 ml microfuge tube the cfDNA with 5 µl 10× phosphorylation buffer, 20 deoxy nucleotide solution mix (10 mM each dNTP), 1 µl of a 1:5 dilution of DNA Polymerase I, 1 µl T4 DNA Polymerase and 1 µl T4 Polynucleotide Kinase provided in the NEBNext™ DNA Sample Prep DNA Reagent Set 1 for 15 minutes at 20° C. The enzymes were then heat inactivated by incubating the reaction mixture at 75° C. for 5 minutes. The mixture was cooled to 4° C., and dA tailing of the blunt-ended DNA was accomplished using 10 µl of the dA-tailing master Mix containing the Klenow fragment (3' to 5' exo minus) (NEBNext™ DNA Sample Prep DNA Reagent Set 1), and incubating for 15 minutes at 37° C. Subsequently, the Klenow fragment was heat inactivated by incubating the reaction mixture at 75° C. for 5 minutes. Following the inactivation of the Mellow fragment, 1 µl of a 1.5 dilution of Illumina Genomic Adaptor Oligo Mix (Part No, 1000521, Illumina Inc., Hayward. Calif.) was used to ligate the Illumina adaptors (Non-Index Y-Adaptors) to the dA-tailed DNA using 4 µl of the T4 DNA ligase provided in the NEB-NextTM DNA Sample Prep DNA Reagent Set 1, by incubating the reaction mixture for 15 minutes at 25° C. The mixture was cooled to 4° C., and the adaptor-ligated cfDNA. was purified from mitigated adaptors, adaptor dimers, and other reagents using magnetic beads provided in the Agencourt AMPure PCR purification system (Part No. A63881; Beckman Coulter Genomics, Danvers, Mass.). Eighteen cycles of PCR were performed to selectively enrich adaptor-ligated cfDNA using Phusion High-Fidelity Master Mix (Finnzymes, Woburn, Mass.) and Illumina's PCR primers complementary to the adaptors (Part No. 1000537 and 1000537). The adaptor-ligated DNA was subjected to PCR (98° C. for 30 seconds; 18 cycles of 98° C. for 10 seconds, 65° C. for 30 seconds, and 72° C. for 30 seconds; final extension at 72° C. for 5 minutes, and hold at 4° C.) using Illumina Genomic PCR Primers (Part Nos. 100537 and 1000538) and the Phusion HF PCR Master Mix provided in the NEBNexfrm DNA Sample Prep DNA Reagent Set 1, according to the manufacturer's instructions. The amplified product was purified using the Agencourt AMPure XP PCR purification system (Agencourt Bioscience Corporation, Beverly, Mass.) according to the manufacturer's instructions available on the world wide web at beckmangenomics dot com/products/AMPureXPProtocol_000387v001.pdf. The purified amplified product was eluted in 40 µl of Qiagen EB Buffer, and the concentration and size distribution of the amplified libraries was analyzed using the Agilent DNA 1000 Kit for the 2100 Bioanalyzer (Agilent technologies Inc., Santa Clara, Calif.).

b. Sequencing

Sequencing of library DNA was performed using the Genome Analyzer II (Illumina Inc., San Diego, Calif., USA) according to standard manufacturer protocols. Copies of the protocol for whole genome sequencing using Illumina/Solexa technology may be found at BioTechniques® Protocol Guide 2007 Published December 2006: p 29, and on the world wide web at biotechniques.com/defaultasp?page=protocol&subsection=article display&id=112378. The DNA library was diluted to 1 nM and denatured. Library DNA (5 pM) was subjected to cluster amplification according to the procedure described in Illumina's Cluster Station User Guide and Cluster Station Operations Guide, available on the world wide web at illumina com/systems/genome analyzer/cluster_station-.ilmn. The amplified DNA was sequenced using Illumina's Genome Analyzer II to obtain single-end reads of 36 bp. Only about 30 bp of random sequence information are needed to identify a sequence as belonging to a specific human chromosome. Longer sequences can uniquely identify more particular targets. In the present case, a large number of 36 bp reads were obtained, covering approximately 10% of the genome.

c. Analysis of Sequencing Data for the Determination of Fetal Fraction

Upon completion of sequencing of the sample, the Illumina "Sequencer Control Software" transferred image and base call files to a Unix server running the Illumina "Genome Analyzer Pipeline" software version 1.51. the 36 bp reads were aligned to an artificial reference genome e.g. a SNP genome, using the BOWTIE program. The artificial reference genome was identified as the grouping of the polymorphic DNA sequences that encompass the alleles comprised in the polymorphic target sequences. For example, the artificial reference genome is a SNP genome comprising SEQ ID NOs: 1-56. Only reads that mapped uniquely to the artificial genome were used for the analysis of fetal fraction. Reads that matched perfectly to the SNP genome were counted as tags and filtered. Of the remaining reads, only reads having one or two mismatches were counted as tags and included in the analysis. Tags mapped to each of the polymorphic alleles were counted, and the fetal fraction was determined as a percent of the ratio of the number of tags mapped to the major allele i.e. maternal allele, and the number of tags mapped to the minor allele i.e. fetal allele.

Example 3

Selection of Autosomal SNPs for the Determination of Fetal Fraction

A set of 28 autosomal SNPs were selected from a list of 92 SNPs (Pakstis et al., Hum Genet 127:315-324 [2010])

and from Applied Biosystems by Life Technologies™ (Carlsbad, Calif.) at world wide address appliedbiosystems.com, and validated for use in multiplexed PCR amplification. Primers were designed to hybridize to a sequence close to the SNPs site on the cfDNA to ensure that it be included in the 36 bp read generated from the massively parallel sequencing on the Illumina Analyzer GII, and to generate amplicons of sufficient length to undergo bridge-amplification during cluster formation. Thus, primers were designed to generate amplicons that were at least 110 bp, which when combined with the universal adaptors (Illumina Inc., San Diego, Calif.) used for cluster amplification, resulted in DNA molecules of at least 200 bp. Primer sequences were identified, and primer sets i.e. forward and reverse primers, were synthesized by Integrated DNA Technologies (San Diego, Calif.), and stored as a 1 µM solution to be used for amplifying polymorphic target sequences as described in Examples 4-7. Table 1 provides the RefSNP (rs) accession ID numbers, the primers used for amplifying the target cfDNA sequence, and the sequences of the amplicons comprising the possible SNP alleles that would be generated using the primers. The SNPs given in Table 1 were used for the simultaneous amplification of 13 target sequences in a multiplexed assay. The panel provided in Table 1 is an exemplary SNP panel. Fewer or more SNPs can be employed to enrich the fetal and maternal DNA for polymorphic target nucleic acids. Additional SNPs that can be used include the SNPs given in Table 2. The SNP alleles are shown in bold and are underlined. Other additional SNPs that can be used to determine fetal fraction according to the present method include rs315791, rs3780962, rs1410059, rs279844, rs38882, rs9951171 (SEQ ID NOS 29 & 30), rs214955, rs6444724, rs2503107, rs1019029, rs1413212, rs1031825, rs891700, rs1005533, rs2831700, rs354439, rs1979255, rs1454361, rs8037429, and rs1490413, which have been analyzed for determining fetal fraction by Taq-Man PCR, and are disclosed in U.S. Provisional applications 61/296,358 and 61/360,837.

TABLE 1

SNP Panel for the Determination of Fetal Fraction

| SNP ID | Chr | Amplicon: Allele 1 | Amplicon: Allele 2 | Forward Primer Sequence, name and SEQ ID NO: | Reverse Primer Sequence, name and SEQ ID NO: |
|---|---|---|---|---|---|
| rs560681 | 1 | CACATGCACAGCCAGCAACCCTGTCAGCAGGAGTTCCCACCAGTTTCTTTCTGAGAACATCTGTTCAGGTTTCTCTCCATCTCTATTTACTCAGGTCACAGGACCTTGGGG (SEQ ID NO: 1) | CACATGCACAGCCAGCAACCCTGTCAGCAGGAGTTCCCACCAGTTTCTTTCTGAGAACATCTGTTCAGGTTTCTCTCCATCTCTGTTTACTCAGGTCACAGGACCTTGGGG (SEQ ID NO: 2) | CACATGCACAGCCAGCAACCC (rs560681_C1_1_F; SEQ ID NO: 57) | CCCCAAGGTCCTGTGACCTGAGT (rs560681_C1_1_R; SEQ ID NO: 58) |
| rs1109037 | 2 | TGAGGAAGTGAGGCTCAGAGGGTAAGAAACTTTGTCACAGAGCTGGTGGTGAGGGTGGAGATTTTACACTCCCTGCCTCCCACACCAGTTTCTCCAGAGTGGAAAGACTTTCATCTCGCACTGGCA (SEQ ID NO: 3) | TGAGGAAGTGAGGCTCAGAGGGTAAGAAACTTTGTCACAGAGCTGGTGGTGAGGGTGGAGATTTTACACTCCCTGCCTCCCACACCAGTTTCTCCGGAGTGGAAAGACTTTCATCTCGCACTGGCA (SEQ ID NO: 4) | TGAGGAAGTGAGGCTCAGAGGGT (rs110937_C2_1_F; SEQ ID NO: 59) | TGCCAGTGCGAGATGAAAGTCTTT (rs110937_C2_1_R; SEQ ID NO: 60) |
| rs9866013 | 3 | GTGCCTTCAGAACCTTTGAGATCTGATTCTATTTTTAAAGCTTCTTAGAAGAGAATTGCAAAGTGGGTTGTTTCTCTAGCCAGACAGGGCAGGCAAATAGGGGTGGCTGGTGGGATGGGA (SEQ ID NO: 5) | GTGCCTTCAGAACCTTTGAGATCTGATTCTATTTTTAAAGCTTCTTAGAAGAGAATTGCAAAGTGGGTTGTTTCTCTAGCCAGACAGGGCAGGTAAATAGGGGTGGCTGGTGGGATGGGA (SEQ ID NO: 6) | GTGCCTTCAGAACCTTTGAGATCTGAT (rs9866013_C3_1_F; SEQ ID NO: 61) | TCCCATCCCACCAGCCACCC (rs9866013_C3_1_R; SEQ ID NO: 62) |
| rs13182883 | 5 | AGGTGTGTCTCTCTTTTGTGAGGGGAGGGGTCCCTTCTGGCCTAGTAGAGGGCCTGGCCTGCAGTGAGCATTCAAATCCTCAAGGAACAGGGTGGGGAGGTGGGACAAAGG (SEQ ID NO: 7) | AGGTGTGTCTCTCTTTTGTGAGGGGAGGGGTCCCTTCTGGCCTAGTAGAGGGCCTGGCCTGCAGTGAGCATTCAAATCCTCGAGGAACAGGGTGGGGAGGTGGGACAAAGG (SEQ ID NO: 8) | AGGTGTGTCTCTCTTTTGTGAGGGG (rs13182883_C5_1_F; SEQ ID NO: 63) | CCTTTGTCCCACCTCCCCACC (rs13182883_C5_1_R; SEQ ID NO: 64) |
| rs13218440 | 6 | CCTCGCCTACTGTGCTGTTTCTAACCATCATGCTTTTCCCTGAATCTCTTGAGTCTTTTTCTGCTGTGGACTGAAACTTGATCCTGAGATTCACCTCT | CCTCGCCTACTGTGCTGTTTCTAACCATCATGCTTTTCCCTGAATCTCTTGAGTCTTTTTCTGCTGTGGACTGAAACTTGATCCTGAGATTCACCTCT | CCTCGCCTACTGTGCTGTTTCTAACC (rs13218440_C6_1_F; SEQ ID NO: 65) | CCATCCCAGCTGAGTATTCCAGGAG (rs13218440_C6_1_R; SEQ ID NO: 66) |

TABLE 1-continued

SNP Panel for the Determination of Fetal Fraction

| SNP ID | Chr | Amplicon: Allele 1 | Amplicon: Allele 2 | Forward Primer Sequence, name and SEQ ID NO: | Reverse Primer Sequence, name and SEQ ID NO: |
|---|---|---|---|---|---|
| | | AGTCCCTCTGAGCA GCCTCCTGGAATAC TCAGCTGGGATGG (SEQ ID NO: 9) | AGTCCCTCTGGGCA GCCTCCTGGAATAC TCAGCTGGGATGG (SEQ ID NO: 10) | | |
| rs7041158 | 9 | AATTGCAATGGTGA GAGGTTGATGGTAA AATCAAACGGAACT TGTTATTTTGTCAT TCTGATGGACTGGA ACTGAGGATTTTCA ATTTCCTCTCCAAC CCAAGACACTTCTC ACTGG (SEQ ID NO: 11) | AATTGCAATGGTGA GAGGTTGATGGTAA AATCAAACGGAACT TGTTATTTTGTCAT TCTGATGGACTGGA ACTGAGGATTTTCA ATTTCCTTTCCAAC CCAAGACACTTCTC ACTGG (SEQ ID NO: 12) | AATTGCAATGGTGA GAGGTTGATGGT (SEQ ID NO: 67) | CCAGTGAGAAGTGT CTTGGGTTGG (SEQ ID NO: 68) |
| rs740598 | 10 | GAAATGCCTTCTCA GGTAATGGAAGGTT ATCCAAATATTTTT CGTAAGTATTTCAA ATAGCAATGGCTCG TCTATGGTTAGTCT CACAGCCACATTCT CAGAACTGCTCAAA CC (SEQ ID NO: 13) | GAAATGCCTTCTCA GGTAATGGAAGGTT ATCCAAATATTTTT CGTAAGTATTTCAA ATAGCAATGGCTCG TCTATGGTTAGTCT CGCAGCCACATTCT CAGAACTGCTCAAA CC (SEQ ID NO: 14) | GAAATGCCTTCTCA GGTAATGGAAGG (SEQ ID NO: 69) | GGTTTGAGCAGTTC TGAGAATGTGGCT (SEQ ID NO: 70) |
| rs10773760 | 12 | ACCCAAAACACTGG AGGGGCCTCTTCTC ATTTTCGGTAGACT GCAAGTGTTAGCCG TCGGGACCAGCTTC TGTCTGGAAGTTCG TCAAATTGCAGTTA AGTCCAAGTATGCC ACATAGCAGATAAG GG (SEQ ID NO: 15) | ACCCAAAACACTGG AGGGGCCTCTTCTC ATTTTCGGTAGACT GCAAGTGTTAGCCG TCGGGACCAGCTTC TGTCTGGAAGTTCG TCAAATTGCAGTTA GGTCCAAGTATGCC ACATAGCAGATAAG GG (SEQ ID NO: 16) | ACCCAAAACACTGG AGGGGCCT (SEQ ID NO: 71) | CCCTTATCTGCTAT GTGGCATACTTGG (SEQ ID NO: 72) |
| rs4530059 | 14 | GCACCAGAATTTAA ACAACGCTGACAAT AAATATGCAGTCGA TGATGACTTCCCAG AGCTCCAGAAGCAA CTCCAGCACACAGA GAGGCGCTGATGTG CCTGTCAGGTGC (SEQ ID NO: 17) | GCACCAGAATTTAA ACAACGCTGACAAT AAATATGCAGTCGA TGATGACTTCCCAG AGCTCCAGAAGCAA CTCCAGCACACGGA GAGGCGCTGATGTG CCTGTCAGGTGC (SEQ ID NO: 18) | GCACCAGAATTTAA ACAACGCTGACAA (SEQ ID NO: 73) | GCACCTGACAGGCA CATCAGCG (SEQ ID NO: 74) |
| rs7205345 | 16 | TGACTGTATACCCC AGGTGCACCCTTGG GTCATCTCTATCAT AGAACTTATCTCAC AGAGTATAAGAGCT GATTTCTGTGTCTG CCTCTCACACTAGA CTTCCACATCCTTA GTGC (SEQ ID NO: 19) | TGACTGTATACCCC AGGTGCACCCTTGG GTCATCTCTATCAT AGAACTTATCTCAC AGAGTATAAGAGCT GATTTCTGTGTCTG CCTGTCACACTAGA CTTCCACATCCTTA GTGC (SEQ ID NO: 20) | TGACTGTATACCCC AGGTGCACCC (SEQ ID NO: 75) | GCACTAAGGATGTG GAAGTCTAGTGTG (SEQ ID NO: 76) |
| rs8078417 | 17 | TGTACGTGGTCACC AGGGGACGCCTGGC GCTGCGAGGGAGGC CCCGAGCCTCGTGC CCCCGTGAAGCTTC AGCTCCCCTCCCCG GCTGTCCTTGAGGC TCTTCTCACACT (SEQ ID NO: 21) | TGTACGTGGTCACC AGGGGACGCCTGGC GCTGCGAGGGAGGC CCCGAGCCTCGTGC CCCCGTGAAGCTTC AGCTCCCCTCCCTG GCTGTCCTTGAGGC TCTTCTCACACT (SEQ ID NO: 22) | TGTACGTGGTCACC AGGGGACG (SEQ ID NO: 77) | AGTGTGAGAAGAGC CTCAAGGACAGC (SEQ ID NO: 78) |
| rs576261 | 19 | CAGTGGACCCTGCT GCACCTTTCCTCCC CTCCCATCAACCTC TTTTGTGCCTCCCC | CAGTGGACCCTGCT GCACCTTTCCTCCC CTCCCATCAACCTC TTTTGTGCCTCCCC | CAGTGGACCCTGCT GCACCTT (SEQ ID NO: 79) | GTGGCAAAGGAGAG AGTTGTGAGG (SEQ ID NO: 80) |

TABLE 1-continued

SNP Panel for the Determination of Fetal Fraction

| SNP ID | Chr | Amplicon: Allele 1 | Amplicon: Allele 2 | Forward Primer Sequence, name and SEQ ID NO: | Reverse Primer Sequence, name and SEQ ID NO: |
|---|---|---|---|---|---|
| | | CTCCGTGTACCACC TTCTCTGTCACCAA CCCTGGCCTCACAA CTCTCTCCTTTGCC AC (SEQ ID NO: 23) | CTCCGTGTACCACC TTCTCTGTCACCAC CCCTGGCCTCACAA CTCTCTCCTTTGCC AC (SEQ ID NO: 24) | | |
| rs2567608 | 20 | CAGTGGCATAGTAG TCCAGGGGCTCCTC CTCAGCACCTCCAG CACCTTCCAGGAGG CAGCAGCGCAGGCA GAGAACCCGCTGGA AGAATCGGCGGAAG TTGTCGGAGAGG (SEQ ID NO: 25) | CAGTGGCATAGTAG TCCAGGGGCTCCTC CTCAGCACCTCCAG CACCTTCCAGGAGG CAGCAGCGCAGGCA GAGAACCCGCTGGA AGGATCGGCGGAAG TTGTCGGAGAGG (SEQ ID NO: 26) | CAGTGGCATAGTAG TCCAGGGGCT (SEQ ID NO: 81) | CCTCTCCGACAACT TCCGCCG (SEQ ID NO: 82) |

TABLE 2

Additional SNPs for the Determination of Fetal Fraction

| SNP ID | Chr | Amplicon: Allele 1 | Amplicon: Allele 2 | Forward Primer Sequence, name and SEQ ID NO: | Reverse Primer Sequence, name and SEQ ID NO: |
|---|---|---|---|---|---|
| rs430046 | 16 | AGGTCTGGGGCCGC TGAATGCCAAGCTGG GAATCTTAAATGTTA AGGAACAAGGTCATA CAATGAATGGTGTGA TGTAAAAGCTTGGGA GGTGATTTCTGAGGG TAGGTGCTGGGTTTA ATGGGAGGA (SEQ ID NO: 27) | AGGTCTGGGGCCGC TGAATGCCAAGCTGG GAATCTTAAATGTTA AGGAACAAGGTCATA CAATGAATGGTGTGA TGTAAAAGCTTGGGA GGTGATTTTTGAGGG TAGGTGCTGGGTTTA ATGGGAGGA (SEQ ID NO: 28) | AGGTCTGGGGCCG CTGAAT (rs430046_C1_1_F; SEQ ID NO: 83) | TCCTCCCATTAAAC CCAGCACCT (rs430046_C1_1_R; SEQ ID NO: 84) |
| rs9951171 | 18 | ACGGTTCTGTCCTGT AGGGGAGAAAAGTCC TCGTTGTTCCTCTGG GATGCAACATGAGAG AGCAGCACACTGAGG CTTTATGGATTGCCC TGCCACAAGTGAACA GG (SEQ ID NO: 29) | ACGGTTCTGTCCTGT AGGGGAGAAAAGTCC TCGTTGTTCCTCTGG GATGCAACATGAGAG AGCAGCACACTGAGG CTTTATGGGTTGCCC TGCCACAAGTGAACA GG (SEQ ID NO: 30) | ACGGTTCTGTCCTG TAGGGGAGA (rs9951171_C1_1_F; SEQ ID NO: 85) | CCTGTTCACTTGTG GCAGGGCA (rs9951171_C1_1_R; SEQ ID NO: 86) |
| rs338882 | 5 | GCGCAGTCAGATGGG CGTGCTGGCGTCTGT CTTCTCTCTCTCCTG CTCTCTGGCTTCATT TTTCTCTCCTTCTGT CTCACCTTCTTTCGT GTGCCTGTGCACACA CACGTTTGGGACAAG GGCTGGA (SEQ ID NO: 31) | GCGCAGTCAGATGGG CGTGCTGGCGTCTGT CTTCTCTCTCTCCTG CTCTCTGGCTTCATT TTTCTCTCCTTCTGT CTCACCTTCTTTCGT GTGCCTGTGCATACA CACGTTTGGGACAAG GGCTGGA (SEQ ID NO: 32) | GCGCAGTCAGATGG GCGTGC (rs338882_C1_1_F; SEQ ID NO: 87) | TCCAGCCCTTGTCC CAAACGTGT (rs338882_C1_1_R; SEQ ID NO: 88) |
| rs10776839 | 9 | GCCGGACCTGCGAAA TCCCAAAATGCCAAA CATTCCCGCCTCACA TGATCCCAGAGAGAG GGGACCCAGTGTTCC CAGCTTGCAGCTGAG GAGCCCGAGGTTGCC GTCAGATCAGAGCCC CAGTTGCCCG (SEQ ID NO: 33) | GCCGGACCTGCGAAA TCCCAAAATGCCAAA CATTCCCGCCTCACA TGATCCCAGAGAGAG GGGACCCAGTGTTCC CAGCTTGCAGCTGAG GAGCCCGAGTTTGCC GTCAGATCAGAGCCC CAGTTGCCCG (SEQ ID NO: 34) | GCCGGACCTGCGAA ATCCCAA (rs10776839_C1_1_F; SEQ ID NO: 89) | CGGGCAACTGGGGC TCTGATC (rs10776839_C1_1_R; SEQ ID NO: 90) |
| rs9905977 | 17 | AGCAGCCTCCCTCGA CTAGCTCACACTACG ATAAGGAAAATTCAT | AGCAGCCTCCCTCGA CTAGCTCACACTACG ATAAGGAAAATTCAT | AGCAGCCTCCCTCG ACTAGCT (rs9905977_C1_1_F; | GGCAGAGGGGAAAG ACGAAAGGA (rs9905977_C1_1_R; |

TABLE 2-continued

Additional SNPs for the Determination of Fetal Fraction

| SNP ID | Chr | Amplicon: Allele 1 | Amplicon: Allele 2 | Forward Primer Sequence, name and SEQ ID NO: | Reverse Primer Sequence, name and SEQ ID NO: |
|---|---|---|---|---|---|
| | | GAGCTGGTGTCCAAG GAGGGCTGGGTGACT CGTGGCTCAGTCAGC ATCAAGATTCCTTTC GTCTTTCCCCTCTGC C (SEQ ID NO: 35) | GAGCTGGTGTCCAAG GAGGGCTGGGTGACT CGTGGCTCAGTCAGC GTCAAGATTCCTTTC GTCTTTCCCCTCTGC C (SEQ ID NO: 36) | SEQ ID NO: 91) | SEQ ID NO: 92) |
| rs1277284 | 4 | TGGCATTGCCTGTAA TATACATAGCCATGG TTTTTTATAGGCAAT TTAAGATGAATAGCT TCTAAACTATAGATA AGTTTCATTACCCCA GGAAGCTGAACTATA GCTACTTTACCCAAA ATCATTAGAATGGTG CTT (SEQ ID NO: 37) | TGGCATTGCCTGTAA TATACATAGCCATGG TTTTTTATAGGCAAT TTAAGATGAATAGCT TCTAAACTATAGATA AGTTTCATTACCCCA GGAAGCTGAACTATA GCTACTTTCCCCAAA ATCATTAGAATGGTG CTT (SEQ ID NO: 38) | TGGCATTGCCTGTA ATATACATAG (rs1277284_C4_1_F; SEQ ID NO: 93) | AAGCACCATTCTAA TGATTTTGG (rs1277284_C4_1_R; SEQ ID NO: 94) |
| rs258684 | 7 | ATGAAGCCTTCCACC AACTGCCTGTATGAC TCATCTGGGACTTC TGCTCTATACTCAAA GTGGCTTAGTCACTG CCAATGTATTTCCAT ATGAGGGACGATGAT TACTAAGGAAATATA GAAACAACAACTGAT C (SEQ ID NO: 39) | ATGAAGCCTTCCACC AACTGCCTGTATGAC TCATCTGGGACTTC TGCTCTATACTCAAA GTGGCTTAGTCACTG CCAATGTATTTCCAT ATGAGGGACGGTGAT TACTAAGGAAATATA GAAACAACAACTGAT C (SEQ ID NO: 40) | ATGAAGCCTTCCAC CAACTG (rs258684_C7_1_F; SEQ ID NO: 95) | GATCAGTTGTTGTT TCTATATTTCCTT (rs258684_C7_1_R; SEQ ID NO: 96) |
| rs1347696 | 8 | ACAACAGAATCAGGT GATTGGAGAAAAGAT CACAGGCCTAGGCAC CCAAGGCTTGAAGGA TGAAAGAATGAAAGA TGGACGGAACAAAAT TAGGACCTTAATTCT TTGTTCAGTTCAG (SEQ ID NO: 41) | ACAACAGAATCAGGT GATTGGAGAAAAGAT CACAGGCCTAGGCAC CCAAGGCTTGAAGGA TGAAAGAATGAAAGA TGGACGGAAGAAAAT TAGGACCTTAATTCT TTGTTCAGTTCAG (SEQ ID NO: 42) | ACAACAGAATCAGG TGATTGGA (rs1347696_C8_4_F; SEQ ID NO: 97) | CTGAACTGAACAAA GAATTAAGGTC (rs1347696_C8_4_F; SEQ ID NO: 98) |
| rs508485 | 11 | TTGGGGTAAATTTTC ATTGTCATATGTGGA ATTTAAATATACCAT CATCTACAAAGAATT CCACAGAGTTAAATA TCTTAAGTTAAACAC TTAAAATAAGTGTTT GCGTGATATTTTGAT GACAGATAAACAGAG TCTAATTCCCACCCC (SEQ ID NO: 43) | TTGGGGTAAATTTTC ATTGTCATATGTGGA ATTTAAATATACCAT CATCTACAAAGAATT CCACAGAGTTAAATA TCTTAAGTTAAACAC TTAAAATAAGTGTTT GCGTGATATTTTGAT GATAGATAAACAGAG TCTAATTCCCACCCC (SEQ ID NO: 44) | TTGGGGTAAATTTT CATTGTCA (rs508485_C11_1_F; SEQ ID NO: 99) | GGGGTGGGAATTAG ACTCTG (rs508485_C11_1_R; SEQ ID NO 100) |
| rs9788670 | 15 | TGCAATTCAAATCAG GAAGTATGACCAAAA GACAGAGATCTTTTT TGGATGATCCCTAGC CTAGCAATGCCTGGC AGCCATGCAGGTGCA ATGTCAACCTTAAAT AATGTATTGCAAACT CAGAGCTGACAAACC TCGATGTTGC (SEQ ID NO: 45) | TGCAATTCAAATCAG GAAGTATGACCAAAA GACAGAGATCTTTTT TGGATGATCCCTAGC CTAGCAATGCCTGGC AGCCATGCAGGTGCA ATGTCAACCTTAAAT AATGTATTGCAAATT CAGAGCTGACAAACC TCGATGTTGC (SEQ ID NO: 46) | TGCAATTCAAATCA GGAAGTATG (rs9788670_c15_2_F; SEQ ID NO: 101) | GCAACATCGAGGTTT GTCAG (rs9788670_c15_2_R; SEQ ID NO: 102) |
| rs8137254 | 22 | CTGTGCTCTGCGAAT AGCTGCAGAAGTAAC TTGGGGACCCAAAAT AAAGCAGAATGCTAA TGTCAAGTCCTGAGA ACCAAGCCCTGGGAC | CTGTGCTCTGCGAAT AGCTGCAGAAGTAAC TTGGGGACCCAAAAT AAAGCAGAATGCTAA TGTCAAGTCCTGAGA ACCAAGCCCTGGGAC | CTGTGCTCTGCGAA TAGCTG (rs8137254_c22_2_F: SEQ ID NO: 103) | ACCATGCTCATGGA GAATCC (rs8137254_c22_2_R; SEQ ID NO: 104) |

TABLE 2-continued

Additional SNPs for the Determination of Fetal Fraction

| SNP ID | Chr | Amplicon: Allele 1 | Amplicon: Allele 2 | Forward Primer Sequence, name and SEQ ID NO: | Reverse Primer Sequence, name and SEQ ID NO: |
|---|---|---|---|---|---|
| | | TCTGGTGCCATTTCG GATTCTCCATGAGCA TGGT (SEQ ID NO: 47) | TCTGGTGCCATTTTG GATTCTCCATGAGCA TGGT (SEQ ID NO: 48) | | |
| rs3143 | 19 | TTTTTCCAGCCAACT CAAGGCCAAAAAAAA TTTCTTAATATAGTT ATTATGCGAGGGGAG GGGAAGCAAAGGAGC ACAGGTAGTCCACAG AATAAGACACAAGAA ACCTCAAGCTGTG (SEQ ID NO: 49) | TTTTTCCAGCCAACT CAAGGCCAAAAAAAA TTTCTTAATATAGTT ATTATGCGAGGGGAG GGGAAGCAAAGGAGC ACAGGTAGTCCACAG AATAGGACACAAGAA ACCTCAAGCTGTG (SEQ ID NO: 50) | TTTTTCCAGCCAAC TCAAGG (rs3143_c19_2_F: SEQ ID NO: 105) | CACAGCTTGAGGTT TCTTGTG (rs3143_c19_2_R; SEQ ID NO: 106) |
| rs2182957 | 13 | TCTTCTCGTCCCCTA AGCAAACAACATCCG CTTGCTTCTGTCTGT GTAACCACAGTGAAT GGGTGTGCACGCTTG ATGGGCCTCTGAGCC CCTGTTGCACAAACC AGAAA (SEQ ID NO: 51) | TCTTCTCGTCCCCTA AGCAAACAACATCCG CTTGCTTCTGTCTGT GTAACCACAGTGAAT GGGTGTGCACGCTTG GTGGGCCTCTGAGCC CCTGTTGCACAAACC AGAAA (SEQ ID NO: 52) | TCTTCTCGTCCCCT AAGCAA (rs2182957_c13_1_F: SEQ ID NO: 107) | TTTCTGGTTTGTGC AACAGG (rs2182957_c13_1_R; SEQ ID NO: 108) |
| rs3739005 | 2 | CACATGGGGGCATTA AGAATCGCCCAGGGA GGAGGAGGGAGAACG CGTGCTTTTCACATT TGCATTTGAATTTTC GAGTTCCCAGGATGT GTTTTTGTGCTCATC GATGT (SEQ ID NO: 53) | CACATGGGGGCATTA AGAATCGCCCAGGGA GGAGGAGGGAGAACG CGTGCTTTTCACATT TGCATTTGAATTTTT GAGTTCCCAGGATGT GTTTTTGTGCTCATC GATGT (SEQ ID NO: 54) | CACATGGGGGCATT AAGAAT (rs3739005_c2_2_F; SEQ ID NO: 109) | ACATCGATGAGCAC AAAAACAC (rs3739005_c2_2_R; SEQ ID NO: 110) |
| rs530022 | 1 | GGGCTCTGAGGTGTG TGAAATAAAAACAAA TGTCCATGTCTGTCC TTTTATGGCATTTTG GGACTTTACATTTCA AACATTTCAGACATG TATCACAACACGAAG GAATAACAGTTCCAG GGATATCT (SEQ ID NO: 55) | GGGCTCTGAGGTGTG TGAAATAAAAACAAA TGTCCATGTCTGTCC TTTTATGGCATTTTG GGACTTTACATTTCA AACATTTCAGACATG TATCACAACACGAGG GAATAACAGTTCCAG GGATATCT (SEQ ID NO: 56) | GGGCTCTGAGGTGTG TGAAA (rs530022_c1_2_F; SEQ ID NO: 111) | AGATATCCCTGGAA CTGTTATTCC (rs530022_c1_2_R; SEQ ID NO: 112) |

Example 4

Determination of Fetal Fraction by Massively Parallel Sequencing of a Target Library To determine the fraction of fetal cfDNA in a maternal sample, target polymorphic nucleic acid sequences each comprising a SNP were amplified and used for preparing a target library for sequencing in a massively parallel fashion.

cfDNA was extracted as described in Example 1. A target sequencing library was prepared as follows. cfDNA contained in 5 µl of purified cfDNA was amplified in a reaction volume of 50 µl containing 7.5 µl of a 1 µM primer mix (Table 1), 10 µl of NEB 5× Mastermix and 27 µl water. Thermal cycling was performed with the Gene Amp9700 (Applied Biosystems) using the following cycling conditions: incubating at 95° C. for 1 minute, followed by 20-30 cycles at 95° C. for 20 seconds, 68° C. for 1 minute, and 68° C. for 30 s, which was followed by a final incubation at 68° C. for 5 minutes. A final hold at 4° C. was added until the samples were removed for combining with the unamplified portion of the purified cfDNA sample. The amplified product was purified using the Agencourt AMPure XP PCR purification system (Part No. A63881; Beckman Coulter Genomics, Danvers, Mass.). A final hold at 4° C. was added until the samples were removed for preparing the target library. The amplified product was analyzed with a 2100 Bioanalyzer (Agilent Technologies, Sunnyvale, Calif.), and the concentration of amplified product determined. A sequencing library of amplified target nucleic acids was prepared as described in Example 2, and was sequenced in a massively parallel fashion using sequencing-by-synthesis with reversible dye terminators and according to the Illumina protocol (BioTechniques® Protocol Guide 2007 Published December 2006: p 29, and on the world wide web at biotechniques.com/default.asp?page=protocol&subsection=article display&id=112378). Analysis and counting of tags mapped to a reference genome consisting of 26 sequences (13 pairs each representing two alleles) comprising a SNP i.e. SEQ ID NO:1-26 was performed as described.

Table 3 provides the tag counts obtained from sequencing the target library, and the calculated fetal fraction derived from sequencing data.

TABLE 3

Determination of Fetal Fraction by Massively Parallel Sequencing of a Library of Polymorphic Nucleic Acids

| SNP | SNP TAG COUNTS | Fetal Fraction (%) |
|---|---|---|
| rs10773760.1\|Chr.12\|length = 128\|allele = A | 236590 | 1.98 |
| rs10773760.2\|Chr.12\|length = 128\|allele = G | 4680 | |
| rs13182883.1\|Chr.5\|length = 111\|allele = A | 3607 | 4.99 |
| rs13182883.2\|Chr.5\|length = 111\|allele = G | 72347 | |
| rs4530059.1\|Chr.14\|length = 110\|allele = A | 3698 | 1.54 |
| rs4530059.1\|Chr.14\|length = 110\|allele = G | 239801 | |
| rs8078417.1\|Chr.17\|length = 110\|allele = C | 1E+06 | 3.66 |
| rs8078417.2\|Chr.17\|length = 110\|allele = T | 50565 | |

Fetal Fraction (Mean ± S.D.) = 12.4 ± 6.6

The results show that polymorphic nucleic acid sequences each comprising at least one SNP can be amplified from cfDNA derived from a maternal plasma sample to construct a library that can be sequenced in a massively parallel fashion to determine the fraction of fetal nucleic acids in the maternal sample.

Example 5

Determination of Fetal Fraction Following Enrichment of Fetal and Maternal Nucleic Acids in a cfDNA Sequencing Library Sample To enrich the fetal and maternal cfDNA contained in a primary sequencing library constructed using purified fetal and maternal cfDNA, a portion of a purified cfDNA sample was used for amplifying polymorphic target nucleic acid sequences, and for preparing a sequencing library of amplified polymorphic target nucleic acids, which was used to enrich the fetal and maternal nucleic acid sequences comprised in the primary library.

The method corresponds to workflow 3 diagrammed in FIG. 3. A target sequencing library was prepared from a portion of the purified cfDNA as described in Example 2. A primary sequencing library was prepared using the remaining portion of the purified cfDNA as described in Example 2. Enrichment of the primary library for the amplified polymorphic nucleic acids comprised in the target library was obtained by diluting the primary and the target sequencing libraries to 10 nM, and combining the target library with the primary library at a ratio of 1:9 to provide an enriched sequencing library. Sequencing of the enriched library and analysis of the sequencing data was performed as described in Example 2.

Table 4 provides the number of sequence tags that mapped to the SNP genome for the informative SNPs identified from sequencing an enriched library derived from plasma samples of pregnant women each carrying a T21, a T13, a T18 and a monosomy X fetus, respectively. Fetal fraction was calculated as follows:

% fetal fraction allele$_x$=((ΣFetal sequence tags for allele$_x$)/(ΣMaternal sequence tags for allele$_x$))×100

Table 4 also provides the number of the sequence tags mapped to the human reference genome. Tags mapped to the human reference genome were used to determine the presence or absence of aneuploidy using the same plasma sample that was utilized for determining the corresponding fetal fraction. Method for using sequence tags counts for determining aneuploidy are described in U.S. Provisional Applications 61/407,017 and 61/455,849778, which are herein incorporated by reference in their entirety.

TABLE 4

Determination of Fetal Fraction by Massively Parallel Sequencing of an Enriched Library of Polymorphic Nucleic Acids

| Sample ID (karyotype) | SNP | SNP TAG COUNTS | FETAL FRACTION (%) |
|---|---|---|---|
| 11409 (47, XY + 21) | rs13182883.1\|Chr.5\|length = 111\|allele = A | 261 | 4.41 |
| | rs13182883.2\|Chr.5\|length = 111\|allele = G | 5918 | |
| | rs740598.1\|Chr.10\|length = 114\|allele = A | 5545 | 7.30 |
| | rs740598.2\|Chr.10\|length = 114\|allele = G | 405 | |
| | rs8078417.1\|Chr.17\|length = 110\|allele = C | 8189 | 6.74 |
| | rs8078417.2\|Chr.17\|length = 110\|allele = T | 121470 | |
| | rs576261.1\|Chr.19\|length = 114\|allele = A | 58342 | 7.62 |
| | rs576261.2\|Chr.19\|length = 114\|allele = C | 4443 | |
| | Fetal Fraction (Mean ± S.D.) = 6.5 ± 1.5 | | |
| 95133 (47, XX + 18) | rs1109037.1\|Chr.2\|length = 126\|allele = A | 12229 | 2.15 |
| | rs1109037.2\|Chr.2\|length = 126\|allele = G | 263 | |
| | rs13218440.1\|Chr.6\|length = 139\|allele = A | 55949 | 3.09 |
| | rs13218440.2\|Chr.6\|length = 139\|allele = G | 1729 | |
| | rs7041158.1\|Chr.9\|length = 117\|allele = C | 7281 | 4.12 |
| | rs7041158.2\|Chr.9\|length = 117\|allele = T | 300 | |
| | rs7205345.1\|Chr.16\|length = 116\|allele = C | 53999 | 2.14 |
| | rs7205345.2\|Chr.16\|length = 116\|allele = G | 1154 | |
| | Fetal Fraction (Mean ± S.D.) = 2.9 ± 0.9 | | |
| 51236 (46, XY + 13) | rs13218440.1\|Chr.6\|length = 139\|allele = A | 1119 | 1.65 |
| | rs13218440.2\|Chr.6\|length = 139\|allele = G | 67756 | |
| | rs560681.1\|Chr.1\|length = 111\|allele = A | 14123 | 5.18 |
| | rs560681.2\|Chr.1\|length = 111\|allele = G | 732 | |
| | rs7205345.1\|Chr.16\|length = 116\|allele = C | 18176 | 1.63 |
| | rs7205345.2\|Chr.16\|length = 116\|allele = G | 296 | |
| | rs9866013.1\|Chr.3\|length = 121\|allele = C | 117 | 2.33 |
| | rs9866013.2\|Chr.3\|length = 121\|allele = T | 5024 | |
| | Fetal Fraction (Mean ± S.D.) = 2.7 ± 1.7 | | |

TABLE 4-continued

Determination of Fetal Fraction by Massively Parallel Sequencing
of an Enriched Library of Polymorphic Nucleic Acids

| Sample ID | SNP | SNP TAG COUNTS | FETAL FRACTION (%) |
|---|---|---|---|
| 54430 (45, XO) | rs1109037.1\|Chr.2\|length = 126\|allele = A | 19841 | 1.80 |
| | rs1109037.2\|Chr.2\|length = 126\|allele = G | 357 | |
| | rs9866013.1\|Chr.3\|length = 121\|allele = C | 12931 | 3.81 |
| | rs9866013.2\|Chr.3\|length = 121\|allele = T | 493 | |
| | rs7041158.1\|Chr.9\|length = 117\|allele = C | 2800 | 4.25 |
| | rs7041158.2\|Chr.9\|length = 117\|allele = T | 119 | |
| | rs740598.1\|Chr.10\|length = 114\|allele = A | 12903 | 4.87 |
| | rs740598.2\|Chr.10\|length = 114\|allele = G | 628 | |
| | rs10773760.1\|Chr.12\|length = 128\|allele = A | 46324 | 4.65 |
| | rs10773760.2\|Chr.12\|length = 128\|allele = G | 2154 | |
| | Fetal Fraction (Mean ± S.D.) = 3.9 ± 1.2 | | |

Example 6

Determination of Fetal Fraction by Massively Parallel Sequencing

Enrichment of Fetal and Maternal Nucleic Acids for Polymorphic Nucleic Acids in a Purified cfDNA Sample To enrich the fetal and maternal cfDNA contained in a purified sample of cfDNA extracted from a maternal plasma sample, a portion of the purified cfDNA was used for amplifying polymorphic target nucleic acid sequences each comprising one SNP chosen from the panel of SNPs given in Table 5.

The method corresponds to workflow 2 diagrammed in FIG. 3. Cell-free plasma was obtained from a maternal blood sample, and cfDNA was purified from the plasma sample as described in Example 1. The final concentration was determined to be 92.8 pg/μl. cfDNA contained in 5 μl of purified cfDNA was amplified in a reaction volume of 50 μl containing 7.5 μl of a 1 uM primer mix (Table 1), 10 μl of NEB 5× Mastermix and 27 μl water. Thermal cycling was performed with the Gene Amp9700 (Applied Biosystems). Using the following cycling conditions: incubating at 95° C. for 1 minute, followed by 30 cycles at 95° C. for 20 seconds, 68° C. for 1 minute, and 68° C. for 30 s, which was followed by a final incubation at 68° C. for 5 minutes. A final hold at 4° C. was added until the samples were removed for combining with the unamplified portion of the purified cfDNA sample. The amplified product was purified using the Agencourt AMPure XP PCR purification system (Part No. A63881; Beckman Coulter Genomics, Danvers, Mass.), and the concentration quantified using the Nanodrop 2000 (Thermo Scientific, Wilmington, Del.). The purified amplification product was diluted 1:10 in water and 0.9 μl (371 pg) added to 40 μl of purified cfDNA sample to obtain a 10% spike. The enriched fetal and maternal cfDNA present in the purified cfDNA sample was used for preparing a sequencing library, and was sequenced as described in Example 2.

Table 5 provides the tag counts obtained for each of chromosomes 21, 18, 13, X and Y i.e. sequence tag density, and the tag counts obtained for the informative polymorphic sequences contained in the SNP reference genome i.e. SNP tag density. The data show that sequencing information can be obtained from sequencing a single library constructed from a purified maternal cfDNA sample that has been enriched for sequences comprising SNPs to simultaneously determine the presence or absence of aneuploidy and the fetal fraction. The presence or absence of aneuploidy was determined using the number of tags mapped to chromosomes as described in U.S. Provisional Applications 61/407,017 and 61/455,849. In the example given, the data show that the fraction of fetal DNA in plasma sample AFR105 was quantifiable from the sequencing results of five informative SNPs and determined to be 3.84%. Sequence tag densities are provided for chromosomes 21, 13, 18, X and Y.

The example shows that the enrichment protocol provides the requisite tag counts for determining aneuploidy and fetal fraction from a single sequencing process.

TABLE 5

Determination of Fetal Fraction by Massively Parallel Sequencing:
Enrichment of Fetal and Maternal Nucleic Acids for Polymorphic
Nucleic Acids in a Purified cfDNA sample

| Aneuploidy | | | | | |
|---|---|---|---|---|---|
| | Chromosome 21 | Chromosome 18 | Chromosome 13 | Chromosome X | Chromosome Y |
| Sequence Tag Density | 178763 | 359529 | 388204 | 572330 | 2219 |
| Karyotype | Unaffected | Unaffected | Unaffected | Unaffected | Unaffected |

| Fetal Fraction | | |
|---|---|---|
| SNP | SNP TAG DENSITY | FETAL FRACTION (%) |
| rs10773760.1\|Chr.12\|length = 128\|allele = A | 18903 | 2.81 |
| rs10773760.2\|Chr.12\|length = 128\|allele = G | 532 | |
| rs1109037.1\|Chr.2\|length = 126\|allele = A | 347 | 5.43 |

TABLE 5-continued

Determination of Fetal Fraction by Massively Parallel Sequencing:
Enrichment of Fetal and Maternal Nucleic Acids for Polymorphic
Nucleic Acids in a Purified cfDNA sample

| | | |
|---|---|---|
| rs1109037.2\|Chr.2\|length = 126\|allele = G | 6394 | |
| rs2567608.1\|Chr.20\|length = 110\|allele = A | 94503 | 1.74 |
| rs2567608.2\|Chr.20\|length = 110\|allele = G | 1649 | |
| rs7041158.1\|Chr.9\|length = 117\|allele = C | 107 | 5.61 |
| rs7041158.2\|Chr.9\|length = 117\|allele = T | 6 | |
| rs8078417.1\|Chr.17\|length = 110\|allele = C | 162668 | 3.61 |
| rs8078417.2\|Chr.17\|length = 110\|allele = T | 5877 | |

Fetal Fraction (Mean ± S.D.) = 3.8 ± 1.7

Example 7

Determination of Fetal Fraction by Massively Parallel Sequencing

Enrichment of Fetal and Maternal Nucleic Acids for Polymorphic Nucleic Acids in a Plasma Sample To enrich the fetal and maternal cfDNA contained in an original plasma sample derived from a pregnant woman, a portion the original plasma sample was used for amplifying polymorphic target nucleic acid sequences each comprising one SNP chosen from the panel of SNPs given in Table 1, and a portion of the amplified product was combined with the remaining original plasma sample.

The method corresponds to workflow 2 diagrammed in FIG. 3. cfDNA contained in 15 µl of cell-free plasma was amplified in a reaction volume of 50 µl containing 9 ul of a 1 µM mixture of primers (15 plexTable 1), 1 µl of Phusion blood DNA polymerase, 25 ul of the 2× Phusion blood PCR buffer containing deoxynucleotide triphosphates (dNTPs: dATP, dCTP, dGTP and dTTP). Thermal cycling was performed with the Gene Amp9700 (Applied Biosystems) using the following cycling conditions: incubating at 95° C. for 3 minutes, followed by 35 cycles at 95° C. for 20 seconds, 55° C. for 30 s, and 70° C. for 1 minute, which was followed by a final incubation at 68° C. for 5 minutes. A final hold at 4° C. was added until the samples were removed for combining with the unamplified portion of the cell-free plasma. The amplified product was diluted 1:2 with water and analyzed using the Bioanalyzer. An additional 3 µl of amplified product was diluted with 11.85 µl of water to obtain a final concentration of 2 ng/µl. 2.2 µl of the diluted amplified product was combined with the remaining plasma sample. The enriched fetal and maternal cfDNA present in the plasma sample was purified as described in Example 1, and used for preparing a sequencing library. Sequencing and analysis of the sequencing data was performed as described in Example 2.

The results are given in Table 6. In the example given, the data show that the fraction of fetal DNA in plasma sample SAC2517 was quantifiable from the sequencing results of one informative SNP and determined to be 9.5%. In the example given, sample SAC2517 was shown by karyotyping to be unaffected for aneuploidies of chromosomes 21, 13, 18, X and Y. Sequence tag densities are provided for chromosomes 21, 13, 18, X and Y. The presence or absence of aneuploidy was determined using tag counts as described in U.S. Provisional Applications 61/407,017 and 61/455,849, which are herein incorporated by reference in their entirety.

The example demonstrates that enriching the mixture of fetal and maternal cfDNA present in a plasma sample for nucleic acid sequences that comprise at least one informative SNP can be used to provide the requisite sequence and SNP tag counts for determining aneuploidy and fetal fraction from a single sequencing process by massively parallel sequencing a library prepared from cfDNA contained in a plasma sample that is enriched for polymorphic nucleic acids.

TABLE 6

Determination of Fetal Fraction by Massively Parallel Sequencing:
Enrichment of Fetal and Maternal Nucleic Acids for Polymorphic
Nucleic Acids Comprising a SNP in a Plasma Sample

| | Aneuploidy | | | | |
|---|---|---|---|---|---|
| | Chromosome 21 | Chromosome 18 | Chromosome 13 | Chromosome X | Chromosome Y |
| Sequence Tag Density | 183851 | 400582 | 470526 | 714055 | 2449 |
| Karyotype | Unaffected | Unaffected | Unaffected | Unaffected | Unaffected |

| Fetal Fraction | | |
|---|---|---|
| SNP | TAG COUNTS | FETAL FRACTION (%) |
| rs10773760.1\|Chr.12\|length = 128\|allele = A | 8536 | 9.5 |
| rs10773760.2\|Chr.12\|length = 128\|allele = G | 89924 | |

Example 8

Determination of Fetal Fraction by Massively Parallel Sequencing of Samples Comprising Amplified Polymorphic Sequences

Tandem SNPs

To determine the fraction of fetal cfDNA in a maternal sample, target polymorphic nucleic acid sequences each comprising a pair of tandem SNPs are amplified and used for preparing a target library for sequencing in a massively parallel fashion. Pairs of tandem SNPs can be selected from rs7277033-rs2110153 (SEQ ID NOS 312 & 313); rs2822654-rs1882882 (SEQ ID NOS 314 & 315); rs368657-rs376635 (SEQ ID NOS 316 & 317); rs2822731-rs2822732 (SEQ ID NOS 318 & 319); rs1475881-rs7275487 (SEQ ID NOS 320 & 321); rs1735976-rs2827016 (SEQ ID NOS 322 & 323); rs447340-rs2824097 (SEQ ID NOS 324 & 325); rs418989-rs13047336 (SEQ ID NOS 326 & 327); rs987980-rs987981 (SEQ ID NOS 328 & 329); rs4143392-rs4143391 (SEQ ID NOS 330 & 331); rs1691324-rs13050434 (SEQ ID NOS 332 & 333); rs11909758-rs9980111 (SEQ ID NOS 334 & 335); rs2826842-rs232414 (SEQ ID NOS 336 & 337); rs1980969-rs1980970 (SEQ ID NOS 338 & 339); rs9978999-rs9979175 (SEQ ID NOS 340 & 341); rs1034346-rs12481852 (SEQ ID NOS 342 & 343); rs7509629-rs2828358 (SEQ ID NOS 344 & 345); rs4817013-rs7277036 (SEQ ID NOS 346 & 347); rs9981121-rs2829696 (SEQ ID NOS 348 & 349); rs455921-rs2898102 (SEQ ID NOS 350 & 351); rs2898102-rs458848 (SEQ ID NOS 352 & 353); rs961301-rs2830208 (SEQ ID NOS 354 & 355); rs2174536-rs458076 (SEQ ID NOS 356 & 357); rs11088023-rs11088024 (SEQ ID NOS 358 & 359); rs1011734-rs1011733 (SEQ ID NOS 360 & 361); rs2831244-rs9789838 (SEQ ID NOS 362 & 363); rs8132769-rs2831440 (SEQ ID NOS 364 & 365); rs8134080-rs2831524 (SEQ ID NOS 366 & 367); rs4817219-rs4817220 (SEQ ID NOS 368 & 369); rs2250911-rs2250997 (SEQ ID NOS 370 & 371); rs2831899-rs2831900 (SEQ ID NOS 372 & 373); rs2831902-rs2831903 (SEQ ID NOS 374 & 375); rs11088086-rs2251447 (SEQ ID NOS 376 & 377); rs2832040-rs11088088 (SEQ ID NOS 378 & 379); rs2832141-rs2246777 (SEQ ID NOS 380 & 381); rs2832959 rs9980934 (SEQ ID NOS 382 & 383); rs2833734-rs2833735 (SEQ ID NOS 384 & 385); rs933121-rs933122 (SEQ ID NOS 386 & 387); rs2834140-rs12626953 (SEQ ID NOS 388 & 389); rs2834485-rs3453 (SEQ ID NOS 390 & 391); rs9974986-rs2834703 (SEQ ID NOS 392 & 393); rs2776266-rs2835001 (SEQ ID NOS 394 & 395); rs1984014-rs1984015 (SEQ ID NOS 396 & 397); rs7281674-rs2835316 (SEQ ID NOS 398 & 399); rs13047304-rs13047322 (SEQ ID NOS 400 & 401); rs2835545-rs4816551 (SEQ ID NOS 402 & 403); rs2835735-rs2835736 (SEQ ID NOS 404 & 405); rs13047608-rs2835826 (SEQ ID NOS 406 & 407); rs2836550-rs2212596 (SEQ ID NOS 408 & 409); rs2836660-rs2836661 (SEQ ID NOS 410 & 411); rs465612-rs8131220 (SEQ ID NOS 412 & 413); rs9980072-rs8130031 (SEQ ID NOS 414 & 415); rs418359-rs2836926 (SEQ ID NOS 416 & 417); rs7278447-rs7278858 (SEQ ID NOS 418 & 419); rs385787-rs367001 (SEQ ID NOS 420 & 421); rs367001-rs386095 (SEQ ID NOS 422 & 423); rs2837296-rs2837297 (SEQ ID NOS 424 & 425); and rs2837381-rs4816672 (SEQ ID NOS 426 & 427). The primers used for amplifying the target sequences comprising the tandem SNPs are designed to encompass both SNP sites. For example, the forward primer is designed to encompass the first SNP, and the reverse primer is designed to encompass the second of the tandem SNP pair i.e. each of the SNP sites in the tandem pair is encompassed within the 36 bp generated by the sequencing method. Paired-end sequencing can be used to identify all sequences encompassing the tandem SNP sites. Exemplary sets of primers that are used to amplify the tandem SNPs disclosed herein are rs7277033-rs2110153_F (SEQ ID NOS 312 & 313): TCCTGGAAACAAAAGTATT (SEQ ID NO:197) and rs7277033-rs2110153_R (SEQ ID NOS 312 & 313): AACCTTACAACAAAGCTAGAA (SEQ ID NO:198), set rs2822654-rs1882882_F (SEQ ID NOS 314 & 315): ACTAAGCCTTGGGGATCCAG (SEQ ID NO:199) and rs2822654-rs1882882_R (SEQ ID NOS 314 & 315): TGCTGTGGAAATACTAAAAGG (SEQ ID NO:200), set rs368657-rs376635_F (SEQ ID NOS 316 & 317): CTCCAGAGGTAATCCTGTGA (SEQ ID NO:201) and rs368657-rs376635_R (SEQ ID NOS 316 & 317): TGGTGTGAGATGGTATCTAGG (SEQ ID NO:202), rs2822731-rs2822732_F (SEQ ID NOS 318 & 319): GTATAATCCATGAATCTTGTTT (SEQ ID NO:203) and rs2822731-rs2822732_R (SEQ ID NOS 318 & 319): TTCAAATTGTATATAAGAGAGT (SEQ ID NO:204), rs1475881-rs7275487_F (SEQ ID NOS 320 & 321): GCAGGAAAGTTATTTTTAAT (SEQ ID NO:205) and rs1475881-rs7275487_R (SEQ ID NOS 320 & 321): TGCTTGAGAAAGCTAACACTT (SEQ ID NO:206), rs1735976-rs2827016F (SEQ ID NOS 322 & 323): CAGTGTTTGGAAATTGTCTG (SEQ ID NO:207) and rs1735976-rs2827016_R (SEQ ID NOS 322 & 323): GGCACTGGGAGATTATTGTA (SEQ ID NO:208), rs447349-rs2824097_F (SEQ ID NOS 324 & 325): TCCTGTTGTTAAGTACACAT (SEQ ID NO:209) and rs447349-rs2824097_R (SEQ ID NOS 324 & 325): GGGCCGTAATTACTTTTG (SEQ ID NO:210), rs418989-rs13047336_F (SEQ ID NOS 326 & 327): ACTCAGTAGGCACTTTGTGTC (SEQ ID NO:211) and rs418989-rs13047336_R (SEQ ID NOS 326 & 327): TCTTCCACCACACCAATC (SEQ ID NO:212), rs987980-rs987981_F (SEQ ID NOS 328 & 329): TGGCTTTTCAAAGGTAAAA (SEQ ID NO:213) and rs987980-rs987981_R (SEQ ID NOS 328 & 329): GCAACGTTAACATCTGAATTT (SEQ ID NO:214), rs4143392-rs4143391_F (SEQ ID NOS 330 & 331): rs4143392-rs4143391 (SEQ ID NO:215) and rs4143392-rs4143391_R (SEQ ID NOS 330 & 331): ATTTTATATGTCATGATCTAAG (SEQ ID NO:216), rs1691324-rs13050434_F (SEQ ID NOS 332 & 333): AGAGATTACAGGTGTGAGC (SEQ ID NO:217) and rs1691324-rs13050434_R (SEQ ID NOS 332 & 333): ATGATCCTCAACTGCCTCT (SEQ ID NO:218), rs11909758-rs9980111_F (SEQ ID NOS 334 & 335): TGAAACTCAAAAGAGAAAAG (SEQ ID NO:219) and rs11909758-rs9980111_R (SEQ ID NOS 334 & 335): ACAGATTTCTACTTAAAATT (SEQ ID NO:220), rs2826842-rs232414_F (SEQ ID NOS 336 & 337): TGAAACTCAAAAGAGAAAAG (SEQ ID NO:221) and rs2826842-rs232414_R (SEQ ID NOS 336 & 337): ACAGATTTCTACTTAAAATT (SEQ ID NO:222), rs2826842-rs232414_F (SEQ ID NOS 336 & 337): GCAAAGGGGTACTCTATGTA (SEQ ID NO:223) and rs2826842-rs232414_R (SEQ ID NOS 336 & 337): TATCGGGTCATCTTGTTAAA (SEQ ID NO:224), rs1980969-rs1980970_F (SEQ ID NOS 338 & 339): TCTAACAAAGCTCTGTCCAAAA (SEQ ID NO:225) and rs1980969-rs1980970_R (SEQ ID NOS 338 & 339): CCA- CACTGAATAACTGGAACA (SEQ ID NO:226), rs9978999-rs9979175_F (SEQ ID NOS 340 & 341): GCAAGCAAGCTCTACCTTC (SEQ ID NO:227) and rs9978999-rs9979175_R (SEQ ID NOS 340 & 341): TGTTCTTCCAAAATTCACATGC (SEQ ID NO:228), rs1034346-rs12481852_F (SEQ ID NOS 342 & 343): ATTTCACTATTCCTTCATTTT (SEQ ID NO:229) and rs1034346-rs12481852_R (SEQ ID NOS 342 & 343): TAATTGTTGCACACTAAATTAC (SEQ ID NO:230), rs4817013-rs7277036_F: (SEQ ID NOS 346 & 347) AAAAAGCCACAGAAATCAGTC (SEQ ID NO:231) and rs4817013-rs7277036_R (SEQ ID NOS 346 & 347): TTCTTATATCTCACTGGGCATT (SEQ ID NO:232), rs9981121-rs2829696_F (SEQ ID NOS 348 & 349): GGATGGTAGAAGAGAAGAAAGG (SEQ ID NO:233) and rs9981121-rs2829696_R (SEQ ID NOS 348 & 349): GGATGGTAGAAGAGAAGAAAGG (SEQ ID NO:234), rs455921-rs2898102_F (SEQ ID NOS 350 & 351): TGCAAAGATGCAGAACCAAC (SEQ ID NO:235) and rs455921-rs2898102_R (SEQ ID NOS 350 & 351): TTTTGTTCCTTGTCCTGGCTGA (SEQ ID NO:236), rs2898102-rs458848_F (SEQ ID NOS 352 & 353): TGCAAAGATGCAGAACCAAC (SEQ ID NO:237) and rs2898102-rs458848_R (SEQ ID NOS 352 & 353): GCCTCCAGCTCTATCCAAGTT (SEQ ID NO:238), rs961301-rs2830208_F (SEQ ID NOS 354 & 355): CCTTAATATCTTCCCATGTCCA (SEQ ID NO:239) and rs961301-rs2830208_R (SEQ ID NOS 354 & 355): ATTGTTAGTGCCTCTTCTGCTT (SEQ ID NO:240), rs2174536-rs458076_F (SEQ ID NOS 356 & 357): GAGAAGTGAGGTCAGCAGCT (SEQ ID NO:241) and rs2174536-rs458076_R (SEQ ID NOS 356 & 357): TTTCTAAATTTCCATTGAACAG (SEQ ID NO:242), rs11088023-rs11088024_F (SEQ ID NOS 358 & 359): GAAATTGGCAATCTGATTCT (SEQ ID NO:243) and rs11088023-rs11088024_R (SEQ ID NOS 358 & 359): CAACTTGTCCTTTATTGATGT (SEQ ID NO:244), rs1011734-rs1011733_F (SEQ ID NOS 360 & 361): CTATGTTGATAAAACATTGAAA (SEQ ID NO:245) and rs1011734-rs1011733_R (SEQ ID NOS 360 & 361): GCCTGTCTGGAATATAGTTT (SEQ ID NO:246), rs2831244-rs9789838_F (SEQ ID NOS 362 & 363): CAGGGCATATAATCTAAGCTGT (SEQ ID NO:247) and rs2831244-rs9789838_R (SEQ ID NOS 362 & 363): CAATGACTCTGAGTTGAGCAC (SEQ ID NO:248), rs8132769-rs2831440_F (SEQ ID NOS 364 & 365): ACTCTCTCCCTCCCCTCT (SEQ ID NO:249) and rs8132769-rs2831440_R (SEQ ID NOS 364 & 365): TATGGCCCCAAAACTATTCT (SEQ ID NO:250), rs8134080-rs2831524_F (SEQ ID NOS 366 & 367): ACAAGTACTGGGCAGATTGA (SEQ ID NO:251) and rs8134080-rs2831524_R (SEQ ID NOS 366 & 367): GCCAGGTTTAGCTTTCAAGT (SEQ ID NO:252), rs4817219-rs4817220_F (SEQ ID NOS 368 & 369): TTTTATATCAGGAGAAACACTG (SEQ ID NO:253) and rs4817219-rs4817220_R (SEQ ID NOS 368 & 369): CCAGAATTTTGGAGGTTTAAT (SEQ ID NO:254), rs2250911-rs2250997_F (SEQ ID NOS 370 & 371): TGTCATTCCTCCTTTATCTCCA (SEQ ID NO:255) and rs2250911-rs2250997_R (SEQ ID NOS 370 & 371): TTCTTTTGCCTCTCCCAAAG (SEQ ID NO:256), rs2831899-rs2831900_F (SEQ ID NOS 372 & 373): ACCCTGGCACAGTGTTGACT (SEQ ID NO:257) and rs2831899-rs2831900_R (SEQ ID NOS 372 & 373): TGGGCCTGAGTTGAGAAGAT (SEQ ID NO:258), rs2831902-rs2831903_F (SEQ ID NOS 374 & 375): AATTTGTAAGTATGTGCAACG (SEQ ID NO:259) and rs2831902-rs2831903_R (SEQ ID NOS 374 & 375): TTTTTCCCATTTCCAACTCT (SEQ ID NO:260), rs11088086-rs2251447_F (SEQ ID NOS 376 & 377): AAAAGATGAGACAGGCAGGT (SEQ ID NO:261) and rs11088086-rs2251447_R (SEQ ID NOS 376 & 377): ACCCCTGTGAATCTCAAAAT (SEQ ID NO:262), rs2832040-rs11088088_F (SEQ ID NOS 378 & 379): GCACTTGCTTCTATTGTTTGT (SEQ ID NO:263) and rs2832040-rs11088088_R (SEQ ID NOS 378 & 379): CCCTTCCTCTCTTCCATTCT (SEQ ID NO:264), rs2832141-rs2246777_F (SEQ ID NOS 380 & 381): AGCACTGCAGGTA (SEQ ID NO:265) and rs2832141-rs2246777_R (SEQ ID NOS 380 & 381): ACAGATACCAAAGAACTGCAA (SEQ ID NO:266), rs2832959 rs9980934_F (SEQ ID NOS 382 & 383): TGGACACCTTTCAACTTAGA (SEQ ID NO:267) and rs2832959 rs9980934_R (SEQ ID NOS 382 & 383): GAACAGTAATGTTGAACTTTTT (SEQ ID NO:268), rs2833734-rs2833735_F (SEQ ID NOS 384 & 385): TCTTGCAAAAAGCTTAGCACA (SEQ ID NO:269) and rs2833734-rs2833735_R (SEQ ID NOS 384 & 385): AAAAAGATCTCAAAGGGTCCA (SEQ ID NO:270), rs933121-rs933122_F (SEQ ID NOS 386 & 387): GCTTTTGCTGAACATCAAGT (SEQ ID NO:271) and rs933121-rs933122_R (SEQ ID NOS 386 & 387): CCTTCCAGCAGCATAGTCT (SEQ ID NO:272), rs2834140-rs12626953_F (SEQ ID NOS 388 & 389): AAATCCAGGATGTGCAGT (SEQ ID NO:273) and rs2834140-rs12626953_R (SEQ ID NOS 388 & 389): ATGATGAGGTCAGTGGTGT (SEQ ID NO:274), rs2834485-rs3453_F (SEQ ID NOS 390 & 391): CATCACAGATCATAGTAAATGG (SEQ ID NO:275) and rs2834485-rs3453_R (SEQ ID NOS 390 & 391): AATTATTATTTTGCAGGCAAT (SEQ ID NO:276), rs9974986-rs2834703_F (SEQ ID NOS 392 & 393): CATGAGGCAAACACCTTTCC (SEQ ID NO:277) and rs9974986-rs2834703_R (SEQ ID NOS 392 & 393): GCTGGACTCAGGATAAAGAACA (SEQ ID NO:278), rs2776266-rs2835001_F (SEQ ID NOS 394 & 395): TGGAAGCCTGAGCTGACTAA (SEQ ID NO:279) and rs2776266-rs2835001_R (SEQ ID NOS 394 & 395): CCTTCTTTTCCCCCAGAATC (SEQ ID NO:280), rs1984014-rs1984015_F (SEQ ID NOS 396 & 397): TAGGAGAACAGAAGATCAGAG (SEQ ID NO:281) and rs1984014-rs1984015_R (SEQ ID NOS 396 & 397): AAAGACTATTGCTAAATGCTTG (SEQ ID NO:282), rs7281674-rs2835316_F (SEQ ID NOS 398 & 399): TAAGCGTAGGGCTGTGTGTG (SEQ ID NO:283) and rs7281674-rs2835316_R (SEQ ID NOS 398 & 399): GGACGGATAGACTCCAGAAGG (SEQ ID NO:284), rs13047304-rs13047322_F (SEQ ID NOS 400 & 401): GAATGACCTTGGCACTTTTATCA (SEQ ID NO:285) and rs13047304-rs13047322_R (SEQ ID NOS 400 & 401): AAGGATAGAGATATACAGATGAATGGA (SEQ ID NO:286), rs2835735-rs2835736_F (SEQ ID NOS 404 & 405): CATGCACCGCGCAAATAC (SEQ ID NO:287) and rs2835735-rs2835736_R (SEQ ID NOS 404 & 405): ATGCCTCACCCACAAACAC (SEQ ID NO:288), rs13047608-rs2835826_F (SEQ ID NOS 406 & 407): TCCAAGCCCTTCTCACTCAC (SEQ ID NO:289) and rs13047608-rs2835826_R (SEQ ID NOS 406 & 407): CTGGGACGGTGACATTTTCT (SEQ ID NO:290), rs2836550-rs2212596_F (SEQ ID NOS 408 & 409): CCCAGGAAGAGTGGAAAGATT (SEQ ID NO:291) and rs2836550-rs2212596_R (SEQ ID NOS 408 & 409): TTAGCTTGCATGTACCTGTGT (SEQ ID NO:292), rs2836660-rs2836661_F (SEQ ID NOS 410 & 411):

AGCTAGATGGGGTGAATTTT (SEQ ID NO:293) and _R: TGGGCTGAGGGGAGATTC (SEQ ID NO:294), rs465612-rs8131220_F (SEQ ID NOS 412 & 413): ATCAAGCTAATTAATGTTATCT (SEQ ID NO:295) and rs465612-rs8131220_R (SEQ ID NOS 412 & 413): AAT-GAATAAGGTCCTCAGAG (SEQ ID NO:296), rs9980072-rs8130031_F (SEQ ID NOS 414 & 415): TTTAATCTGATCATTGCCCTA (SEQ ID NO:297) and rs9980072-rs8130031_R (SEQ ID NOS 414 & 415): AGCT-GTGGGTGACCTTGA (SEQ ID NO:298), rs418359-rs2836926_F (SEQ ID NOS 416 & 417): TGTCCCACCAT-TGTGTATTA (SEQ ID NO:299) and rs418359-rs2836926_R (SEQ ID NOS 416 & 417): TCAGACTTGAAGTCCAGGAT (SEQ ID NO:300), rs7278447-rs7278858_F (SEQ ID NOS 418 & 419): GCT-TCAGGGGTGTTAGTTTT (SEQ ID NO:301) and rs7278447-rs7278858_R (SEQ ID NOS 418 & 419): CTTT-GTGAAAAGTCGTCCAG (SEQ ID NO:302), rs385787-rs367001_F (SEQ ID NOS 420 & 421): CCATCATG-GAAAGCATGG (SEQ ID NO:303) and rs385787-rs367001_R (SEQ ID NOS 420 & 421): TCATCTCCATGACTGCACTA (SEQ ID NO:304), rs367001-rs386095_F (SEQ ID NOS 422 & 423): GAGAT-GACGGAGTAGCTCAT (SEQ ID NO:305) and rs367001-rs386095_R (SEQ ID NOS 422 & 423): CCCAGCTG-CACTGTCTAC (SEQ ID NO:306), rs2837296-rs2837297_F (SEQ ID NOS 424 & 425): TCTTGTTCCAATCACAGGAC (SEQ ID NO:307) and rs2837296-rs2837297_R (SEQ ID NOS 424 & 425): ATGCTGTTAGCTGAAGCTCT (SEQ ID NO:308), and rs2837381-rs4816672_F (SEQ ID NOS 426 & 427): TGAAAGCTCCTAAAGCAGAG (SEQ ID NO:309) and rs2837381-rs4816672_R (SEQ ID NOS 426 & 427): TTGAAGAGATGTGCTATCAT (SEQ ID NO:310). Polynucleotide sequences e.g. GC clamp sequences, can be included to ensure specific hybridization of AT-rich primers (Ghanta et al., PLOS ONE 5(10): doi10.1371/journal.pone.0013184 [2010], available on the world wide web at plosone.org). An example of a GC clamp sequence that can be included either 5' of the forward primer or 3' of the reverse primer is GCCGCCTGCAGCCCGCGC-CCCCCGTGCCCCCGCCCCGCCGCCGGC-CCGGGCGCC (SEQ ID NO:311). Polymorphic sequences can be used alone or in combination with unamplified cfDNA to determine either fetal fraction or the presence or absence of aneuploidy and fetal fraction in a maternal sample as described for polymorphic SNP sequences. Sample preparation and enrichment of cfDNA sequencing library, a purified cfDNA sample, and a plasma sample is performed according to the method described in Examples 5, 6, and 7, respectively. All sequencing libraries are prepared as described in Example 2a., and sequencing is performed as described in Example 2b. Analysis of the sequencing data for the determination of fetal aneuploidy is performed as described in Example 5. Concomitant to the analysis for determining aneuploidy, the sequencing data is analyzed to determine the fetal fraction as follows. Following the transfer of the image and base call files to the Unix server miming the Illumina "Genome Analyzer Pipeline" software version 1.51 as described in Example 3a., the 36 bp reads are aligned to a 'tandem SNP genome' using the BOWTIE program. The tandem SNP genome is identified as the grouping of the DNA sequences that encompass the alleles of the 58 tandem SNP pairs disclosed above. Only reads that mapped uniquely to the tandem SNP genome are used for the analysis of fetal fraction. Reads that match perfectly to the tandem SNP genome are counted as tags and filtered. Of the remaining reads, only reads having one or two mismatches are counted as tags and included in the analysis. Tags mapped to each of the tandem SNP alleles are counted, and the fetal fraction is determined essentially as described in Example 6 above but accounting for tags mapped to the two tandem SNP alleles x and y present on each of the amplified polymorphic target nucleic acid sequences that are amplified to enrich the samples i.e.

% fetal fraction allele$_{x+y}$=(($\Sigma$Fetal sequence tags for allele$_{x+y}$)/($\Sigma$Maternal sequence tags for allele$_{x+y}$))$\times$100

Only informative tandem SNPs are used to determine the fetal fraction.

Optionally, the fraction of fetal nucleic acids in the mixture of fetal and maternal nucleic acids is calculated for each of the informative allele (allele$_{x+y}$) as follows:

% fetal fraction allele$_{x+y}$=((2$\times\Sigma$Fetal sequence tags for allele$_{x+y}$)/($\Sigma$Maternal sequence tags for allele$_{x+y}$))$\times$100, to compensate for the presence of 2 sets of tandem fetal alleles, one being masked by the maternal background.

The percent fetal fraction is calculated for at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, or more informative sets of tandem alleles. In one embodiment, the fetal fraction is the average fetal fraction determined for at least 3 informative sets of tandem alleles.

Example 9

Determination of Fetal Fraction by Massively Parallel Sequencing of Samples Comprising Amplified Polymorphic Sequences STRs To determine the fraction of fetal cfDNA in a maternal sample, target polymorphic nucleic acid sequences each comprising an STR are amplified and used for preparing a target library for sequencing in a massively parallel fashion.

Peripheral blood samples are obtained from pregnant subjects, and cfDNA is purified from the plasma fraction as described in Examples 1 and 2 STRs that are amplified are chosen from the codis and non-codis STRs disclosed in Table 7, and amplification of the polymorphic STR sequences is obtained using the corresponding sets of primers provided. For example, the STRs listed in Table 7 are amplified using the corresponding primers (SEQ ID NOs: 113-197), and the amplified product is used to generate a target sequencing library. The STR target sequencing library is prepared as described for the preparation of the SNP target library as described in Example 8. STRs CSF1PO, D13S317, D16S539, D18S51, D21S11, D2S1338D7S820, and FGA have been analyzed previously for determining fetal fraction, and are disclosed in U.S. Provisional applications 61/296,358 and 61/360,837.

TABLE 7

CODIS and NON-CODIS miniSTRs

| STR Locus (Marker Name) | Chromosome Location | Size Range (bp) | GenBank Accession | Primer Sequences (Forward/Reverse) |
|---|---|---|---|---|
| Codis miniSTR loci* | | | | |
| CSF1PO | 5q33.1 | 89-129 | X14720 | ACAGTAACTGCCTTCATAGATAG (CSF1PO_F; SEQ ID NO: 113) GTGTCAGACCCTGTTCTAAGTA (CSF1PO_R; SEQ ID NO: 114) |
| FGA | 4q31.3 | 125-281 | M64982 | AAATAAAATTAGGCATATTTACAAGC (FGA_F; SEQ ID NO: 115) GCTGAGTGATTTGTCTGTAATTG (FGA_R; SEQ ID NO: 116) |
| TH01 | 11p15.5 | 51-98 | D00269 | CCTGTTCCTCCCTTATTTCCC (TH01_F; SEQ ID NO: 117) GGGAACACAGACTCCATGGTG (TH01_R; SEQ ID NO: 118) |
| TPOX | 2p25.3 | 65-101 | M68651 | CTTAGGGAACCCTCACTGAATG (TPOX_F; SEQ ID NO: 119) GTCCTTGTCAGCGTTTATTTGC (TPOX_R; SEQ ID NO: 120) |
| vWA | 12p13.31 | 88-148 | M25858 | AATAATCAGTATGTGACTTGGATTGA (vWA_F; SEQ ID NO: 121) ATAGGATGGATGGATAGATGGA (vWA_R; SEQ ID NO: 122) |
| D3S1358 | 3p21.31 | 72-120 | NT_005997 | CAGAGCAAGACCCTGTCTCAT (D3S1358_F; SEQ ID NO: 123) TCAACAGAGGCTTGCATGTAT (D3S1358_R; SEQ ID NO: 124) |
| D5S818 | 5q23.2 | 81-117 | AC008512 | GGGTGATTTTCCTCTTTGGT (D5S818_F; SEQ ID NO: 125) AACATTTGTATCTTTATCTGTATCCTTATTTAT (D5S818_R; SEQ ID NO: 126) |
| D7S820 | 7q21.11 | 136-176 | AC004848 | GAACACTTGTCATAGTTTAGAACGAAC (D7S820_F; SEQ ID NO: 127) TCATTGACAGAATTGCACCA (D7S820_R; SEQ ID NO: 128) |
| D8S1179 | 8q24.13 | 86-134 | AF216671 | TTTGTATTTCATGTGTACATTCGTATC (D7S820_F; SEQ ID NO: 129) ACCTATCCTGTAGATTATTTTCACTGTG (D7S820_R; SEQ ID NO: 130) |
| D13S317 | 13q31.1 | 88-132 | AL353628 | TCTGACCCATCTAACGCCTA (D13S317_F; SEQ ID NO: 131) CAGACAGAAAGATAGATAGATGATTGA (D13S317_R; SEQ ID NO: 132) |
| D16S539 | 16q24.1 | 81-121 | AC024591 | ATACAGACAGACAGACAGGTG (D16S539_F; SEQ ID NO: 133) GCATGTATCTATCATCCATCTCT (D16S539_R; SEQ ID NO: 134) |
| D18S51 | 18q21.33 | 113-193 | AP001534 | TGAGTGACAAATTGAGACCTT (D18S51_F; SEQ ID NO: 135) GTCTTACAATAACAGTTGCTACTATT (D18S51_R; SEQ ID NO: 136) |
| D21S11 | 21q21.1 | 153-221 | AP000433 | ATTCCCCAAGTGAATTGC (D21S11_F; SEQ ID NO: 137) GGTAGATAGACTGGATAGATAGACGA (D21S11_R; SEQ ID NO: 138) |
| D2S1338 | 2q35 | 90-142 | AC01036 | TGGAAACAGAAATGGCTTGG (D2S1338_F; SEQ ID NO: 139) GATTGCAGGAGGGAAGGAAG (D2S1338_R; SEQ ID NO: 140) |

TABLE 7-continued

CODIS and NON-CODIS miniSTRs

| STR Locus (Marker Name) | Chromosome Location | Size Range (bp) | GenBank Accession | Primer Sequences (Forward/Reverse) |
|---|---|---|---|---|
| Penta D | 21q22.3 | 94-167 | AP001752 | GAGCAAGACACCATCTCAAGAA (Penta D_F; SEQ ID NO: 141)<br>GAAATTTTACATTTATGTTTATGATTCTCT (Penta D_R; SEQ ID NO: 142) |
| Penta E | 15q26.2 | 80-175 | AC027004 | GGCGACTGAGCAAGACTC (Penta E_F; SEQ ID NO: 143)<br>GGTTATTAATTGAGAAAACTCCTTACA (Penta E_R; SEQ ID NO: 144) |
| Non-Codis miniSTR loci* ||||||
| D22S1045 | 22q12.3 | 82-115 | AL022314 (17) | ATTTTCCCCGATGATAGTAGTCT (D22S1045_F; SEQ ID NO: 145)<br>GCGAATGTATGATTGGCAATATTTTT (D22S1045_R; SEQ ID NO: 146) |
| D20S1082 | 20q13.2 | 73-101 | AL158015 | ACATGTATCCCAGAACTTAAAGTAAAC (D20S1082_F; SEQ ID NO: 147)<br>GCAGAAGGGAAAATTGAAGCTG (D20S1082_R; SEQ ID NO: 148) |
| D20S482 | 20p13 | 85-126 | AL121781 (14) | CAGAGACACCGAACCAATAAGA (D20S482_F; SEQ ID NO: 149)<br>GCCACATGAATCAATTCCTATAATAAA (D20S482_R; SEQ ID NO: 150) |
| D18S853 | 18p11.31 | 82-104 | AP005130 (11) | GCACATGTACCCTAAAACTTAAAAT (D18S853_F; SEQ ID NO: 151)<br>GTCAACCAAAACTCAACAAGTAGTAA (D18S853_R; SEQ ID NO: 152) |
| D17S1301 | 17q25.1 | 114-139 | AC016888 (12) | AAGATGAAATTGCCATGTAAAAATA (D17S1301_F; SEQ ID NO: 153)<br>GTGTGTATAACAAAATTCCTATGATGG (D17S1301_R; SEQ ID NO: 154) |
| D17S974 | 17p13.1 | 114-139 | AC034303 (10) | GCACCCAAAACTGAATGTCATA (D17S974_F; SEQ ID NO: 155)<br>GGTGAGAGTGAGACCCTGTC (D17S974_R; SEQ ID NO: 156) |
| D14S1434 | 14q32.13 | 70-98 | AL121612 (13) | TGTAATAACTCTACGACTGTCTGTCTG (D14S1434_F; SEQ ID NO: 157)<br>GAATAGGAGGTGGATGGATGG (D14S1434_R; SEQ ID NO: 158) |
| D12ATA63 | 12q23.3 | 76-106 | AC009771 (13) | GAGCGAGACCCTGTCTCAAG (D12ATA63_F; SEQ ID NO: 159)<br>GGAAAAGACATAGGATAGCAATTT (D12ATA63_R; SEQ ID NO: 160) |
| D11S4463 | 11q25 | 88-116 | AP002806 (14) | TCTGGATTGATCTGTCTGTCC (D11S4463_F; SEQ ID NO: 161)<br>GAATTAAATACCATCTGAGCACTGAA (D11S4463_R; SEQ ID NO: 162) |
| D10S1435 | 10p15.3 | 82-139 | AL354747 (11) | TGTTATAATGCATTGAGTTTTATTCTG (D10S1435_F; SEQ ID NO: 163)<br>GCCTGTCTCAAAAATAAAGAGATAGACA (D10S1435_R; SEQ ID NO: 164) |
| D10S1248 | 10q26.3 | 79-123 | AL391869 (13) | TTAATGAATTGAACAAATGAGTGAG (D10S1248_F; SEQ ID NO: 165)<br>GCAACTCTGGTTGTATTGTCTTCAT (D10S1248_R; SEQ ID NO: 166) |
| D9S2157 | 9q34.2 | 71-107 | AL162417 (10) | CAAAGCGAGACTCTGTCTCAA (D9S2157_F; SEQ ID NO: 167)<br>GAAAATGCTATCCTCTTTGGTATAAAT (D9S2157_R; SEQ ID NO: 168) |

TABLE 7-continued

CODIS and NON-CODIS miniSTRs

| STR Locus (Marker Name) | Chromosome Location | Size Range (bp) | GenBank Accession | Primer Sequences (Forward/Reverse) |
|---|---|---|---|---|
| D9S1122 | 9q21.2 | 93-125 | AL161789 (12) | GGGTATTTCAAGATAACTGTAGATAGG (D9S1122_F; SEQ ID NO: 169)<br>GCTTCTGAAAGCTTCTAGTTTACC (D9S1122_R; SEQ ID NO: 170) |
| D8S1115 | 8p11.21 | 63-96 | AC090739 (9) | TCCACATCCTCACCAACAC (D8S1115_F; SEQ ID NO: 171)<br>GCCTAGGAAGGCTACTGTCAA (D8S1115_R; SEQ ID NO: 172) |
| D6S1017 | 6p21.1 | 81-110 | AL035588 (10) | CCACCCGTCCATTTAGGC (D6S1017_F; SEQ ID NO: 173)<br>GTGAAAAAGTAGATATAATGGTTGGTG (D6S1017_R; SEQ ID NO: 174) |
| D6S474 | 6q21 | 107-136 | AL357514 (17) | GGTTTTCCAAGAGATAGACCAATTA (D6S474_F; SEQ ID NO: 175)<br>GTCCTCTCATAAATCCCTACTCATATC (D6S474_R; SEQ ID NO: 176) |
| D5S2500 | 5q11.2 | 85-126 | AC008791 (17) | CTGTTGGTACATAATAGGTAGGTAGGT (D5S2500_F; SEQ ID NO: 177)<br>GTCGTGGGCCCCATAAATC (D5S2500_R; SEQ ID NO: 178) |
| D4S2408 | 4p15.1 | 85-109 | AC110763 (9) | AAGGTACATAACAGTTCAATAGAAAGC (D4S2408_F; SEQ ID NO: 179)<br>GTGAAATGACTGAAAAATAGTAACCA (D4S2408_R; SEQ ID NO: 180) |
| D4S2364 | 4q22.3 | 67-83 | AC022317 (9) | CTAGGAGATCATGTGGGTATGATT (D4S2364U_F; SEQ ID NO: 181)<br>GCAGTGAATAAATGAACGAATGGA (D4S236_4R; SEQ ID NO: 182) |
| D3S4529 | 3p12.1 | 111-139 | AC117452 (13) | CCCAAAATTACTTGAGCCAAT (D3S452_F; SEQ ID NO: 183)<br>GAGACAAAATGAAGAAACAGACAG (D3S452_R; SEQ ID NO: 184) |
| D3S3053 | 3q26.31 | 84-108 | AC069259 (9) | TCTTTGCTCTCATGAATAGATCAGT (D3S3053_F; SEQ ID NO: 185)<br>GTTTGTGATAATGAACCCACTCAG (D3S3053_R; SEQ ID NO: 186) |
| D2S1776 | 2q24.3 | 127-161 | AC009475 (11) | TGAACACAGATGTTAAGTGTGTATATG (D2S1776_F; SEQ ID NO: 187)<br>GTCTGAGGTGGACAGTTATGAAA (D2S1776_R; SEQ ID NO: 188) |
| D2S441 | 2p14 | 78-110 | AC079112 (12) | CTGTGGCTCATCTATGAAAACTT (D2S441_F; SEQ ID NO: 189)<br>GAAGTGGCTGTGGTGTTATGAT (D2S441_R; SEQ ID NO: 190) |
| D1S1677 | 1q23.3 | 81-117 | AL513307 (15) | TTCTGTTGGTATAGAGCAGTGTTT (D1S1677_F; SEQ ID NO: 191)<br>GTGACAGGAAGGACGGAATG (D1S1677_R; SEQ ID NO: 192) |
| D1S1627 | 1p21.1 | 81-100 | AC093119 (13) | CATGAGGTTTGCAAATACTATCTTAAC (D1S1627_F; SEQ ID NO: 193)<br>GTTTTAATTTTCTCCAAATCTCCA (D1S1627_R; SEQ ID NO: 194) |
| D1GATA113 | 1p36.23 | 81-105 | Z97987 (11) | TCTTAGCCTAGATAGATACTTGCTTCC (D1GATA113F; SEQ ID NO: 195)<br>GTCAACCTTTGAGGCTATAGGAA (D1GATA113R; SEQ ID NO: 196) |

*(Butler et al., *J Forensic Sci* 5:1054-1064; Hill et al., Poster #44- 17th International Symposium on Human Identification- 2006)

Sequencing of the library enriched for polymorphic STR sequences is performed using a NGS technology e.g. sequencing by synthesis. Sequence reads of lengths that encompass the STRs e.g. miniSTRs of at least 100 bp, to a reference STR genome consisting of the polymorphic sequences which were amplified in the sample. Informative STR alleles are identified by differences in the length of the repeats, and the number of STR sequence tags are counted, and used to determine the fetal fraction. Optionally, amplification of the polymorphic STR sequences is performed to enrich a plasma sample, a purified cfDNA sample or a cfDNA sequencing library sample, as described in Examples 5, 6, and 7, respectively.

Example 10

Determination of Fetal Fraction by Capillary Electrophoresis of Polymorphic Sequences Comprising STRs To determine fetal fraction in maternal samples comprising fetal and maternal cfDNA, peripheral blood samples were collected from volunteer pregnant women carrying either male or female fetuses. Peripheral blood samples were obtained and processed to provide purified cfDNA as described in Example 1

Ten microliters of cfDNA samples were analyzed using the AmpFlSTR® MiniFiler™ PCR amplification kit (Applied Biosystems, Foster City, Calif.) according to the manufacturer's instructions. Briefly, cfDNA contained in 10 µl was amplified in a reaction volume of 25 µl containing 5 µL fluorescently labeled primers (AmpF/STR® MiniFiler™ Primer Set), and the AmpF/STR® MiniFiler™ Master Mix, which includes AmpliTaq Gold® DNA polymerase and associated buffer, salt (1.5 mM MgCl2), and 200 µM deoxynucleotide triphosphates (dNTPs: dATP, dCTP, dGTP and dTTP). The fluorescently labeled primers are forward primers that are labeled with 6FAM™, VIC™, NED™, and PET™ dyes. Thermal cycling was performed with the Gene Amp9700 (Applied Biosystems) using the following cycling conditions: incubating at 95° C. for 10 minutes, followed by 30 cycles at 94° C. for 20 seconds, 59° C. for 2 minute, and 72° C. for 1 minute, which was followed by a final incubation at 60° C. for 45 minutes. A final hold at 4° C. was added until the samples were removed for analysis. The amplified product was prepared by diluting 1 ul of amplified product in 8.7 ul Hi-Di™ formamide (Applied Biosystems) and 0.3 µl GeneScan™-500 LIZ internal size standard (Applied Biosystems), and analyzed with an ABI PRISM3130xl Genetic Analyzer (Applied Biosystems) using Data Collection HID_G5_POP4 (Applied Biosystems), and a 36-cm capillary array. All genotyping was performed with GeneMapper_ID v3.2 software (Applied Biosystems) using manufacturer provided allelic ladders and bins and panels.

All genotyping measurement were performed on the Applied Biosystems 3130xl Genetic Analyzer, using a ±0.5-nt "window" around the size obtained for each allele to allow for detection and correct assignment of alleles. Any sample allele whose size was outside the ±0.5-nt window was determined to be OL i.e. "Off Ladder". OL alleles are alleles of a size that is not represented in the AmpF/STR® MiniFiler™ Allelic Ladder or an allele that does not correspond to an allelic ladder, but whose size is just outside a window because of measurement error. The minimum peak height threshold of >50 RFU was set based on validation experiments performed to avoid typing when stochastic effects are likely to interfere with accurate interpretation of mixtures. The calculation of fetal fraction is based on averaging all informative markers. Informative markers are identified by the presence of peaks on the electropherogram that fall within the parameters of preset bins for the STRs that are analyzed.

Calculations of fetal fraction were performed using the average peak height for major and minor alleles at every STR locus determined from triplicate injections. The rules applied to the calculation are:

1. off-ladder allele (OL) data for alleles are not included in the calculation; and
2. only peak heights derived from >50 RFU (relative fluorescence units) are included in the calculation
3. if only one bin is present the marker is deemed non-informative; and
4. if a second bin is called but the peaks of the first and second bins are within 50-70% of their relative fluorescence units (RFU) in peak height, the minority fraction is not measured and the marker is deemed not informative.

The fraction of the minor allele for any given informative marker is calculated by dividing the peak height of the minor component by the sum of the peak height for the major component, and expressed as a percent was first calculated for each informative locus as $$\text{fetal fraction} = (\Sigma \text{peak height of minor allele}/\Sigma \text{peak height of major allele(s)}) \times 100,$$

The fetal fraction for a sample comprising two or more informative STRs, would be calculated as the average of the fetal fractions calculated for the two or more informative markers.

Table 8 provides the data obtained from analyzing cfDNA of a subject pregnant with a male fetus.

TABLE 8

Fetal Fraction Determined in cfDNA of a Pregnant Subject by Analysis of STRs

| STR | Allele 1 | Allele 2 | Allele 3 | Allele 1 Height | Allele 2 Height | Allele 3 Height | Fetal Fraction | Fetal Fraction (Mean/STR) |
|---|---|---|---|---|---|---|---|---|
| AMEL | X | Y | | 3599 | 106 | | 2.9 | |
| AMEL | X | Y | | 3602 | 110 | | 3.1 | |
| AMEL | X | Y | | 3652 | 109 | | 3.0 | 3.0 |
| CSF1PO | 11 | 12 | | 2870 | 2730 | | | |
| CSF1PO | 11 | 12 | | 2924 | 2762 | | | |
| CSF1PO | 11 | 12 | | 2953 | 2786 | | | |
| D13S317 | 11 | 12 | | 2621 | 2588 | | | |
| D13S317 | 11 | 12 | | 2680 | 2619 | | | |
| D13S317 | 11 | 12 | | 2717 | 2659 | | | |
| D16S539 | 9 | 11 | | 1056 | 1416 | | | |
| D16S539 | 9 | 11 | | 1038 | 1394 | | | |

TABLE 8-continued

Fetal Fraction Determined in cfDNA of a Pregnant Subject by Analysis of STRs

| STR | Allele 1 | Allele 2 | Allele 3 | Allele 1 Height | Allele 2 Height | Allele 3 Height | Fetal Fraction | Fetal Fraction (Mean/STR) |
|---|---|---|---|---|---|---|---|---|
| D16S539 | 9 | 11 | | 1072 | 1437 | | | |
| D18S51 | 13 | 15 | | 2026 | 1555 | | | |
| D18S51 | 13 | 15 | | 2006 | 1557 | | | |
| D18S51 | 13 | 15 | | 2050 | 1578 | | | |
| D21S11 | 28 | 31.2 | | 2450 | 61 | | 2.5 | |
| D21S11 | 28 | 31.2 | | 2472 | 62 | | 2.5 | |
| D21S11 | 28 | 31.2 | | 2508 | 67 | | 2.7 | 2.6 |
| D2S1338 | 20 | 23 | | 3417 | 3017 | | | |
| D2S1338 | 20 | 23 | | 3407 | 3020 | | | |
| D2S1338 | 20 | 23 | | 3493 | 3055 | | | |
| D7S820 | 9 | 12 | 13 | 2373 | 178 | 1123 | 5.1 | |
| D7S820 | 9 | 12 | 13 | 2411 | 181 | 1140 | 5.1 | |
| D7S820 | 9 | 12 | 13 | 2441 | 182 | 1156 | 5.1 | 5.1 |
| FGA | 17.2 | 22 | 25 | 68 | 1140 | 896 | 3.3 | |
| FGA | 17.2 | 22 | 25 | 68 | 1144 | 909 | 3.1 | |
| FGA | 17.2 | 22 | 25 | 68 | 1151 | 925 | 3.3 | 3.2 |

Fetal Fraction = 3.5

The results show that cfDNA can be used for determining the presence or absence of fetal DNA as indicated by the detection of a minor component at one or more STR alleles, for determining the percent fetal fraction, and for determining fetal gender as indicated by the presence or absence of the Amelogenin allele.

Example 11

Preamplification of cfDNA for Determining Fetal Fraction by Capillary Electrophoresis of Polymorphic Sequences Comprising STRs To improve the sensitivity of the STR assay in detecting and quantifying the STR alleles in the minor contributor of the cfDNA sample, the number of starting genomes in the artificial samples was increased by a modified whole genome amplification strategy.

Peripheral blood samples were collected and processed as described in Example 2. Cell-free DNA was extracted from 1 ml cell-free plasma using the Roche MagNA Pure Compact Nucleic Acid Isolation Kit I Large Volume (Roche Applied Science, IN) using the MagNA Pure Compact Instrument, and eluted in 50 µl of elution buffer. Ten microliters of the extracted cfDNA were used to quantify the cfDNA, and the remainder was stored (see storage instructions WI0035 Clinical Sample Storage). The concentration of the plasma extracted cfDNA was determined by fluorescence-based quantitation with UV absorbance measurements using the Qubit™ Quantitation Platform (Invitrogen).

The concentration of cfDNA quantified in plasma samples prepared using the MagnaPure Nucleic Acid Isolation Kit I from 16 pregnant subjects was determined to range between 20 and 100 pg/µl. As the fetal component of plasma cfDNA is known to contribute 3-10% of the total plasma cfDNA, artificial plasma samples were created by spiking aliquots of cfDNA derived from plasma of female volunteer subjects with cfDNA extracted from plasma of male volunteer subjects to mimic the ratios of fetal to maternal cfDNA found in the pregnant subjects. Artificial samples were created to contain 200-1000 pg of extracted female cfDNA that was spiked with 45-150 pg of extracted male cfDNA in a total volume of 10 µl. Each artificial sample was spiked to contain 3%, 5% and 10% male cfDNA.

Artificial samples having concentrations of total cfDNA of less than approximately 50 pg/µl, were preamplified using the modified improved primer extension amplification PCR (mIPEP) amplification according to the method of Hanson and Ballantyne, (Hanson and Ballantyne, Analytical Biochem 346:246-257 [2005]) as follows. Ten microliters of spiked plasma cfDNA were amplified in a 25 µl reaction volume containing 1 mM dNTPs, 2.5 mM MgCl$_2$ (Applied Biosystems), 1× Expand High Fidelity Buffer (No. 3), 10.5 U Expand High Fidelity Enzyme Mix (Roche Diagnostics), and 40 µM PEP primer (5'-NNNNNNNNNNNNNNN-3', Qiagen). The amplification was performed in a GeneAmp PCR System 9700 Thermocycler under the following conditions: (1) 20 and 30 cycles of 94° C. for 1 minute, 37° C. for 2 minutes, and 0.1° C./s ramp to 55° C. for 4 minutes. The amplification product was purified using a Qiagen column. The concentration of the amplification product was determined using the Qubit™ Quantitation Platform as described above. STR analysis was performed as described in Example 9 above, except that only peak heights >100 RFU were included in the calculations.

The results are shown in Tables 9, 10 and 11. The results provided in Table 9 show that the cfDNA contained in 10 µl cfDNA of artificial samples ART23 and ART24 having a starting concentration of cfDNA of 46.2 and 50.2 pg/µl, respectively, was amplified by approximately 5 and 10 fold following 20 and 30 cycles of PCR amplification, respectively.

These data indicate that a pre-amplification of cfDNA using the mIPEP method provided enhanced levels of total cfDNA rendering the level of the minor component more amenable to the STR analysis.

TABLE 9

Preamplification with mIPEP

| SAMPLE | cfDNA without mIPEP (pg/µl) | cfDNA with mIPEP: 20 PCR cycles (pg/50 µl) | cfDNA with mIPEP: 30 PCR cycles (pg/50 µl) |
|---|---|---|---|
| ART23 | 46.2 | 2265 | 4125 |
| ART24 | 50.2 | 2085 | 3875 |

Table 10 shows triplicate measurements profiling 9 loci of the cfDNA of spiked samples ART23 and ART24 following the mIPEP procedure with 20 and 30 cycles of amplification, as described above.

The data in Table 11 indicate that pre-amplification of cfDNA enables the detection and quantification of the minor component at most loci tested in artificially mixed samples having a starting cfDNA concentration that would otherwise not permit an accurate analysis of the minor STR alleles.

TABLE 10 mIPEP Preamplification and Detection of Minor Component

| STR Locus | Allele | ART23 (453 pg) mIPEP amplified 20 cycles Allele Height | ART23 (825 pg) mIPEP amplified 20 cycles Allele Height | ART23 (462 pg) Extracted unamplified cfDNA Allele Height | Allele | ART24 (417 pg) mIPEP amplified 30 cycles Allele Height | ART24 (775 pg) mIPEP amplified 30 cycles Allele Height | ART24 (502 pg) Extracted unamplified cfDNA Allele Height |
|---|---|---|---|---|---|---|---|---|
| AMEL | X/Y | 291/95 | 397/170 | 535/832 | X/Y | 695/359 | 1878/1148 | 1564/1959 |
| AMEL | X/Y | 425/147 | 428/188 | 675/1048 | X/Y | 1216/619 | 1551/954 | 1573/1943 |
| AMEL | X/Y | 267/94 | 455/203 | 664/1043 | X/Y | 718/363 | 1479/924 | 1621/2024 |
| CSF1PO | 10/11 | 800/979 | 725/1009 | 1429/1325 | 11/12 | 2029/1317 | 4159/2317 | 2990/3083 |
| CSF1PO | 10/11 | 1147/1432 | 789/1102 | 1779/1650 | 11/12 | 3449/2223 | 3460/113/ 1890 | 2996/3118 |
| CSF1PO | 10/11 | 729/906 | 831/1162 | 1783/1657 | 11/12 | 2006/1309 | 3362/1840 | 3072/3183 |
| D13S317 | 12 | 743 | 515 | 1229 | 11 | 955 | 1490 | 3634 |
| D13S317 | 12 | 1079 | 563 | 1534 | 11 | 1631 | 1198 | 3631 |
| D13S317 | 12 | 668 | 583 | 1520 | 11 | 968 | 1170 | 3795 |
| D16S539 | 9/10 | 239/140 | 370/466 | 835/676 | 10/11 | 513/512 | 1173/1472 | 1678/973 |
| D16S539 | 9/10 | 347/203 | 64*(OL)/391/ 489 | 1046/864 | 10/11 | 859/870 | 973/1212 | 1730/999 |
| D16S539 | 9/10 | 227/134 | 441/515 | 1055/860 | 10/11 | 530/513 | 960/1183 | 1784/1044 |
| D18S51 | 14/15 | 359/464 | 363/220 | 785/541 | 12/18 | 1044/576 | 1840/786 | 2559/1507 |
|  |  | 512/645 | 391/226 | 999/672 | 12/18 | 1769/994 | 1511/643 | 2565/1469 |
|  |  | 313/402 | 409/245 | 994/685 | 12/18 | 1033/567 | 1496/631 | 2643/1523 |
| D21S11 | 29/32 | 103/104 | 114/173 | 605/413 | 31.2 | 381 | 661 | 3276 |
|  |  | 149/153 | 130/182 | 759/523 | 31.2 | 650 | 536 | 3028 |
|  |  | 85/86 | 131/196 | 760/525 | 31.2 | 380 | 520 | 3282 |
| D2S1338 | 18/20 | 572/383 | 428/363 | 1116/1013 | 19/20 | 1066/433 | 2315/1243 | 2962/2968 |
|  |  | 827/553 | 454/386 | 1428/1279 | 19/20 | 1821/757 | 1901/101 | 2942/2942 |
|  |  | 530/351 | 482/408 | 1431/1275 | 19/20 | 1063/444 | 1859/1012 | 3072/3067 |
| D7S820 | 11/12 | 262/167 | 149/270 | 557/627 | 11/12 | 256/138 | 520/322 | 1550/1548 |
|  |  | 62/366/231 | 162/292 | 699/775 | 11/12 | 448/236 | 419/258 | 1484/1466 |
|  |  | 224/146 | 169/307 | 689/779 | 11/12 | 253/141 | 406/250 | 1579/1573 |
| FGA | 21/23 | 263/146 | 181/88 | 596/365 | 22/24 | 228/244 | 375/429 | 1272/1064 |
|  |  | 384/215 | 191/92 | 762/450 | 22/24 | 409/425 | 303/345 | 1221/1023 |
|  |  | 230/136 | 202/102 | 749/456 | 22/24 | 232/250 | 297/348 | 1298/1087 |

*"OL" means "Off Ladder measurement"

TABLE 11

Fetal Fraction Determined in a Sample Following Preamplification Using mIPEP

| STR marker | Allele 1/ Height | Allele 2/ Height | Allele 3/ Height | Allele 4/ Height | Percent minor fraction/STR - minor >100 RFU | Percent minor fraction/STR - minor <100 RFU |
|---|---|---|---|---|---|---|
| Amelogenin | X/2799 | Y/207 |  |  |  |  |
| Amelogenin | X/2751 | Y/198 |  |  |  |  |
| Amelogenin | X/3109 | Y/232 |  |  |  |  |
|  | X/2886 | Y/212 |  |  | 7 |  |
| CSF1PO | 10/2377 | 11/1869 | 12/508 |  |  |  |
| CSF1PO | 10/2299 | 11/1814 | 12/498 |  |  |  |
| CSF1PO | 10/2616 | 11/206 | 12/562 |  |  |  |
|  | 10/2431 | 11/1917 | 12/523 |  | 12 |  |
| D13S317 | 10/1232 | 11/1600 | 13/186 |  |  |  |
| D13S317 | 10/1208 | 11/1548 | 13/182 |  |  |  |
| D13S317 | 10/1386 | 11/1758 | 13/212 |  |  |  |
|  | 10/1275 | 11/1635 | 13/193 |  | 12 |  |
| D16S539 | 11/757 | 12/933 |  |  |  |  |
| D16S539 | 11/729 | 12/885 |  |  |  |  |
| D16S539 | 11/836 | 12/1031 |  |  |  |  |
|  | 11/774 | 12/950 |  |  | 12 |  |
| D18S51 | OL/80 | 14/3137 | 15/371 |  |  |  |
| D18S51 | 11/73 | 14/3082 | 15/362 |  |  |  |
| D18S51 | OL/83 | 14/3488 | 15/413 |  |  |  |
|  | OL | 14/3236 | 15/382 |  |  |  |

TABLE 11-continued

Fetal Fraction Determined in a Sample Following Preamplification Using mIPEP

| STR marker | Allele 1/ Height | Allele 2/ Height | Allele 3/ Height | Allele 4/ Height | Percent minor fraction/STR - minor >100 RFU | Percent minor fraction/STR - minor <100 RFU |
|---|---|---|---|---|---|---|
| D21S11 | 29/953 | 30/941 | | | | |
| D21S11 | 29/921 | 30/908 | | | | |
| D21S11 | 29/1046 | 30/1045 | | | | |
| | 29/973 | 30/965 | | | | |
| D2S1338 | 17/461 | 18/366 | 20/2280 | 24/1760 | | |
| D2S1338 | 17/460 | 18/360 | 20/2240 | 24/1712 | | |
| D2S1338 | 17/508 | 18/409 | 20/2563 | 24/1971 | | |
| | 17/476 | 18/378 | 20/2361 | 24/1814 | 20 | |
| D7S820 | 8/1409 | 9/60 | 12/1059 | | | |
| D7S820 | 8/1380 | 9/60 | 12/1036 | | | |
| D7S820 | 8/1561 | 9/69 | 12/1166 | | | |
| | 8/1450 | 9/63 | 12/1087 | | | 2 |
| FGA | 19/825 | 21/850 | 25/279 | | | |
| FGA | 19/807 | 21/841 | 25/265 | | | |
| FGA | 19/913 | 21/958 | 25/306 | | | |
| | 19/848 | 21/883 | 25/283 | | 16 | |
| % fetal fraction >100RFU for minor allele → 12 | | | | | 12 | |
| % fetal fraction including <100RFU for minor allele → 11 | | | | | | 11 |

Example 12

Correlation of Fetal Fraction Determined by Analysis of Fetal and Maternal SNPs and STRs To verify that the calculated fetal fraction i.e. fraction of minor nucleic acid component, determined using the SNP and STR assay as described in the preceding Examples provided an accurate measurement of the fetal fraction, the percent fetal fraction of cfDNA in the plasma from the same pregnant subjects was compared.

Peripheral blood samples were obtained from 48 volunteer subjects, 24 of the subjects were pregnant with male fetuses, and 24 were pregnant with female fetuses. cfDNA was prepared as described in Example 1, Fetal fraction using SNPs was determined by massively parallel sequencing by synthesis as described in Example 5, and fetal fraction using STRs was determined using capillary electrophoresis as described in Example 10

Figure 6:
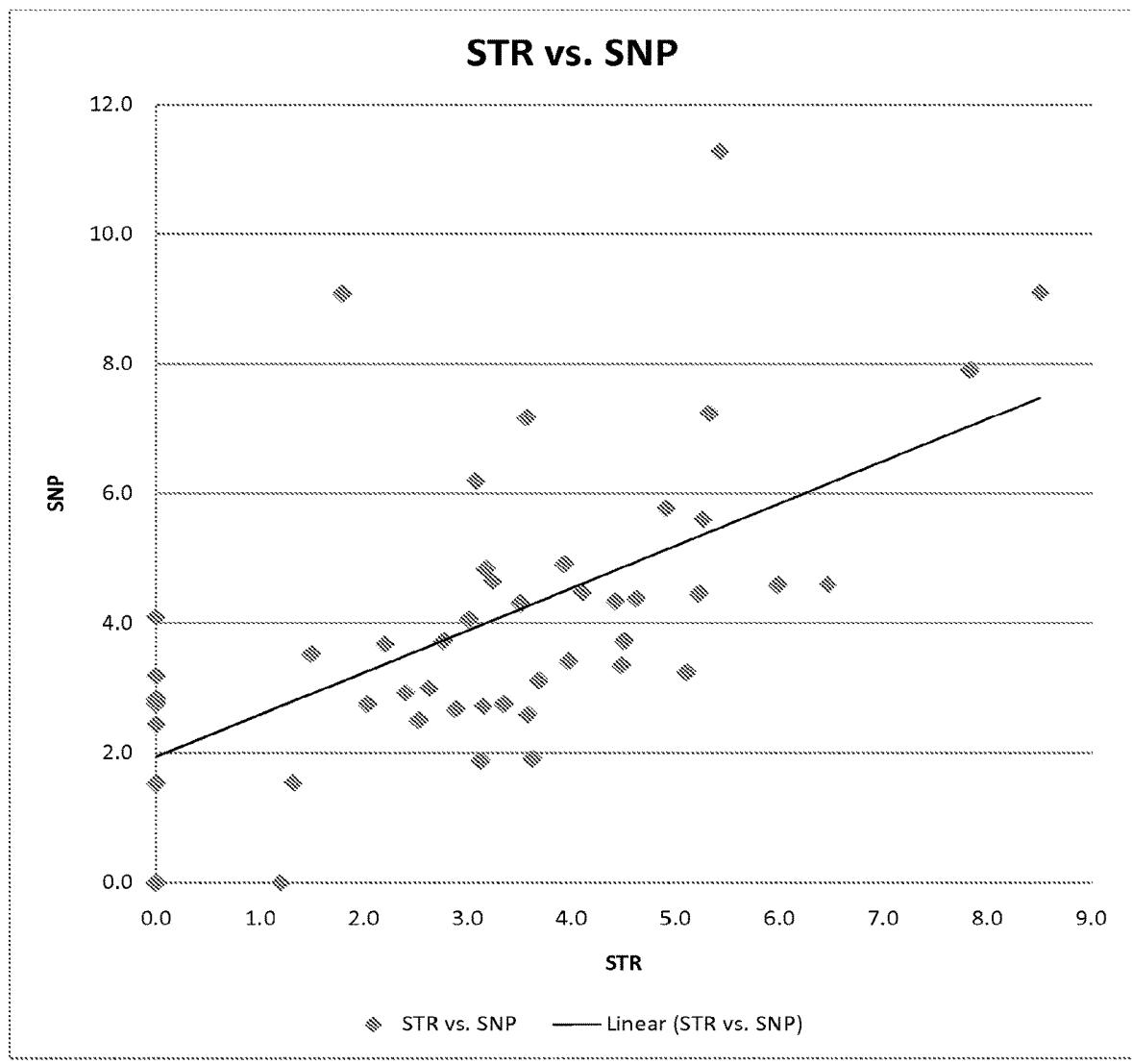
FIG. 6 illustrates the correlation of fetal fraction determined by massively parallel sequencing size separation of polymorphic sequences comprising SNPs and STRs.

The results shown in FIG. 6 indicate that a positive correlation exists between the fraction determined using the STR assay and the fraction determined using the SNP sequencing. These data further validate the use of polymorphic sequences comprising STRs or SNPs for determining the fraction of fetal cfDNA in a plasma sample.

Example 13

Use of Fetal Fraction to Set Thresholds and Estimate Minimum Sample Size in Aneuploidy Detection Counts of sequence matches to different chromosomes are manipulated to generate a score which will vary with chromosomal copy number that can be interpreted to identify chromosomal amplification or deletion. For example, such a score could be generated by comparing the relative amount of a sequence tags on a chromosome undergoing copy number changes to a chromosome known to be a euploid. Examples of scores that can be used to identify amplification or deletion include but are not limited to: counts for the chromosome of interest divided by counts of another chromosome from the same experimental run, the counts for the chromosome of interest divided by the total number of counts from the experimental run, comparison of counts from the sample of interest versus a separate control sample. Without loss of generality, it can be assumed that scores will increase as copy number increases. Knowledge of fetal fraction can be used to set "cutoff" thresholds to call "aneuploidy", "normal", or "marginal" (uncertain) states. Then, calculations are performed to estimate the minimum number of sequences required to achieve adequate sensitivity (i.e. probability of correctly identifying an aneuploidy state).

Figure 7:
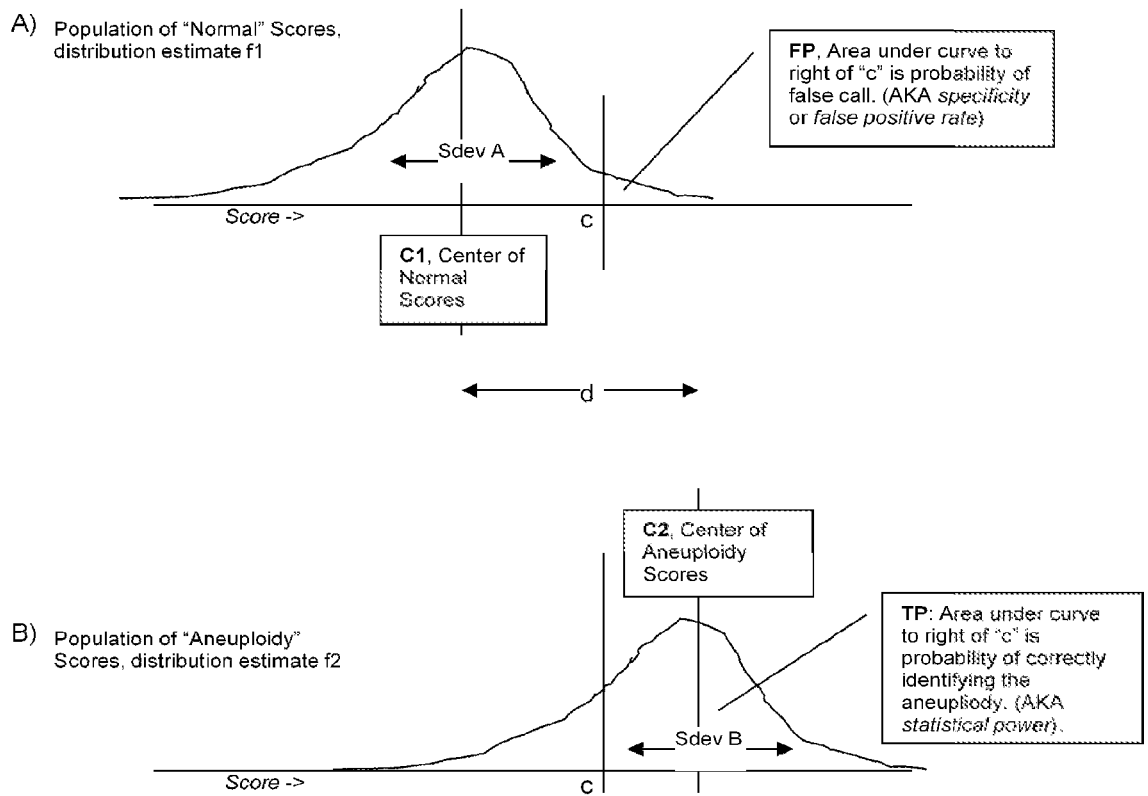
FIG. 7 illustrates an embodiment of use of fetal fraction for determining cutoff thresholds for aneuploidy detection.

FIG. 7 is a plot of two different populations of scores. The x-axis is score and the y-axis is frequency. Scores on samples of chromosomes without aneuploidy can have a distribution shown in FIG. 7A. FIG. 7B illustrates a hypothetical distribution of a population of scores on samples with an amplified chromosome. Without loss of generality, the graphs and equations show the case of a univariate score where the aneuploidy condition represents an amplification of copy number. Multivariate cases and/or reduction/deletion abnormalities are simple extensions or rearrangements of the given descriptions and are intend to fall within the scope of this art.

The amount of "overlap" between the populations can determine how well normal and aneuploidy cases can be discriminated. In general, increasing fetal fraction, ff, increases discrimination power by separating the two population centers (by moving "C2," the "Center of Aneuploidy Scores", and increasing "d," causing the populations to overlap less. Furthermore, an increase in the absolute value of the magnitude, m, (for example having four copies of the chromosome instead of a trisomy) of the amplification will also increase separation of population centers leading to higher power (i.e. higher probability of correctly identifying aneuploidy states).

Increasing the number of sequences generated, N, reduces standard deviations "sdevA" and/or "sdevB," the spread of the two populations of scores, which also causes the populations to overlap less.

Setting Thresholds and Estimating Sample Size

The following procedure can be used to set "c", the critical value for calling "aneuploidy", "normal", or "marginal" (uncertain) states. Without loss of generality, one sided statistical tests are used below.

First, an acceptable false positive rate, FP (sometimes also called "type I error" or "specificity"), is decided, which is the probability of a false positive or falsely calling aneuploidy. For example, FP can be at least, or about 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, or 0.1.

Second, the value of "c" can be determined by solving the equation: FP=integral from c to infinity of (f1(x)dx).

$$FP = \int_c^\infty f1(x)dx \quad \text{(Equation 1)}$$

Once a critical value, c, has been determined, the minimum number sequences required to achieve a certain TP=True positive rate can be estimated. The true positive rate can be, for example, about 0.5, 0.6, 0.7, 0.8, or 0.9. In one embodiment, the true positive rate can be 0.8. In other words, N is the minimum number of sequences required to identify aneuploidy 100*TP percent of the time. N=minimum number such that TP=integral from c to infinity of f2(x,ff)dx>0.8. N is determined by solving $$\min_N \text{ s.t. } \left\{ TB \geq \int_c^\infty f2(x, N)dx \right\} \quad \text{(Equation 2)}$$

In classical statistical tests f1 and f2 are often F, non-central F distributions (a special case of t and non-central t distributions) although that is not a necessary condition for this application.

Setting "Levels" of Thresholds to Give More Control of Errors

Thresholds can also be set in stages using the above methods. For example, a threshold can be set for high confidence calling of "aneuploidy", say ca, using FP 0.001 and a "marginal" threshold, say cb, using FP 0.05. In this case if Score, S:
(S>ca) then call "Trisomy"
(cb>S<=ca) then call "Marginal"
(S<cb) then call "Normal"

Some Trivial Generalizations Falling within Scope of this Art

Different values for thresholds such as TP, FP, etc can be used. Procedures can be run in any order. For example, one can start with N and solve for c, etc. Distributions can depend on ff so that f1(x,N,ff), f2(x,N,ff), and/or other variables. The above integral equations can be solved by reference to tables or by iterative computer methods. A non-centrality parameter can be estimated and power can be read from standard statistical tables. Statistical power and sample sizes may be derived from calculation or estimation of expected mean squares. Closed form theoretical distributions such as f, t, non-central t, normal, etc. or estimates (kernel or other) can be used to model the distributions f1, f2. Empirical threshold setting and parameter selection using Receiver Operator Characteristic Curves (ROC) can be used and collated with fetal fraction. Various estimates of distribution spread (variance, mean absolute deviation, inter quartile range, etc.) may be used. Various estimates of distribution center (mean, median, etc.) can be used. Two sided as opposed to one sided statistical tests can be used. The simple hypothesis test can be reformulated as linear or non-linear regression. Combinatorial methods, simulation (e.g., monte carlo), maximization (e.g., expectation maximization), iterative, or other methods can be used independently or in conjunction with the above to establish statistical power or thresholds.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for determining the fraction of fetal cell-free DNA (cfDNA) in a maternal blood sample comprising a mixture of fetal and maternal cfDNA, the method comprising:
 (a) isolating said mixture of cfDNA from said sample;
 (b) amplifying a plurality of predetermined polymorphic target nucleic acids in said mixture, wherein each of said predetermined polymorphic target nucleic acids comprises at least one single nucleotide polymorphism (SNP);
 (c) preparing a sequencing library using at least a portion of the amplified product obtained in step (b);
 (d) performing massively parallel sequencing of at least a portion of said library obtained in step (c) to provide a plurality of polymorphic sequence reads;
 (e) mapping a plurality of the sequence reads to polymorphic sites in a reference genome to obtain a plurality of mapped sequence tags, wherein said polymorphic sites comprise allelic sequences for said at least one SNP in each of said plurality of predetermined target nucleic acids;
 (f) quantifying sequence tags aligned to each of said allelic sequences to obtain a quantitative value for each of said allelic sequences;
 (g) identifying a plurality of informative SNPs from the number of sequence tags obtained in step (f), wherein said informative SNPs are identified by the difference in allelic sequences and the number of sequence tags aligned to each of the possible allelic sequences for each SNP; and
 (h) for each of said informative SNPs, calculating said fraction of fetal cfDNA from the quantitative values obtained in (f).

2. The method of claim 1, wherein amplifying said plurality of predetermined polymorphic target nucleic acids in step (b) comprises performing PCR.

3. The method of claim 1, wherein said massively parallel sequencing is sequencing-by-synthesis with reversible dye terminators.

4. The method of claim 1, wherein said massively parallel sequencing is sequencing-by-ligation.

5. The method of claim 1, wherein said sequencing is single molecule sequencing.

6. The method of claim 1, wherein said sequencing comprises an amplification.

7. The method of claim 1, wherein said maternal sample is selected from blood, plasma, serum, urine and saliva.

8. The method of claim 1, wherein said method is a fetal gender-independent method.

9. The method of claim 1, wherein said plurality of polymorphic nucleic acids are located on a plurality of different chromosomes.

10. The method of claim 1, wherein said plurality of polymorphic sites are located on a chromosome other than chromosome 13, 18, 21, X or Y.

11. The method of claim 10, wherein said plurality of different chromosomes are selected from chromosomes 1-22.

12. The method of claim 1, wherein said plurality of polymorphic nucleic acids comprises at least 10 informative polymorphic sites.

13. The method of claim 1, further comprising setting at least one threshold for calling an aneuploidy, a normal or a no call state, wherein the at least one threshold is based on the calculated fraction of fetal cfDNA obtained in step (h).

14. The method of claim 1, further comprising estimating the probability of correctly identifying an aneuploidy, wherein the probability is based on the calculated fraction of fetal cfDNA obtained in step (h).

15. A method comprising:
(a) obtaining a plasma sample from a human patient; and
(b) detecting whether fetal cell-free DNA (cfDNA) is present in the plasma sample by contacting nucleic acids from the plasma sample with primers configured to amplify polymorphic target nucleic acids and detecting binding between fetal cfDNA and the primers;
wherein said contacting comprises mixing said primers with cfDNA isolated from said plasma sample; and
wherein said detecting binding comprises:
(b1) amplifying a plurality of predetermined polymorphic target nucleic acids in said plasma sample, wherein each of said predetermined polymorphic target nucleic acids comprises at least one single nucleotide polymorphism (SNP);
(b2) preparing a sequencing library using at least a portion of the amplified product obtained in step (b1);
(b3) performing massively parallel sequencing of at least a portion of said library obtained in step (b2) to provide a plurality of polymorphic sequence reads;
(b4) mapping a plurality of the sequence reads to polymorphic sites in a reference genome to obtain a plurality of mapped sequence tags, wherein said polymorphic sites comprise allelic sequences for said at least one SNP in each of said plurality of predetermined target nucleic acids.

16. The method of claim 15, the method further comprising:
(c) quantifying sequence tags aligned to each of said allelic sequences to obtain a quantitative value for each of said allelic sequences; and
(d) identifying a plurality of informative SNPs from the number of sequence tags obtained in step (c), wherein said informative SNPs are identified by the difference in allelic sequences and the number of sequence tags aligned to each of the possible allelic sequences for each SNP.

17. The method of claim 16, the method further comprising:
(e) for each of said informative SNPs, calculating a fraction of fetal cfDNA from the quantitative values obtained in (c).

18. A method for determining the relative abundance of fetal cell-free DNA (cfDNA) in a maternal blood sample comprising a mixture of fetal and maternal cfDNA, said method comprising:
(a) providing digital sequence information comprising sequence reads obtained from massively parallel sequencing of a plurality of amplified polymorphic target nucleic acids from a mixture of fetal and maternal cfDNA,
wherein the plurality of amplified polymorphic target nucleic acids are amplicons of specific target sequences, each target sequence comprising at least one single nucleotide polymorphism (SNP);
(b) mapping a plurality of the sequence reads to polymorphic sites in a reference genome to obtain a plurality of mapped sequence tags;
(c) for each of a plurality of polymorphic sites in the reference genome:
(i) quantifying mapped sequence tags that map to a first allele of the polymorphic site to obtain a quantitative value for the first allele;
(ii) quantifying mapped sequence tags that map to a second allele of the polymorphic site to obtain a quantitative value for the second allele;
(iii) determining a parameter from the quantitative value for the first allele and the quantitative value for the second allele;
(iv) comparing the parameter to one or more cutoff values associated with the relative abundance of fetal cfDNA in the maternal sample; and
(v) classifying the polymorphic site as an (i) informative SNP or a (ii) non-informative SNP, based on the comparison of the parameter to the one or more cutoff values;
(d) determining the relative abundance of fetal cfDNA in the maternal blood sample based on the parameter obtained in step (c) for each of a plurality of informative SNPs.

* * * * *

UNITED STATES PATENT AND TRADEMARK OFFICE
CERTIFICATE OF CORRECTION

PATENT NO. : 10,612,096 B2
APPLICATION NO. : 15/299335
DATED : April 7, 2020
INVENTOR(S) : Richard P. Rava et al.

It is certified that error appears in the above-identified patent and that said Letters Patent is hereby corrected as shown below:

In the Specification

Column 1, Line 8 delete "Aug. 23, 2012" and insert --May 1, 2012--.

Signed and Sealed this
Eighteenth Day of August, 2020

Andrei Iancu
*Director of the United States Patent and Trademark Office*

SEQUENCE LISTING

```
<160> NUMBER OF SEQ ID NOS: 427

<210> SEQ ID NO 1
<211> LENGTH: 111
<212> TYPE: DNA
<213> ORGANISM: Homo sapiens

<400> SEQUENCE: 1
cacatgcaca gccagcaacc ctgtcagcag gagttcccac cagtttcttt ctgagaacat      60
ctgttcaggt ttctctccat ctctatttac tcaggtcaca ggaccttggg g              111

<210> SEQ ID NO 2
<211> LENGTH: 111
<212> TYPE: DNA
<213> ORGANISM: Homo sapiens

<400> SEQUENCE: 2
cacatgcaca gccagcaacc ctgtcagcag gagttcccac cagtttcttt ctgagaacat      60
```

```
ctgttcaggt ttctctccat ctctgtttac tcaggtcaca ggaccttggg g          111
```

<210> SEQ ID NO 3
<211> LENGTH: 126
<212> TYPE: DNA
<213> ORGANISM: Homo sapiens

<400> SEQUENCE: 3

```
tgaggaagtg aggctcagag ggtaagaaac tttgtcacag agctggtggt gagggtggag   60
attttacact ccctgcctcc cacaccagtt tctccagagt ggaaagactt tcatctcgca  120
ctggca                                                             126
```

<210> SEQ ID NO 4
<211> LENGTH: 126
<212> TYPE: DNA
<213> ORGANISM: Homo sapiens

<400> SEQUENCE: 4

```
tgaggaagtg aggctcagag ggtaagaaac tttgtcacag agctggtggt gagggtggag   60
attttacact ccctgcctcc cacaccagtt tctccggagt ggaaagactt tcatctcgca  120
ctggca                                                             126
```

<210> SEQ ID NO 5
<211> LENGTH: 121
<212> TYPE: DNA
<213> ORGANISM: Homo sapiens

<400> SEQUENCE: 5

```
gtgccttcag aacctttgag atctgattct attttttaaag cttcttagaa gagagattgc  60
aaagtgggtt gtttctctag ccagacaggg caggcaaata ggggtggctg gtgggatggg  120
a                                                                  121
```

<210> SEQ ID NO 6
<211> LENGTH: 121
<212> TYPE: DNA
<213> ORGANISM: Homo sapiens

<400> SEQUENCE: 6

```
gtgccttcag aacctttgag atctgattct attttttaaag cttcttagaa gagagattgc  60
aaagtgggtt gtttctctag ccagacaggg caggtaaata ggggtggctg gtgggatggg  120
a                                                                  121
```

<210> SEQ ID NO 7
<211> LENGTH: 111
<212> TYPE: DNA
<213> ORGANISM: Homo sapiens

<400> SEQUENCE: 7

```
aggtgtgtct ctcttttgtg aggggagggg tcccttctgg cctagtagag ggcctggcct   60
gcagtgagca ttcaaatcct caaggaacag ggtggggagg tgggacaaag g           111
```

<210> SEQ ID NO 8
<211> LENGTH: 111
<212> TYPE: DNA
<213> ORGANISM: Homo sapiens

<400> SEQUENCE: 8

```
aggtgtgtct ctcttttgtg agggagggg tcccttctgg cctagtagag ggcctggcct    60
gcagtgagca ttcaaatcct cgaggaacag ggtggggagg tgggacaaag g           111
```

<210> SEQ ID NO 9
<211> LENGTH: 139
<212> TYPE: DNA
<213> ORGANISM: Homo sapiens

<400> SEQUENCE: 9

```
cctcgcctac tgtgctgttt ctaaccatca tgcttttccc tgaatctctt gagtctttt    60 ctgctgtgga ctgaaacttg atcctgagat tcacctctag tccctctgag cagcctcctg  120
gaatactcag ctgggatgg                                               139
```

<210> SEQ ID NO 10
<211> LENGTH: 139
<212> TYPE: DNA
<213> ORGANISM: Homo sapiens

<400> SEQUENCE: 10

```
cctcgcctac tgtgctgttt ctaaccatca tgcttttccc tgaatctctt gagtctttt    60 ctgctgtgga ctgaaacttg atcctgagat tcacctctag tccctctggg cagcctcctg  120
gaatactcag ctgggatgg                                               139
```

<210> SEQ ID NO 11
<211> LENGTH: 117
<212> TYPE: DNA
<213> ORGANISM: Homo sapiens

<400> SEQUENCE: 11

```
aattgcaatg gtgagaggtt gatggtaaaa tcaaacggaa cttgttattt tgtcattctg    60
atggactgga actgaggatt ttcaatttcc tctccaaccc aagacacttc tcactgg     117
```

<210> SEQ ID NO 12
<211> LENGTH: 117
<212> TYPE: DNA
<213> ORGANISM: Homo sapiens

<400> SEQUENCE: 12

```
aattgcaatg gtgagaggtt gatggtaaaa tcaaacggaa cttgttattt tgtcattctg    60
atggactgga actgaggatt ttcaatttcc tttccaaccc aagacacttc tcactgg     117
```

<210> SEQ ID NO 13
<211> LENGTH: 114
<212> TYPE: DNA
<213> ORGANISM: Homo sapiens

<400> SEQUENCE: 13

```
gaaatgcctt ctcaggtaat ggaaggttat ccaaatattt ttcgtaagta tttcaaatag    60
caatggctcg tctatggtta gtctcacagc cacattctca gaactgctca aacc        114
```

<210> SEQ ID NO 14
<211> LENGTH: 114
<212> TYPE: DNA
<213> ORGANISM: Homo sapiens

<400> SEQUENCE: 14

```
gaaatgcctt ctcaggtaat ggaaggttat ccaaatattt ttcgtaagta tttcaaatag    60
caatggctcg tctatggtta gtctcgcagc cacattctca gaactgctca aacc        114
```

```
<210> SEQ ID NO 15
<211> LENGTH: 128
<212> TYPE: DNA
<213> ORGANISM: Homo sapiens

<400> SEQUENCE: 15
acccaaaaca ctggaggggc ctcttctcat tttcggtaga ctgcaagtgt tagccgtcgg      60
gaccagcttc tgtctggaag ttcgtcaaat tgcagttaag tccaagtatg ccacatagca     120
gataaggg                                                              128

<210> SEQ ID NO 16
<211> LENGTH: 128
<212> TYPE: DNA
<213> ORGANISM: Homo sapiens

<400> SEQUENCE: 16
acccaaaaca ctggaggggc ctcttctcat tttcggtaga ctgcaagtgt tagccgtcgg      60
gaccagcttc tgtctggaag ttcgtcaaat tgcagttagg tccaagtatg ccacatagca     120
gataaggg                                                              128

<210> SEQ ID NO 17
<211> LENGTH: 110
<212> TYPE: DNA
<213> ORGANISM: Homo sapiens

<400> SEQUENCE: 17
gcaccagaat ttaaacaacg ctgacaataa atatgcagtc gatgatgact tcccagagct      60
ccagaagcaa ctccagcaca cagagaggcg ctgatgtgcc tgtcaggtgc                 110

<210> SEQ ID NO 18
<211> LENGTH: 110
<212> TYPE: DNA
<213> ORGANISM: Homo sapiens

<400> SEQUENCE: 18
gcaccagaat ttaaacaacg ctgacaataa atatgcagtc gatgatgact tcccagagct      60
ccagaagcaa ctccagcaca cggagaggcg ctgatgtgcc tgtcaggtgc                 110

<210> SEQ ID NO 19
<211> LENGTH: 116
<212> TYPE: DNA
<213> ORGANISM: Homo sapiens

<400> SEQUENCE: 19
tgactgtata ccccaggtgc acccttgggt catctctatc atagaactta tctcacagag      60
tataagagct gatttctgtg tctgcctctc acactagact tccacatcct tagtgc         116

<210> SEQ ID NO 20
<211> LENGTH: 116
<212> TYPE: DNA
<213> ORGANISM: Homo sapiens

<400> SEQUENCE: 20
tgactgtata ccccaggtgc acccttgggt catctctatc atagaactta tctcacagag      60
tataagagct gatttctgtg tctgcctgtc acactagact tccacatcct tagtgc         116

<210> SEQ ID NO 21
```

<211> LENGTH: 110
<212> TYPE: DNA
<213> ORGANISM: Homo sapiens

<400> SEQUENCE: 21
tgtacgtggt caccagggga cgcctggcgc tgcgagggag gccccgagcc tcgtgccccc    60
gtgaagcttc agctcccctc cccggctgtc cttgaggctc ttctcacact               110

<210> SEQ ID NO 22
<211> LENGTH: 110
<212> TYPE: DNA
<213> ORGANISM: Homo sapiens

<400> SEQUENCE: 22
tgtacgtggt caccagggga cgcctggcgc tgcgagggag gccccgagcc tcgtgccccc    60
gtgaagcttc agctcccctc cctggctgtc cttgaggctc ttctcacact               110

<210> SEQ ID NO 23
<211> LENGTH: 114
<212> TYPE: DNA
<213> ORGANISM: Homo sapiens

<400> SEQUENCE: 23
cagtggaccc tgctgcacct ttcctcccct cccatcaacc tcttttgtgc ctcccccctcc   60 gtgtaccacc ttctctgtca ccaaccctgg cctcacaact ctctcctttg ccac          114

<210> SEQ ID NO 24
<211> LENGTH: 114
<212> TYPE: DNA
<213> ORGANISM: Homo sapiens

<400> SEQUENCE: 24
cagtggaccc tgctgcacct ttcctcccct cccatcaacc tcttttgtgc ctcccccctcc   60 gtgtaccacc ttctctgtca ccaccctgg cctcacaact ctctcctttg ccac           114

<210> SEQ ID NO 25
<211> LENGTH: 110
<212> TYPE: DNA
<213> ORGANISM: Homo sapiens

<400> SEQUENCE: 25
cagtggcata gtagtccagg ggctcctcct cagcacctcc agcacttcc aggaggcagc     60 agcgcaggca gagaacccgc tggaagaatc ggcggaagtt gtcggagagg               110

<210> SEQ ID NO 26
<211> LENGTH: 110
<212> TYPE: DNA
<213> ORGANISM: Homo sapiens

<400> SEQUENCE: 26
cagtggcata gtagtccagg ggctcctcct cagcacctcc agcacttcc aggaggcagc     60 agcgcaggca gagaacccgc tggaaggatc ggcggaagtt gtcggagagg               110

<210> SEQ ID NO 27
<211> LENGTH: 129
<212> TYPE: DNA
<213> ORGANISM: Homo sapiens

<400> SEQUENCE: 27
aggtctgggg gccgctgaat gccaagctgg gaatcttaaa tgttaaggaa caaggtcata    60

```
caatgaatgg tgtgatgtaa aagcttggga ggtgatttct gagggtaggt gctgggttta      120
atgggagga                                                              129

<210> SEQ ID NO 28
<211> LENGTH: 129
<212> TYPE: DNA
<213> ORGANISM: Homo sapiens

<400> SEQUENCE: 28
aggtctgggg gccgctgaat gccaagctgg gaatcttaaa tgttaaggaa caaggtcata      60
caatgaatgg tgtgatgtaa aagcttggga ggtgattttt gagggtaggt gctgggttta      120
atgggagga                                                              129

<210> SEQ ID NO 29
<211> LENGTH: 107
<212> TYPE: DNA
<213> ORGANISM: Homo sapiens

<400> SEQUENCE: 29
acggttctgt cctgtagggg agaaaagtcc tcgttgttcc tctgggatgc aacatgagag      60
agcagcacac tgaggcttta tggattgccc tgccacaagt gaacagg                    107

<210> SEQ ID NO 30
<211> LENGTH: 107
<212> TYPE: DNA
<213> ORGANISM: Homo sapiens

<400> SEQUENCE: 30
acggttctgt cctgtagggg agaaaagtcc tcgttgttcc tctgggatgc aacatgagag      60
agcagcacac tgaggcttta tgggttgccc tgccacaagt gaacagg                    107

<210> SEQ ID NO 31
<211> LENGTH: 127
<212> TYPE: DNA
<213> ORGANISM: Homo sapiens

<400> SEQUENCE: 31
gcgcagtcag atgggcgtgc tggcgtctgt cttctctctc tcctgctctc tggcttcatt      60
tttctctcct tctgtctcac cttctttcgt gtgcctgtgc acacacacgt ttgggacaag      120
ggctgga                                                                127

<210> SEQ ID NO 32
<211> LENGTH: 127
<212> TYPE: DNA
<213> ORGANISM: Homo sapiens

<400> SEQUENCE: 32
gcgcagtcag atgggcgtgc tggcgtctgt cttctctctc tcctgctctc tggcttcatt      60
tttctctcct tctgtctcac cttctttcgt gtgcctgtgc atacacacgt ttgggacaag      120
ggctgga                                                                127

<210> SEQ ID NO 33
<211> LENGTH: 130
<212> TYPE: DNA
<213> ORGANISM: Homo sapiens

<400> SEQUENCE: 33
```

```
gccggacctg cgaaatccca aaatgccaaa cattcccgcc tcacatgatc ccagagagag    60
gggacccagt gttcccagct tgcagctgag gagcccgagg ttgccgtcag atcagagccc   120
cagttgcccg                                                           130
```

<210> SEQ ID NO 34
<211> LENGTH: 130
<212> TYPE: DNA
<213> ORGANISM: Homo sapiens

<400> SEQUENCE: 34

```
gccggacctg cgaaatccca aaatgccaaa cattcccgcc tcacatgatc ccagagagag    60
gggacccagt gttcccagct tgcagctgag gagcccgagt ttgccgtcag atcagagccc   120
cagttgcccg                                                           130
```

<210> SEQ ID NO 35
<211> LENGTH: 121
<212> TYPE: DNA
<213> ORGANISM: Homo sapiens

<400> SEQUENCE: 35

```
agcagcctcc ctcgactagc tcacactacg ataaggaaaa ttcatgagct ggtgtccaag    60
gagggctggg tgactcgtgg ctcagtcagc atcaagattc ctttcgtctt tcccctctgc   120
c                                                                    121
```

<210> SEQ ID NO 36
<211> LENGTH: 121
<212> TYPE: DNA
<213> ORGANISM: Homo sapiens

<400> SEQUENCE: 36

```
agcagcctcc ctcgactagc tcacactacg ataaggaaaa ttcatgagct ggtgtccaag    60
gagggctggg tgactcgtgg ctcagtcagc gtcaagattc ctttcgtctt tcccctctgc   120
c                                                                    121
```

<210> SEQ ID NO 37
<211> LENGTH: 138
<212> TYPE: DNA
<213> ORGANISM: Homo sapiens

<400> SEQUENCE: 37

```
tggcattgcc tgtaatatac atagccatgg tttttatag gcaatttaag atgaatagct     60
tctaaactat agataagttt cattacccca ggaagctgaa ctatagctac tttacccaaa   120
atcattagaa tggtgctt                                                  138
```

<210> SEQ ID NO 38
<211> LENGTH: 138
<212> TYPE: DNA
<213> ORGANISM: Homo sapiens

<400> SEQUENCE: 38

```
tggcattgcc tgtaatatac atagccatgg tttttatag gcaatttaag atgaatagct     60
tctaaactat agataagttt cattacccca ggaagctgaa ctatagctac tttccccaaa   120
atcattagaa tggtgctt                                                  138
```

<210> SEQ ID NO 39
<211> LENGTH: 136

-continued

<212> TYPE: DNA
<213> ORGANISM: Homo sapiens

<400> SEQUENCE: 39
atgaagcctt ccaccaactg cctgtatgac tcatctgggg acttctgctc tatactcaaa    60
gtggcttagt cactgccaat gtatttccat atgagggacg atgattacta aggaaatata   120
gaaacaacaa ctgatc                                                   136

<210> SEQ ID NO 40
<211> LENGTH: 136
<212> TYPE: DNA
<213> ORGANISM: Homo sapiens

<400> SEQUENCE: 40
atgaagcctt ccaccaactg cctgtatgac tcatctgggg acttctgctc tatactcaaa    60
gtggcttagt cactgccaat gtatttccat atgagggacg gtgattacta aggaaatata   120
gaaacaacaa ctgatc                                                   136

<210> SEQ ID NO 41
<211> LENGTH: 118
<212> TYPE: DNA
<213> ORGANISM: Homo sapiens

<400> SEQUENCE: 41
acaacagaat caggtgattg gagaaaagat cacaggccta ggcacccaag gcttgaagga    60
tgaaagaatg aaagatggac ggaacaaaat taggacctta attctttgtt cagttcag    118

<210> SEQ ID NO 42
<211> LENGTH: 118
<212> TYPE: DNA
<213> ORGANISM: Homo sapiens

<400> SEQUENCE: 42
acaacagaat caggtgattg gagaaaagat cacaggccta ggcacccaag gcttgaagga    60
tgaaagaatg aaagatggac ggaagaaaat taggacctta attctttgtt cagttcag    118

<210> SEQ ID NO 43
<211> LENGTH: 150
<212> TYPE: DNA
<213> ORGANISM: Homo sapiens

<400> SEQUENCE: 43
ttggggtaaa ttttcattgt catatgtgga atttaaatat accatcatct acaaagaatt    60
ccacagagtt aaatatctta agttaaacac ttaaaataag tgtttgcgtg atattttgat   120
gacagataaa cagagtctaa ttcccacccc                                    150

<210> SEQ ID NO 44
<211> LENGTH: 150
<212> TYPE: DNA
<213> ORGANISM: Homo sapiens

<400> SEQUENCE: 44
ttggggtaaa ttttcattgt catatgtgga atttaaatat accatcatct acaaagaatt    60
ccacagagtt aaatatctta agttaaacac ttaaaataag tgtttgcgtg atattttgat   120
gatagataaa cagagtctaa ttcccacccc                                    150

<210> SEQ ID NO 45

```
<211> LENGTH: 145
<212> TYPE: DNA
<213> ORGANISM: Homo sapiens

<400> SEQUENCE: 45
tgcaattcaa atcaggaagt atgaccaaaa gacagagatc ttttttggat gatccctagc      60
ctagcaatgc ctggcagcca tgcaggtgca atgtcaacct taaataatgt attgcaaact     120
cagagctgac aaacctcgat gttgc                                           145

<210> SEQ ID NO 46
<211> LENGTH: 145
<212> TYPE: DNA
<213> ORGANISM: Homo sapiens

<400> SEQUENCE: 46
tgcaattcaa atcaggaagt atgaccaaaa gacagagatc ttttttggat gatccctagc      60
ctagcaatgc ctggcagcca tgcaggtgca atgtcaacct taaataatgt attgcaaatt     120
cagagctgac aaacctcgat gttgc                                           145

<210> SEQ ID NO 47
<211> LENGTH: 124
<212> TYPE: DNA
<213> ORGANISM: Homo sapiens

<400> SEQUENCE: 47
ctgtgctctg cgaatagctg cagaagtaac ttggggaccc aaaataaagc agaatgctaa      60
tgtcaagtcc tgagaaccaa gccctgggac tctggtgcca tttcggattc tccatgagca     120
tggt                                                                  124

<210> SEQ ID NO 48
<211> LENGTH: 124
<212> TYPE: DNA
<213> ORGANISM: Homo sapiens

<400> SEQUENCE: 48
ctgtgctctg cgaatagctg cagaagtaac ttggggaccc aaaataaagc agaatgctaa      60
tgtcaagtcc tgagaaccaa gccctgggac tctggtgcca ttttggattc tccatgagca     120
tggt                                                                  124

<210> SEQ ID NO 49
<211> LENGTH: 118
<212> TYPE: DNA
<213> ORGANISM: Homo sapiens

<400> SEQUENCE: 49
tttttccagc caactcaagg ccaaaaaaaa tttcttaata tagttattat gcgaggggag      60
gggaagcaaa ggagcacagg tagtccacag aataagacac aagaaacctc aagctgtg       118

<210> SEQ ID NO 50
<211> LENGTH: 118
<212> TYPE: DNA
<213> ORGANISM: Homo sapiens

<400> SEQUENCE: 50
tttttccagc caactcaagg ccaaaaaaaa tttcttaata tagttattat gcgaggggag      60
gggaagcaaa ggagcacagg tagtccacag aataggacac aagaaacctc aagctgtg       118
```

<210> SEQ ID NO 51
<211> LENGTH: 110
<212> TYPE: DNA
<213> ORGANISM: Homo sapiens

<400> SEQUENCE: 51
tcttctcgtc ccctaagcaa acaacatccg cttgcttctg tctgtgtaac cacagtgaat    60
gggtgtgcac gcttgatggg cctctgagcc cctgttgcac aaaccagaaa              110

<210> SEQ ID NO 52
<211> LENGTH: 110
<212> TYPE: DNA
<213> ORGANISM: Homo sapiens

<400> SEQUENCE: 52
tcttctcgtc ccctaagcaa acaacatccg cttgcttctg tctgtgtaac cacagtgaat    60
gggtgtgcac gcttggtggg cctctgagcc cctgttgcac aaaccagaaa              110

<210> SEQ ID NO 53
<211> LENGTH: 110
<212> TYPE: DNA
<213> ORGANISM: Homo sapiens

<400> SEQUENCE: 53
cacatggggg cattaagaat cgcccaggga ggaggaggga gaacgcgtgc ttttcacatt    60
tgcatttgaa ttttcgagtt cccaggatgt gttttttgtgc tcatcgatgt              110

<210> SEQ ID NO 54
<211> LENGTH: 110
<212> TYPE: DNA
<213> ORGANISM: Homo sapiens

<400> SEQUENCE: 54
cacatggggg cattaagaat cgcccaggga ggaggaggga gaacgcgtgc ttttcacatt    60
tgcatttgaa tttttgagtt cccaggatgt gttttttgtgc tcatcgatgt              110

<210> SEQ ID NO 55
<211> LENGTH: 128
<212> TYPE: DNA
<213> ORGANISM: Homo sapiens

<400> SEQUENCE: 55
gggctctgag gtgtgtgaaa taaaaacaaa tgtccatgtc tgtcctttta tggcattttg    60
ggactttaca tttcaaacat ttcagacatg tatcacaaca cgaaggaata acagttccag   120
ggatatct                                                            128

<210> SEQ ID NO 56
<211> LENGTH: 128
<212> TYPE: DNA
<213> ORGANISM: Homo sapiens

<400> SEQUENCE: 56
gggctctgag gtgtgtgaaa taaaaacaaa tgtccatgtc tgtcctttta tggcattttg    60
ggactttaca tttcaaacat ttcagacatg tatcacaaca cgagggaata acagttccag   120
ggatatct                                                            128

<210> SEQ ID NO 57
<211> LENGTH: 21
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 57
cacatgcaca gccagcaacc c                                              21

<210> SEQ ID NO 58
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
ccccaaggtc ctgtgacctg agt                                            23

<210> SEQ ID NO 59
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
tgaggaagtg aggctcagag ggt                                            23

<210> SEQ ID NO 60
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
tgccagtgcg agatgaaagt cttt                                           24

<210> SEQ ID NO 61
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
gtgccttcag aacctttgag atctgat                                        27

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
tcccatccca ccagccaccc                                                20

<210> SEQ ID NO 63
<211> LENGTH: 25
<212> TYPE: DNA
<213> ORGANISM: Artificial Sequence
```

<220> FEATURE:
<223> OTHER INFORMATION: Description of Artificial Sequence: Synthetic
      primer

<400> SEQUENCE: 63
aggtgtgtct ctcttttgtg agggg                                           25

<210> SEQ ID NO 64
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
cctttgtccc acctccccac c                                               21

<210> SEQ ID NO 65
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
cctcgcctac tgtgctgttt ctaacc                                          26

<210> SEQ ID NO 66
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
ccatcccagc tgagtattcc aggag                                           25

<210> SEQ ID NO 67
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
aattgcaatg gtgagaggtt gatggt                                          26

<210> SEQ ID NO 68
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
ccagtgagaa gtgtcttggg ttgg                                            24

<210> SEQ ID NO 69
<211> LENGTH: 27
<212> TYPE: DNA
<213> ORGANISM: Artificial Sequence
<220> FEATURE:

```
<223> OTHER INFORMATION: Description of Artificial Sequence: Synthetic
      primer

<400> SEQUENCE: 69
gaaatgcctt ctcaggtaat ggaaggt                                            27

<210> SEQ ID NO 70
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
ggtttgagca gttctgagaa tgtggct                                            27

<210> SEQ ID NO 71
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
acccaaaaca ctggaggggc ct                                                 22

<210> SEQ ID NO 72
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
cccttatctg ctatgtggca tacttgg                                            27

<210> SEQ ID NO 73
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
gcaccagaat ttaaacaacg ctgacaa                                            27

<210> SEQ ID NO 74
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
gcacctgaca ggcacatcag cg                                                 22

<210> SEQ ID NO 75
<211> LENGTH: 24
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 75
tgactgtata ccccaggtgc accc                                          24

<210> SEQ ID NO 76
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
gcactaagga tgtggaagtc tagtgtg                                       27

<210> SEQ ID NO 77
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
tgtacgtggt caccagggga cg                                            22

<210> SEQ ID NO 78
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
agtgtgagaa gagcctcaag gacagc                                        26

<210> SEQ ID NO 79
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
cagtggaccc tgctgcacct t                                             21

<210> SEQ ID NO 80
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
gtggcaaagg agagagttgt gagg                                          24

<210> SEQ ID NO 81
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
cagtggcata gtagtccagg ggct                                                  24

<210> SEQ ID NO 82
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
cctctccgac aacttccgcc g                                                     21

<210> SEQ ID NO 83
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
aggtctgggg gccgctgaat                                                       20

<210> SEQ ID NO 84
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
tcctcccatt aaacccagca cct                                                   23

<210> SEQ ID NO 85
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
acggttctgt cctgtagggg aga                                                   23

<210> SEQ ID NO 86
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
cctgttcact tgtggcaggg ca                                                    22

<210> SEQ ID NO 87
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 87
gcgcagtcag atgggcgtgc                                                20

<210> SEQ ID NO 88
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88 tccagcccctt gtcccaaacg tgt                                           23

<210> SEQ ID NO 89
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
gccggacctg cgaaatccca a                                              21

<210> SEQ ID NO 90
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90
cgggcaactg gggctctgat c                                              21

<210> SEQ ID NO 91
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
agcagcctcc ctcgactagc t                                              21

<210> SEQ ID NO 92
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92
ggcagagggg aaagacgaaa gga                                            23

<210> SEQ ID NO 93
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93
```
tggcattgcc tgtaatatac atag                                          24

<210> SEQ ID NO 94
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94
aagcaccatt ctaatgattt tgg                                           23

<210> SEQ ID NO 95
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 95
atgaagcctt ccaccaactg                                               20

<210> SEQ ID NO 96
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 96
gatcagttgt tgtttctata tttcctt                                       27

<210> SEQ ID NO 97
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 97
acaacagaat caggtgattg ga                                            22

<210> SEQ ID NO 98
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 98
ctgaactgaa caaagaatta aggtc                                         25

<210> SEQ ID NO 99
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 99
ttggggtaaa ttttcattgt ca          22

<210> SEQ ID NO 100
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 100
ggggtgggaa ttagactctg          20

<210> SEQ ID NO 101
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 101
tgcaattcaa atcaggaagt atg          23

<210> SEQ ID NO 102
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 102
gcaacatcga ggtttgtcag          20

<210> SEQ ID NO 103
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 103
ctgtgctctg cgaatagctg          20

<210> SEQ ID NO 104
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 104
accatgctca tggagaatcc          20

<210> SEQ ID NO 105
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 105
tttttccagc caactcaagg          20

<210> SEQ ID NO 106
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 106
cacagcttga ggtttcttgt g                                           21

<210> SEQ ID NO 107
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 107
tcttctcgtc ccctaagcaa                                             20

<210> SEQ ID NO 108
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 108
tttctggttt gtgcaacagg                                             20

<210> SEQ ID NO 109
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 109
cacatggggg cattaagaat                                             20

<210> SEQ ID NO 110
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 110
acatcgatga gcacaaaaac ac                                          22

<210> SEQ ID NO 111
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 111
gggctctgag gtgtgtgaaa                                             20

<210> SEQ ID NO 112
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 112
agatatccct ggaactgtta ttcc                                           24

<210> SEQ ID NO 113
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 113
acagtaactg ccttcataga tag                                            23

<210> SEQ ID NO 114
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 114
gtgtcagacc ctgttctaag ta                                             22

<210> SEQ ID NO 115
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 115
aaataaaatt aggcatattt acaagc                                         26

<210> SEQ ID NO 116
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 116
gctgagtgat ttgtctgtaa ttg                                            23

<210> SEQ ID NO 117
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 117
cctgttcctc ccttatttcc c                                              21

<210> SEQ ID NO 118
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 118
gggaacacag actccatggt g                                        21

<210> SEQ ID NO 119
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 119
cttagggaac cctcactgaa tg                                       22

<210> SEQ ID NO 120
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 120
gtccttgtca gcgtttattt gc                                       22

<210> SEQ ID NO 121
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 121
aataatcagt atgtgacttg gattga                                   26

<210> SEQ ID NO 122
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 122
ataggatgga tggatagatg ga                                       22

<210> SEQ ID NO 123
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 123
cagagcaaga ccctgtctca t                                        21

<210> SEQ ID NO 124

```
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 124
tcaacagagg cttgcatgta t                                              21

<210> SEQ ID NO 125
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 125
gggtgatttt cctctttggt                                                20

<210> SEQ ID NO 126
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 126
aacatttgta tctttatctg tatccttatt tat                                 33

<210> SEQ ID NO 127
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 127
gaacacttgt catagtttag aacgaac                                        27

<210> SEQ ID NO 128
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 128
tcattgacag aattgcacca                                                20

<210> SEQ ID NO 129
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 129
tttgtatttc atgtgtacat tcgtatc                                        27

<210> SEQ ID NO 130
<211> LENGTH: 28
```

<212> TYPE: DNA
<213> ORGANISM: Artificial Sequence
<220> FEATURE:
<223> OTHER INFORMATION: Description of Artificial Sequence: Synthetic
      primer

<400> SEQUENCE: 130
acctatcctg tagattattt tcactgtg                                          28

<210> SEQ ID NO 131
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 131
tctgacccat ctaacgccta                                                   20

<210> SEQ ID NO 132
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 132
cagacagaaa gatagataga tgattga                                           27

<210> SEQ ID NO 133
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 133
atacagacag acagacaggt g                                                 21

<210> SEQ ID NO 134
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 134
gcatgtatct atcatccatc tct                                               23

<210> SEQ ID NO 135
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 135
tgagtgacaa attgagacct t                                                 21

<210> SEQ ID NO 136
<211> LENGTH: 26
<212> TYPE: DNA

<213> ORGANISM: Artificial Sequence
<220> FEATURE:
<223> OTHER INFORMATION: Description of Artificial Sequence: Synthetic
      primer

<400> SEQUENCE: 136
gtcttacaat aacagttgct actatt                                      26

<210> SEQ ID NO 137
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 137
attccccaag tgaattgc                                               18

<210> SEQ ID NO 138
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 138
ggtagataga ctggatagat agacga                                      26

<210> SEQ ID NO 139
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 139
tggaaacaga aatggcttgg                                             20

<210> SEQ ID NO 140
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 140
gattgcagga gggaaggaag                                             20

<210> SEQ ID NO 141
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 141
gagcaagaca ccatctcaag aa                                          22

<210> SEQ ID NO 142
<211> LENGTH: 30
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 142
gaaattttac atttatgttt atgattctct                                      30

<210> SEQ ID NO 143
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 143
ggcgactgag caagactc                                                   18

<210> SEQ ID NO 144
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 144
ggttattaat tgagaaaact ccttaca                                         27

<210> SEQ ID NO 145
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 145
attttccccg atgatagtag tct                                             23

<210> SEQ ID NO 146
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 146
gcgaatgtat gattggcaat attttt                                          26

<210> SEQ ID NO 147
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 147
acatgtatcc cagaacttaa agtaaac                                         27

<210> SEQ ID NO 148
<211> LENGTH: 22
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 148
gcagaaggga aaattgaagc tg                                              22

<210> SEQ ID NO 149
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 149
cagagacacc gaaccaataa ga                                              22

<210> SEQ ID NO 150
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 150
gccacatgaa tcaattccta taataaa                                         27

<210> SEQ ID NO 151
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 151
gcacatgtac cctaaaactt aaaat                                           25

<210> SEQ ID NO 152
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 152
gtcaaccaaa actcaacaag tagtaa                                          26

<210> SEQ ID NO 153
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 153
aagatgaaat tgccatgtaa aaata                                           25

<210> SEQ ID NO 154
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 154
gtgtgtataa caaaattcct atgatgg                                              27

<210> SEQ ID NO 155
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 155
gcacccaaaa ctgaatgtca ta                                                   22

<210> SEQ ID NO 156
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 156
ggtgagagtg agaccctgtc                                                      20

<210> SEQ ID NO 157
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 157
tgtaataact ctacgactgt ctgtctg                                              27

<210> SEQ ID NO 158
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 158
gaataggagg tggatggatg g                                                    21

<210> SEQ ID NO 159
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 159
gagcgagacc ctgtctcaag                                                      20

<210> SEQ ID NO 160
<211> LENGTH: 24
<212> TYPE: DNA
<213> ORGANISM: Artificial Sequence
<220> FEATURE:
<223> OTHER INFORMATION: Description of Artificial Sequence: Synthetic
      primer -continued

<400> SEQUENCE: 160
ggaaaagaca taggatagca attt                                           24

<210> SEQ ID NO 161
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 161
tctggattga tctgtctgtc c                                              21

<210> SEQ ID NO 162
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 162
gaattaaata ccatctgagc actgaa                                         26

<210> SEQ ID NO 163
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 163
tgttataatg cattgagttt tattctg                                        27

<210> SEQ ID NO 164
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 164
gcctgtctca aaaataaaga gatagaca                                       28

<210> SEQ ID NO 165
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 165
ttaatgaatt gaacaaatga gtgag                                          25

<210> SEQ ID NO 166
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 166
gcaactctgg ttgtattgtc ttcat                                         25

<210> SEQ ID NO 167
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 167
caaagcgaga ctctgtctca a                                             21

<210> SEQ ID NO 168
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 168
gaaaatgcta tcctctttgg tataaat                                       27

<210> SEQ ID NO 169
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 169
gggtatttca agataactgt agatagg                                       27

<210> SEQ ID NO 170
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 170
gcttctgaaa gcttctagtt tacc                                          24

<210> SEQ ID NO 171
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 171
tccacatcct caccaacac                                                19

<210> SEQ ID NO 172
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 172
```
gcctaggaag gctactgtca a                                          21

<210> SEQ ID NO 173
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 173
ccacccgtcc atttaggc                                              18

<210> SEQ ID NO 174
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 174 gtgaaaagt agatataatg gttggtg                                     27

<210> SEQ ID NO 175
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 175
ggttttccaa gagatagacc aatta                                      25

<210> SEQ ID NO 176
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 176
gtcctctcat aaatccctac tcatatc                                    27

<210> SEQ ID NO 177
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 177
ctgttggtac ataataggta ggtaggt                                    27

<210> SEQ ID NO 178
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 178

```
gtcgtgggcc ccataaatc                                                  19

<210> SEQ ID NO 179
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 179
aaggtacata acagttcaat agaaagc                                         27

<210> SEQ ID NO 180
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 180
gtgaaatgac tgaaaatag taacca                                           26

<210> SEQ ID NO 181
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 181
ctaggagatc atgtgggtat gatt                                            24

<210> SEQ ID NO 182
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 182
gcagtgaata aatgaacgaa tgga                                            24

<210> SEQ ID NO 183
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 183
cccaaaatta cttgagccaa t                                               21

<210> SEQ ID NO 184
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 184
gagacaaaat gaagaaacag acag                                            24
```

<210> SEQ ID NO 185
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 185
tctttgctct catgaataga tcagt                                           25

<210> SEQ ID NO 186
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 186
gtttgtgata atgaacccac tcag                                            24

<210> SEQ ID NO 187
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 187
tgaacacaga tgttaagtgt gtatatg                                         27

<210> SEQ ID NO 188
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 188
gtctgaggtg gacagttatg aaa                                             23

<210> SEQ ID NO 189
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 189
ctgtggctca tctatgaaaa ctt                                             23

<210> SEQ ID NO 190
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 190
gaagtggctg tggtgttatg at                                              22

<210> SEQ ID NO 191
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 191
ttctgttggt atagagcagt gttt                                          24

<210> SEQ ID NO 192
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 192
gtgacaggaa ggacggaatg                                               20

<210> SEQ ID NO 193
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 193
catgaggttt gcaaatacta tcttaac                                       27

<210> SEQ ID NO 194
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 194
gttttaattt tctccaaatc tcca                                          24

<210> SEQ ID NO 195
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 195
tcttagccta gatagatact tgcttcc                                       27

<210> SEQ ID NO 196
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 196
gtcaaccttt gaggctatag gaa                                           23

```
<210> SEQ ID NO 197
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 197
tcctggaaac aaaagtatt                                                19

<210> SEQ ID NO 198
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 198
aaccttacaa caaagctaga a                                             21

<210> SEQ ID NO 199
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 199
actaagcctt ggggatccag                                               20

<210> SEQ ID NO 200
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 200
tgctgtggaa atactaaaag g                                             21

<210> SEQ ID NO 201
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 201
ctccagaggt aatcctgtga                                               20

<210> SEQ ID NO 202
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 202
tggtgtgaga tggtatctag g                                             21

<210> SEQ ID NO 203
```

```
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 203
gtataatcca tgaatcttgt tt                                              22

<210> SEQ ID NO 204
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 204
ttcaaattgt ataagaga gt                                                22

<210> SEQ ID NO 205
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 205
gcaggaaagt tattttttaat                                                20

<210> SEQ ID NO 206
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 206
tgcttgagaa agctaacact t                                               21

<210> SEQ ID NO 207
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 207
cagtgtttgg aaattgtctg                                                 20

<210> SEQ ID NO 208
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 208
ggcactggga gattattgta                                                 20

<210> SEQ ID NO 209
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 209
tcctgttgtt aagtacacat                                               20

<210> SEQ ID NO 210
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 210
gggccgtaat tacttttg                                                 18

<210> SEQ ID NO 211
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 211
actcagtagg cactttgtgt c                                             21

<210> SEQ ID NO 212
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 212
tcttccacca caccaatc                                                 18

<210> SEQ ID NO 213
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 213
tggcttttca aaggtaaaa                                                19

<210> SEQ ID NO 214
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 214
gcaacgttaa catctgaatt t                                             21

<210> SEQ ID NO 215

<400> SEQUENCE: 215
```

000

<210> SEQ ID NO 216
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 216
attttatatg tcatgatcta ag                                              22

<210> SEQ ID NO 217
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 217
agagattaca ggtgtgagc                                                  19

<210> SEQ ID NO 218
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 218
atgatcctca actgcctct                                                  19

<210> SEQ ID NO 219
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 219
tgaaactcaa aagagaaaag                                                 20

<210> SEQ ID NO 220
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 220
acagatttct acttaaaatt                                                 20

<210> SEQ ID NO 221
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 221
tgaaactcaa aagagaaaag                                           20

<210> SEQ ID NO 222
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 222
acagatttct acttaaaatt                                           20

<210> SEQ ID NO 223
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 223 gcaaagggt actctatgta                                            20

<210> SEQ ID NO 224
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 224
tatcgggtca tcttgttaaa                                           20

<210> SEQ ID NO 225
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 225
tctaacaaag ctctgtccaa aa                                        22

<210> SEQ ID NO 226
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 226
ccacactgaa taactggaac a                                         21

<210> SEQ ID NO 227
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 227
gcaagcaagc tctctacctt c                                         21

<210> SEQ ID NO 228
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 228
tgttcttcca aaattcacat gc                                              22

<210> SEQ ID NO 229
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 229
atttcactat tccttcattt t                                               21

<210> SEQ ID NO 230
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 230
taattgttgc acactaaatt ac                                              22

<210> SEQ ID NO 231
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 231
aaaaagccac agaaatcagt c                                               21

<210> SEQ ID NO 232
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 232
ttcttatatc tcactgggca tt                                              22

<210> SEQ ID NO 233
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 233
ggatggtaga agagaagaaa gg                                              22

<210> SEQ ID NO 234
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 234
ggatggtaga agagaagaaa gg                                           22

<210> SEQ ID NO 235
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 235
tgcaaagatg cagaaccaac                                              20

<210> SEQ ID NO 236
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 236
ttttgttcct tgtcctggct ga                                           22

<210> SEQ ID NO 237
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 237
tgcaaagatg cagaaccaac                                              20

<210> SEQ ID NO 238
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 238
gcctccagct ctatccaagt t                                            21

<210> SEQ ID NO 239
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 239
ccttaatatc ttcccatgtc ca                                           22

<210> SEQ ID NO 240
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 240
attgttagtg cctcttctgc tt                                    22

<210> SEQ ID NO 241
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 241
gagaagtgag gtcagcagct                                       20

<210> SEQ ID NO 242
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 242
tttctaaatt tccattgaac ag                                    22

<210> SEQ ID NO 243
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 243
gaaattggca atctgattct                                       20

<210> SEQ ID NO 244
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 244
caacttgtcc tttattgatg t                                     21

<210> SEQ ID NO 245
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 245
ctatgttgat aaaacattga aa                                    22

<210> SEQ ID NO 246

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 246
gcctgtctgg aatatagttt                                                20

<210> SEQ ID NO 247
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 247
cagggcatat aatctaagct gt                                             22

<210> SEQ ID NO 248
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 248
caatgactct gagttgagca c                                              21

<210> SEQ ID NO 249
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 249
actctctccc tccctct                                                   18

<210> SEQ ID NO 250
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 250
tatggcccca aaactattct                                                20

<210> SEQ ID NO 251
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 251
acaagtactg ggcagattga                                                20

<210> SEQ ID NO 252
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 252
gccaggttta gctttcaagt                                                   20

<210> SEQ ID NO 253
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 253
ttttatatca ggagaaacac tg                                                22

<210> SEQ ID NO 254
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 254
ccagaatttt ggaggtttaa t                                                 21

<210> SEQ ID NO 255
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 255
tgtcattcct cctttatctc ca                                                22

<210> SEQ ID NO 256
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 256
ttcttttgcc tctcccaaag                                                   20

<210> SEQ ID NO 257
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 257
accctggcac agtgttgact                                                   20

<210> SEQ ID NO 258
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 258
tgggcctgag ttgagaagat                                               20

<210> SEQ ID NO 259
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 259
aatttgtaag tatgtgcaac g                                             21

<210> SEQ ID NO 260
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 260
tttttcccat ttccaactct                                               20

<210> SEQ ID NO 261
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 261
aaaagatgag acaggcaggt                                               20

<210> SEQ ID NO 262
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 262
acccctgtga atctcaaaat                                               20

<210> SEQ ID NO 263
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 263
gcacttgctt ctattgtttg t                                             21

<210> SEQ ID NO 264
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 264
cccttcctct cttccattct                                                    20

<210> SEQ ID NO 265
<211> LENGTH: 13
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 265
agcactgcag gta                                                           13

<210> SEQ ID NO 266
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 266
acagatacca aagaactgca a                                                  21

<210> SEQ ID NO 267
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 267
tggacacctt tcaacttaga                                                    20

<210> SEQ ID NO 268
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 268
gaacagtaat gttgaacttt tt                                                 22

<210> SEQ ID NO 269
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 269
tcttgcaaaa agcttagcac a                                                  21

<210> SEQ ID NO 270
<211> LENGTH: 21
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 270
aaaaagatct caaagggtcc a                                           21

<210> SEQ ID NO 271
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 271
gcttttgctg aacatcaagt                                             20

<210> SEQ ID NO 272
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 272
ccttccagca gcatagtct                                              19

<210> SEQ ID NO 273
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 273
aaatccagga tgtgcagt                                               18

<210> SEQ ID NO 274
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 274
atgatgaggt cagtggtgt                                              19

<210> SEQ ID NO 275
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 275
catcacagat catagtaaat gg                                          22

<210> SEQ ID NO 276
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 276
aattattatt ttgcaggcaa t                                              21

<210> SEQ ID NO 277
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 277
catgaggcaa acacctttcc                                                20

<210> SEQ ID NO 278
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 278
gctggactca ggataaagaa ca                                             22

<210> SEQ ID NO 279
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 279
tggaagcctg agctgactaa                                                20

<210> SEQ ID NO 280
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 280
ccttcttttc ccccagaatc                                                20

<210> SEQ ID NO 281
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 281
taggagaaca gaagatcaga g                                              21

<210> SEQ ID NO 282
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 282
aaagactatt gctaaatgct tg        22

<210> SEQ ID NO 283
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 283
taagcgtagg gctgtgtgtg        20

<210> SEQ ID NO 284
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 284
ggacggatag actccagaag g        21

<210> SEQ ID NO 285
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 285
gaatgacctt ggcacttta tca        23

<210> SEQ ID NO 286
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 286
aaggatagag atatacagat gaatgga        27

<210> SEQ ID NO 287
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 287
catgcaccgc gcaaatac        18

<210> SEQ ID NO 288
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 288
atgcctcacc cacaaacac                                                19

<210> SEQ ID NO 289
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 289
tccaagccct tctcactcac                                               20

<210> SEQ ID NO 290
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 290
ctgggacggt gacattttct                                               20

<210> SEQ ID NO 291
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 291
cccaggaaga gtggaaagat t                                             21

<210> SEQ ID NO 292
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 292
ttagcttgca tgtacctgtg t                                             21

<210> SEQ ID NO 293
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 293
agctagatgg ggtgaatttt                                               20

<210> SEQ ID NO 294
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 294
```
tgggctgagg ggagattc                                                  18

<210> SEQ ID NO 295
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 295
atcaagctaa ttaatgttat ct                                             22

<210> SEQ ID NO 296
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 296
aatgaataag gtcctcagag                                                20

<210> SEQ ID NO 297
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 297
tttaatctga tcattgccct a                                              21

<210> SEQ ID NO 298
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 298
agctgtgggt gaccttga                                                  18

<210> SEQ ID NO 299
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 299
tgtcccacca ttgtgtatta                                                20

<210> SEQ ID NO 300
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 300
tcagacttga agtccaggat                                                   20

<210> SEQ ID NO 301
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 301
gcttcagggg tgttagtttt                                                   20

<210> SEQ ID NO 302
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 302
ctttgtgaaa agtcgtccag                                                   20

<210> SEQ ID NO 303
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 303
ccatcatgga aagcatgg                                                     18

<210> SEQ ID NO 304
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 304
tcatctccat gactgcacta                                                   20

<210> SEQ ID NO 305
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 305
gagatgacgg agtagctcat                                                   20

<210> SEQ ID NO 306
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 306
cccagctgca ctgtctac                                                     18

<210> SEQ ID NO 307
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 307
tcttgttcca atcacaggac                                            20

<210> SEQ ID NO 308
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 308
atgctgttag ctgaagctct                                            20

<210> SEQ ID NO 309
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 309
tgaaagctcc taaagcagag                                            20

<210> SEQ ID NO 310
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 310
ttgaagagat gtgctatcat                                            20

<210> SEQ ID NO 311
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 311
gccgcctgca gcccgcgccc cccgtgcccc cgccccgccg ccggcccggg cgcc       54

<210> SEQ ID NO 312
<211> LENGTH: 601
<212> TYPE: DNA
<213> ORGANISM: Homo sapiens

<400> SEQUENCE: 312
catagtgaca ggtatatgcc caactaactg tggaaaacag ttctttcttt caaccttact    60
catcaccctc acggtctgtt tatgaggctc tcctccacca gccagaaagg atgacgtgcc   120
atacctgcaa aacttataca gcatcaacag aatgaatctt tccaacaagc cgaaacattg   180

```
agtattgtgg cacagaatat gccccaccca ttactcaatc tagatatcct tttattccac    240
cgtctcatga ttttctttttt cctggaaaac aaaagtattt ctttcatagc ccagctagca    300
ygataaatca gcgagtcaga attctagctt tgttgtaagg ttttgcgaat atctgatcct    360
cttattttgt acttttctat ttcctaggca aatctgagta tttcacccag ttttccttaa    420
ctaggcattg aaaactcagt ttttttctta caaaccttca tgtcttcctg ctcatttgca    480
cagtcttatc ttgcacctcc tataaaatgg agaaacttga cattaaaacg taattttat    540 tacattttga gggattccca gagaattttt ccccaatctc cttaggtagg gacttcttta    600
c                                                                   601

<210> SEQ ID NO 313
<211> LENGTH: 601
<212> TYPE: DNA
<213> ORGANISM: Homo sapiens

<400> SEQUENCE: 313
gtgggaacta tagtaaagaa gtccctacct aaggagattg gggaaaaatt ctctgggaat     60
ccctcaaaat gtaataaaaa ttcgttttta atgtcaagtt tctccatttt ataggaggtg    120
caagataaga ctgtgcaaat gagcaggaag acatgaaggt ttgtaagaaa aaaactgagt    180
tttcaatgcc tagttaagga aaactgggtg aaatactcag atttgcctag gaaatagaaa    240
agtacaaaat aagaggatca gatattcgca aaaccttaca acaaagctag aattctgact    300
ygctgattta tcgtgctagc tgggctatga agaaatact tttgttttcc aggaaaagaa    360
aaatcatgag acggtggaat aaaaggatat ctagattgag taatgggtgg ggcatattct    420
gtgccacaat actcaatgtt tcggcttgtt ggaaagattc attctgttga tgctgtataa    480
gttttgcagg tatggcacgt catcctttct ggctggtgga ggagagcctc ataaacagac    540
cgtgagggtg atgagtaagg ttgaaagaaa gaactgtttt ccacagttag ttgggcatat    600
a                                                                   601

<210> SEQ ID NO 314
<211> LENGTH: 650
<212> TYPE: DNA
<213> ORGANISM: Homo sapiens

<400> SEQUENCE: 314
tttattggtc ctgactggta caaatactga taaaaaggat tttaagatca tattcatact     60
tttggggaat gagagccaca attaattaac aatgtctgcc atgagattgg atgcaagagt    120
atggcactca tactattcct acttctgtct aattacacta tttgtttctg tgtgcaaaaa    180
tctttggtag gtggtggatg tgcccaagac acagggaaga aaaagaagta aacagggaag    240
tacaacacag actctgaaat ggggcatcat ggaagacgga gctttgtcgt cttggtcttt    300
gctgtatatt cacttcctac aacagtgcta aatccttgt ggatgcttaa atatattaaa     360
tgaatgcata aatgaaaaga gtaaataaag agtgtatatg aaagtatgta gataaaattc    420
ttcactaagc cttggggatc cagctgcttm aggactaaga ccgtatctag ctcctttag    480 tatttccaca gcatgccatg gagatacatg tttctgatta tatatgatac atggaaatta    540
tatgttgttg aatgagtgat tgagtaaatg tgtactaggg cagctaatca taaatatttc    600
tactattgct aaaatgactg gatttatcca ttccttctga gagtttatac                650

<210> SEQ ID NO 315
```

<211> LENGTH: 626
<212> TYPE: DNA
<213> ORGANISM: Homo sapiens

<400> SEQUENCE: 315

```
ctgcttaagg actaagaccr tatctagctc cttttagtat ttccacagca tgccatggag      60
atacatgttt ctgattatat atgatacatg gaaattatat gttgttgaat gagtgattga     120
gtaaatgtgt actagggcag ctaatcataa atatttctac tattgctaaa atgactggat     180
ttatccattc cttctgagag tttatactga ttgcttatat tgtatcaaat accgtaactg     240
agggcaatgt ttactcaaac taatagcacc attcaaattt atgcaaacaa taacactata     300
tctttaaaat gttttcacta aaagctgcat aaagagtgta ttcaacaaca atagaataat     360
tttacaatct tttttcttgc ttaatggcca tttgtgcctt ctgacatgct gctagccatt     420
caaaggtcac actaccttga agttgaagat caagacaaat gattagactc ataaaagaca     480
aatcacgtct ttctggacag gtgattatta ataattaatt agcatttaaa catgtattat     540
ttaagttctt tttaagttat aaagtctttg atttgctaaa cagtttaaat aatgaataaa     600
acataaaata ataatagtta ccattt                                           626
```

<210> SEQ ID NO 316
<211> LENGTH: 1113
<212> TYPE: DNA
<213> ORGANISM: Homo sapiens

<400> SEQUENCE: 316

```
caagagctgc atctcactcc aattttctt ctccctataa ccttatctag attcccagtt       60
gagggaaccg atgacctaat tcctctcagt ttaaatgcaa cacaggagca aattccaaat     120
atctatgctg gtcttgctgg gattgcagaa ccccagggtg gttatcctcc tccagaggta     180
atcctgtgat cagcactaac rccacatacc agcccttttca tcagcttgtt ggagaagcat    240
ctttacttcc caccaagcag tgacctagat accatctcac accagttaga atcaggatca     300
ttaaaaagtc aagaaaaaac agatgctgaa gaggatgtgg agaaatagga atgcttttac     360
actgttagtg ggaatgtaaa ttagttcaac cattgtcaaa gacagtgtgg cgatccctca     420
cagatctaga accagaaata ccatttgacc cagcaatccc attactgggt ctatacccaa     480
aggattataa attactctac tataaagaca catgcacaca tatgtttatt gcagcaccat     540
tcacaatagc aaagaattgc aaccaaccct aatgcccatc aatgacagac tggataaaga     600
aaatctggca catatacacc atggaatact acgcagccat aaaaaaggat gagtttatgt     660
cctttacagg gacatggatg aagctggaaa ccatcattct cagcaaacta acacaggaac     720
agaaaaccaa acacatgttc tcactcacaa gtgggagttg aacaatgaga cacatggac     780
acagggaggg gaacatcaca caccactgct tgtcagggg tggggggcta ggggaaggat     840
agcattagga gaaataccta atgtagatga agggttgatg ggtgcagcaa accaccatgg     900
catgtgtata cctgtgtaac aaacctccat gttctgcacg tgtatcccag aacttaaagt     960
acaatacaaa aaaaaaaaa agtgtaatcc agtttacatt ttcaaggtca aagtgggtac     1020
aatgctatct atcttgggct aagaagagaa aaggaaaaat tcttgcttta aatcttagaa     1080
gtctggtttt tttccctgtt ttgtaccccca tcc                                 1113
```

<210> SEQ ID NO 317
<211> LENGTH: 1113
<212> TYPE: DNA
<213> ORGANISM: Homo sapiens

<400> SEQUENCE: 317

```
ttcccagttg agggaaccga tgacctaatt cctctcagtt taaatgcaac acaggagcaa      60
attccaaata tctatgctgg tcttgctggg attgcagaac cccagggtgg ttatcctcct     120
ccagaggtaa tcctgtgatc agcactaacg ccacatacca gcccttcat cagcttgttg     180
gagaagcatc tttacttccc rccaagcagt gacctagata ccatctcaca ccagttagaa     240
tcaggatcat aaaaagtca agaaaaaaca gatgctgaag aggatgtgga gaaataggaa     300
tgcttttaca ctgttagtgg gaatgtaaat tagttcaacc attgtcaaag acagtgtggc     360
gatccctcac agatctagaa ccagaaatac catttgaccc agcaatccca ttactgggtc     420
tatacccaaa ggattataaa ttactctact ataaagacac atgcacacat atgtttattg     480
cagcaccatt cacaatagca aagaattgca accaaccta atgcccatca atgacagact     540
ggataaagaa aatctggcac atatacacca tggaatacta cgcagccata aaaaggatg     600
agtttatgtc ctttacaggg acatggatga agctggaaac catcattctc agcaaactaa     660
cacaggaaca gaaaaccaaa cacatgttct cactcacaag tgggagttga acaatgagaa     720
cacatggaca cagggagggg aacatcacac accactgctt gtcagggggt gggggggctag     780
gggaaggata gcattaggag aaatacctaa tgtagatgaa gggttgatgg gtgcagcaaa     840
ccaccatggc atgtgtatac ctgtgtaaca aacctccatg ttctgcacgt gtatcccaga     900
acttaaagta caatacaaaa aaaaaaaaaa gtgtaatcca gtttacattt tcaaggtcaa     960
agtgggtaca atgctatcta tcttgggcta agaagagaaa aggaaaaatt cttgctttaa    1020
atcttagaag tctggttttt ttccctgttt tgtaccccat cctcttggtc tctctagata    1080
tatttaagac tcacatagga cttgtctttt cta                                 1113
```

<210> SEQ ID NO 318
<211> LENGTH: 1001
<212> TYPE: DNA
<213> ORGANISM: Homo sapiens

<400> SEQUENCE: 318

```
tcatcaacta aatagttgat gagggaaat tgttctgtat atgttcatac ttcagctaat      60
caattaaaaa tgatgaaata ataagattac catttgcaa accctaatg caatgttgga      120
tccaggcaat gatcatcaat ggccactaaa atcacacaaa aggagataac cagaaatatgt     180
gctttgtgat ggaagcatta aatacaacta atgagatatt gtttataaga aagaaaggaa     240
gcaagaaagc aatcacacca agctctgtat ctagctacca catttaagga aaaaagaga     300
cagaagagca tgttaaatgt taccaagaag atacagtcag tcggaaaaaa tacagacaag     360
aaaatacaga gcaaacaac ccagcttctt cagcaaatca atataaaaaa attttaagaa     420
agagttaaag tataaactga gagacttcag aaacatatta tccaagtata atccatgaat     480
cttgtttaaa tatagatcaa rtaaaccact ataccaaaaa catcaaaaga caactgggta     540
aatttttaa atgactagct atttgatgtt aaggaagtaa tgttactctc ttatatacaa     600
tttgaaataa tctagcgagg agcagcaaat gtgcggctat gaggaagaaa cacaattggc     660
cattcttgaa tcattagctg gatggtggct atatgggggt agattttact actctctaat     720
tttacatata tttaaaatgt tccataataa attgttgagt tatcaaaaga aatatttcta     780
tataatagct aaaattattt ataaaagtta gtggtctcat aactttattt atttatttac     840
ttattttgag accgagtctc cctctgttat gcaggctgga gtgcagtggc tccatctcgg     900
```

```
ctcactgcaa acttcacctc ctggattgaa gcgattctcc tgcctcagcc ccccgagta      960 gctgggatta caggcttgca ccccacgcc cagctaattt t                          1001

<210> SEQ ID NO 319
<211> LENGTH: 601
<212> TYPE: DNA
<213> ORGANISM: Homo sapiens

<400> SEQUENCE: 319
agctaccaca tttaaggaaa aaagagaca gaagagcatg ttaaatgtta ccaagaagat      60
acagtcagtc ggaaaaaata cagacaagaa aatacagagc aaaacaaccc agcttcttca    120
gcaaatcaat ataaaaaaat tttaagaaag agttaaagta taaactgaga gacttcagaa    180
acatattatc caagtataat ccatgaatct tgtttaaata tagatcaaat aaaccactat    240
accaaaaaca tcaaaagaca actgggtaaa ttttttaaat gactagctat ttgatgttaa    300
rgaagtaatg ttactctctt atatacaatt tgaaataatc tagcgaggag cagcaaatgt    360
gcggctatga ggaagaaaca caattggcca ttcttgaatc attagctgga tggtggctat    420 atggggtag attttactac tctctaattt tacatatatt taaatgttc cataataaat      480 tgttgagtta tcaaaagaaa tatttctata taatagctaa aattatttat aaaagttagt    540
ggtctcataa ctttatttat ttatttactt attttgagac cgagtctccc tctgttatgc    600
a                                                                    601

<210> SEQ ID NO 320
<211> LENGTH: 601
<212> TYPE: DNA
<213> ORGANISM: Homo sapiens

<400> SEQUENCE: 320
ccaactgatc taattagata aacttagtca atatatttga atcccacatt ccagcagcta    60
ttttctccat ttgcttttat tgctgtttgt ggtgagtttg atatataatt ttaaggtgtt    120
aacatcccta acttatgtat gggtacagct cataaatacg aacctgtgtc atgcaactca    180
tatatgactg tgttcaaaat aatgtgtatt agactgtaaa acgattttaa tattttaaat    240
aactttcctg catttgtcgg tttcagcagg aaagttattt ttaataactt ccctgtattt    300
sttggtttca gtattaatta atctcattaa tgctaaactt tgtgatccta ggttaaaaaa    360
catattcaag atagcttcag aatgtttggt atacaaatag gtctggctaa atataagtgt    420
tagctttctc aagcatctaa atgctggcgg gcttttaaaa aaccagggct ttaaggagaa    480
aacacctgct ctgtggtttt gtagcagata tgaagtattc aaatttctta ataaatagaa    540
aaagaaatat ataacagaaa caggttgcac ttgtctttct cattaagcag gtggttagta    600
c                                                                    601

<210> SEQ ID NO 321
<211> LENGTH: 501
<212> TYPE: DNA
<213> ORGANISM: Homo sapiens

<400> SEQUENCE: 321
agctcataaa tacgaacctg tgtcatgcaa ctcatatatg actgtgttca aaataatgtg    60
tattagactg taaaacgatt ttaatatttt aaataacttt cctgcatttg tcggtttcag    120
caggaaagtt attttaata acttcccctgt atttgttggt ttcagtatta attaatctca    180
ttaatgctaa actttgtgat cctaggttaa aaacatatt caagatagct tcagaatgtt    240
```

```
tggtatacaa rtaggtctgg ctaaatataa gtgttagctt tctcaagcat ctaaatgctg    300
gcgggctttt aaaaaaccag ggctttaagg agaaaacacc tgctctgtgg ttttgtagca    360
gatatgaagt attcaaattt cttaataaat agaaaagaa atatataaca gaaacaggtt     420
gcacttgtct ttctcattaa gcaggtggtt agtaccatta tttgcattct catagcctta    480
atatacattt tccttctcta g                                              501

<210> SEQ ID NO 322
<211> LENGTH: 601
<212> TYPE: DNA
<213> ORGANISM: Homo sapiens

<400> SEQUENCE: 322
ttttgagttt ctactttagt gtcttagtgc tttctcgata tgggagaatt catgtcctcc     60
attcagaagt atgcactaag taagaggtat catgtctggt tcttgattag gtactaatct   120
tgaaatatta tcctacaata ggttagagca cgtatatctc ctgataatat attgaatatg   180
atagatttaa ataattggtt aactaaatac taaagcaaat tgctgcacgt atcatttatt   240
attcattgtg tagaaagtgc ctgactcagt gtttggaaat tgtctgactt ttcctcatat   300
rtagtgtggt ttcatgttat tgtatataag acctgacatg aactctgttt acaataatct   360
cccagtgcca taaagaccat aataaataat ataaccaatt ggtttcttta tgctgtcatt   420 tatagggca tatggcatta gtggaggatt accttgtatt acccatagtg cttagagtat    480
gaatcacaca tgcaccttga aggaaaagag gtgcaatgta ataagaaacc agatattgaa   540
aatgcaagtt ttgttatgtt attctgggta tgttaacctt tattcctgcc ctccatatgc   600
a                                                                    601

<210> SEQ ID NO 323
<211> LENGTH: 501
<212> TYPE: DNA
<213> ORGANISM: Homo sapiens

<400> SEQUENCE: 323
aagaggtatc atgtctggtt cttgattagg tactaatctt gaaatactat cctacagtag    60
gttagagcac gtatatctcc tgataatata ttgaatatga tagatttaaa taattggtta   120
actaaatact aaagcaaatt gctgcacgta tcatttatta ttcattgtgt agaaagtgcc   180
tgactcagtg tttggaaatt gtctgacttt tcctcatata tagtgtggtt tcatgttatt   240
gtatataaga mctgacatga accctgttta caataatctc ccagtgccat aaagaccata   300
ataaataata taaccaattg gtttctttat gctgtcattt attagggcat atggcattag   360
tggaggatta ccttgtatta cccatagtgc ttagagtatg aatcacacat gccacttgaa   420
ggaaaagagg tgcaatgtaa taagaaacca gatattgaaa atgcaagttt tgttatgtta   480
ttctgggtat gttaaccttt a                                              501

<210> SEQ ID NO 324
<211> LENGTH: 854
<212> TYPE: DNA
<213> ORGANISM: Homo sapiens

<400> SEQUENCE: 324
tttcagcact gagagccaga gtggaattgt ctccttcatt gccactgcct tcacgttttg     60
tgtgtcgtat ctgttttgtg atcactgaga cccaagaacc cccgacttgc cgacatacta   120
```

| | |
|---|---|
| tgtggccccg agagaggact tgagctctct gggtttcatc attaccatca attaaataaa | 180 |
| caggacagta gcttcttcct tggattgtta atttaaggct ctggataata catgtaaccg | 240 |
| ccttatgata gagcagaatt gtaagtaggc tcatggtaga atcgttcaat gacatttccc | 300 |
| tttcctttgg gagaaacaga aattcacagg tctaattctt ttcctattaa tagttcctgr | 360 |
| ccattattcc agaactgtcc taaaggaatt ctttctcctt aaggacacca cctcccagga | 420 |
| gggtatttaa agatttgcac aggccgggca cggtggctca tgcttgtaat cccagcagtt | 480 |
| tgggaggcca aggcgggtgg atcacttgtg ctcaggggtt caagaccggc ctggccaaca | 540 |
| tggtgaaacc ctatctctac aaaaacaca aagttagct gggcctggct atgcatgcct | 600 |
| gtaattccag ctactcggga ggctgaggct ggagaatagc ttgaaccagg aggtggaga | 660 |
| taacagtgag ctgagatgcc actatgacac tccagcctgg gtgacagagc aagactctct | 720 |
| ctcaaaaaaa aaaaaagatt tttatagtcc agtattcaac gttcatagta cacctttctt | 780 |
| atcctagtaa atcttctttt atcaaggtat atgatcccat atagtagtta actcttactc | 840 |
| ttactttatg acaa | 854 |

<210> SEQ ID NO 325
<211> LENGTH: 501
<212> TYPE: DNA
<213> ORGANISM: Homo sapiens

<400> SEQUENCE: 325

| | |
|---|---|
| aaatacttac tattaaatat gagaaactgt ggtgtttatc ggtaagatcc acgaaggaag | 60 |
| aagttttaaa gaaaatact ttaaccgtgg aaaaaaaaa ctttaatgtc tattatcgaa | 120 |
| taggggccgt aattactttt gcaaaataaa aaacaaaca agactagcta tagtgtaaat | 180 |
| gtaatcgtta tgcttttttaa tgaaacaatt aagtaggttg cccatttaca attagcctga | 240 |
| ttttctcctg ygtggtatta tgtgtactta acaacaggac ccagtggaaa ttcactcatt | 300 |
| taacaaagtc tgcctacatg gtttcaaata tgggcctaac ttgaaaattc agtcataatt | 360 |
| aaatctaagg actaaaacaa atctgtataa aaagattctg ctaaataagg gaaaattcaa | 420 |
| gtctagggct acattctgaa agatattgaa gtagaacctc tgcagcaaga ctaggcttgg | 480 |
| aaagtgcggg gaggagggaa a | 501 |

<210> SEQ ID NO 326
<211> LENGTH: 601
<212> TYPE: DNA
<213> ORGANISM: Homo sapiens

<400> SEQUENCE: 326

| | |
|---|---|
| ccacatcaga aacatgagga aattctacat ggtaaaaaca gcaacaacca aaaaatactt | 60 |
| aaagtcaaca aaccaggaaa agacatctct gaatatagga atgccaaacc tttaacacaa | 120 |
| taaaacacag attatatttc agaaggctat attatatgtg tataccaaca tcaatatgtc | 180 |
| cagagtagct gcacagagtt ccatatttta gtctttataa gttcccctcc tcaccctact | 240 |
| cagtaggcac tttgtgtcta gaaacttctg tgtcaacagt tttccctctc tctggaattc | 300 |
| mtcaggacag aagtgattgg tgtggtggaa gagggttgtg ctaagagtga agttatatga | 360 |
| aagtaggatg gaggttagca agtagttaaa gtccagaaag gcaataaggt gttaaggaag | 420 |
| aacttttcca ttttacaggt ctgagcaagc aggaaatcaa ctctacaaac tttgaaactt | 480 |
| ggtaaatatg aaaacattct caataccatt tgtcatttaa taaatacaaa ttatactatt | 540 |
| ttactgcttg catctagaag tttgtcaaag atctcgtctt aattattcat tgtgtcggcg | 600 |

```
a                                                                601

<210> SEQ ID NO 327
<211> LENGTH: 601
<212> TYPE: DNA
<213> ORGANISM: Homo sapiens

<400> SEQUENCE: 327
gacgagatct tgacaaact  tctagatgca agcagtaaaa tagtataatt tgtatttatt      60
aaatgacaaa tggtattgag aatgttttca tatttaccaa gtttcaaagt ttgtagagtt     120
gatttcctgc ttgctcagac ctgtaaaatg gaaaagttct tccttaacac cttattgcct     180
ttctggactt taactacttg ctaacctcca tcctactttc atataacttc actcttagca     240
caaccctctt ccaccacacc aatcacttct gtcctgatga attccagaga gagggaaaac     300
ygttgacaca gaagtttcta gacacaaagt gcctactgag tagggtgagg aggggaactt     360
ataaagacta aaatatggaa ctctgtgcag ctactctgga catattgatg ttggtataca     420
catataatat agccttctga aatataatct gtgttttatt gtgttaaagg tttggcattc     480
ctatattcag agatgtcttt tcctggtttg ttgactttaa gtattttttg gttgttgctg     540
ttttttaccat gtagaatttc ctcatgtttc tgatgtggaa agtataagaa tatcagccag     600
a                                                                601

<210> SEQ ID NO 328
<211> LENGTH: 811
<212> TYPE: DNA
<213> ORGANISM: Homo sapiens

<400> SEQUENCE: 328
taaataatct ctaattagta taatgggtgt tcttagtgca gtgggtactt ttaaagtgct      60
ttgtggcttt tgatgaaaat tgtcttagta tttaaaactt tttcttaccc aattttttgt     120
tcccatcgaa ttagcaatgc tgtaaagaaa ggcatcttat tccattttt  gttgctataa     180
aggaatactt gaggctgggt aatttataaa gatgaaaagt ttatttggct cgcaattctg     240
gatggctgga aggttaagta ctgggccaca gcatctggtg ggggcctcga gctgcttcta     300
gtcataatgg aaggtgaagg gtgtaaagat catgtgacaa gggaggaaag aagagaagga     360
aggaggtgct ggttctttct atcaaccaat tcgcaagaga actaatagag aaagaactca     420
cttagccctg tgggaacaca ttaatctatt cataagggat ctggctgtat gatacaaaca     480
cctcccatta ggccccacct ccaaattgta tcccattggg gatcaaattt caaaagaga      540
tttggaagga acaaacaaac catatctaag ccatagtaaa aggaatggct tttcaaaggt     600
aaaatttact ragtgtatta atattttacc aatttccagc caggagagta tgaatgttgc     660
attattacat tgctttgaaa caaagcatta gtcttaattc agaagtttaa attcagatgt     720
taacgttgca tatttaataa tgcacaacca gtactaaaat cctcattgaa atgacaaata     780
attttatttc gaatccctta tagaggttca c                                   811

<210> SEQ ID NO 329
<211> LENGTH: 811
<212> TYPE: DNA
<213> ORGANISM: Homo sapiens

<400> SEQUENCE: 329
tgtcttagta tttaaaactt tttcttaccc aattttttgt tcccatcgaa ttagcaatgc      60
```

```
tgtaaagaaa ggcatcttat tccatttttt gttgctataa aggaatactt gaggctgggt      120
aatttataaa gatgaaaagt ttatttggct cgcaattctg gatggctgga aggttaagta      180
ctgggccaca gcatctggtg ggggcctcga gctgcttcta gtcataatgg aaggtgaagg      240
gtgtaaagat catgtgacaa gggaggaaag aagagaagga aggaggtgct ggttctttct      300
atcaaccaat tcgcaagaga actaatagag aaagaactca cttagccctg tgggaacaca      360
ttaatctatt cataagggat ctggctgtat gatacaaaca cctcccatta ggccccacct      420
ccaaattgta tcccattggg gatcaaattt caaaagaga  tttggaagga acaaacaaac      480
catatctaag ccatagtaaa aggaatggct tttcaaaggt aaaatttact aagtgtatta      540 atatttacc  aatttccagc caggagagta tgaatgttgc attattacat tgctttgaaa       600
caaagcatta ktcttaattc agaagtttaa attcagatgt taacgttgca tatttaataa      660
tgcacaacca gtactaaaat cctcattgaa atgacaaata atttttattc gaatccctta     720
tagaggttca caatgtttta acaatgtagt tttgactaaa tagaagtagt caaaacctgt      780
cagattggaa atagtattta taaaacataa a                                     811

<210> SEQ ID NO 330
<211> LENGTH: 601
<212> TYPE: DNA
<213> ORGANISM: Homo sapiens

<400> SEQUENCE: 330
gctcatcaat tttgacttaa gaaaattcta gcaacattta tagattttgc caaaattcag      60
cttcttccca atcaatcta  taagaaggct cttccttaaa cataatttt  atatctatga      120 actgcactag catttactat atatttttat cactctcacc attactggat aataaataaa      180
agctcattaa aagagttaac aaaacatatt tattttaggc atcctgaaaa aaagattcaa      240
ttttattatc atttctacaa taagtattga agaaggaga  atttaaatta cttcatatac      300
stgataaagg aaaacatatg caaggcaaat aaacatctta gatcatgaca tataaaataa      360
tagattatta ctaaagatta aaatactttc ttaagaatta aagcaattct aaaagcaata      420
gtaaataaca ttctttctag tgatcagaca ctggatacta tgtttgagat agacagtgaa      480
ttgggaatgt tgttttacag aagctcctac cttgcaagga caggcaagtt taaatgtcag      540
ctagaaaact atcttgagtt ttcagtaatg taagattttc ctattcaatt tcacacttta      600
a                                                                      601

<210> SEQ ID NO 331
<211> LENGTH: 601
<212> TYPE: DNA
<213> ORGANISM: Homo sapiens

<400> SEQUENCE: 331
agaaaattct agcaacattt atagattttg ccaaaattca gcttcttccc aaatcaatct      60
ataagaaggc tcttccttaa acataatttt tatatctatg aactgcacta gcatttacta      120 tatatttta  tcactctcac cattactgga taataaataa aagctcatta aaagagttaa      180
caaaacatat ttattttagg catcctgaaa aaagattca  attttattat catttctaca      240
ataagtattg aagaaggag  aatttaaatt acttcatata cctgataaag gaaaacatat      300
rcaaggcaaa taacatctt  agatcatgac atataaaata atagattatt actaaagatt      360 aaatacttt  cttaagaatt aaagcaattc taaaagcaat agtaaataac attctttcta      420
gtgatcagac actggatact atgtttgaga tagacagtga attgggaatg ttgttttaca      480
```

| | |
|---|---|
| gaagctccta ccttgcaagg acaggcaagt ttaaatgtca gctagaaaac tatcttgagt | 540 |
| tttcagtaat gtaagatttt cctattcaat ttcacactttt aaatttttata tatatataaaa | 600 |
| a | 601 |

<210> SEQ ID NO 332
<211> LENGTH: 1110
<212> TYPE: DNA
<213> ORGANISM: Homo sapiens

<400> SEQUENCE: 332

| | |
|---|---|
| tgtagaagtt cttatcactt cctggccttt tggctaagat caagtgtgaa atgtagaagt | 60 |
| tcctctaagc tttacttccc tcaaaaacta gttttatctt gtcagcagga ttcacttaaa | 120 |
| aagacaaatt cagattatga attttttttct tttttacagg gtctgctctg ttgcccaggc | 180 |
| tggagtgcag aggcacaatc tcggctcact gcagcctccg cctcctgggt tcaagcaatt | 240 |
| ctcttgcctc agcctcccga gtaactggga ttacaggcat gtgccaccac ccagctaatt | 300 |
| tttgtatttt tagtagagat ggggtttcac cacattggtc aggctggtct cgaactgctg | 360 |
| gcctcaagtg atccacttgc ctcggcctcc caaagtgcag agattacagg tgtgagccac | 420 |
| cgtgcccagc ctcataaccg tttcaactac ttttttcactt gacaagcaga tgtgaagtta | 480 |
| acaaagtcac ccatatttga aataaagata gtatattcct gggyaggca gaggcagttg | 540 |
| aggatcatga ataactatg ttggcatagt tatttaggtg ttgatactgt tattatgcca | 600 |
| ttgaaagtta aacagagaac cctctgggta catgttttat accaatgcac actatcttat | 660 |
| tagtccctct cataatgtgc agtcatcatt actgttacgg gttgaggtgt ccccatcctc | 720 |
| tatgggacac ctctatgttg aagtctcaga ttccctagaa tctcagaatg tgaccttgtt | 780 |
| tggaaacaga tttgctacag acgcaattag ttgagatgcg cttatatggg taggtcctaa | 840 |
| ttcagtgact ggtgtcctta aaaaaatgga aatgtacaca cggtggtaga catgcataga | 900 |
| gggaagagag atggagaaaa tggtcaccta caagccaaag acaggggtct ggagcagatc | 960 |
| cttccctcac agccctcaga aggaaccaat cttgccaata ccttgatttt ggacttccac | 1020 |
| ctccagaact ataacacatt tctgttcttc aagcaatttg tagccatttg ttacagctaa | 1080 |
| tacaatcaca catagaaatg acttgtaaat | 1110 |

<210> SEQ ID NO 333
<211> LENGTH: 691
<212> TYPE: DNA
<213> ORGANISM: Homo sapiens

<400> SEQUENCE: 333

| | |
|---|---|
| taaaacatgt acccagaggg ttctctgttt aactttcaat ggcataataa cagtatcaac | 60 |
| acctaaataa ctatgccaac atagttattt catgatcctc aactgcctct gcctaccca | 120 |
| ggaatatact atctttattt caaatatggg tgactttgtt aacttcacat ctgcttgtca | 180 |
| agtgaaaaag tagttgaaac rgttatgagg ctgggcacgg tggctcacac ctgtaatctc | 240 |
| tgcactttgg gaggccgagg caagtggatc acttgaggcc agcagttcga gaccagcctg | 300 |
| accaatgtgg tgaaacccca tctctactaa aaatacaaaa attagctggg tggtggcaca | 360 |
| tgcctgtaat cccagttact cgggaggctg aggcaagaga attgcttgaa cccaggaggc | 420 |
| ggaggctgca gtgagccgag attgtgcctc tgcactccag cctgggcaac agagcagacc | 480 |
| ctgtaaaaaa gaaaaaaatt cataatctga atttgtctttt ttaagtgaat cctgctgaca | 540 |

```
agataaaact agtttttgag ggaagtaaag cttagaggaa cttctacatt tcacacttga      600
tcttagccaa aaggccagga agtgataaga acttctacat tttaagttat tcacaagata      660
actattaatg aacctgaaat agtttgtaaa g                                    691

<210> SEQ ID NO 334
<211> LENGTH: 640
<212> TYPE: DNA
<213> ORGANISM: Homo sapiens

<400> SEQUENCE: 334 aaacctttt  cctgttttac tattactaaa ggtggcacaa cagcaacctc aacaactttg       60
caccatgcca acactgatgt ttacacccag cacagcattt ttggtctcta tttttattct      120
cctctgaatg taatgaggat tcctagatgg ctagccaatt cgaatattta aggcaactga      180
aagttagaat gtttctgaaa catagtgttg ttgccagaga gtacgaaagt tttcaagaat      240
atcgggcaat tctgaaagta caagaagcc  agattaaatg aataacact ggcgaagttt       300 tagcaaggtg actctcatat aatgatcatt atcattacca cagttaaaag aaaagagttg      360
tttatgaaag gccatgtgtc tgcaatgaaa ctcaaaagag aaaagttaac aggtgcaara      420
ggtagtttta ttataaaagg agggtaggca acaagaatat gtttaatttt tcttcctttt      480
catgagtaag acaagagtt  tcatatatgt gaatattttt atttaatttt aagtagaaat      540 ctgttttta  aatatgggta tatgcttatt tgtgtaagtg taagaaacag aagtaagtac      600
agcaaaccag aaataggcca aacactcctg agcataattt                            640

<210> SEQ ID NO 335
<211> LENGTH: 919
<212> TYPE: DNA
<213> ORGANISM: Homo sapiens

<400> SEQUENCE: 335
tacacccagc acagcatttt tggtctctat ttttattctc ctctgaatgt aatgaggatt       60
cctagatggc tagccaattc gaatatttaa ggcaactgaa agttagaatg tttctgaaac      120
atagtgttgt tgccagagag tacgaaagtt ttcaagaata tcgggcaatt ctgaaagtac      180
aaagaagcca gattaaatga ataacactg  gcgaagtttt agcaaggtga ctctcatata      240
atgatcatta tcattaccac agttaaaaga aaagagttgt ttatgaaagg ccatgtgtct      300
gcaatgaaac tcaaaagaga aaagttaaca ggtgcaaaag gtagttttat tataaaagga      360
gggtaggcaa caagaatatg tttaattttt cttcctttc  atgagtaagg acaagagtkt      420
catatatgtg aatatttta  tttaatttta agtagaaatc tgtttttaaa atatgggtat      480
atgcttattt gtgtaagtgt aagaaacaga agtaagtaca gcaaaccaga aataggccaa      540
acactcctga gcataatttt acttggtaga ttattcctga aacttaagga atcatctttg      600
aactcttttc ctcacttgac ttccaggatt caccatgcac ttgtgatttt cctttcattt      660
cactctccgt tcctcctcag tctttttttc tcccccaggt ctttttttgtt catcttaaac      720 tctaaattt  agaatatccc aggggtctgc cttcggcctt ctcttttata tctacactgg      780
cctcatacat aatcttaacc aagtcattat tttaaatacc tacaatatac tgaaaacttc      840
taaatttgta ttttaattct tgacttcttc catacagtct agatttgtat gtccataggc      900
tgacatcatt ggctgatac                                                   919

<210> SEQ ID NO 336
<211> LENGTH: 1001
```

```
<212> TYPE: DNA
<213> ORGANISM: Homo sapiens

<400> SEQUENCE: 336
ttactaaata ttctccaaca aatatatact tagtatatac tattagtgat gcatgctttc       60
aaatatttgg actatatcaa tgaatgaaac aaaaaattat ttgcccttaa ggagcttaga      120
ttctaacaga tggattcaga tgattttat gccttatttc gtaggtttaa aagagcaatg       180
gggaaaaggg aagaagagag ggattgaaaa tattgagaag gttgggagac ttagcaattt      240
taagtaaggt agtgagggta ggttttattg gcaaagtgat ttttcagcag agactgggaa      300
agatgaacgt ggtatcctgg aggaaagcct cccaggcaga gttaagctgc taacaaaagt      360
gcccttaggc tggagtgggc ttgtttgatt aaggaacaaa gaggtcagca tggttgcact      420
agagagaaaa aatcagatgg cgtaaggaga tgaaatcaga agatacgag gctaggcaaa       480
ggggtactct atgtaatgaa yatgacctgg cagtactgac atctcctgag ggactgttag      540
aagtgcagac tcttgtatct tttctcaagt ctatgaaatc tagacttcat tttaacaaga      600
tgacccgata tttacataca cattaaagtt ccagaagcac tgatataaca cattgtaaga      660
tcgcacagga cttcaattct ttttctggtt tttagaggca gtcctttggg gtgttttgtg      720
tagagtataa tgacctgaaa tatctaggat cactctagct actatcttga ggaaagagtg      780
caataaggcg aacagttca gaggcaatgg tggtcttcta aatgaaagac acacagcact       840
caaaccaggc agttgaggag ggatgggaag aagttgtcaa attctagaca tattttaaag      900
gtagtgtcca gagaatttcc ttagatgcgt aggaacatgg aggataggac atagggtgga      960
aataaacgaa ataagaaac tgaagctgat tctgacattt t                         1001

<210> SEQ ID NO 337
<211> LENGTH: 1576
<212> TYPE: DNA
<213> ORGANISM: Homo sapiens

<400> SEQUENCE: 337 ataccttta agtgacatcc tagtgaatct ccatttgtca cgagacctca agctttccag        60
ttctggcaca aagtgattac tcataccatc acttcaaaat gatgattatc ttcatttatt      120
ttagttatat tgaacaaaat atacatttaa aaaatctaat tactaaatat ctccaacaa       180
atatatactt agtatatact attagtgatg catgctttca aatatttgga ctatatcaat      240
gaatgaaaca aaaaattatt tgcccttaag gagcttagat tctaacagat ggattcagat      300
gatttttatg ccttatttcg taggtttaaa agagcaatgg ggaaaaggga agaagagagg      360
gattgaaaat attgagaagg ttgggagact tagcaatttt aagtaaggta gtgagggtag      420
gttttattgg caaagtgatt tttcagcaga gactgggaaa gatgaacgtg gtatcctgga      480
ggaaagcctc ccaggcagag ttaagctgct aacaaaagtg cccttaggct ggagtgggct      540
tgtttgatta aggaacaaag aggtcagcat ggttgcacta gagagaaaaa atcagatggc      600
gtaaggagat gaaatcagaa agatacgagg ctaggcaaag gggtactcta tgtaatgaac      660
atgacctggc agtactgaca tctcctgagg gactgttaga agtgcagact cttgtatctt      720
ttctcaartc tatgaaatct agacttcatt ttaacaagat gacccgatat ttacatacac      780
attaaagttc cagaagcact gatataacac attgtaagat cgcacaggac ttcaattctt      840
tttctggttt ttagaggcag tcctttgggg tgttttgtgt agagtataat gacctgaaat      900
atctaggatc actctagcta ctatcttgag gaaagagtgc aataaggcgg aacagttcag      960
```

```
aggcaatggt ggtcttctaa atgaaagaca cacagcactc aaaccaggca gttgaggagg    1020
gatgggaaga agttgtcaaa ttctagacat attttaaagg tagtgtccag agaatttcct    1080
tagatgcgta ggaacatgga ggataggaca tagggtggaa ataaacgaaa taagaaaact    1140
gaagctgatt ctgacatttt agacctaaaa tctcaactaa aagttgccaa gatgggaaaa    1200
actaggtgca tcttgtttgg tgagtggaaa tcagccttgt gaattaagac ttaaactgat    1260
gtctttaatc ccgtagaaat accatgaagg cagtagaaga tggctaaaga gaggtctaga    1320
ctgtaggtac aaatttaaaa gtcacttgca tttggatgct taaagtcagg atattgtgaa    1380
gtcaacagag gaataaataa atgcagagag gggaaagaaa aggcccatag actgagccat    1440
tgtctggttt atttacatat tagtatatat tttcttaaag atgtttgcta tataataatg    1500
agttacctaa agtgtgactt ttctaaattt atggggaatt ttctacattg tgttatggca    1560
ctactaaaaa taataa                                                   1576

<210> SEQ ID NO 338
<211> LENGTH: 1275
<212> TYPE: DNA
<213> ORGANISM: Homo sapiens

<400> SEQUENCE: 338
gtaaaactaa ttataattaa aatcaaaata tttactgaac ctacttactc ctataatttg      60
cgttgctggt taaacccag ctataaaaat tttgatcaaa aatttttatt ttgtaaatga     120
tctgacacag cataaatgtt aatcacattt ctttatttta tttgcagatt aatttgagta    180
atttgaaaaa ttattaatgt tacttaatta ctctcaacac cttacagtgt ctcctgtaag    240
cactattggt gatactgaat ttaagttaca tttaacaact atcagaaaat agttttaaa    300 gtaaaaatta tgatttggag tttaccaact aaatcttgtt agctttcact gcctctattg    360
agaagagcag cagttcttat cttcctcctt tttcttcttt aattaacaag agattatttg    420
tatcatagcc ataaaatcag ttcaggtatt acatgaacga caccctgac tgcaatggtg    480 tagtttattg tattagtcca ttttcatgct gctgataaag acatacataa gactgggtaa    540
tttataaaga aatagaagtt taacggactc acagttccat gtggctgggg aagcctcaca    600
atcatgatcg aaggcaaaag gcacatctta catggcaaca ggcaagagag aatgagagcc    660
aagtgaaagg agaaacccct tataaaacct tcagacctca tgagacttat tcactaccac    720
aagaacagta tgtgagaaac agtcccatga tccagttatc tcccactggg tccctcccac    780
cacacaaggg aattatggga actgcaattc aagatgaaat gtgggtggaa gcacaacgga    840
actatatcat gatcaaagca ttattgtttt ctctgataag ctgatctaga aagtgctgct    900
tgtgatcagc tttggtgacc atgatcagtg aaatggttaa ggaaatctac agattttgta    960
ggtttgtgcc ttgacagacg accggtatct gtttctcttt tcatgatgaa gtatctaaca    1020
aagctctgtc caaattttg aatttctcgt taaawgcatc atgattatag aacagaggtt    1080
acaatcaatt attcagtcac acaatcactc tcatcagtca ttaaggtgca tacctggtgt    1140
tccagttatt cagtgtggta taacaaacta cctggaactt aatggcttga aatagtcacc    1200
attacattat gattgtccat tctctgcatc aataattagg atttggcaaa gagggaatgg    1260
tttgtttaca gacag                                                    1275

<210> SEQ ID NO 339
<211> LENGTH: 1275
<212> TYPE: DNA
<213> ORGANISM: Homo sapiens
```

<400> SEQUENCE: 339

```
gtaaaactaa ttataattaa aatcaaaata tttactgaac ctacttactc ctataatttg      60
cgttgctggt taaaacccag ctataaaaat tttgatcaaa aattttttat ttgtaaatga     120
tctgacacag cataaatgtt aatcacattt ctttatttta tttgcagatt aatttgagta     180
atttgaaaaa ttattaatgt tacttaatta ctctcaacac cttacagtgt ctcctgtaag     240
cactattggt gatactgaat ttaagttaca tttaacaact atcagaaaat agttttaaa      300
gtaaaaatta tgatttggag tttaccaact aaatcttgtt agctttcact gcctctattg     360
agaagagcag cagttcttat cttcctcctt tttcttcttt aattaacaag agattatttg     420
tatcatagcc ataaaatcag ttcaggtatt acatgaacga caccctgac tgcaatggtg      480
tagtttattg tattagtcca tttcatgct gctgataaag acatacataa gactgggtaa      540
tttataaaga aatagaagtt taacggactc acagttccat gtggctgggg aagcctcaca     600
atcatgatcg aaggcaaaag gcacatctta catggcaaca ggcaagagag aatgagagcc     660
aagtgaaagg agaaacccct tataaaacct tcagacctca tgagacttat tcactaccac     720
aagaacagta tgtgagaaac agtcccatga tccagttatc tcccactggg tccctcccac     780
cacacaaggg aattatggga actgcaattc aagatgaaat gtgggtggaa gcacaacgga     840
actatatcat gatcaaagca ttattgtttt ctctgataag ctgatctaga aagtgctgct     900
tgtgatcagc tttggtgacc atgatcagtg aaatggttaa ggaaatctac agattttgta     960
ggtttgtgcc ttgacagacg accggtatct gtttctcttt tcatgatgaa gtatctaaca    1020
aagctctgtc caaattttg aatttctcgt taaatgcatc atgattatag aacagaggtt     1080
acaatcaatt attcagtcac acaatcactc tcatcagtca ttaaggtgcr tacctggtgt    1140
tccagttatt cagtgtggta taacaaacta cctggaactt aatggcttga aatagtcacc    1200
attacattat gattgtccat tctctgcatc aataattagg atttggcaaa gagggaatgg    1260
tttgtttaca gacag                                                    1275
```

<210> SEQ ID NO 340
<211> LENGTH: 1001
<212> TYPE: DNA
<213> ORGANISM: Homo sapiens

<400> SEQUENCE: 340

```
gaaacaaaaa attgcttttt atatattgat attttttgcac ggatttctta ggattttcta     60
tgtacatgac catgtcatct gcaaatgaaa tagttttatt tctttatcaa tccggatgaa    120
tttattaaaa ttatcttgcc taatttccca aatagggcct ccatgttgaa cataagtggt    180
ggcaagggtg atctgttgct aatctcagtg gatgatattc agtgttttac aatgatcttc    240
gacagctctg gctgttaaat tatcatagtc tgtatggcct aaacaaacaa aatacttatg    300
attatggggg aggctgggat atccaagatc aagttgctgg caggtctagc aacctgccac    360
tgggaagccc tgcttcccag ttttcagatg gccaccttct tatagtatct tcaccaaaga    420
tagggcagag agagcaagca agctctctac cttctcatat aagggcacta atccccaccat    480
gaaggcgcca ctgtcatgac stgattatgt cacaaagacc ccggggcaaa tattaccact    540
gtgaggagta cagttttagc atgtgaattt tggaagaaca caaacattta gtacagagtg    600
actattaagt atgttattaa ctatggagtt tttgtaggca ttttttaaca cattgagaaa    660
gtttcctcta ttcctacttt tgttgagaag tttttatgat gacaaggcat tacatttat     720
```

```
ccaatgactt ttctgtgtgt attgagatga ctgatttgtt ctgccaattt aaatccattg    780
ttgattctct ctaggatttt ttttatttca gttattaaat ttttcaacag gagaattact    840
gtcttgttct tttttttgta atttctgtcc ccttactggt attccatatt taataaggca    900
tcataatagt actcttcttt agtttcttaa agatggtttt ctttagtttt taacatattt    960
atgtctattt agaagtcttt gttaagtctg acatctgagc t                       1001

<210> SEQ ID NO 341
<211> LENGTH: 1001
<212> TYPE: DNA
<213> ORGANISM: Homo sapiens

<400> SEQUENCE: 341
ggatttctta ggattttcta tgtacatgac catgtcatct gcaaatgaaa tagttttatt     60
tctttatcaa tccggatgaa tttattaaaa ttatcttgcc taatttccca aatagggcct    120
ccatgttgaa cataagtggt ggcaagggtg atctgttgct aatctcagtg gatgatattc    180
agtgttttac aatgatcttc gacagctctg gctgttaaat tatcatagtc tgtatggcct    240
aaacaaacaa aatacttatg attatggggg aggctgggat atccaagatc aagttgctgg    300
caggtctagc aacctgccac tgggaagccc tgcttcccag ttttcagatg ccaccttct    360 tatagtatct tcaccaaaga tagggcagag agagcaagca agctctctac cttctcatat    420
aagggcacta atcccaccat gaaggcgcca ctgtcatgac ctgattatgt cacaaagacc    480
ccggggcaaa tattaccact stgaggagta cagttttagc atgtgaattt tggaagaaca    540
caaacattta gtacagagtg actattaagt atgttattaa ctatggagtt tttgtaggca    600
ttttttaaca cattgagaaa gtttcctcta ttcctacttt tgttgagaag tttttatgat    660
gacaaggcat tacattttat ccaatgactt ttctgtgtgt attgagatga ctgatttgtt    720
ctgccaattt aaatccattg ttgattctct ctaggatttt ttttatttca gttattaaat    780
ttttcaacag gagaattact gtcttgttct tttttttgta atttctgtcc ccttactggt    840
attccatatt taataaggca tcataatagt actcttcttt agtttcttaa agatggtttt    900
ctttagtttt taacatattt atgtctattt agaagtcttt gttaagtctg acatctgagc    960
tctctcaaag tttctgctga tttttttttt cctatgtttg g                       1001

<210> SEQ ID NO 342
<211> LENGTH: 701
<212> TYPE: DNA
<213> ORGANISM: Homo sapiens

<400> SEQUENCE: 342
ggaaaccctg gcctcttgat cacactttcc tggagtttag tcccctctgc aatatgtacc     60
tgggagtcat aagaaatgcc agttacaaaa acttcctgta cagatatcct agcactcaac    120
tggaaaccgg ggagagtcac aattctgtct ttccagccat atgtaactga atggagatc    180 ttttcacccct gagccagggg tgatgggaaa gggagctggg catggctcaa tgtttagcct    240
tttcttggtc ttcaagattt catagacatt cttaaataca tgtttctttc aatgaagttt    300 gccccttagga caattcacag ctacattagg tacttttaa ataatacttt tgaccatccg    360
tggttatttc attgaagaaa atctatagag cacctcagcc atcattccag aagtgactat    420
cctcctcagt aatggttctt attctaattt taaatatcat tgatgtagaa cattctattt    480
cactattcct tcatttttatt rttatgggaa attatataca gttctccaga tttttaaagc    540
cttgctaaca tgttttaagt cacacaaata ttcttctgtg ggaaaatgac agtaatttag    600
```

```
tgtgcaacaa ttatatagaa ctatttttca aacttataaa cgaagtgaaa ttctaaataa    660
aatcatttat caaacacaaa aatttgagcc agaataagga a                        701

<210> SEQ ID NO 343
<211> LENGTH: 701
<212> TYPE: DNA
<213> ORGANISM: Homo sapiens

<400> SEQUENCE: 343
aatgccagtt acaaaaactt cctgtacaga tatcctagca ctcaactgga aaccggggag     60
agtcacaatt ctgtctttcc agccatatgt aactgaaatg agatcttttt caccctgagc    120
caggggtgat gggaaaggga gctggtcatg gctcaatgtt tagccttttc ttggtcttca    180
agatttcata gacattctta aatacatgtt tcttcaatg aagtttgccc ttaggacaat     240
tcacagctac attaggtact ttttaaataa tacttttgac catccgtggt tatttcattg    300
aagaaaatct atagagcacc tcagccatca ttccagaagt gactatcctc ctcagtaatg    360
gttcttattc taattttaaa tatcattgat gtagaacatt ctatttcact attccttcat    420
tttattatta tgggaaatta tatacagttc tccagatttt taaagccttg ctaacatgtt    480
ttaagtcaca caaatattct yctgtgggaa aatgacagta atttagtgtg caacaattat    540
atagaactat ttttcaaact tataaacgaa gtgaaattct aaataaaatc atttatcaaa    600
cacaaaaatt tgagccagaa taaggaatgt aaattacaat ttaaacacag attataaact    660
atcttacttt taaaatgtta aaattcctaa cttgtttgaa a                       701

<210> SEQ ID NO 344
<211> LENGTH: 768
<212> TYPE: DNA
<213> ORGANISM: Homo sapiens

<400> SEQUENCE: 344
ctaaaatcta ccattatatg atatccttcc caatacataa attaaaaaaa aaaacactgt     60
agaggaaaaa gcaatatttt gaaatgatat gcttttcttt gtttgtcttc aaacaattac    120
atcttcatca taatggttgt attagtctgt ttttacactg ctataaagaa ttgcctgaga    180
ctgagtaaca tataaagaaa aaagttttaa ttgaccacag tttcacaggc ttaataggaa    240
gcatgactgg gaaacttaga atcatggcag aagaggaagg ggaagcaagg atcttcttca    300
catggtagca ggagagagag cacaaagggg gacacgctac acactttcaa caacgagat    360 ctcctgagaa ctctatcggg agaacagcaa gagggaagtt cacccctatg attcaatcag    420
ctcccaccgg gcttctcccc tgacacatga ggaattacaa ttggatgaga gatttgggtg    480
gggacacaca gacaaaccat atcaactgtc atggacttaa acaattgtct ttgaattgtc    540 tttttttcata cttttatttg catctttyca ctaaaaagat gacacaaagt aatcctagtt    600
tacatttttt accatgtaat tccatattac ttttcctga aagttactta ttttaaatc     660 tcaaagctct tcatacttat ggtttgatct gcacttacaa ctggatctca gaaagattga    720
attctcccat cataccaagt tcatgtctct cactcttaat atttgttc                768

<210> SEQ ID NO 345
<211> LENGTH: 701
<212> TYPE: DNA
<213> ORGANISM: Homo sapiens

<400> SEQUENCE: 345
```

| aaatgatatg cttttctttg tttgtcttca aacaattaca tcttcatcat aatggttgta | 60 |
| ttagtctgtt tttacactgc tataaagaat tgcctgagac tgagtaacat ataaagaaaa | 120 |
| aagtttaat tgaccacagt ttcacaggct taataggaag catgactggg aaacttagaa | 180 |
| tcatggcaga agaggaaggg gaagcaagga tcttcttcac atggtagcag agagagagc | 240 |
| acaaaggggg acacgctaca cactttcaaa caacgagatc tcctgagaac tctatcggga | 300 |
| gaacagcaag agggaagttc acccctatga ttcaatcagc tcccaccggg cttctcccct | 360 |
| gacacatgag gaattacaat ggatgagag atttgggtgg ggacacacag acaaaccata | 420 |
| tcaactgtca tggacttaaa caattgtctt tgaattgtct ttttcatac ttttatttgc | 480 |
| atcttttcac taaaaagatg rcacaaagta atcctagttt catttttta ccatgtaatt | 540 |
| ccatattact ttttcctgaa agttacttat ttttaaatct caaagctctt catacttatg | 600 |
| gtttgatctg cacttacaac tggatctcag aaagattgaa ttctcccatc ataccaagtt | 660 |
| catgtctctc actcttaata tttgttccca agacaacaat t | 701 |

<210> SEQ ID NO 346
<211> LENGTH: 6758
<212> TYPE: DNA
<213> ORGANISM: Homo sapiens

<400> SEQUENCE: 346

| agagtgggcc attgttctga ctagtctggg gctccccaaa gaactggtat ctgtctcacc | 60 |
| tgactcagaa caatgataag gctgtagatc ttttttggaag tctatgaaaa caggcacaat | 120 |
| gaaggcagca tgttagagat ataattccac aggaagatgc caggtaaaac aaaagagaaa | 180 |
| aagcaggaac aagctgatta ggaaatttgt gatgactaaa agtatataca caagcccaaa | 240 |
| taagatactc caaagatgtt tgataggttc tagatctcta gatatactgc tcaatgaaag | 300 |
| tgtcccctg aacaaagcca gtctgcaaag actgggtgag atgatttttt ttaaatgtca | 360 |
| agtctcagca acaacaaaaa tgacaagaca tgcacagaag caagaaaata taacacaatc | 420 |
| aaagaaaaaa aagccacaga atcagtcct agagaaaacy gatctatgag ctgcctgaca | 480 |
| ataattataa aataactatc ataaaaatgc ccagtgagat ataagaaaac acagacaact | 540 |
| aaatgaatca ggaaaatgat gcatgaacaa aatgggcata tcaacagaga tggaaatgac | 600 |
| aaagataaac aaacagaaat tttggagctt aaaaatacag taagtaaagt gaataattca | 660 |
| ctaaaaatat tcaatagcag actagatcag gcagaagaaa atatcaatga acttgaagac | 720 |
| agatcatcaa gtcagaggaa caacagcaac aaaaaagaat gaaaaagtg aagacagcct | 780 |
| aagggactta ggagtcagta ccaaggaaat caatatatac gttatagatg tatcagaaga | 840 |
| aaaagggaga aaaatgaaaa gaaagcatat ttgaaaaaat aatagctgaa gaattctcaa | 900 |
| tttcaaagag agaaattgat atacaaattc aagaagttca aaagactcta gccataataa | 960 |
| atctaaagag actcacacta agacatatta tcatcaaact gtcaaaatca aagcaaagaa | 1020 |
| attgtgaaat ctgccaagga aaagtgactc atcacacata agagatataa cataagattg | 1080 |
| tcacaggatt tctgaacaga cactttgcag gtcagaggga agtagggtga catattccag | 1140 |
| gtgctgaaag aagaaaacac cctgccaacc aagaatatgg catccagaaa aacttttccta | 1200 |
| gaagaatgaa ggagaaattt agactttccc aaataaacaa agctgaggg agttcattac | 1260 |
| taccagacct gctctgcaaa atgctaaaga gaaaccttca ggtgaaacaa aaagatgcta | 1320 |
| gacagtaaca caaaaccact cataaataac ttcttcagta aaaataatac atcgacaaat | 1380 |
| atggtaacct gtattaatac tggtgcacaa attcactttc aaattttata aataagaatt | 1440 |

```
taaaggatga aaacatctaa aactaactat aaatctatat aatgaatata caatatataa    1500
aaaaatttgt gatcacaata acataaaatg ggggaggtag agctgtatag gggtagagct    1560
tttgtatgca attgaaatta ccatcagttt aaactgaact gttataacat taagatgttt    1620
tatgtaattg caatggtaac tatattctat agaatatatt aaaagaaaaa agaaaatagg    1680
aagggaatca aagcatgtcc ttgtaaaaaa gtcaatgaaa gcaaaagaaa ggcagaaaga    1740
gtgaaaagga ggaataaaaa gttataagac ataaaaaaaa tgaaaatagt aatagtcctg    1800
ccatatcagt aattacatta aatataaatg gattaaactc cctaatcaaa tcatagattg    1860
gtttgcaaga actaacttta caattaaaga cacacagctg acggtgaagg gagaaaaaaa    1920
acttccatgc agtgaccaaa atagaggagg gtggctgtat tactgtcaga caaaataaaa    1980
tttaagtcaa aaactgttac aagagtaaaa gaagggcatt atacagttaa aaagtaaat    2040 tcgccaggca gacacaacaa ttataaatat caatacataa aataagagc tcctaaatat    2100 atgcagcaaa cagacataat tgaagaaaga aataaaatagc taaaatggta gaagacttta    2160 ataccccccac ttacaataat gtataaaata acaagacaga atgtaaataa aaatgtagag    2220
aatttgagca acactgtaga ccaattggac ctaataaaata tactcagaat aatccatcca    2280
accaaagcag aaacagaata tacattcttt tcaagtacac atttgacatt ctctgggatt    2340
aactacatgt tatgcaacaa acaagtctca acaatgttta aaagtctgat attacacaaa    2400
gtattgtttc tgatgacgat ggaaagaacc tagaagccaa tagcaaaaag aaaatagaaa    2460
atccacacat atgtgaaaat taaactacat gcaattaagc aaagggccaa agaagaagaa    2520
gaaaaaagaa acaccgtga aacaaataaa aacaaaaata cagcatatga aaatgcatgg    2580
gatgcagcaa aagtgatggt aagagaaatg tttatagtta taaatgcaaa ccttaaaaaa    2640
gaagaaagaa aacaaaaata ctcaaattaa caactttaca agtcaagaag gtagagaaaa    2700
aagaacaaac tataccaaaa gctaacacag aaagaaaaga ataaagatta aaaacaaaaa    2760
caatttaaaa aatagcagaa ctaaagttg gttctttgaa aagatcaaca gaattgacaa    2820
tttcttagct acattaagaa aaatacaaga ctcaaataac acaatcagt ggtgaaaggg    2880 ggtattataa ctgatgccac agaaatacaa aaggatcata agggactact acaaattgta    2940
tgacaacaaa ttgagtaacc taggatacct tgataaattc caaaaaatgc acaatatact    3000
gaatcatgaa tacatgaccc ttataaatca agactaaatc ataagaaat agaaaatatc    3060 aacagaccaa taattagtaa ggagaataaa ctagtaatca gaaacctccc aacaagaaa    3120 agcttaggac caaatggctt tactggagaa ttctaccaac cattaaaagg ataattaaga    3180
ccaatcttcc tcaaactttt aaaacaaatg ttaaagagga ggaaactctt tcaatctcat    3240
tcataaggtc agcattatcc ttataccaaa accagacaaa gacactatta aaaaactta    3300 gaccaatatc cctgatgaat ttcgatgcaa gaatcctcag caaaatacta tcaaacaatt    3360
caacagcata cttaaatgat tatatgctgt aatcaagatg catttattct ttgaatgcaa    3420
gtgtaattca acacataaaa ttcaatcaat gtaatacacc acattaacag aatgagagac    3480
aaaaaccaca taattatatc aactgatgca gaaaaaaatc tgacacagtt caacaccttt    3540
tgtgataaaa acactcaaca aactaggaaa agaaggaaac aactttaaca catcatatgc    3600
tcactgatga aaatctacaa gttctttata aaagatcagg aacaagacaa taatctgcat    3660
tgttaccact tctattatac gtagtattgg aagttctaat cagagcaaat taggcaagaa    3720
aaataaataa aaggcatcca aagtgggaag gaagtaaaat aatctctttt tacagatgat    3780
```

```
ataaccttag aattagaaaa tcctaaaaat ttcacatacc aagaaaaagc gtgttaaaat    3840
taataagtaa attcagcaag ttgactgata caaaatcaac acagaaagct cagttgtgtg    3900
tctgtgtgtc tcatacacta acaatgaaca atctgaaaag gagattaaga aaacaatttc    3960
atttacaata gcatcaggaa aaaaaataaa tacttaggaa caaacttaac caaggggttg    4020
gaattcctgt atactgaaaa ctacaaatat tgccaaaaga aaataaagga gacacaaata    4080
agtgatatgt ttttaatatg tccacccaaa gtgatcttca gattcaatga aatccctatc    4140
aaagttataa tggcattttt ctgcaggaat gtaaaaattt atcctaaaat tcatatagaa    4200
tctctaggta ccctgagggc caaacaattt tgagaaaaaa aaaagaacaa aattggagga    4260
ctcacacttc cagattacaa gaatatttac aaattacata tttacaaaaa aaattacaaa    4320
gccacaataa tcaaaacaac gtgggatttg cataaaggca gatatataga ccagtggaat    4380
agtattgaga gtccagaaat aaaccctag gtatatcatc aaatgacatt tgacaaagtg    4440
ctggtaccac tcaatgggaa tgggacaatt tgttcaacaa atagagcaaa gaaaactaaa    4500
catccatgtg caaagaata aatctggacc cttatattac actatagaca aaattaattc    4560
aaaatggatt aaagatctaa atgaaagatc taaaactata aaactcctag gagaaaacag    4620
aggaaaaatt tcatgctaat ttggcaacat tttgtgatgt gacaccaaaa gcagagtcaa    4680
taaaagcaaa aattagacag atggaaatcc atcatagttt ataacttttg gtcattaaag    4740
aacagtcaac agagtgaaaa ggcaatctat aaaatggggg aaaaacagaa aatatgtgca    4800
aatcacagat atctgatagg ggattcatat ccagaataaa taaagaactc ctatatctca    4860
acaacaaaaa atctaatcca atcaaaaaat gggccaaggg agtgaagata catttctcca    4920
aagatgttat acaaatggcc aggaagcata tgaaaagatg ttcaatgtca ctaatcatca    4980
gagaaatgca aatcaaaacc acagtgcaat atcacttcac attcattaga atggcttctg    5040
tcatgaacaa cagaaaataa caagtgttga tgagtgtgta gagaaattga gacctttata    5100
taattttggc agaaattcaa aatggtgcaa ccactataaa aaatgatatg gaggtcctca    5160
aaaaattaaa aatagaacta ccatatgatc cacaatccca cctctgggta catattcaaa    5220
agaattgaaa gcagggtgtt gaagatatat ttgcacactc tttatagcag cactgttcac    5280
aatagccaag agatgaaagt aacccaaagg ttcatgaagc aatgaataaa caaaatatat    5340
tatgtacata gagtaaaata ctgtgcagct ttaaagagaa aggaaatctt atactatgct    5400
acaacatgaa tggaacttta gggcattata gtaagtaaaa taagccagtt ttttttaaag    5460
gacaaataaa cactatacga ttctacttaa gtatttaatg ttgtcaaatt tataaatata    5520
gaatgtagaa tagtggttac cctgagctgg gggaaagggg caaaggggaa ttgttatttt    5580
aatgggtata gtttcagttc tgcaaaatga aaaggttctg gaaatctgtt tcacaatgtt    5640
gtaaatataa ttactctgaa attgtacact taaaaatggt taagatgaca aatagagttg    5700
tgatgtcttc ttttgttatt atatagaaaa acttttttcat atgataatag tctttgtttt    5760
taagctgact tgctgatat taatataatc cttccatttt tctttaaaat gctatatgct    5820
ttcacataat tttgctttac gttgatgtat ttatacataa ggtgggtttc ttatagatac    5880
cacgttgtgt gtcttttta tctaagttga tagacttgcc ttttgttagg gtatttaaat    5940
aatttatatt taatgtaatt attgatatag ttgagtgtgt tgattttttgt tttctatttg    6000 ctccatctgt tgttggttct cattattcct ctgtttctac cttcttttgt actaattatt    6060 atatttatt atttttcatc tcaactgttg gcttattagc cacattgctt ttaaaatttt    6120
taatgattgc tctagggttt ataataaaca aaatgttagc attttctacc atcaaatatt    6180
```

```
tttacactat tcatgtatac ttcaatttct ttcttcccat cctttgaact atatcttcat    6240
acattttact ctacatttgt tataaactcag tgctttgaaa gtcaattatt tttgtctttg    6300
acagtcaatg attttttaaag agtttaacag tgaaaaaaaa tggctttcat cttttttccat   6360 tagatttcat actccttctg cctgaagaat ttcttttaat agaccttgta ctgcgggtct    6420
caggcaagaa attctctcag cctttgttgg tttgaaaaac tgcttattac acctttgttt    6480
ttgaaagata ttttcactag gtatagaagt ctgggttgac agttctcatt gtttgtcaca    6540 gcattttttaa gatgcccatt caattgtctt gtcttgtata attttggatt agtctggtgt    6600
atttcttacc tttgttcctc tctgtgcaat gcttcaacca tcccacttca ggctgccttt    6660 aagatgttttt cttttccctt aatctttagt ttttagctgg ttgacagtga cgcatctaag   6720
tgtagtgtat gaggttgctt ttattgtcac tgttgttg                             6758

<210> SEQ ID NO 347
<211> LENGTH: 6758
<212> TYPE: DNA
<213> ORGANISM: Homo sapiens

<400> SEQUENCE: 347
agagtgggcc attgttctga ctagtctggg gctccccaaa gaactggtat ctgtctcacc      60
tgactcagaa caatgataag gctgtagatc ttttttggaag tctatgaaaa caggcacaat    120
gaaggcagca tgttagagat ataattccac aggaagatgc caggtaaaac aaaagagaaa    180
aagcaggaac aagctgatta ggaaatttgt gatgactaaa agtatataca caagcccaaa    240
taagatactc caaagatgtt tgataggttc tagatctcta gatatactgc tcaatgaaag    300 tgtcccccctg aacaaagcca gtctgcaaag actgggtgag atgattttttt ttaaatgtca   360 agtctcagca acaacaaaaa tgacaagaca tgcacagaag caagaaaata taacacaatc    420
aaagaaaaaa aagccacaga aatcagtcct agagaaaact gatctatgag ctgcctgama    480
ataattataa aataactatc ataaaaatgc ccagtgagat ataagaaaac acagacaact    540
aaatgaatca ggaaaatgat gcatgaacaa aatgggcata tcaacagaga tggaaatgac    600
aaagataaac aaacagaaat tttggagctt aaaaatacag taagtaaagt gaataattca    660
ctaaaaatat tcaatagcag actagatcag gcagaagaaa atatcaatga acttgaagac    720
agatcatcaa gtcagaggaa caacagcaac aaaaaagaat gaaaaagtg aagacagcct     780 aagggactta ggagtcagta ccaaggaaat caatatatac gttatagatg tatcagaaga    840
aaaagggaga aaatgaaaaa gaaagcatat ttgaaaaaat aatagctgaa gaattctcaa    900
tttcaaagag agaaattgat atacaaattc aagaagttca aaagactcta gccataataa    960
atctaaagag actcacacta agacatatta tcatcaaact gtcaaaatca aagacaaaga   1020
attgtgaaat ctgccaagga aaagtgactc atcacacata agagatataa cataagattg    1080
tcacaggatt tctgaacaga cactttgcag gtcagaggga agtagggtga catattccag    1140
gtgctgaaag aagaaaacac cctgccaacc aagaatatgg catccagaaa aactttccta    1200
gaagaatgaa ggagaaattt agactttccc aaataaacaa aagctgaggg agttcattac    1260
taccagacct gctctgcaaa atgctaaaga gaaaccttca ggtgaaacaa aaagatgcta    1320
gacagtaaca caaaccacct cataaaataac ttcttcagta aaaataatac atcgacaaat    1380
atggtaacct gtattaatac tggtgcacaa attcactttc aaattttata aataagaatt    1440
taaaggatga aaacatctaa aactaactat aaatctatat aatgaatata caatatataa    1500
```

```
aaaaatttgt gatcacaata acataaaatg ggggaggtag agctgtatag gggtagagct      1560
tttgtatgca attgaaatta ccatcagttt aaactgaact gttataacat taagatgttt      1620
tatgtaattg caatggtaac tatattctat agaatatatt aaaagaaaa agaaaatagg       1680 aagggaatca aagcatgtcc ttgtaaaaaa gtcaatgaaa gcaaagaaa ggcagaaaga       1740 gtgaaaagga ggaataaaaa gttataagac ataaaaaaaa tgaaaatagt aatagtcctg      1800
ccatatcagt aattcatta aatataaatg gattaaactc cctaatcaaa tcatagattg       1860
gtttgcaaga actaacttta caattaaaga cacacagctg acggtgaagg gagaaaaaaa      1920
acttccatgc agtgaccaaa atagaggagg gtggctgtat tactgtcaga caaaataaaa      1980
tttaagtcaa aaactgttac aagagtaaaa gaagggcatt atacagttaa aaaagtaaat      2040
tcgccaggca gacacaacaa ttataaatat caatacataa aataagagc tcctaaatat       2100 atgcagcaaa cagacataat tgaagaaaga aataaatagc taaaatggta gaagacttta     2160 ataccccccac ttacaataat gtataaaata acaagacaga atgtaaataa aaatgtagag     2220
aatttgagca acactgtaga ccaattggac ctaataaata tactcagaat aatccatcca     2280
accaaagcag aaacagaata tacattcttt tcaagtacac atttgacatt ctctgggatt     2340
aactacatgt tatgcaacaa acaagtctca acaatgttta aaagtctgat attacacaaa     2400
gtattgtttc tgatgacgat ggaaagaacc tagaagccaa tagcaaaaag aaaatagaaa     2460
atccacacat atgtggaaat taaactacat gcaattaagc aaagggccaa agaagaagaa     2520
gaaaaaagaa aacaccgtga acaaataaa aacaaaaata cagcatatga aaatgcatgg     2580
gatgcagcaa aagtgatggt aagagaaatg tttatagtta taaatgcaaa ccttaaaaaa     2640
gaagaaagaa aacaaaaata ctcaaattaa caactttaca agtcaagaag gtagagaaaa     2700
aagaacaaac tataccaaaa gctaacacag aaagaaaaga ataaagatta aaaacaaaaa     2760
caatttaaaa aatagcagaa ctaaagttg gttctttgaa aagatcaaca gaattgacaa     2820
tttcttagct acattaagaa aaatacaaga ctcaaataac acaatcagt ggtgaaaggg       2880 ggtattataa ctgatgccac agaaatacaa aaggatcata agggactact acaaattgta     2940
tgacaacaaa ttgagtaacc taggatacct tgataaattc caaaaaatgc acaatatact     3000
gaatcatgaa tacatgaccc ttataaatca agactaaatc ataagaaat agaaaatatc      3060 aacagaccaa taattagtaa ggagaataaa ctagtaatca gaaccctccc aacaaagaaa     3120
agcttaggac caaatggctt tactggagaa ttctaccaac cattaaaagg ataattaaga     3180
ccaatcttcc tcaaactttt aaacaaatg ttaaagagga ggaaactctt tcaatctcat       3240
tcataaggtc agcattatcc ttataccaaa accagacaaa gacactatta aaaaaactta     3300
gaccaatatc cctgatgaat ttcgatgcaa gaatcctcag caaaatacta tcaaacaatt     3360
caacagcata cttaaatgat tatatgctgt aatcaagatg catttattct ttgaatgcaa     3420
gtgtaattca acacataaaa ttcaatcaat gtaatacacc acattaacag aatgagagac     3480
aaaaaccaca taattatatc aactgatgca gaaaaaatc tgacacagtt caacacctt       3540 tgtgataaaa acactcaaca aactaggaaa agaaggaaac aactttaaca catcatatgc     3600
tcactgatga aaatctacaa gttctttata aagatcagg acaagacaa taatctgcat       3660 tgttaccact tctattatac gtagtattgg aagttctaat cagagcaaat taggcaagaa     3720
aaataaataa aaggcatcca aagtggaaag gaagtaaaat aatctctttt tacagatgat     3780
ataaccttag aattagaaaa tcctaaaaat ttcacatacc aagaaaaagc gtgttaaaat     3840
taataagtaa attcagcaag ttgactgata caaaatcaac acagaaagct cagttgtgtg     3900
```

```
tctgtgtgtc tcatacacta acaatgaaca atctgaaaag gagattaaga aaacaatttc    3960
atttacaata gcatcaggaa aaaaaataaa tacttaggaa caaacttaac caaggggttg    4020
gaattcctgt atactgaaaa ctacaaatat tgccaaaaga aaataaagga gacacaaata    4080
agtgatatgt ttttaatatg tccacccaaa gtgatcttca gattcaatga aatccctatc    4140
aaagttataa tggcattttt ctgcaggaat gtaaaaattt atcctaaaat tcatatagaa    4200
tctctaggta ccctgagggc caaacaattt tgagaaaaaa aaaagaacaa aattggagga    4260
ctcacacttc cagattacaa gaatatttac aaattacata tttacaaaaa aaattacaaa    4320
gccacaataa tcaaaacaac gtgggatttg cataaaggca gatatataga ccagtggaat    4380
agtattgaga gtccagaaat aaacccttag gtatatcatc aaatgacatt tgacaaagtg    4440
ctggtaccac tcaatgggaa tgggacaatt tgttcaacaa atagagcaaa gaaaactaaa    4500
catccatgtg caaaagaata aatctggacc cttatattac actatagaca aaattaattc    4560
aaaatggatt aaagatctaa atgaaagatc taaaactata aaactcctag gagaaaacag    4620
aggaaaaatt tcatgctaat ttggcaacat tttgtgatgt gacaccaaaa gcagagtcaa    4680
taaaagcaaa aattagacag atggaaatcc atcatagttt ataacttttg gtcattaaag    4740
aacagtcaac agagtgaaaa ggcaatctat aaaatggggg aaaaacagaa aatatgtgca    4800
aatcacagat atctgatagg ggattcatat ccagaataaa taagaactc ctatatctca    4860 acaacaaaaa atctaatcca atcaaaaaat gggccaaggg agtgaagata catttctcca    4920
aagatgttat acaatggcc aggaagcata tgaaaagatg ttcaatgtca ctaatcatca    4980
gagaaatgca aatcaaaacc acagtgcaat atcacttcac attcattaga atggcttctg    5040
tcatgaacaa cagaaaataa caagtgttga tgagtgtgta gagaaattga gacctttata    5100
taattttggc agaaattcaa aatggtgcaa ccactataaa aaatgatatg gaggtcctca    5160
aaaaattaaa aatagaacta ccatatgatc cacaatccca cctctgggta catattcaaa    5220
agaattgaaa gcagggtgtt gaagatatat ttgcacactc tttatagcag cactgttcac    5280
aatagccaag agatgaaagt aacccaaagg ttcatgaagc aatgaataaa caaaatatat    5340
tatgtacata gagtaaaata ctgtgcagct ttaaagagaa aggaaatctt atactatgct    5400
acaacatgaa tggaacttta gggcattata gtaagtaaaa taagccagtt ttttttaaag    5460
gacaaataaa cactatacga ttctacttaa gtatttaatg ttgtcaaatt tataaatata    5520
gaatgtagaa tagtggttac cctgagctgg gggaaggggg caaaggggaa ttgttatttt    5580
aatgggtata gtttcagttc tgcaaaatga aaaggttctg gaaatctgtt tcacaatgtt    5640
gtaaatataa ttactctgaa attgtacact taaaaatggt taagatgaca aatagagttg    5700
tgatgtcttc ttttgttatt atatagaaaa acttttcat atgataatag tctttgtttt    5760
taagctgact ttgctgatat taatataatc cttccatttt tctttaaaat gctatatgct    5820
ttcacataat tttgctttac gttgatgtat ttatacataa ggtgggtttc ttatagatac    5880
cacgttgtgt gtcttttttta tctaagttga tagacttgcc ttttgttagg gtatttaaat    5940
aatttatatt taatgtaatt attgatatag ttgagtgtgt tgattttgt tttctatttg    6000 ctccatctgt tgttggttct cattattcct ctgtttctac cttcttttgt actaattatt    6060
atatttattt attttcatc tcaactgttg gcttattagc cacattgctt ttaaaatttt    6120
taatgattgc tctagggttt ataataaaca aaatgttagc attttctacc atcaaatatt    6180
tttacactat tcatgtatac ttcaatttct ttcttcccat cctttgaact atatcttcat    6240
```

| | |
|---|---|
| acatttact ctacatttgt tataactcag tgctttgaaa gtcaattatt tttgtctttg | 6300 |
| acagtcaatg attttaaag agtttaacag tgaaaaaaaa tggctttcat cttttccat | 6360 |
| tagatttcat actccttctg cctgaagaat ttctttaat agaccttgta ctgcgggtct | 6420 |
| caggcaagaa attctctcag cctttgttgg tttgaaaaac tgcttattac acctttgttt | 6480 |
| ttgaaagata ttttcactag gtatagaagt ctgggttgac agttctcatt gtttgtcaca | 6540 |
| gcatttttaa gatgcccatt caattgtctt gtcttgtata attttggatt agtctggtgt | 6600 |
| atttcttacc tttgttcctc tctgtgcaat gcttcaacca tcccacttca ggctgccttt | 6660 |
| aagatgtttt cttttcctt aatctttagt tttagctgg ttgacagtga cgcatctaag | 6720 |
| tgtagtgtat gaggttgctt ttattgtcac tgttgttg | 6758 |

<210> SEQ ID NO 348
<211> LENGTH: 501
<212> TYPE: DNA
<213> ORGANISM: Homo sapiens

<400> SEQUENCE: 348

| | |
|---|---|
| gaccatgtta tgacattta gtgcttgcta agcagtaaat actgacttac tttcctgcta | 60 |
| cactcttcag agcagaaaga gaaatctaca aaagggcaa tgtagttggg atccaccaca | 120 |
| gccttgagac tgggccatgt ttctacagct tacccacatt ttaccccac tttctctgag | 180 |
| aaacaatgca aactggagaa caaggtcaga gaagttatct tggatggtag aagagaagaa | 240 |
| aggagaagaa rggataagca gaaaatcaaa aagggcataa aaaaattact ggggaaaata | 300 |
| attcttagtc actcaccatt tcttatgttt gtgaaaacag aaacgaggag caagtgttgt | 360 |
| tgtaagaatt gttcttgccc ctccccctcc accacccaca tctgtcaagc tatccctgtt | 420 |
| tcactgtttc ctctgcactc tctattaact tctttgtcct cctcttttct tttcctacag | 480 |
| caaagacttt ttgtcatgtt t | 501 |

<210> SEQ ID NO 349
<211> LENGTH: 501
<212> TYPE: DNA
<213> ORGANISM: Homo sapiens

<400> SEQUENCE: 349

| | |
|---|---|
| tgacttactt tcctgctaca ctcttcagag cagaaagaga atctacaaa aagggcaatg | 60 |
| tagttgggat ccaccacagc cttgagactg ggccatgttt ctacagctta cccacatttt | 120 |
| accccacctt tctctgagaa acaatgcaaa ctggagaaca aggtcagaga agttatcttg | 180 |
| gatggtagaa gagaagaaag gagaagaaag gataagcaga aaatcaaaaa gggcataaaa | 240 |
| aaattactgg rgaaaataat tcttagtcac tcaccatttc ttatgtttgt gaaaacagaa | 300 |
| acgaggagca agtgttgttg taagaattgt tcttgcccct ccccctccac cacccacatc | 360 |
| tgtcaagcta tccctgtttc actgtttcct ctgcactctc tattaacttc tttgtcctcc | 420 |
| tcttttcttt tcctacagca aagacttttt gtcatgtttt gtttcttttt ctattgtttc | 480 |
| tttccctttt ctaatccttg a | 501 |

<210> SEQ ID NO 350
<211> LENGTH: 1148
<212> TYPE: DNA
<213> ORGANISM: Homo sapiens

<400> SEQUENCE: 350

| | |
|---|---|
| tatgagattt aatgttaaga aataaaatgt aggatctaaa acgtaatcta tagcataatc | 60 |

| | | |
|---|---|---|
| tcaaaaatgg tttagaaatg acataataat acagacattt gtgggtggta ggattatgca | 120 |
| tattttata tattttaaa tatattttc aaaagcttcc tataaagaat gtaattcttt | 180 |
| cccaattcca aatctagctt aaacataatt ttacaaaaat tattctctca gaatgtaaac | 240 |
| tagtaccacc tctatggaaa acattatgga gatttcctaa agagttaaaa gtagatctac | 300 |
| catttgatcc agcaatctta atactgggta tctacccgga ggaaaagaag tcattgtatg | 360 |
| aaaaagacac ttgtacacat atgtttacag gaccacaatt cacaaatgca agatgcaga | 420 |
| accaacctaa gtggccastg actaatgaga ggataaagaa gatgtggcat atatatatca | 480 |
| gggactacta ctcagccatt acaaggaaca aaataatgtc ttttgcaaca acttggatag | 540 |
| agctggaggc cattattcta agtaaagtaa ttcaggaatt ggaaaaccaa aaaccgtatg | 600 |
| ttctctctta taagtgggaa ctaagttagg aataagcaaa ggcacacaga gggacatatt | 660 |
| ggactttaga gactcacgag gaggagggta ataggggact agggattaaa agaaaaacta | 720 |
| gacattaggt acaaggtacc ctacttaagt gcactaaaat ctcagaattc accactacgt | 780 |
| aattcaacta agtaacaaga aaccacttgt accccaaaag ctactgaaat aaaaattatt | 840 |
| ctctcaaaaa ttttaagccc taaacttcag ttcctattgt ttatatttac taagaaaaac | 900 |
| aacagaaaac actgttttaa aaatggtgga ttttttttaag gttaaaggta tataagacag | 960 |
| ctgcctaagg aaacgcagat acccctgtac cttgttgttg ttgttgtttt tcacttttt | 1020 |
| aaaaaacata gagatgggat ctccttatgc tgcccaggct tgtctcaaac tcctgagctc | 1080 |
| aagcaatcct ctgacctcag actctcaaag ttttgggact acaggcgaca gtcaccatgc | 1140 |
| cagccaat | 1148 |

<210> SEQ ID NO 351
<211> LENGTH: 1148
<212> TYPE: DNA
<213> ORGANISM: Homo sapiens

<400> SEQUENCE: 351

| | | |
|---|---|---|
| tatgagattt aatgttaaga aataaaatgt aggatctaaa acgtaatcta tagcataatc | 60 |
| tcaaaaatgg tttagaaatg acataataat acagacattt gtgggtggta ggattatgca | 120 |
| tattttata tattttaaa tatattttc aaaagcttcc tataaagaat gtaattcttt | 180 |
| cccaattcca aatctagctt aaacataatt ttacaaaaat tattctctca gaatgtaaac | 240 |
| tagtaccacc tctatggaaa acattatgga gatttcctaa agagttaaaa gtagatctac | 300 |
| catttgatcc agcaatctta atactgggta tctacccgga ggaaaagaag tcattgtatg | 360 |
| aaaaagacac ttgtacacat atgtttacag gaccacaatt cacaaatgca agatgcaga | 420 |
| accaacctaa gtggccactg actaatgaga ggataaagaa gatgtggcat atatayatca | 480 |
| gggactacta ctcagccatt acaaggaaca aaataatgtc ttttgcaaca acttggatag | 540 |
| agctggaggc cattattcta agtaaagtaa ttcaggaatt ggaaaaccaa aaaccgtatg | 600 |
| ttctctctta taagtgggaa ctaagttagg aataagcaaa ggcacacaga gggacatatt | 660 |
| ggactttaga gactcacgag gaggagggta ataggggact agggattaaa agaaaaacta | 720 |
| gacattaggt acaaggtacc ctacttaagt gcactaaaat ctcagaattc accactacgt | 780 |
| aattcaacta agtaacaaga aaccacttgt accccaaaag ctactgaaat aaaaattatt | 840 |
| ctctcaaaaa ttttaagccc taaacttcag ttcctattgt ttatatttac taagaaaaac | 900 |
| aacagaaaac actgttttaa aaatggtgga ttttttttaag gttaaaggta tataagacag | 960 |

```
ctgcctaagg aaacgcagat acccctgtac cttgttgttg ttgttgtttt tcactttttt    1020
aaaaaacata gagatgggat ctccttatgc tgcccaggct tgtctcaaac tcctgagctc    1080
aagcaatcct ctgacctcag actctcaaag ttttgggact acaggcgaca gtcaccatgc    1140
cagccaat                                                             1148
```

<210> SEQ ID NO 352
<211> LENGTH: 1148
<212> TYPE: DNA
<213> ORGANISM: Homo sapiens

<400> SEQUENCE: 352

```
tatgagattt aatgttaaga aataaaatgt aggatctaaa acgtaatcta tagcataatc     60
tcaaaaatgg tttagaaatg acataataat acagacattt gtgggtggta ggattatgca    120 tattttata tatttttaaa tatattttc aaaagcttcc tataaagaat gtaattcttt     180
cccaattcca aatctagctt aaacataatt ttacaaaaat tattctctca gaatgtaaac    240
tagtaccacc tctatggaaa acattatgga gatttcctaa agagttaaaa gtagatctac    300
catttgatcc agcaatctta atactgggta tctacccgga ggaaaagaag tcattgtatg    360
aaaaagacac ttgtacacat atgtttacag gaccacaatt cacaaatgca agatgcaga     420 accaacctaa gtggccactg actaatgaga ggataaagaa gatgtggcat atatayatca    480
gggactacta ctcagccatt acaaggaaca aaataatgtc ttttgcaaca acttggatag    540
agctggaggc cattattcta agtaaagtaa ttcaggaatt ggaaaaccaa aaaccgtatg    600
ttctctctta taagtgggaa ctaagttagg aataagcaaa ggcacacaga gggacatatt    660
ggactttaga gactcacgag gaggagggta ataggggact agggattaaa agaaaaacta    720
gacattaggt acaaggtacc ctacttaagt gcactaaaat ctcagaattc accactacgt    780
aattcaacta gtaacaaga aaccacttgt accccaaaag ctactgaaat aaaaattatt      840
ctctcaaaaa ttttaagccc taaacttcag ttcctattgt ttatatttac taagaaaaac    900
aacagaaaac actgttttaa aaatggtgga ttttttaag gttaaaggta tataagacag      960
ctgcctaagg aaacgcagat acccctgtac cttgttgttg ttgttgtttt tcactttttt    1020
aaaaaacata gagatgggat ctccttatgc tgcccaggct tgtctcaaac tcctgagctc    1080
aagcaatcct ctgacctcag actctcaaag ttttgggact acaggcgaca gtcaccatgc    1140
cagccaat                                                             1148
```

<210> SEQ ID NO 353
<211> LENGTH: 1148
<212> TYPE: DNA
<213> ORGANISM: Homo sapiens

<400> SEQUENCE: 353

```
tatgagattt aatgttaaga aataaaatgt aggatctaaa acgtaatcta tagcataatc     60
tcaaaaatgg tttagaaatg acataataat acagacattt gtgggtggta ggattatgca    120 tattttata tatttttaaa tatattttc aaaagcttcc tataaagaat gtaattcttt     180
cccaattcca aatctagctt aaacataatt ttacaaaaat tattctctca gaatgtaaac    240
tagtaccacc tctatggaaa acattatgga gatttcctaa agagttaaaa gtagatctac    300
catttgatcc agcaatctta atactgggta tctacccgga ggaaaagaag tcattgtatg    360
aaaaagacac ttgtacacat atgtttacag gaccacaatt cacaaatgca agatgcaga     420 accaacctaa gtggccactg actaatgaga ggataaagaa gatgtggcat atatatatca    480
```

```
gggactactr ctcagccatt acaaggaaca aaataatgtc ttttgcaaca acttggatag    540
agctggaggc cattattcta agtaaagtaa ttcaggaatt ggaaaaccaa aaaccgtatg    600
ttctctctta taagtgggaa ctaagttagg aataagcaaa ggcacacaga gggacatatt    660
ggactttaga gactcacgag gaggagggta ataggggact agggattaaa agaaaaacta    720
gacattaggt acaaggtacc ctacttaagt gcactaaaat ctcagaattc accactacgt    780
aattcaacta gtaacaaga  aaccacttgt accccaaaag ctactgaaat aaaaattatt    840
ctctcaaaaa ttttaagccc taaacttcag ttcctattgt ttatatttac taagaaaaac    900
aacagaaaac actgttttaa aaatggtgga ttttttaag  gttaaaggta tataagacag    960
ctgcctaagg aaacgcagat accctgtac  cttgttgttg ttgttgtttt tcacttttt    1020 aaaaaacata gagatgggat ctccttatgc tgcccaggct tgtctcaaac tcctgagctc   1080
aagcaatcct ctgacctcag actctcaaag ttttgggact acaggcgaca gtcaccatgc   1140
cagccaat                                                           1148

<210> SEQ ID NO 354
<211> LENGTH: 611
<212> TYPE: DNA
<213> ORGANISM: Homo sapiens

<400> SEQUENCE: 354
caaaacctca accttccaga taagtctaag ggtgagaact tcacacaaga tgaataagaa     60
ccaatttctt ccagggcgat gttgaacctg gaaatgaaag ccaatctctc ttggaaggcc    120
tggtttgtag aaatgtcagt ctttgtttca agctgtggga gaatgagaag caagactta    180 gggaagagg  aataaaatag atgtgcagaa ataacagagt gagaaagtct tcagggtgtc    240
gctagcccta attgcaggca tccctgaatc ctagaccttg gattgcaaga gactccttaa    300
tatcttccca tgtccacatt tgcttcacat agtttgaatg tggcttctat tatatacaga    360
tacaagattc aaatccaacc tctaygatga ctggtcttgt gaataagcag aagaggcact    420
aacaatatga cgtgagggat tcagggaaga gcactttctt gagcacatat cttccctggt    480
ctgccagctg tagtttatga aattccacaa tgaggatgaa atggaatcac catttacaga    540
gtactctcca gatgtctaac cctaagctag gtaccttcaa aatattatct agtttagata    600 atcaacccttt                                                         611

<210> SEQ ID NO 355
<211> LENGTH: 601
<212> TYPE: DNA
<213> ORGANISM: Homo sapiens

<400> SEQUENCE: 355
ttctctagtc caaagggttg attatctaaa ctagataata ttttgaaggt acctagctta     60
gggttagaca tctggagagt actctgtaaa tggtgattcc atttcatcct cattgtggaa    120
tttcataaac tacagctggc agaccaggga agatatgtgc tcaagaaagt gctcttccct    180
gaatccctca cgtcatattg ttagtgcctc ttctgcttat tcacaagacc agtcatcata    240
gaggttggat ttgaatcttg tatctgtata taatagaagc acattcaaa  ctatgtgaag    300 yaaatgtgga catgggaaga tattaaggag tctcttgcaa tccaaggtct aggattcagg    360
gatgcctgca attagggcta gcgacaccct gaagactttc tcactctgtt atttctgcac    420
atctatttta ttcctctttc cctaaagtct tgcttctcat tctcccacag cttgaaacaa    480
```

| | |
|---|---|
| agactgacat tctacaaac caggccttcc aagagagatt ggctttcatt tccaggttca | 540 |
| acatcgccct ggaagaaatt ggttcttatt catcttgtgt gaagttctca cccttagact | 600 |
| t | 601 |

<210> SEQ ID NO 356
<211> LENGTH: 527
<212> TYPE: DNA
<213> ORGANISM: Homo sapiens

<400> SEQUENCE: 356

| | |
|---|---|
| gctctagaat atggcattcc agaagtggga tgctacaaat agtctcattg agagtcaact | 60 |
| tgcacaatgt atcgtcctac ccttacatca atttctgaaa caacttctct ttgcacttcc | 120 |
| cctatagtta catgcataat aaattctgac aactcttatg aagtcatgga ataactttct | 180 |
| tcttatgttt cctatcaatg tcattagccc tttatcttgt ttgagtttcc atcagcaatg | 240 |
| ttttcaagtc ccaagatcat tcatgtatcc acaagcaatg atacgccaga tttggacaaa | 300 |
| taatactgaa tactatctta ttttcactgc catgatcaag gcagtgtgga ttgctgccaa | 360 |
| gtccaagaga agtgaggtca gcagctgcaa gccacctccg tcatttagaa aagcttcatg | 420 |
| atgtagtgtg tcgtttcgat gtgacactgt ctcacagagt taaaatgatg tgmaaggaac | 480 |
| tgttcaatgg aaatttagaa atttctcttt ttctcaattt tagtgta | 527 |

<210> SEQ ID NO 357
<211> LENGTH: 601
<212> TYPE: DNA
<213> ORGANISM: Homo sapiens

<400> SEQUENCE: 357

| | |
|---|---|
| gaacaagatt ttcctgcttt taaaaatact acattaaagc tgaaaattta ggccaaaatt | 60 |
| ttcaagtggt aatagttaca ggcaattcat ctttctggtc agaaaagggt gttactgcag | 120 |
| ctatttctgc ctgaaactgg gtggcactac tactttttt ttttttttttt taactgagca | 180 |
| gacattttcc ttacactaaa attgagaaaa agagaaattt ctaaatttcc attgaacagt | 240 |
| tccttgcaca tcattttaac tctgtgagac agtgtcacat cgaaacgaca cactacatca | 300 |
| ygaagctttt ctaaatgacg gaggtggctt gcagctgctg acctcacttc tcttggactt | 360 |
| ggcagcaatc cacactgcct tgatcatggc agtgaaaata agatagtatt cagtattatt | 420 |
| tgtccaaatc tggcgtatca ttgcttgtgg atacatgaat gatcttggga cttgaaaaca | 480 |
| ttgctgatgg aaactcaaac aagataaagg gctaatgaca ttgataggaa acataagaag | 540 |
| aaagttattc catgacttca taagagttgt cagaatttat tatgcatgta actacagggg | 600 |
| a | 601 |

<210> SEQ ID NO 358
<211> LENGTH: 1001
<212> TYPE: DNA
<213> ORGANISM: Homo sapiens

<400> SEQUENCE: 358

| | |
|---|---|
| gcttaatacc tgagtgatgg aatattctgt tcaacaaacc cctctgacat aggtttgcct | 60 |
| atataataaa cctgttcatg tactcctgaa cctaaaagtt taaaaagat tatgtagaaa | 120 |
| acccaaagga atctataaaa agtctactag agctagagtg attttaacaa gatttcaata | 180 |
| cacaaattca aatgtctttc tatatattaa tgacaatcaa caataaaatt ttaaaacatt | 240 |
| attaaagtat aatgaaaata tcaactgttt agggagaaat gtaacaagaa tggtgaagga | 300 |

```
cctatacact aaaaagcttc aatatgttgt tgagattaac tgaagaaggt ctaaatagat      360
ttttttttca tgtctcggaa gacttaatat gtgaagatac caattcttcc ccaaatgatc      420
aacaggtgaa atgcaatccc aatcaaaatc ccagcaatta ttttaagggg gaaattggca      480
atctgattct aaaattcata yggaaaaaaa caatggagtt agaataacta aaacaagtcc      540 gaaaagaaa agaaatgga ggactaatgc tacctgattt caagtcttat cgtataaatc       600
tacatcaata aaggacaagt tggtattggg ttaaagatag ataaatacat cagtggaata      660
gaatattgaa tccagaataa atccacacat atatggataa aataccaga caattcagtg       720 gagatggttt tgtttttaca acaaatgtta ctggaacaaa ttgatatatg tattagtcag      780
atatggctgc cataacaaag aaccacaaac aggtggttta ataatggaa ataaatttcc       840 tcagaattct ggagtatgga agcccaagat caagttgctg ggaggattcg tttcttctga      900
gtgtctcttt ttttgatgac agatgactat cttttaccaa tgtcttcact tggttttccc      960
tctgtgtgtg cctaggtcct attctccaat tcctataagg a                         1001
```

<210> SEQ ID NO 359
<211> LENGTH: 1001
<212> TYPE: DNA
<213> ORGANISM: Homo sapiens

<400> SEQUENCE: 359

```
ctaaaagttt aaaaagatt atgtagaaaa cccaaaggaa tctataaaaa gtctactaga       60
gctagagtga ttttaacaag atttcaatac acaaattcaa atgtctttct atatattaat     120
gacaatcaac aataaaattt taaaacatta ttaaagtata atgaaaatat caactgttta     180
gggagaaatg taacaagaat ggtgaaggac ctatacacta aaaagcttca atatgttgtt     240
gagattaact gaagaaggtc taaatagatt ttttttttcat gtctcggaag acttaatatg     300
tgaagatacc aattcttccc caaatgatca acaggtgaaa tgcaatccca atcaaaatcc     360
cagcaattat tttaagggggg aaattggcaa tctgattcta aaattcatat ggaaaaaaac     420
aatggagtta gaataactaa aacaagtccg aaaagaaaa agaaatggag gactaatgct     480
acctgatttc aagtcttatc rtataaatct acatcaataa aggacaagtt ggtattgggt     540
taaagataga taaatacatc agtggaatag aatattgaat ccagaataaa tccacacata     600
tatggataaa ataccagac aattcagtgg agatggtttt gttttttacaa caaatgttac     660 tggaacaaat tgatatatgt attagtcaga tatggctgcc ataacaaaga accacaaaca     720
ggtggtttaa ataatggaaa taaatttcct cagaattctg gagtatggaa gcccaagatc     780
aagttgctgg gaggattcgt tcttctgag tgtctctttt tttgatgaca gatgactatc     840
ttttaccaat gtcttcactt ggttttccct ctgtgtgtgc ctaggtccta ttctccaatt     900
cctataagga aaccagtcat attggattag ggcccactct aatggcccca ttttacttgc     960
attatctctt taaagacact atctccagat gtagccacac t                         1001
```

<210> SEQ ID NO 360
<211> LENGTH: 1058
<212> TYPE: DNA
<213> ORGANISM: Homo sapiens

<400> SEQUENCE: 360

```
catgattagc tatgctactt tccactgctc ttagtatact gagaggcagc ataagtaaaa       60
ctaaaatatc tgaagatagc aatagactat ttaaagtaga agaagtatgc tatttttgtt     120
```

```
ttgttttcat ttcgaaggaa atatgcaaag gtttattgag tatttcagct tctcttacag    180 taggttttt ttggattctt tctgtgtttg tctatgttga taaaacattg aaatgccata    240
tagctcaaag gtcattcact taagaaatct aagtactgat aacatcttag ccccgattct    300
tcataggcat tgttaagcct attataattt tggtwcagag agaaggtaaa ctatattcca    360
gacaggcata taaagcaatt tctcctataa ttggagttca cgaaaaattc acatatttct    420
ttttaatagt aactctcaca gcaagaacat atgtttgtaa ataatacatc acagaatctt    480
attggcagac aaggaaattc ctaaaatatt ttttactgcc acatcaatta agatatataa    540
aataccttat atagaagatg tttgcaccca ggccaaacaa atcaaacaag aatagaagca    600
ctgacagtct tatttcaaaa ttggtttaac ttgtatttac aggatattgt agtaccttat    660
aaagttgatt gctgattggc cgtcttttac agaattctgt cagattgtta ttatttcttg    720
taaagattga ttcaaacaaa taaaaattgt caggattgga tatgtcctat agtgaggtgt    780
agttatgtca catgagattt ttaattacaa agaaatggaa aataaaatga aatagaatt    840 gagactcccc tgtcacctca caaatatgtt gaaatacaat gaaatttcca aagatgttaa    900
agcatataaa gttgaataat tcttattatg tattaaactt acagaaattt aatttcttta    960
ctttataaga ggtagtgaaa atataaaatt aattatgaag acagagtagt cttagtcaga   1020
catggcccta taaagcatat tcccattcgt tacatcaa                            1058
```

<210> SEQ ID NO 361
<211> LENGTH: 1058
<212> TYPE: DNA
<213> ORGANISM: Homo sapiens

<400> SEQUENCE: 361

```
catgattagc tatgctactt tccactgctc ttagtatact gagaggcagc ataagtaaaa     60
ctaaaatatc tgaagatagc aatagactat ttaaagtaga agaagtatgc tattttttgtt   120 ttgttttcat ttcgaaggaa atatgcaaag gtttattgag tatttcagct tctcttacag    180 taggttttt ttggattctt tctgtgtttg tctatgttga taaaacattg aaatgccaya    240
tagctcaaag gtcattcact taagaaatct aagtactgat aacatcttag ccccgattct    300
tcataggcat tgttaagcct attataattt tggtacagag agaaggtaaa ctatattcca    360
gacaggcata taaagcaatt tctcctataa ttggagttca cgaaaaattc acatatttct    420
ttttaatagt aactctcaca gcaagaacat atgtttgtaa ataatacatc acagaatctt    480
attggcagac aaggaaattc ctaaaatatt ttttactgcc acatcaatta agatatataa    540
aataccttat atagaagatg tttgcaccca ggccaaacaa atcaaacaag aatagaagca    600
ctgacagtct tatttcaaaa ttggtttaac ttgtatttac aggatattgt agtaccttat    660
aaagttgatt gctgattggc cgtcttttac agaattctgt cagattgtta ttatttcttg    720
taaagattga ttcaaacaaa taaaaattgt caggattgga tatgtcctat agtgaggtgt    780
agttatgtca catgagattt ttaattacaa agaaatggaa aataaaatga aatagaatt    840 gagactcccc tgtcacctca caaatatgtt gaaatacaat gaaatttcca aagatgttaa    900
agcatataaa gttgaataat tcttattatg tattaaactt acagaaattt aatttcttta    960
ctttataaga ggtagtgaaa atataaaatt aattatgaag acagagtagt cttagtcaga   1020
catggcccta taaagcatat tcccattcgt tacatcaa                            1058
```

<210> SEQ ID NO 362
<211> LENGTH: 956

<210> SEQ ID NO 362
<211> LENGTH: 956
<212> TYPE: DNA
<213> ORGANISM: Homo sapiens

<400> SEQUENCE: 362

| | | | | | |
|---|---|---|---|---|---|
| aaaacaagga | acaaacaaac | aaaaatgtta | caaccgaaca | acagactttt | gagtcatgtt | 60 |
| tcaggccaag | aggtgatgag | ttactgtagt | tgcttgagct | ggttggtgaa | atattacctg | 120 |
| gcaacaaaac | tgaaatagaa | ggtggcttag | taaaatgcag | attcagaatg | agtgccttaa | 180 |
| ggttaaggca | tataagacca | aactgatttt | cttttttcacg | aggtcttcag | gtaaggccat | 240 |
| tgtagaagat | accttgtttg | cgaacttcag | taaattactt | cacttgtctc | atattttcat | 300 |
| tttcaggatg | gaggcttgag | attgaattgt | agtgcaatta | ggtaaatttt | tacccatttt | 360 |
| aaatataata | ttaaaatatt | aattataaat | taccttatttt | gaatctggaa | taatatttat | 420 |
| tgcagggcat | ataatctaag | ctgtaaacgt | cctgtyagaa | gacaacatat | tcatcttgct | 480 |
| aaggtataag | ctatatgact | ggcactgtgc | tcaactcaga | gtcattgaat | gaacagtatt | 540 |
| tatttaatct | atgaatgaga | gcacttcaag | tatacagaaa | gatatctcaa | aagattcagc | 600 |
| cttacattgc | tcataacttc | aatgacttag | atgaaaacct | cctgaacatt | tttatcagtt | 660 |
| gtataggtac | cccaaatcat | aagggaatgt | ttatcaatta | gatgatgaaa | tggggatgca | 720 |
| actacatcat | ggcaggctaa | agcaatagaa | tgactttgac | aagaggaaat | tacatagagg | 780 |
| cacctgagtc | tcctaaacca | atttcaaagg | tatgagaggg | gggtgatata | aataaatagt | 840 |
| tgatagatga | aaaaactcag | aagttatagt | tgacagcaat | tttaatataa | tatgaaaaat | 900 |
| gtggttggac | ttttagggaa | aaaaacctaa | taaaatctaa | tggaaattag | tggtcc | 956 |

<210> SEQ ID NO 363
<211> LENGTH: 956
<212> TYPE: DNA
<213> ORGANISM: Homo sapiens

<400> SEQUENCE: 363

| | | | | | |
|---|---|---|---|---|---|
| caaccgaaca | acagactttt | gagtcatgtt | tcaggccaag | aggtgatgag | ttactgtagt | 60 |
| tgcttgagct | ggttggtgaa | atattacctg | gcaacaaaac | tgaaatagaa | ggtggcttag | 120 |
| taaaatgcag | attcagaatg | agtgccttaa | ggttaaggca | tataagacca | aactgatttt | 180 |
| cttttttcacg | aggtcttcag | gtaaggccat | tgtagaagat | accttgtttg | cgaacttcag | 240 |
| taaattactt | cacttgtctc | atattttcat | tttcaggatg | gaggcttgag | attgaattgt | 300 |
| agtgcaatta | ggtaaatttt | tacccatttt | aaatataata | ttaaaatatt | aattataaat | 360 |
| taccttatttt | gaatctggaa | taatatttat | tgcagggcat | ataatctaag | ctgtaaacgt | 420 |
| cctgtcagaa | gacaacatat | tcatcttgct | aaggtrtaag | ctatatgact | ggcactgtgc | 480 |
| tcaactcaga | gtcattgaat | gaacagtatt | tatttaatct | atgaatgaga | gcacttcaag | 540 |
| tatacagaaa | gatatctcaa | aagattcagc | cttacattgc | tcataacttc | aatgacttag | 600 |
| atgaaaacct | cctgaacatt | tttatcagtt | gtataggtac | cccaaatcat | aagggaatgt | 660 |
| ttatcaatta | gatgatgaaa | tggggatgca | actacatcat | ggcaggctaa | agcaatagaa | 720 |
| tgactttgac | aagaggaaat | tacatagagg | cacctgagtc | tcctaaacca | atttcaaagg | 780 |
| tatgagaggg | gggtgatata | aataaatagt | tgatagatga | aaaaactcag | aagttatagt | 840 |
| tgacagcaat | tttaatataa | tatgaaaaat | gtggttggac | ttttagggaa | aaaaacctaa | 900 |
| taaaatctaa | tggaaattag | tggtccactc | atttctccac | ctaggatgtt | aaaaat | 956 |

<210> SEQ ID NO 364

<211> LENGTH: 601
<212> TYPE: DNA
<213> ORGANISM: Homo sapiens

<400> SEQUENCE: 364

```
gtaaaacaca tagatcgctg tatccttgtt cagtaagcta caacatactc gtatctcctg      60
aaatcctggg cttaaatcga ggtctcaaag gctttgtttt gttttgttgt atggttgtat     120
ggtgagtgtg tgtgtgtgtg tgtgtgtgtg tgtttattct cctgaaattc tcctcctcac     180
ttgacttaag ctaaaagata acgtcctct tcctttcagc cacagatggt gatggataaa      240
ttgaatgtca ttcacattat tcccttaaaa taaactctct ccctcccctc tcccgtctca     300
wccttgtccc tttctttata taatgggtaa tgcgttaatg tcagcagaat agttttgggg     360
ccataatggc aagtatcacg tggatggttt agcattgttt ttagaatgct gtgaatttgg     420
gtatatgtga gttttgggga agttttgca actatatgtt tgttaattaa atgaggacta      480
taaagtaata taaaattatg tttctggaac atattttgga agctataaag tcatctgtat     540
ttattatcca cagacataat gtcattgttc aggtcctgca accttcttat aatcaacata     600
c                                                                      601
```

<210> SEQ ID NO 365
<211> LENGTH: 601
<212> TYPE: DNA
<213> ORGANISM: Homo sapiens

<400> SEQUENCE: 365

```
agtaagctac aacatactcg tatctcctga aatcctgggc ttaaatcgag gtctcaaagg      60
ctttgttttg ttttgttgta tggttgtatg gtgagtgtgt gtgtgtgtgt gtgtgtgtgt     120
gtttattctc ctgaaattct cctcctcact tgacttaagc taaaagataa cgtcctctt      180
cctttcagcc acagatggtg atggataaat gaatgtcat tcacattatt cccttaaaat      240
aaactctctc cctcccctct cccgtctcat ccttgtccct ttctttatat aatgggtaat     300
kcgttaatgt cagcagaata gttttggggc cataatggca agtatcacgt ggatggttta     360
gcattgtttt tagaatgctg tgaatttggg tatatgtgag ttttggggaa agttttgcaa     420
ctatatgttt gttaattaaa tgaggactat aaagtaatat aaaattatgt ttctggaaca     480
tattttggaa gctataaagt catctgtatt tattatccac agacataatg tcattgttca     540
ggtcctgcaa ccttcttata atcaacatac gtgggcccag ggattttatg tatcttcgcc     600
t                                                                      601
```

<210> SEQ ID NO 366
<211> LENGTH: 1079
<212> TYPE: DNA
<213> ORGANISM: Homo sapiens

<400> SEQUENCE: 366

```
gaatttatgg tctgatggag aagggaatca ttaaagttct atgtagtgag atatccccaa      60
ggggtgtatt aggcttacca ccactggaat ctggatagat gaagacagag tggcagggaa     120
gtcgtattaa ggttctgttt ctgctgggag ccacaggtcc tcaggaagca acaagtactg     180
ggcagattga tactgtagct rggctctagc tctatacctc tagaataaag gttacaaact     240
agcaacttga aagctaaacc tggcccacag atatgtttta tttggctctt acactgtttt     300
aaaaatatt accaacatt aaaactggga agttttatga aaaacccag acttctggat        360
tctgttgaaa aaaaaaatca gaagatctgg caatactgag ctgacattcc tatatgacaa     420
```

```
caattggctg atctatgca gcttctctcc aaaaagcaaa gaatgtgttc ttgcttaaca      480
cagtccccac cactccctca tattctccaa tcctggacct gagcgtcatt tgctatgtat      540
cgccatttgc catgaagttt tacactctac agaaatataa ttttttttgta gaagactatg     600 ctttaatcaa gatcaggata atataaagtg agatctgaaa gtggaaaaaa gataaatgtc      660
caacaatgat agactggatt aagaaaatgt ggcacatata caccgtggag tactatgcag      720
ccaaaaaaaa cgatgagttc atgtcctttg tagggacatg gatgaagctg aaaccacca       780 ttctcagcaa actatcgcaa ggacaaaaaa ccaaacgccg catgttctca ctcataggtg      840
ggaattgaac aatgagaaca cttgggcaca ggaaggggaa catcacacac cgggccctgt      900
tgtggggtgg ggggaggagg gagggatagc atttggagat atacctaatg ttaaatgact      960
agtttctggg tgcagcacac catcatggca catgtataca tatgtaacta acctgcacat     1020
tgtgcacatg taccctaaaa cttaaagtat aattttttaaa aaagatatt ttcttatct      1079

<210> SEQ ID NO 367
<211> LENGTH: 501
<212> TYPE: DNA
<213> ORGANISM: Homo sapiens

<400> SEQUENCE: 367
ataaattttc tcttccctca agaatttatg gtctgatgga gaagggaatc attaaagttc       60
tatgtagtga gatatcccca aggggtgtat taggcttacc accactggaa tctggataga      120
tgaagacaga gtggcaggga agtcgtatta aggttctgtt tctgctggga gcccacaggtc     180 ctcaggaagc aacaagtact gggcagattg atactgtagc tgggctctag ctctatacct      240
ctagaataaa kgttacaaac tagcaacttg aaagctaaac ctggcccaca gatatgtttt      300
atttggctct tacactgttt taaaaatat taccaacatt taaaactggg aagttttatg       360
aaaaaaccca gacttctgga ttctgttgaa aaaaaaaatc agaagatctg gcaatactga      420
gctgacattc ctatatgaca acaattggct ggatctatgc agcttctctc caaaaagcaa      480
agaatgtgtt cttgcttaac a                                                501

<210> SEQ ID NO 368
<211> LENGTH: 1001
<212> TYPE: DNA
<213> ORGANISM: Homo sapiens

<400> SEQUENCE: 368
tgaagaagcc gcctggcttc ttgtttcttc tcatagcaaa atgcaatgag aaagagataa       60
tttgagaaaa gaaccgttta acaaaaaga aaccaagaca taatgatttt ggaaattctc       120
agtttattca gactgcaaaa gatattaaaa taaagaaact cagtaacagg gatagataat      180
ctaaagaaaa agcctaggac acggctgtag taaccttctg tttttatacc tcagcaattt      240
gctaatgcct caaaagatc aaaagtactc aaatataaag ggctctttga agagattaga      300
tttcctcaat caaaccaaag agcatcgagg aagcttaagg ttactgtccc tcacatatct      360
cagcagaagg caaaaataga agactgatta tctaagaaag atctctgaaa gagtctcata      420
ttatggagtg aacccctgtg gcatacatgg agacccact tggttcttga gaattttata      480
tcaggagaaa cactgtcagt ytgtattgaa aggaacagag aaaatacgaa attaaagaag      540
actattaaac ctccaaaatt ctggcaggaa agaagcttac acagctactc agttgcaaag      600
atctgccact tttcatatac atgaaaggac tcagaggagg aagccacagg tttagaagga      660
```

```
aaagctaaaa gcaacatcgt attagtcttg gatctaggaa cctaatttct ctagcagaat    720
ctagaaatgg cttgggacaa gtgattgttt tttacctag gattttctcc ctcttgaaaa     780
caggactgtc tgtaactatt atcctatgcc tgccctacca tcatatttca gaaacaggta    840
acttatgttt tcactttcaa agattcacaa taaagagaaa ttgtacctca gaatggatta    900
taccagagct ttcctcatgc ataaattaaa taatttaggt tatgtgattt gaagcttttg    960
agtgggtgag gtgacatttt ggatgctgag ttggtgccgt a                       1001
```

<210> SEQ ID NO 369
<211> LENGTH: 1001
<212> TYPE: DNA
<213> ORGANISM: Homo sapiens

<400> SEQUENCE: 369

```
tcttctcata gcaaaatgca atgagaaaga gataatttga gaaagaacc gtttaaacaa      60 aaagaaacca agacataatg attttggaaa ttctcagttt attcagactg caaagatat     120 taaaataaag aaactcagta acagggatag ataatctaaa gaaaaagcct aggacacggc    180
tgtagtaacc ttctgttttt atacctcagc aatttgctaa tgcctcaaaa agatcaaaag    240
tactcaaata taagggctc tttgaagaga ttagatttcc tcaatcaaac caagagcat      300 cgaggaagct taaggttact gtccctcaca tatctcagca aaggcaaaa atagaagact     360 gattatctaa gaaagatctc tgaaagagtc tcatattatg gagtgaaccc ctgtggcata    420
catgggagac ccacttggtt cttgagaatt ttatatcagg agaaacactg tcagtctgta    480
ttgaaaggaa cagagaaaat rcgaaattaa agaagactat taaacctcca aaattctggc    540
aggaaagaag cttacacagc tactcagttg caaagatctg ccacttttca tatacatgaa    600
aggactcaga ggaggaagcc acaggtttag aaggaaaagc taaaagcaac atcgtattag    660
tcttggatct aggaacctaa tttctctagc agaatctaga aatggcttgg gacaagtgat    720
tgttttttta cctaggattt tctccctctt gaaaacagga ctgtctgtaa ctattatcct    780
atgcctgccc taccatcata tttcagaaac aggtaactta tgttttcact ttcaaagatt    840
cacaataaag agaaattgta cctcagaatg gattatacca gagctttcct catgcataaa    900
ttaaataatt taggttatgt gatttgaagc ttttgagtgg gtgaggtgac attttggatg    960
ctgagttggt gccgtagtga gtccagaatt ctgcggaact t                      1001
```

<210> SEQ ID NO 370
<211> LENGTH: 601
<212> TYPE: DNA
<213> ORGANISM: Homo sapiens

<400> SEQUENCE: 370

```
ctctagactc ctcctgtatt taatttagc cacttttta gggcctacaa ttttagatct       60
ccacagggct cttgaaactt cttgaacctc atcagtaaca tgtccattag tggcatgacc    120
caagagttct agaacatcta ttcagcaagt gtgtatctgg taagtgaata ttccttctat    180
gtgttccctt ttgcatcaaa ctacacactg tcattcctcc tttatctcca aaagcttgaa    240
aattcctcac ttgtatctca ttctttctct cttagaaaac tgatcacctc tgatgaatta    300
raacggaatg accaagcttt gggagaggca aaagaatctc ggtgttaaag actcagagtt    360
taagaagcaa caaaaagatt atacagatgt gaatatgtga ccttcctcca ccagggcatg    420
ttgccttgga gtaagataat ctaagcacac acttcatagc ctgagaacaa ttttggaagt    480
ctttgcttta tggatattta cataaagcaa atatggatat ttacctaaag gctggaccaa    540
```

```
ggcctaattc ctctagagcc ccttgatcat gaacaccatt cctgtcatga ttcttaaggt    600
c                                                                    601

<210> SEQ ID NO 371
<211> LENGTH: 601
<212> TYPE: DNA
<213> ORGANISM: Homo sapiens

<400> SEQUENCE: 371
acaagctcca gccatggacg caattccttc tagaagcaaa atttatctct agactcctcc     60
tgtattttaa tttagccact tttttagggc ctacaatttt agatctccac agggctcttg    120
aaacttcttg aacctcatca gtaacatgtc cattagtggc atgacccaag agttctagaa    180
catctattca gcaagtgtgt atctggtaag tgaatattcc ttctatgtgt tcccttttgc    240
atcaaactac acactgtcat tcctccttta tctccaaaag cttgaaaatt cctcacttgt    300
rtctcattct ttctctctta gaaaactgat cacctctgat gaattagaac ggaatgacca    360
agctttggga gaggcaaaag aatctcggtg ttaaagactc agagtttaag aagcaacaaa    420
aagattatac agatgtgaat atgtgacctt cctccaccag gcatgttgc cttggagtaa    480
gataatctaa gcacacactt catagcctga gaacaatttt ggaagtcttt gctttatgga    540
tatttacata aagcaaatat ggatatttac ctaaaggctg gaccaaggcc taattcctct    600
a                                                                    601

<210> SEQ ID NO 372
<211> LENGTH: 701
<212> TYPE: DNA
<213> ORGANISM: Homo sapiens

<400> SEQUENCE: 372
gaagatgcac tctaatgttt tttcccagaa gctctgtagg tttagctttt acctttctgg     60
gtttgttttg ttttgttttt tgagatggag tcccactcgt gtcacccagg ctggagtaca    120
atggtgcaat ctcggttcac tgcaacctcc acctcccggg ttcaagcaat tccctgtct    180
ccacctctcg agtagctggg atgggaggcg cctgccacca tacctggcta attttcatat    240
ttttagtaaa gatagggttt caccatgtta gccaggctgg tctcgaactc ctgacctcaa    300
gtgatccacc cgcctcagct tcccaaagtg ctgggattac aggcgtgagc cactgcgccc    360
agccctagct ttttggtcta tgattcctcc caaattaatt tctgtgaacc attaccttaa    420
gatgttgaga tttaatgtcc agaatctcat tgttcaccct ttgaaaatta agaaccctg    480
gcacagtgtt gactggagcc wcttaccta atagaaaata aagctcacat atatccataa    540
tgaaaagcag agaccagcac aaccatagtc acctgacagt tttaaaatcc aaggccagga    600
tcttctcaac tcaggcccac tcacttactc cacaacatac ttcttctttc ctcagcatct    660
actacttgtg ctgggacctt ggtcttccca ttgttcatgt c                       701

<210> SEQ ID NO 373
<211> LENGTH: 701
<212> TYPE: DNA
<213> ORGANISM: Homo sapiens

<400> SEQUENCE: 373
agatggagtc ccactcgtgt cacccaggct ggagtacaat ggtgcaatct cggttcactg     60
caacctccac ctcccggggtt caagcaattc ccctgtctcc acctctcgag tagctgggat    120
```

| | |
|---|---|
| gggaggcgcc tgccaccata cctggctaat tttcatatttt ttagtaaaga tagggtttca | 180 |
| ccatgttagc caggctggtc tcgaactcct gacctcaagt gatccacccg cctcagcttc | 240 |
| ccaaagtgct gggattacag gcgtgagcca ctgcgcccag ccctagcttt tggtctatg | 300 |
| attcctccca aattaatttc tgtgaaccat taccttaaga tgttgagatt taatgtccag | 360 |
| aatctcattt gttcaccttt gaaaattaag aaaccctggc acagtgttga ctggagccac | 420 |
| ttaccttaat agaaaataaa gctcacatat atccataatg aaaagcagag accagcacaa | 480 |
| ccatagtcac ctgacagttt waaaatccaa ggccaggatc ttctcaactc aggcccactc | 540 |
| acttactcca caacatactt cttctttcct cagcatctac tacttgtgct gggaccttgg | 600 |
| tcttcccatt gttcatgtca ttcttttcct cacagttccc attcttttct ccctgaaata | 660 |
| aagaaatttc aaaatatacc atgtttcatg aaaaagacaa a | 701 |

<210> SEQ ID NO 374
<211> LENGTH: 701
<212> TYPE: DNA
<213> ORGANISM: Homo sapiens

<400> SEQUENCE: 374

| | |
|---|---|
| gatttccacc ctcaggtgat ggggatggtt gaacatccaa cacctgaaac aggacagacg | 60 |
| atattgacag tacttgttag ttgcatataa tcacagacca gtggaaacag atgaaccaca | 120 |
| cagggccaca gcggggtttc actggggaac agagtgaaca atcaggaggt gtgggaggca | 180 |
| ggtttagtag tttaaagagg ttgaggtgtc cccctggatc ccatgggagg atcacattgg | 240 |
| ctcatttgaa ttatcatacg gactggcagg gaactgaaat cttctactca gggataagca | 300 |
| gaaactgtcc ctggtttcct tgataaaaag ggttgtttga taggggaccct tatccatggg | 360 |
| aggaaagtga ggagggaaat ttgtggctaa gccattcaag gccctcccag ttttactaga | 420 |
| tgtcaaggca gcacacgtaa tattgggact taattttagc cacataacta ataaatttgt | 480 |
| aagtatgtgc aacggctcac rcttgcttcc agaatggcac ctaaaaaaca gatttacctc | 540 |
| tccccaaatt cagatatgga attaaatgta atgtcaggaa aattgtctaa gagttggaaa | 600 |
| tgggaaaaaa atgttctttt ggtggagtta tggactccag aggttatcag attctattga | 660 |
| ataacgtact tttgattgta tttgtaacaa ttaggctatt t | 701 |

<210> SEQ ID NO 375
<211> LENGTH: 1001
<212> TYPE: DNA
<213> ORGANISM: Homo sapiens

<400> SEQUENCE: 375

| | |
|---|---|
| gcatataatc acagaccagt ggaaacagat gaaccacaca gggccacagc ggggtttcac | 60 |
| tggggaacag agtgaacaat caggaggtgt gggaggcagg tttagtagtt taaagaggtt | 120 |
| gaggtgtccc cctggatccc atgggaggat cacattggct catttgaatt atcatacgga | 180 |
| ctggcaggga actgaaatct tctactcagg ataagcaga aactgtccct ggtttccttg | 240 |
| ataaaaaggg ttgtttgata ggggacctta tccatgggag gaaagtgagg agggaaattt | 300 |
| gtggctaagc cattcaaggc cctcccagtt ttactagatg tcaaggcagc acacgtaata | 360 |
| ttgggactta attttagcca cataactaat aaatttgtaa gtatgtgcaa cggctcacac | 420 |
| ttgcttccag aatggcacct aaaaaacaga tttacctctc cccaaattca gatatggaat | 480 |
| taaatgtaat gtcaggaaaa ytgtctaaga gttggaaatg ggaaaaaaat gttcttttgg | 540 |
| tggagttatg gactccagag gttatcagat tctattgaat aacgtacttt tgattgtatt | 600 |

```
tgtaacaatt aggctatttg tgaactcggt aggggtagaa atcgagttgt agaaaatgga      660
tggtaatgca agtgattttt gaccatatca atgcaaatga attctgttgg tagaaatatt      720
catttccaca ctgtagatga ccctaaacat atgtcattac attatatttt attgccttat      780
agactattaa ccaattttga atcatacagt agcaaattta tttcagcatt cttgtgtgta      840
tgtgtttata tatacacgtg catatgtatt taagatatat aattgtatat tcttcaaatt      900
cttctttgaa caggtttgaa cctcttatta gtttcctcat taaggaattt aataagacct      960
ttaatgcatg tttgtatttt catgagagtc attattttac c                         1001

<210> SEQ ID NO 376
<211> LENGTH: 695
<212> TYPE: DNA
<213> ORGANISM: Homo sapiens

<400> SEQUENCE: 376
tgctccttca ttagtgcaat ggaacagcaa atcaggatac tttcacagtt ctcttaagtg       60
agcctagaag tggggagctg cttgttcaca aacttgaagc ctgaatatgt taatattctt      120
tcagtggccg gacgcggtgg ctcatgcctg taatcccaac actttgggag gccgaggtag      180
gcagatcaac ctgaagtcag gagttcgagg ccagcctggc caacatggtg aaaccccacc      240
tgttggtctg tactaaaaat agaaaaatta gctgggcatg gtggcgcatg cctgtaatcc      300
cagctactca ggaggctgtg cagaagaat cgcctgcacc tgggaggcag aggttgcttt       360
gagttgatat cgtgtcactg cactccagcc tgggcaacag agtgagatcc tttcagaaac      420
ctgctgtctg tatttggata caattaaaaa aaaaaaaaag atgagacagg caggtgcgaa      480
agaaataaaa gtcamaactg atccagttgg gaaactcaga attgacagtt acgtgtcctt      540
tcatttattg atattttgag attcacaggg gtttaaactt tattttttcca agactgaata      600 gttcccacct cccttccata tataaaattt gagtagctgg ggagatttaa aagaggctcc      660 ccataaaactc agaagttaaa agagacaagg gtccc                                695

<210> SEQ ID NO 377
<211> LENGTH: 601
<212> TYPE: DNA
<213> ORGANISM: Homo sapiens

<400> SEQUENCE: 377
aaccccacct gttggtctgt actaaaaata gaaaaattag ctgggcatgg tggcgcatgc       60
ctgtaatccc agctactcag gaggctgtgg cagaagaatc gcctgcacct gggaggcaga      120
ggttgctttg agttgatatc gtgtcactgc actccagcct gggcaacaga gtgagatcct      180
ttcagaaacc tgctgtctgt atttggatac aattaaaaaa aaaaaaaga tgagacaggc      240 aggtgcgaaa gaaataaaag tcacaactga tccagttggg aaactcagaa ttgacagtta      300
sgtgtccttt catttattga tattttgaga ttcacagggg tttaaacttt attcttccaa      360
gactgaatag ttcccacctc ccttccatat ataaaatttg agtagctggg gagatttaaa      420
agaggctccc cataaaactca gaagttaaaa gagacaaggg tcccagtaaa tacaaaatga      480
ttggggttga ggaggcagat tttctgtcct cagtgaagtt tgttggttgg ttggttggtt      540
ggttggttaa ttggttggtt tttgagtcag ggtctcactt tgtcacccaa gctggagtgc      600
a                                                                     601

<210> SEQ ID NO 378
```

<211> LENGTH: 663
<212> TYPE: DNA
<213> ORGANISM: Homo sapiens

<400> SEQUENCE: 378

```
tgtagcaaca ggagggatga gacccaaagg tctgaaaagc cagtatttta agaagtcttg      60
gaaaatgtgg aggttgaaaa atctaacagg agtgcttgct tcagcagcaa tttagagtag     120
attagcatgg cctctgcgcc aggatgacat gcacattcct aaaagtgttc cgtgttttaa     180
aaaaaagaga gagacagaat ctaaggggat gtgtacattt gctagagcta ctataacaaa     240
gtaccagagg cagggtcact tcaacaacag aaatttattt ctcacagttc tggaggctag     300
acgtccaaga ttaaggtgtt gactgggttg aattcagccc ataacaggaa ataaggagtt     360
aaataaagca cttgcttcta ttgtttgtac ctaaacttaa cagaayacag taagtaacaa     420
gtcattggga tgcagaaaag aaaaagaga gtgaaggaag agagaaggt gaagggagaa      480
tggaagagag gaagggaggg aggaaagaaa agtttgatga atgattgcag tctaaactgg     540
ttcaaacaag agatcttgtt taattaagga attcatccca tctctgccta ttaggaggag     600
gaaaaagtct aaaatagaag atggtgaaag ttggatgacc ccaggcatta aggccattca     660
tct                                                                  663
```

<210> SEQ ID NO 379
<211> LENGTH: 662
<212> TYPE: DNA
<213> ORGANISM: Homo sapiens

<400> SEQUENCE: 379

```
ttaagaagtc ttggaaaatg tggaggttga aaatctaac aggagtgctt gcttcagcag      60
caatttagag tagattagca tggcctctgc gccaggatga catgcacatt cctaaaagtg     120
ttccgtgttt taaaaaaaag agagagacag aatctaaggg gatgtgtaca tttgctagag     180
ctactataac aaagtaccag aggcagggtc acttcaacaa cagaaattta tttctcacag     240
ttctggaggc tagacgtcca agattaaggt gttgactggg ttgaattcag cccataacag     300
gaaataagga gttaaataaa gcacttgctt ctattgtttg tacctaaact taacagaaca     360
cagtaagtaa caagtcattg ggatgcagaa agaaaaaag agagtgaagg aaggagaraa     420
ggtgaaggga gaatggaaga gaggaaggga gggaggaaag aaaagtttga tgaatgattg     480
cagtctaaac tggttcaaac aagagatctt gtttaattaa ggaattcatc ccatctctgc     540
ctattaggag gaggaaaaag tctaaaatag aagatggtga agttggatg accccaggca      600
ttaaggccat tcatctttaa ctgttatgct tggatcatgc aaatgtgtct ggtagctaca     660
ag                                                                   662
```

<210> SEQ ID NO 380
<211> LENGTH: 615
<212> TYPE: DNA
<213> ORGANISM: Homo sapiens

<400> SEQUENCE: 380

```
ttccatacat tccttccaca ccattgccct taacctttca aattcctgct taaaactaat      60
cccatttta tggctgacct caccctgtat caaaaactcc gacatccctt tacgacagag     120
agcacaaact agtggtccaa aatgtcatgg gggtcttctc agagttgttt tttcaatcag     180
gaaatttcac ataaaaatat ggatttctga tttctctttt aaaaacagaa aaacgagcca     240
ccagtgggag cactgcaggt atctgtgtga gaccygtact tcacaactcc tgctttccct     300
```

```
ccataaagta gcttgcattt tccacattga ctttgcagtt ctttggtatc tgtattggtt    360
ttaagataat ttctactata tcacatatct cctcacagta caaagatatc attttctttc    420
ccttttcttt ttaaaaaatt tgtattttta attttgtgg gtacacagta gatatttatg    480
gggcatatga ggtattttat aggcatataa tatgtactag ggtaagtggg gtattcatca    540
cctcaagcat ttatcctttc tttgtgtaaa atatagcatt ttctgaacac tatgaatact    600
taagtacaag gatca                                                    615
```

<210> SEQ ID NO 381
<211> LENGTH: 994
<212> TYPE: DNA
<213> ORGANISM: Homo sapiens

<400> SEQUENCE: 381

```
tcaaagtgta acaaatttcc tttcctcata aactagcaga cattctatcc cctcattatt     60
gtaacacatt tctaatatct ttctcaaatt gtcttcctgt attacaatgc actcaccttg    120
gcttagaatg tctgagacaa gaaaatctat tcaccattcc cacagatgac tccctcactc    180
tcctcccaag tcttccatac attccttcca ccattgcc cttaacctttt caaattcctg    240 cttaaaacta atcccatttt tatggctgac ctcaccctgt atcaaaaact ccgacatccc    300
tttacgacag agagcacaaa ctagtggtcc aaaatgtcat gggggtcttc tcagagttgt    360 ttttcaatc aggaaatttc acataaaaat atggatttct gatttctctt ttaaaaacag    420
aaaaacgagc caccagtggg agcactgcag gtatctgtgt gagacctgta cttcacaact    480
cctgctttcc ctccataaag yagcttgcat tttccacatt gactttgcag ttctttggta    540
tctgtattgg ttttaagata atttctacta tatcacatat ctcctcacag tacaaagata    600
tcattttctt tccctttttct ttttaaaaaa tttgtatttt taatttttgt gggtacacag    660
tagatattta tggggcatat gaggtatttt ataggcatat aatatgtact agggtaagtg    720
gggtattcat caccctcaagc atttatcctt tctttgtgta aaatatagca ttttctgaac    780
actatgaata cttaagtaca aggatcaagt cataggattt ggaattgatt tttaaaatat    840
gttgaccaaa gtgctcttat catcaaactt aacatcacta atgaaggatg aacatcccaa    900
atctgaaaat ccaaaatcca aaatgctcca taatctaaaa cttgttgagc accaacatga    960
tgcttaaagg aaatgctcct ggagcatttc agat                                994
```

<210> SEQ ID NO 382
<211> LENGTH: 1001
<212> TYPE: DNA
<213> ORGANISM: Homo sapiens

<400> SEQUENCE: 382

```
ctatgagaaa tattttaaa gtggttagga acaattcata gcactgacat gttatcagta     60 aaatagaag aaaataaatt aatattatga aatattaatt atatttcatt aattatgtaa    120
tatgaattat gttttagctc aaatatttcc caagggacaa ttaagtaaat gaaaaataca    180
cacagattaa aataataaat agagaaggag atattaatga ggtacaaaaa gaaaaaatac    240
atgtaatcac atgaaatgct attatttgaa agattaacaa aacttgtaaa ctacctgcta    300
acttgatcaa agaaaaaaat cgagaaacca tatgcgcaat taatagtaag agggaaataa    360
acattgaaac agaagacatt tgaaatacca tataagactg ggtttcagag ctctatgtac    420
gtaaattgat aatgtcctgg agaagtgcag atgaccaaaa tggacacctt tcaacttaga    480
```

| | |
|---|---|
| aatcataaac agattcattt ycttaaagtt aatgaaaaga attaacagac cctcctcaaa | 540 |
| aaagacatat atgcggccta caatcatatg aaaaaaagtt caacattact gttcattaga | 600 |
| gaaatgcaaa tcaaaaccac aatgagatac catctcacac cagtcagaat ggctattatt | 660 |
| aagaagtcaa aaaataaaag atgctggcga ggttgtggag aaaaaagaat gcttttatac | 720 |
| acttggtggg aatgtaaatt agttcagtca ttgtggaaga ctttgatgat tcctagaaga | 780 |
| cctaaataca gaactactat ttgacccaac aatcccatta ctgggtatat actcaaatga | 840 |
| ctataaatca ttctattata aagacacatg catggatatg ttcattacag cactatgcac | 900 |
| aatagcaaag acttggaatc aacatgaatg tccatcaatg atagactaga taaagaaaat | 960 |
| gtggtacaca tataccatgg aatactatgc agccataaaa a | 1001 |

<210> SEQ ID NO 383
<211> LENGTH: 1001
<212> TYPE: DNA
<213> ORGANISM: Homo sapiens

<400> SEQUENCE: 383

| | |
|---|---|
| tcagtaaaaa tagaagaaaa taaattaata ttatgaaata ttaattatat ttcattaatt | 60 |
| atgtaatatg aattatgttt tagctcaaat atttcccaag ggacaattaa gtaaatgaaa | 120 |
| aatacacaca gattaaaata ataaatagag aaggagatat taatgaggta caaaagaaa | 180 |
| aaatacatgt aatcacatga aatgctatta tttgaaagat taacaaaact tgtaaactac | 240 |
| ctgctaactt gatcaaagaa aaaatcgag aaccatatg cgcaattaat agtaagaggg | 300 |
| aaataaacat tgaaacagaa gacatttgaa ataccatata agactgggtt tcagagctct | 360 |
| atgtacgtaa attgataatg tcctggagaa gtgcagatga ccaaaatgga cacctttcaa | 420 |
| cttagaaatc ataaacagat tcatttcctt aaagttaatg aaaagaatta acagaccctc | 480 |
| ctcaaaaaag acatatatgc rgcctacaat catatgaaaa aagttcaac attactgttc | 540 |
| attagagaaa tgcaaatcaa aaccacaatg agataccatc tcacaccagt cagaatggct | 600 |
| attattaaga agtcaaaaaa taaagatgc tggcgaggtt gtggagaaaa aagaatgctt | 660 |
| ttatacactt ggtgggaatg taaattagtt cagtcattgt ggaagacttt gatgattcct | 720 |
| agaagaccta aatacagaac tactatttga cccaacaatc ccattactgg gtatatactc | 780 |
| aaatgactat aaatcattct attataaaga cacatgcatg gatatgttca ttacagcact | 840 |
| atgcacaata gcaaagactt ggaatcaaca tgaatgtcca tcaatgatag actagataaa | 900 |
| gaaaatgtgg tacacatata ccatggaata ctatgcagcc ataaaatga aggagatcat | 960 |
| gcccttttgca gggacacgaa tagaggtgga ggccattatc c | 1001 |

<210> SEQ ID NO 384
<211> LENGTH: 501
<212> TYPE: DNA
<213> ORGANISM: Homo sapiens

<400> SEQUENCE: 384

| | |
|---|---|
| agttgcttga aagcaaagtt ctcgcagtag ctctctatct agaaggaggc attttattta | 60 |
| tgtaaggaag tcacctaaaa gaaaattcat ttgttatggt gtggctttaa gagttactta | 120 |
| cttttaatgg aatcccccag ataataataa attctgaaaa aaaaaaatca gaatcatggc | 180 |
| atgttaaaac tggatacatt cctagaaata gatggaaact gctcttgcaa aaagcttagc | 240 |
| acatgttaaa rcattttaga aacaatttgc caaagtttat ttagtctagt gatttcgaca | 300 |
| ggttaaatgg acccttgag atcttttttc ctcaagtaca aaggctcact tgcttaatga | 360 | acacagtccc agaaaagcag ggggctgaac cttggctcta ccatcttacc taagattcta    420 gagttagcaa agggtttcca caagcccaaa ttattatgtt taatcttttc aattatctgt    480 gaagcattag gttggtgcaa a    501

<210> SEQ ID NO 385
<211> LENGTH: 501
<212> TYPE: DNA
<213> ORGANISM: Homo sapiens

<400> SEQUENCE: 385
gaggcatttt atttatgtaa ggaagtcacc taaaagaaaa ttcatttgtt atggtgtggc    60
tttaagagtt acttactttt aatggaatcc cccagataat aataaattct gaaaaaaaaa    120
aatcagaatc atggcatgtt aaaactggat acattcctag aaatagatgg aaactgctct    180
tgcaaaaagc ttagcacatg ttaaagcatt ttagaaacaa tttgccaaag tttatttagt    240
ctagtgattt ygacaggtta aatggaccct ttgagatctt ttttcctcaa gtacaaaggc    300
tcacttgctt aatgaacaca gtcccagaaa agcaggggc tgaaccttgg ctctaccatc    360
ttacctaaga ttctagagtt agcaaagggt tccacaagc ccaaattatt atgtttaatc    420
ttttcaatta tctgtgaagc attaggttgg tgcaaaagta actgcaggtt ttgacattaa    480
aactggcaaa aactgcaata a    501

<210> SEQ ID NO 386
<211> LENGTH: 703
<212> TYPE: DNA
<213> ORGANISM: Homo sapiens

<400> SEQUENCE: 386
gacaccagtt agcatattgt cgcggggag aggggtggga aaggcgagag aacagcatgt    60
ggtccagagg ccatacccag atggaggctg cagtcagctc cccagtcaaa ggcaaagccc    120
aagtcaaagc catgcttccc tcttgcccac ctgctccaat gccacccaca gagagtgcgc    180
cacagctcac aggatgcagg tctggttgaa tcttaacaat aactttgtaa gggaggtgtc    240
attagctcca ttctcctggc aggaggatga ggctcaaggc agctaaaggc ttttgctgaa    300
catcaagtgg tgagccagga ctcaawgcca gatcttcttg tttccctgtt aggtgtatgt    360
agcacaactg gtatctgcag actatgctgc tggaagggct agccgtcact gttatcacag    420
cgactgctgc ctgagatatg ccaggtactg ctgcaagaag tttacaaata taagctcact    480
tgatcttcat aacatactac ctaggtacaa tcattatatt tatttgacag atacagagac    540 agagggaca cagaaaggat tagtaacttg ccccaaacca cacagccagc aaggtgtaag    600
tgagcacctg cagtctagat gagacaccac tcaaaacgtc attttctgg cagccccgtg    660 cagttaccac agtggtcacc ccagtggtca gctaaaggcc aag    703

<210> SEQ ID NO 387
<211> LENGTH: 704
<212> TYPE: DNA
<213> ORGANISM: Homo sapiens

<400> SEQUENCE: 387
gcatattgtc gcggggaga ggggtgggaa aggcgagaga acagcatgtg gtccagaggc    60
catacccaga tggaggctgc agtcagctcc ccagtcaaag gcaaagccca agtcaaagcc    120
atgcttccct cttgcccacc tgctccaatg ccacccacag agagtgcgcc acagctcaca    180

| | |
|---|---|
| ggatgcaggt ctggttgaat cttaacaata actttgtaag ggaggtgtca ttagctccat | 240 |
| tctcctggca ggaggatgag gctcaaggca gctaaaggct tttgctgaac atcaagtggt | 300 |
| gagccaggac tcaatgccag atcttcttgt ttccctgtta ggtgtwtgta gcacaactgg | 360 |
| tatctgcaga ctatgctgct ggaagggcta gccgtcactg ttatcacagc gactgctgcc | 420 |
| tgagatatgc caggtactgc tgcaagaagt ttacaaatat aagctcactt gatcttcata | 480 |
| acatactacc taggtacaat cattatattt atttgacaga tacagagaca gaggggacac | 540 |
| agaaaggatt agtaacttgc cccaaaccac acagccagca aggtgtaagt gagcacctgc | 600 |
| agtctagatg agacaccact caaaacgtca tttttctggc agccccgtgc agttaccaca | 660 |
| gtggtcaccc cagtggtcag ctaaaggcca agcccaccgt ttct | 704 |

<210> SEQ ID NO 388
<211> LENGTH: 975
<212> TYPE: DNA
<213> ORGANISM: Homo sapiens

<400> SEQUENCE: 388

| | |
|---|---|
| gacttaagac aagggggtct taatttgatt atttttttct gttttatatg atttctatga | 60 |
| aaactacaac aaaataaagt taattctatt taagtgactt tttaatgaat tgcctttgtt | 120 |
| agaaaaaaaa ttaagtgttt ttgtctcact ctgtcaccca ggctggagca cagtggtgtg | 180 |
| atcatggctt actgcagcca tgacctcccg ggctcaggtg atcctcccac ctcagcttcc | 240 |
| caaatagatg ggactacagt tgtgtgccac aacgcctggc taattttttgt attttttttgt | 300 |
| agagacaggg tctcaccagg ttgcccaggc tgatcttgaa ctccttggct caagcgatcc | 360 |
| acccacctca gcctccctga gtgctgggat tacaggcatg agccagcgca cccagccaga | 420 |
| attacatttt tttaaatggt actgtcctag aaaatccagg atgtgcagtg atcaygtatg | 480 |
| aatgcatgga cctgcacaca caggagtgaa caaaagaccc acccctgcca ggtcaccact | 540 |
| catatctcac cccagcccac gctagctcac actcctcccc acacaccact gacctcatca | 600 |
| ttgctaggta cccacttgac ttctcaacag gttcaagaca attggccttc ctcgtctctt | 660 |
| ctagaaacac cctcttttct gggctttgtg taacacctgg tctttctccc ctctctggcc | 720 |
| acttctcagc ttttctttt ctttctttct tttttttttt tttttttttg ccacttcctc | 780 |
| ttcctctaca tcaagcttgt ccaacccaca gcccaggaca gctttgaatg cagcctaaca | 840 |
| caaattcgta agctttctta aaacattatg agatgtgtgt gtgtgtgtgt gtgtgtgtgt | 900 |
| gtgtgtgtgt gtgtgtgtgt gtttagctca tcagctatcg ttattgttag tgtattttat | 960 |
| gtgtggccca agaca | 975 |

<210> SEQ ID NO 389
<211> LENGTH: 976
<212> TYPE: DNA
<213> ORGANISM: Homo sapiens

<400> SEQUENCE: 389

| | |
|---|---|
| gactttttaa tgaattgcct tgttagaaa aaaaattaag tgtttttgtc tcactctgtc | 60 |
| acccaggctg gagcacagtg gtgtgatcat ggcttactgc agccatgacc tcccgggctc | 120 |
| aggtgatcct cccacctcag cttcccaaat agatgggact acagttgtgt gccacaacgc | 180 |
| ctggctaatt tttgtatttt tttgtagaga cagggtctca ccaggttgcc caggctgatc | 240 |
| ttgaactcct tggctcaagc gatccaccca cctcagcctc cctgagtgct gggattacag | 300 |
| gcatgagcca gcgcacccag ccagaattac attttttta atggtactgt cctagaaaat | 360 |

```
ccaggatgtg cagtgatcac gtatgaatgc atggacctgc acacacagga gtgaacaaaa    420
gacccacccc tgccaggtca ccactcatat ctcaccccag cccacgctag ctcacrctcc    480
tccccacaca ccactgacct catcattgct aggtacccac ttgacttctc aacaggttca    540
agacaattgg ccttcctcgt ctcttctaga aacaccctct tttctgggct tgtgtaaca     600 cctggtcttt ctcccctctc tggccacttc tcagcttttc ttttcttttc tttctttttt    660
tttttttttt ttttgccact tcctcttcct ctacatcaag cttgtccaac ccacagccca    720
ggacagcttt gaatgcagcc taacacaaat tcgtaagctt tcttaaaaca ttatgagatg    780
tgtgtgtgtg tgtgtgtgtg tgtgtgtgtg tgtgtgttta gctcatcagc                840
tatcgttatt gttagtgtat tttatgtgtg gcccaagaca tttcttcttc cagtgtggcc    900
cagggaagcc aaaagattgg acacccctgc tctacaacat tcaatatag gccttttcta    960 tgtttcattc tagatt                                                     976
```

<210> SEQ ID NO 390
<211> LENGTH: 801
<212> TYPE: DNA
<213> ORGANISM: Homo sapiens

<400> SEQUENCE: 390

```
atccagacgg tgcccatact ccctgctctg tctagatggt gtccacattc cctgctccgt     60
ctagactgtg cccatattcg ctgctggctg caaatgcgag gagttgacag cagcctcccc    120
tttacaaggc aggaggtgcc actgttcgcc attgtctcca cctagggctt cacttgcttt    180
ctatctgcag acatcagagg gacccacatc tctctgttct gacacgctgt gtgttgatgg    240
cagagtttaa ttatccacat gcaatcttac tttccttatt cccaagtccg tggggctgcc    300
tcatcaaagc attgtaagaa ctgataacca tcttctagaa gtatcatagt gatattaaga    360
acacacatca cagatcatag taaatggctt taattttta rcgaaatctc actactgcaa    420
atgcattgtt gtcctagcta atgaatgcat agagtattgc ctgcaaaata ataattgaga    480 ttctatttt aagaagctta gaacagtaca tggtgcatag caaagactct gtgtatgtga    540
agccagattt taaaatatgg taacaagtgt ctgaaaatat gtggctcaat ttgtctcccg    600
gttacttttc cctctccccc tttaaaatgt agaggaagga gaagaagaga taagaggttt    660
gtgagtgaag acaagggccc tttaaggcct gggaagacta cgccatagg gatctccctc     720 tgccttaaaa ggcacaggaa tcttagtggg gaaaagaag tggtgataaa tagccagtcc     780
gtgtgcctgg aatatcaaag t                                               801
```

<210> SEQ ID NO 391
<211> LENGTH: 801
<212> TYPE: DNA
<213> ORGANISM: Homo sapiens

<400> SEQUENCE: 391

```
ccctgctccg tctagactgt gcccatattc gctgctggct gcaaatgcga ggagttgaca     60
gcagcctccc ctttacaagg caggaggtgc cactgttcgc cattgtctcc acctagggct    120
tcacttgctt tctatctgca gacatcagag ggacccacat ctctctgttc tgacacgctg    180
tgtgttgatg gcagagttta attatccaca tgcaatctta ctttccttat cccaagtcc     240 gtggggctgc ctcatcaaag cattgtaaga actgataacc atcttctaga agtatcatag    300
tgatattaag aacacacatc acagatcata gtaaatggct ttaatttttt agcgaaatct    360
```

```
cactactgca aatgcattgt tgtcctagct aatgaatgca yagagtattg cctgcaaaat    420
aataattgag attctatttt taagaagctt agaacagtac atggtgcata gcaaagactc    480
tgtgtatgtg aagccagatt ttaaaatatg gtaacaagtg tctgaaaata tgtggctcaa    540
tttgtctccc ggttactttt ccctctcccc ctttaaaatg tagaggaagg agaagaagag    600
ataagaggtt tgtgagtgaa gacaagggcc ctttaaggcc tgggaagact aacgccatag    660
ggatctccct ctgccttaaa aggcacagga atcttagtgg ggaaaaagaa gtggtgataa    720
atagccagtc cgtgtgcctg aatatcaaa gtcagtgcgt gccagggatc acactgcggg    780
tcacgtgcac tctgggtctc t                                              801

<210> SEQ ID NO 392
<211> LENGTH: 601
<212> TYPE: DNA
<213> ORGANISM: Homo sapiens

<400> SEQUENCE: 392
ttggcctggg gctgattcct ccaaagcaat gtgtctcttc gcagagtctc ttagagctgc     60
aaggcagtat gggatcatca gagaggatgc taggaagctt cagaaatgga ggtcctggta    120
gaaagggtcc tttggcgtgg cctctgaaga gtccaaatgt gggacaagac cctccgaaag    180
cggtggcctg ggagccaca ggtggggcag ccagcacgga agagggtggc tttgctacca    240
ttgggaaaac ttatcctcca catcctcatg aggcaaacac cttcctacc ttaccgctcc    300 ycagtggcct ccctgttgcc ttcttattca agactaagac cctctagaat gttctttatc    360
ctgagtccag ctgattgtct atactaatat cagtacgggg tgtagatgag gacaaccagt    420
gtgcctggct gccaggcacc ccctccccaa accccaggag tttctggaac attccaactc    480
tgcttgaggg tatccatgca gcatctacta ctgtgagcag gtggtctgat ctgtggaaaa    540
cttctatgat tcacctgagg gtaactgccc tttgtgattt gaaagaatga tgctaacaga    600
a                                                                    601

<210> SEQ ID NO 393
<211> LENGTH: 601
<212> TYPE: DNA
<213> ORGANISM: Homo sapiens

<400> SEQUENCE: 393
gcagagtctc ttagagctgc aaggcagtat gggatcatca gagaggatgc taggaagctt     60
cagaaatgga ggtcctggta gaaagggtcc tttggcgtgg cctctgaaga gtccaaatgt    120
gggacaagac cctccgaaag cggtggcctg ggagccaca ggtggggcag ccagcacgga    180
agagggtggc tttgctacca ttgggaaaac ttatcctcca catcctcatg aggcaaacac    240 cttcctacc ttaccgctcc tcagtggcct ccctgttgcc ttcttattca agactaagac    300
yctctagaat gttctttatc ctgagtccag ctgattgtct atactaatat cagtacgggg    360
tgtagatgag gacaaccagt gtgcctggct gccaggcacc ccctccccaa accccaggag    420
tttctggaac attccaactc tgcttgaggg tatccatgca gcatctacta ctgtgagcag    480
gtggtctgat ctgtggaaaa cttctatgat tcacctgagg gtaactgccc tttgtgattt    540
gaaagaatga tgctaacaga aagtgttgtc atttctgaac ttttctgaac tctgcagcga    600
g                                                                    601

<210> SEQ ID NO 394
<211> LENGTH: 1001
```

```
<212> TYPE: DNA
<213> ORGANISM: Homo sapiens

<400> SEQUENCE: 394
agatttggat ggggacacaa aaccaaacca tatcataggt taaattgtgt ctcccacccc      60
aaaaatgtgt atgttgaagt cctaaccttc agtactcaga atgtgacatt atttggaaat    120
agggtcattg cagatggagt tagttaagat gaggtcatta ggatgagtcc ctaatccaat    180
atgactggtc ctcttacaaa aaggggaagt ttggacacag agccatgcac atgggtggga    240
agaatcccaa atgaacggat aggcagaggg ttggagagat gcatcaacaa ggaacaccaa    300
agattgccag caaccccccag aagctggggg agaggcctgg aacagattct ccctcacagc    360
ctgagaggaa ccaagctggc tgacaccttg atctcaggtt accggccttg agaactgaga    420
gaccctgggt ttctgttgtt taagcctctc agggtgcagc actttattat ggaagcctga    480
gctgactaat acaggtgtct ytatatctca ctgagggaaa gtgacaggaa agtaagaacc    540
atttatgtcc aagagtccag aggagtcaac cagattctgg gggaaaagaa ggtacaatgc    600
tggcctctcc atgcagccta gtccccaaca cttgtagggc ccagggcaag atctaaagca    660
ctctctcacc tatgcatcta tatgctgtaa ctcagataaa caaactatta ataatatat    720
gtgtcttgcc tctcaatctg acaattacac ctttataata gcaacatagg aaaataacta    780
aaactatggt tttaggcaa ccaaatacca gcaaatgta ataattccta ttattagata    840
tgtttaagtg ttctgctggt gggtcagcat ctttggtaga gtcataaaat taaaatgtac    900
ataattaatt aaatattata tgtttattcc ctaacattta ttctgtcat ttcttttttc    960
ttttttcag acagtctcac tcttttgccc aggccggagt g                       1001

<210> SEQ ID NO 395
<211> LENGTH: 1001
<212> TYPE: DNA
<213> ORGANISM: Homo sapiens

<400> SEQUENCE: 395
ttgtgtctcc caccccaaaa atgtgtatgt tgaagtccta accttcagta ctcagaatgt     60
gacattattt ggaaataggg tcattgcaga tggagttagt taagatgagg tcattaggat    120
gagtccctaa tccaatatga ctggtgctct tacaaaaagg ggaagtttgg acacagagcc    180
atgcacatgg gtgggaagaa tcccaaatga acggataggc agagggttgg agagatgcat    240
caacaaggaa caccaaagat tgccagcaac ccccagaagc tgggggagag gcctggaaca    300
gattctccct cacagcctga gaggaaccaa gctggctgac accttgatct caggttaccg    360
gccttgagaa ctgagagacc ctgggtttct gttgtttaag cctctcaggg tgcagcactt    420
tattatggaa gcctgagctg actaatacag gtgtctctat atctcactga gggaaagtga    480
caggaaagta agaaccattt rtgtccaaga gtccagagga gtcaaccaga ttctggggga    540
aaagaaggta caatgctggc ctctccatgc agcctagtcc ccaacacttg tagggccag    600
ggcaagatct aaagcactct ctcacctatg catctatatg ctgtaactca gataaacaaa    660
ctattaaata atatatgtgt cttgcctctc aatctgacaa ttacaccttt ataatagcaa    720
cataggaaaa taactaaaac tatggttttt aggcaaccaa ataccagcaa atgtaataa    780
ttcctattat tagatatgtt taagtgttct gctggtgggt cagcatcttt ggtagagtca    840
taaaattaaa atgtacataa ttaattaaat attatatgtt tattccctaa catttatttc    900
tgtcatttct ttttctttt tttcagacag tctcactctt ttgcccaggc cggagtgcag    960
```

```
tggcgtgatc tcagctcact gcaacctccg cctcccaggt t                        1001
```

<210> SEQ ID NO 396
<211> LENGTH: 1218
<212> TYPE: DNA
<213> ORGANISM: Homo sapiens

<400> SEQUENCE: 396

```
gataaagaaa ggtcatcctc aatttcaatt tactttatat attctttgag aggtaaccgt     60
gtcttatctc cccccaaaat tccttttaaa aggaaatttc caaagatgct ctattctgtg    120
aataaagcat tgtgccacag ccgagaggat ccagcaatga acatgagatt gcccttgatt    180
cataaggtct acaagctagt aaggatagag aacactttaa aataaaaaaa aatagttttt    240
ggtatattta tattgtgtat ttggtataat tgagttttct acattctcat atatgtattt    300
catattttga agaatatgca gaaaataatc aagcttccaa ataaacattt ttttttaaga    360
actgcacaag tgagaattta ggagaacaga agatcagagg gctgcacrgg ctaaactaga    420
caatgagccc atgcaagtaa gttaagagga gaagcgggta agtatgcacc tgctttgtct    480
aggtgaccag caagcattta gcaatagtct tttcaaaaca acagctcctt atattgtcaa    540
atctcaagaa gtaatattta tggttaaaaa aatctcagac ccaacagaaa atccatgagg    600
gagatggttt tggaaacgca gaattttcag ctatgatatc cttttataaa caagcagata    660
cttttcccca aatataattca atgcctcagt ctacctcctg ctgaaaccac taacaccacc    720
actaaagctc gactatatgg gaaaatttag gtgtcacttt caaaatatgt cctagcataa    780
aggcaattaa aaaatgtaaa gcaccaaaga tgcaagagag acataaatga ataaaatatc    840
tggcacgaaa gttttcaaaa gcttgggaat ctgattcaaa aaaaaataaa atcagccaag    900
cagtgttagt aagttagcca atcaggtttc aagaaggcag aaagacaaaa tcaacatcac    960
cagcatttga caccgctact ggggggaaaaa aggggatgg agttcgttta tggccttttt   1020
aaaaatgcca ttacttggac aagagtcata acagagaagc actgcttatt tcagttctgt   1080
taactgtaaa tatcagagcc aacacccaga aaagttcac cattagccaa ttggttttgc   1140
ctggccaatt ggagatggta ataggcctgc tatggatgac attctttctg atataagttg   1200
tttcttgctt tttctccc                                                  1218
```

<210> SEQ ID NO 397
<211> LENGTH: 1218
<212> TYPE: DNA
<213> ORGANISM: Homo sapiens

<400> SEQUENCE: 397

```
gataaagaaa ggtcatcctc aatttcaatt tactttatat attctttgag aggtaaccgt     60
gtcttatctc cccccaaaat tccttttaaa aggaaatttc caaagatgct ctattctgtg    120
aataaagcat tgtgccacag ccgagaggat ccagcaatga acatgagatt gcccttgatt    180
cataaggtct acaagctagt aaggatagag aacactttaa aataaaaaaa aatagttttt    240
ggtatattta tattgtgtat ttggtataat tgagttttct acattctcat atatgtattt    300
catattttga agaatatgca gaaaataatc aagcttccaa ataaacattt ttttttaaga    360
actgcacaag tgagaattta ggagaacaga agatcagagg gctgcacggg ctaaactaga    420
caatgagccc atgcaagtaa gttaagagga gaagcgggta agtatgcacc tgctttgtct    480
aggwgaccag caagcattta gcaatagtct tttcaaaaca acagctcctt atattgtcaa    540
atctcaagaa gtaatattta tggttaaaaa aatctcagac ccaacagaaa atccatgagg    600
```

```
gagatggttt tggaaacgca gaattttcag ctatgatatc cttttataaa caagcagata    660
ctttccccaa atataattca atgcctcagt ctacctcctg ctgaaaccac taacaccacc    720
actaaagctc gactatatgg gaaaattag gtgtcacttt caaaatatgt cctagcataa    780
aggcaattaa aaaatgtaaa gcaccaaga tgcaagagag acataaatga ataaaatatc    840
tggcacgaaa gttttcaaaa gcttgggaat ctgattcaaa aaaaaataaa atcagccaag    900
cagtgttagt aagttagcca atcaggtttc aagaaggcag aaagacaaaa tcaacatcac    960
cagcatttga caccgctact gggggaaaaa aggggatgg agttcgttta tggcctttttt   1020 aaaaatgcca ttacttggac aagagtcata acagagaagc actgcttatt tcagttctgt   1080
taactgtaaa tatcagagcc aacacccaga aaaagttcac cattagccaa ttggttttgc   1140
ctggccaatt ggagatggta ataggcctgc tatggatgac attctttctg atataagttg   1200
tttcttgctt tttctccc                                                  1218

<210> SEQ ID NO 398
<211> LENGTH: 1072
<212> TYPE: DNA
<213> ORGANISM: Homo sapiens

<400> SEQUENCE: 398
cacttaaaag ctctggaaac ctacgagatt atctttaaaa tcgtggggac caaatggctg     60
gccaaggact tgtttctgta caggtgcgat tgcttctctg ctgtgttcct ttttattacc    120
caagtaaccg gtatttcagc tcacaagatg agaaaatgac aaacaggcaa ataagcgta    180 gggctgtgtg tgcaacagtt watcataaag ccatcaccag gagacgtcac tgggcgcctt    240
ctggagtcta tccgtcctaa ctttgctttc tttcttttt tttttaaatt taagttctag    300
ggtacatatg cacaacgtgc aggtttgtca cacatgtata catgtgccat gttggtgtgc    360
tgcacccatt aactcgtcat ttacattagg tgtatctcct agtgctatcc ctccccactc    420
ccccgacccc atgacaggcc ccagtgtgtg atgttcccct tcctgtgtcc aagtgttctc    480
attgttcaat ccccacctat gagtgagaac atgccatgtt tggttttttg tccttgcgat    540
agtttgctga gaatgatggt ttccagcttc atccatgtcc ctacaaagga catgaactca    600 tccttttta tggctacata gtattccatg gtgtatatgt gccacatttt cttaatccag    660
tctatcatcg atggacattt gggttggttc caagtctttg ctattgtgac tagtgttgca    720
ataaatatac gtgtggatgt gtctttatag cagtttgatt tataatcctt tgggtatata    780
cccagtaacg ggatggctgg gtcaaatggt atttctagtt ctagatcctt gaggaatcgc    840
cacactgact tccacaatgg ttgaactagt taacagtccc accaacagtg tgaaagtgtt    900
cctatttctc cacatcctct ccagcacccc attttgactt tgctataagg gaactttagc    960
atctgaacgt gcggacagct tcattgctgg cttgttacgt aacagtgttt tgtgaccatc   1020
tcatgtcata cccacacatc gaaaccagca gtttaaatgg ccagctgttt gc           1072

<210> SEQ ID NO 399
<211> LENGTH: 1072
<212> TYPE: DNA
<213> ORGANISM: Homo sapiens

<400> SEQUENCE: 399
agattatctt taaaatcgtg gggaccaaat ggctggccaa ggacttgttt ctgtacaggt     60
gcgattgctt ctctgctgtg ttcctttttta ttacccaagt aaccggtatt tcagctcaca   120
```

```
agatgagaaa atgacaaaca ggcaaaataa gcgtagggct gtgtgtgcaa cagtttatca      180
taaagccatc accaggagac rtcactgggc gccttctgga gtctatccgt cctaactttg      240
ctttctttct tttttttttt aaatttaagt tctagggtac atatgcacaa cgtgcaggtt      300
tgtcacacat gtatacatgt gccatgttgg tgtgctgcac ccattaactc gtcatttaca      360
ttaggtgtat ctcctagtgc tatccctccc cactcccccg acccatgac aggcccagt       420 gtgtgatgtt ccccttcctg tgtccaagtg ttctcattgt tcaatcccca cctatgagtg      480
agaacatgcc atgtttggtt ttttgtcctt gcgatagttt gctgagaatg atggtttcca      540
gcttcatcca tgtccctaca aaggacatga actcatcctt ttttatggct acatagtatt      600
ccatggtgta tatgtgccac attttcttaa tccagtctat catcgatgga catttgggtt      660
ggttccaagt ctttgctatt gtgactagtg ttgcaataaa tatacgtgtg gatgtgtctt      720
tatagcagtt tgatttataa ccctttgggt atatacccag taacgggatg gctgggtcaa      780
atggtatttc tagttctaga tccttgagga tcgccacac tgacttccac aatggttgaa      840
ctagttaaca gtcccaccaa cagtgtgaaa gtgttcctat ttctccacat cctctccagc      900
accccatttt gactttgcta taagggaact ttagcatctg aacgtgcgga cagcttcatt      960
gctggcttgt tacgtaacag tgttttgtga ccatctcatg tcatacccac acatcgaaac     1020
cagcagttta aatggccagc tgtttgcttg tgaaaactcc cctcggctgg ct            1072

<210> SEQ ID NO 400
<211> LENGTH: 948
<212> TYPE: DNA
<213> ORGANISM: Homo sapiens

<400> SEQUENCE: 400 aaatttctt tgctgaagtg tcttttcaaa ttttttgcctt ttaaaaaaat tgagttgtct       60
taatattgag tcgtaaggtt ctttatatat tctggctata tgtcctttgt cagatatatg      120
tcttgcaaat atttttctccc agtctgtggc ttaccttttc catttttaaa ctgtgtttta     180
taaaaaaaag aagttttttt agatcaaagt ccatttttaat catttttttct tttatagttc     240 atgcttttg tgtctcattt aagaaatctt tccctactcc aatgtcacaa atatattctc       300
tgagaagctt aacagttttt gcaactaaat ttaggtctat gatccgtttt gacttaattt      360
ttccatatgg tgtcatgtaa cagttgagat tttttttccta tgcaggcaga tattcaatgg    420
ttcaagtacc atttattgaa atggctatct tttctccact gaatgacctt ggcacttta      480 tcaaacatca actggccaca yacaggtgag tctacttctg gacacttacc ctgttccatt     540
catctgtata tctctatcct tacaccaaca cgcatagtct tgaatactag ggcaagttaa      600
ttttaagatg tctcctggat atgtaaaaat tatatctgag ttgaactaca gtttatttat      660
atatccaggc agcaaataaa tgtgagaatc tggaggtgag ggaagagatc agagatacca      720
ccttggaaac catcaattta gagatgattc ttaaggcagg ggactaaggg acactctgta     780
ggacacagac atagagaagg gaagggggctg cggcctgaac accccacctg catgctcact    840
cacatacttt cgtcggcctg tgttaacgaa gtgctgggtc tccccagcct ctctcatctg     900
taagcagtgc caacaacgtc caacacagtt ccatccaatt tggatctg                 948

<210> SEQ ID NO 401
<211> LENGTH: 920
<212> TYPE: DNA
<213> ORGANISM: Homo sapiens

<400> SEQUENCE: 401
```

```
aattttttgcc ttttaaaaaa attgagttgt cttaatattg agtcgtaagg ttctttatat      60
attctggcta tatgtccttt gtcagatata tgtcttgcaa atattttctc ccagtctgtg     120
gcttaccttt tccatttttta aactgtgttt tataaaaaaa agaagttttt ttagatcaaa    180
gtccatttta atcattttt cttttatagt tcatgctttt tgtgtctcat ttaagaaatc     240
tttccctact ccaatgtcac aaatatattc tctgagaagc ttaacagtttt ttgcaactaa   300 atttaggtct atgatccgtt ttgacttaat ttttccatat ggtgtcatgt aacagttgag    360 attttttttcc tatgcaggca gatattcaat ggttcaagta ccatttattg aaatggctat  420
cttttctcca ctgaatgacc ttggcactt tatcaaacat caactggcca cacacaggtg    480
agtctacttc tggacactta ycctgttcca ttcatctgta tatctctatc cttacaccaa   540
cacgcatagt cttgaatact agggcaagtt aattttaaga tgtctcctgg atatgtaaaa   600
attatatctg agttgaacta cagtttattt atatatccag gcagcaaata aatgtgagaa   660
tctggaggtg agggaagaga tcagagatac caccttggaa accatcaatt tagagatgat  720
tcttaaggca ggggactaag ggacactctg taggacacag acatagagaa gggaaggggc   780
tgcggcctga acaccccacc tgcatgctca ctcacatact ttcgtcggcc tgtgttaacg   840
aagtgctggg tctccccagc ctctctcatc tgtaagcagt gccaacaacg tccaacacag   900
ttccatccaa tttggatctg                                                920

<210> SEQ ID NO 402
<211> LENGTH: 701
<212> TYPE: DNA
<213> ORGANISM: Homo sapiens

<400> SEQUENCE: 402
tgtgctgctt ccattccata ggcacctgat cctaagtgtt aaccaatccc agaactctcc    60
ccttatttct tgctgcatgt tttgaattga tgtgataaac aatgtgattc gagcgtctta   120
actcagccta tgagcctctc tattctgtga ctgctggaat aggctgcttg gccatgttct   180
tggaagctac caccatatca rggtaatttc ccacacaaca ttccagcccc tgctttcccc   240
tctggcctta tctagggcca ttccccaact caggtgaatg cagactccaa atgtactgag   300
ctgtgtgcag gggccaggtg caaatgcttt ctgtgcatct gcacatgctg ttctacctgg   360
gaagtccttt cctcctttca cctatttta ccttaaacct cagacatcat ctaccctgga   420
aagtccttcc tgacctcacg catctaagta ggtccccccc ataatcccta tccatgcctt  480
ctatagtact taacatggtg acctttaatt gttcatttac ttagctctct gctctcccac   540
actgtgaact ccttacaaac agggaatgtc atctctgaat gaatctttca tctccatgta   600
acacatgcct ccaaccctac ctagcacaca atctggcata taacaggcac tcaataaacc   660
ttcaatgaat gccttgatca agtacaagga acataagcaa a                        701

<210> SEQ ID NO 403
<211> LENGTH: 701
<212> TYPE: DNA
<213> ORGANISM: Homo sapiens

<400> SEQUENCE: 403
ttaaccaatc ccagaactct ccccttattt cttgctgcat gttttgaatt gatgtgataa    60
acaatgtgat tcgagcgtct taactcagcc tatgagcctc tctattctgt gactgctgga   120
ataggctgct tggccatgtt cttggaagct accaccatat cagggtaatt tcccacacaa   180
```

```
cattccagcc cctgctttcc yctctggcct tatctagggc cattccccaa ctcaggtgaa    240
tgcagactcc aaatgtactg agctgtgtgc aggggccagg tgcaaatgct ttctgtgcat    300
ctgcacatgc tgttctacct gggaagtcct ttcctccttt cacctatttt taccttaaac    360
ctcagacatc atctaccctg gaaagtcctt cctgacctca cgcatctaag taggtccccc    420
ccataatccc tatccatgcc ttctatagta cttaacatgg tgacctttaa ttgttcattt    480
acttagctct ctgctctccc acactgtgaa ctccttacaa cagggaatg tcatctctga     540 atgaatcttt catctccatg taacacatgc ctccaaccct acctagcaca aatctggca     600 tataacaggc actcaataaa ccttcaatga atgccttgat caagtacaag gaacataagc    660
aaatttcctg tggaaaaaaa gaattgtatt aagttctttg g                        701

<210> SEQ ID NO 404
<211> LENGTH: 601
<212> TYPE: DNA
<213> ORGANISM: Homo sapiens

<400> SEQUENCE: 404
atgttcactt acacatcttt cttcactta attgaatcct ttattttgt cttagaatct      60 tctgaatatt gaaacagag aactatactg gaagaacata gtgtattaag actcatggag    120
agggagatgt gatactgtgt cactgaggtc gttccagtca taggagaaat gttaccactg    180
gattgaggtc tggtacattt taaaagatga tttaattcta tgatatgtgt tcaacttgca    240
ctaggatagt ttttacttc acctttgttc catgcaccgc gcaaatacct gggaacccctt    300 rttgcccaac tcaagagcca gagtcctctg tcatcattt gcctctctcc taagtgacag    360
gactgagtgc agacttggtg tttgtgggtg aggcatgtgg actgacaggc aggcttcagt    420
ttatttagcg agtgtgagcc ctggcaggaa gattctcttt ctctgcttgc caggttgagg    480
aggcctcatt aagcagtttg aacttgtggt tttggcgtgt ctagtcctgg tgcaggtggc    540
ttggtatcct cacaggcatt tctttggcct cacccttggg gtgactgttc acttgtgttt    600
g                                                                  601

<210> SEQ ID NO 405
<211> LENGTH: 601
<212> TYPE: DNA
<213> ORGANISM: Homo sapiens

<400> SEQUENCE: 405
tcttctgaat attgaaaaca gagaactata ctggaagaac atagtgtatt aagactcatg     60
gagagggaga tgtgatactg tgtcactgag gtcgttccag tcataggaga aatgttacca    120
ctggattgag gtctggtaca ttttaaaaga tgatttaatt ctatgatatg tgttcaactt    180
gcactaggat agttttttact tcacccttttg ttccatgcac cgcgcaaata cctgggaacc    240
cttgttgccc aactcaagag ccagagtcct ctgtcatcat tttgcctctc tcctaagtga    300
saggactgag tgcagacttg gtgtttgtgg gtgaggcatg tggactgaca ggcaggcttc    360 agtttatttta gcgagtgtga gccctggcag gaagattctc tttctctgct tgccaggttg    420
aggaggcctc attaagcagt ttgaacttgt ggttttggcg tgtctagtcc tggtgcaggt    480
ggcttggtat cctcacaggc atttctttgg cctcacccct ggggtgactg ttcacttgtg    540
tttgagcggc tgggactcag taggttcact ggagtaggta tttctttaga gccactggcg    600
g                                                                  601
```

<210> SEQ ID NO 406
<211> LENGTH: 701
<212> TYPE: DNA
<213> ORGANISM: Homo sapiens

<400> SEQUENCE: 406

```
cagctccttg gcaagcctgc tccttcccca gcaaatggaa acaccattct gaacacctgg    60
gcattgtctc tgatgtccct tttcatctcc ctactctcac acaatccagc tgcctctctg   120
ccttccacgg atattaagaa cgtccaccat ctcctgagtc caagcccttc tcactcacct   180
ctttcttgaa ctaatttctt yctgtttttt tccagtcctc ccttctgttc atgtctctcc   240
tctgcacact tccattttct ggttcagaaa atgtcaccgt cccagtcaca cttgccttat   300
ggctgttgtg tcataaatac agttgacact tgaacaacat gggtttgaac tgcatggatt   360
cacttataca catattttt caatacaaat atatttaaaa attttggaga tttgcaacaa    420
tttgaaaaaa cttgcagatg aacagcatag catagaaata ttgaaaaatt aagaaaaagg   480
tatgtcatga atgcataaaa catatgcaga tactagtcta ttttaacctt tactgccata   540
aaatatacac aaatctatta taaaaggtta agtttatca aagcttatgc acacaaacac    600
ttatagacca tatagggagc cattcagtag agagaaatgt aagcgaacgt aaaggtgtgc   660
tatttaatca caactgcata cacactgtac cactgcacta a                       701
```

<210> SEQ ID NO 407
<211> LENGTH: 701
<212> TYPE: DNA
<213> ORGANISM: Homo sapiens

<400> SEQUENCE: 407

```
gggcattgtc tctgatgtcc cttttcatct ccctactctc acacaatcca gctgcctctc    60
tgccttccac ggatattaag aacgtccacc atctcctgag tccaagccct tctcactcac   120
ctctttcttg aactaatttc tttctgtttt tttccagtcc tccttctgt tcatgtctct    180
cctctgcaca cttccatttt stggttcaga aaatgtcacc gtcccagtca cacttgcctt   240
atggctgttg tgtcataaat acagttgaca cttgaacaac atgggtttga actgcatgga   300
ttcacttata cacatatttt ttcaatacaa atatatttaa aaattttgga gatttgcaac   360
aatttgaaaa aacttgcaga tgaacagcat agcatagaaa tattgaaaaa ttaagaaaaa   420
ggtatgtcat gaatgcataa acatatgca gatactagtc tattttaacc tttactgcca    480
taaaatatac acaaatctat tataaaaggt taagtttat caaagcttat gcacacaaac    540
acttatagac catatagga gccattcagt agagagaaat gtaagcgaac gtaaaggtgt    600
gctatttaat cacaactgca tacacactgt accactgcac taatttcaga gccacctcct   660
gttgtgattg tggtgagccc aagtgttgtg aggatctgct t                       701
```

<210> SEQ ID NO 408
<211> LENGTH: 501
<212> TYPE: DNA
<213> ORGANISM: Homo sapiens

<400> SEQUENCE: 408

```
caggtagggt aagcaaatga acacaaattc aaactcggaa ttcaaaacca gcctctgtgt    60
attcctgagg accatactgt ctgctaagtg tagagaaagg cacatcctgg ttcaacagca   120
gagaaagcaa acaggaggca ctttctgtga gtcatctcca ccacgggcc ctctcttttg    180
tgatccagcg atacttgttc acagtcaaag cccaggaaga gtggaaagat taacctttgt   240
```

```
gagccaaacc rtgtgacact tgattacttg acagaactaa tccttctgtc ctgatgacag    300
aaattcaact acacaggtac atgcaagcta atatctgttg taatgcctcc cagtttctct    360
ggagaattcc ttagtttcct ggacatctct gaaatgcaaa gttttggcaa cgagtctctg    420
aattaacctc tgaaaatctc acccagccaa gatggccttc ttgagaagac tgaagaacat    480
ggttggtttc aggctgagct g                                              501
```

<210> SEQ ID NO 409
<211> LENGTH: 604
<212> TYPE: DNA
<213> ORGANISM: Homo sapiens

<400> SEQUENCE: 409

```
cactttctgt gagtcatctc caccacaggg ccctctcttt tgtgatccag cgatacttgt     60
tcacagtcaa agcccaggaa gagtggaaag attaaccttt gtgagccaaa ccgtgtgaca    120
cttgattact tgacagaact aatccttctg tcctgatgac agaamttcaa ctacacaggt    180
acatgcaagc taatatctgt tgtaatgcct cccagtttct ctggagaatt ccttagtttc    240
ctggacatct ctgaaatgca agttttggc aacgagtctc tgaattaacc tctgaaaatc    300
tcacccagcc aagatggcct tcttgagaag actgaagaac atggttggtt tcaggctgag    360
ctggaagtgg tttacctccc aggagaggtt ccccacagtg gtgtttaagg catggggtgg    420
accaacacca ggaagactca gacatcacac cacccacctt caactcagtc acatccacct    480
acattttctg aaaacaaaag gcagtctccc caaaaagcac tgagactctt gtgtaggtaa    540
tctgagcaga caccaacttc ccagggcttc cttttatcca ggagagcttg gctgttcttt    600
ttaa                                                                 604
```

<210> SEQ ID NO 410
<211> LENGTH: 701
<212> TYPE: DNA
<213> ORGANISM: Homo sapiens

<400> SEQUENCE: 410

```
ctccttccgc catggttgta agtttcctga cgcctcccag tcatgcttcc cgtacagcct     60
gcagaactgc gagtcaatga atccctttt ctccacaaat tacccagtct caggtagttc    120
cttacagcag cgtgggaaca gactcaagag ctgaagcaag caaggccgtt agcaaggagc    180
gggctgggga gagcactcca ggcagaggga acagccaggg ccagggcctt gagacagacg    240
tgagccagga tatctgagga acagcagaga agccagtgtg gccgcagcta atgaggaac    300 aatgtgtgag ttccctgggg cggccaaaac aaacaccacg gacggggggcc ttcaaccaca    360 gacaccgatt tcctcacagc tctggaggcg aaaagtccaa gaaaactgca cggagtatct    420
atgaggccct gatggagacc tgacctggtc cacacccatg gcctggcaag ctagatgggg    480
tgaattttca cctgccacag ycgcaagtca aagccaccgg cttctctctt ctccctccca    540
ttgctcctga cagccagggt taatattttg cctcatgtaa acaggaggc atccaccga    600 gaatctcccc tcagcccaca taagctctgc agagagggct gtgttgctcc agttcccacc    660
tggacatgag cactttgaag ggcagcttcc ctcccggggt c                        701
```

<210> SEQ ID NO 411
<211> LENGTH: 612
<212> TYPE: DNA
<213> ORGANISM: Homo sapiens

<400> SEQUENCE: 411

```
gggctgggga gagcactcca ggcagaggga acagccaggg ccagggcctt gagacagacg    60
tgagccagga tatctgagga acagcagaga agccagtgtg gccgcagcta aatgaggaac   120
aatgtgtgag ttccctgggg cggccaaaac aaacaccacg gacggggggcc ttcaaccaca   180
gacaccgatt tcctcacagc tctggaggcg aaaagtccaa gaaaactgca cggagtatct   240
atgaggccct gatggagacc tgacctggtc cacacccatg gcctggcaag ctagatgggg   300
tgaattttca cctgccacag tcgcaagtca agccaccgg cttctctctt ctccctccca    360
ttgctcctga cagccagggt taatattttg cctcatgtaa acagggaggc ayccacccga   420
gaatctcccc tcagcccaca taagctctgc agagagggct gtgttgctcc agttcccacc   480
tggacatgag cactttgaag ggcagcttcc ctcccggggt ctggctgagc tcagggtagg   540
cgtcagtctg catggattgg atggaggaag gctgtgcgtg gcaggagatg acactgccct   600
tgggctgtgt gg                                                       612

<210> SEQ ID NO 412
<211> LENGTH: 1001
<212> TYPE: DNA
<213> ORGANISM: Homo sapiens

<400> SEQUENCE: 412
ttggggaagg aagcactggg gggaaggaag cactgggctt gggacagggc tgggcgctgc    60
ctcttcactg gaccatgaca aggttgttac ctcaccaagg agaggtgcaa aaagcttagg   120
ggcttggatt tctagatttc agtgccaact atgccactta ctggctttat ccttggggaa   180
tttatctact ctgtgacccct cagtttttttt atcttaatta ttaatacata cctcataatg   240
tgactgtgag gattcactta ataatatatg gaaaaccata gaatagtgcc cagcatctag   300
gaagtgccac agccccttc agaagctagt gaaacctgca gaccactttt cagagtgata   360
ttattatttt tttctaggtt tactgagtta taattgaaaa aataaaaatg gaatatagat   420
gtacaacatg aagctctgat gcatatatcc attgtgaaat gatgaccaca atcaagctaa   480
ttaatgttat ctatcacttc wcatagttca accttttttt gtggtgagag tactgaagat   540
ctactctctt agcaattttc aaatctaaaa tacattatta ttaacacagt cactgtgccg   600
tacgttagct ctgaggacct tattcatttt atacctaaaa gtctgtatcc tttaaccaac   660
ctctcctaat ttcccactgt catccctact gccacctctg gtaaccagcc ttctgctctg   720
tttctgagtc caaccttctt agattccaca tatgagtgag atcatgctgt gcagtgtttg   780
tttttctgtg tctggcttgc tttcacttag cataatgtcc tccaggtcca cccatgttgt   840
tgcaaatggc agaatcttct tcttgttaaa gactgaataa tatccctgtg tgtgcgtgca   900
tgtgtgtgtg tgtttgtgtg tgtgtgtgta tcacattttc ttcatccatt catccatcaa   960
tggacactaa gcactaaggt tgattccgta tcttggctat t                      1001

<210> SEQ ID NO 413
<211> LENGTH: 2480
<212> TYPE: DNA
<213> ORGANISM: Homo sapiens

<400> SEQUENCE: 413
aacattactt ggggaaggaa gcactggggg gaaggaagca ctgggcttgg acagggctg    60
ggcgctgcct cttcactgga ccatgacaag gttgttacct caccaaggag aggtgcaaaa   120
agcttagggg cttggatttc tagatttcag tgccaactat gccacttact ggctttatcc   180
```

```
ttggggaatt tatctactct gtgaccctca gttttttat cttaattatt aatacatacc        240
tcataatgtg actgtgagga ttcacttaat aatatatgga aaaccataga atagtgccca        300
gcatctagga agtgccacag cccccttcag aagctagtga aacctgcaga ccacttttca        360
gagtgatatt attatttttt tctaggttta ctgagttata attgaaaaaa taaaaatgga        420
atatagatgt acaacatgaa gctctgatgc atatatccat tgtgaaatga tgaccacaat        480
caagctaatt aatgttatct atcacttcac atagttcaac cttttttgt ggtgagagta         540
ctgaagatct actctcttag caattttcaa atctaaaata cattattatt aacacagtca        600
ctgtgccrta cgttagctct gaggaccttta ttcattttat acctaaaagt ctgtatcctt       660
taaccaacct ctcctaattt cccactgtca tccctactgc cacctctggt aaccagcctt       720
ctgctctgtt tctgagtcca accttcttag attccacata tgagtgagat catgctgtgc       780
agtgtttgtt tttctgtgtc tggcttgctt tcacttagca taatgtcctc caggtccacc      840
catgttgttg caaatggcag aatcttcttc ttgttaaaga ctgaataata tccctgtgtg       900
tgcgtgcatg tgtgtgtgtg tttgtgtgtg tgtgtgtatc acattttctt catccattca      960
tccatcaatg gacactaagc actaaggttg attccgtatc ttggctattg tgaataatgc      1020
tgcaataaac atatgagtcc agatacctct tcaagatact gatttcattt cctttaaata       1080
tatgcccaga agtgggattg ctggatcata tggtagttct atatttagta tcttgaggaa       1140
tttccatact gttttcata atgattgtag caatctatat tcccatcaac agtgtacaag        1200
ggttccattt tctacatggc cttaccaacg tttgttatca cttatctttt tgataataga       1260
tattctagca ggtgtgaggt ggtatctcat tgtggttta atttgcattt tcctgatgat        1320
tagtggtgta gagcatcttt tcatattccc attggtaatt cgtatatctt cctttgagaa       1380
atatttattc agatcttttg cccattgtta gctgagttat atgtgagttg gttttggttt      1440
gttgttgttt tttgtttttg ctattgagct gagttccttg tatattttgg atattaaatc      1500
cttctcagct gtatggttga cagatacatt cttgcattct gtaagttgca tctgtaggtt     1560
gcaacagagt ctctttactc tgttgattgc ttgctttact gtgtgaaagc ttttttagct      1620
tgatgtaatt gtgtttgtct attttttgctt ttgttgcttg tacttttagt gtcatatcca    1680
aaaagttatt gcccagacca gtgtcatccc ctatgttttc ttctagtaat tttaaagttt      1740
caggtcttat gtctatgtct ttaatccatt ttgagttaat ttttgtgtag ggtttaagat       1800
aagaatccaa ttttattttt attttttgta tatggatatc caatttcccc aacaccattt     1860
attgaaaatt ctatccttc tttgttgtgt attaacatca gaataatatt tttaaataca       1920
taaaattcag aagatgacaa aggaaaccaa ttacattgaa atgcatacag agttataatt       1980
ctgaaagagc aatatatgtg cctctttgta aacacatcat atatcaaact gcagtgaccg     2040
ttctaacaac tattgcaatt tcaaagtcat gttgagtagg aggagtactt tgagattctg      2100
aaacaacgtt cttgtgctat gaaatatcca tgatttgat tggtgatggt atcccaggtc       2160
ttgttaatgc tgctgtaatc tgttgcttcc attccatagt tgaataaaat gcttgatatc      2220
tgttggaaat tagtaaaaat aaaaacgtat ttttttccat ccaagttcat tctcagaccc      2280
tgaagagtca cttctctgga ttctgcagca aagttcccag ctggggcagc aagatttagg     2340
caattgaaaa gaacatacac cttgttctca gtggcaaacc acatggaaag ctttaaatgt     2400
cagagaagaa ttctgccatt ttgctgactt ttttgtagtt ctcctaataa acaagtgtta    2460
agtgacaagc ttttcagagg                                                  2480
```

<210> SEQ ID NO 414
<211> LENGTH: 601
<212> TYPE: DNA
<213> ORGANISM: Homo sapiens

<400> SEQUENCE: 414

| | | | | | |
|---|---|---|---|---|---|
| cccccccccc | ccccgcagat | ctcaggtggg | cattttttgaa | cttaactaga | taacaaaaca | 60 |
| cagctaagac | aagtccttttt | ctccagcaaa | gatggcaatg | ctctaataac | tctgagcata | 120 |
| ttaaagattc | tccaagactc | tagcctctgc | tgcaaaaaca | catacaaata | cctactacta | 180 |
| ctgctgctgt | gatgatgatg | atgacagcaa | tagtgagaat | attttaaata | tgccaggcac | 240 |
| ggtggcaact | gctttccaaa | tattatcata | tttaatctga | tcattgccct | atgaggtagg | 300 |
| ragtattctg | attcccattt | tataaataag | gaacccgagg | cttagagagc | atcggtgact | 360 |
| tgttcaaggt | cacccacagc | tgtcaagtga | cagaacttcg | ataaaaatcc | agactccttt | 420 |
| aatggagtat | ggagggaggt | cagaaaacat | aggaagtaag | ggattgtgat | tgacaatgtg | 480 |
| tccttgcaaa | gggacaggtt | aagagacaca | agggcagctg | tctgaggtgt | gccattcacc | 540 |
| agcttcagga | gagaagtggc | aggctacctc | cagctatcca | gccctatcca | gccaaggaag | 600 |
| c | | | | | | 601 |

<210> SEQ ID NO 415
<211> LENGTH: 601
<212> TYPE: DNA
<213> ORGANISM: Homo sapiens

<400> SEQUENCE: 415

| | | | | | |
|---|---|---|---|---|---|
| caaaacacag | ctaagacaag | tccttttctc | cagcaaagat | ggcaatgctc | taataactct | 60 |
| gagcatatta | aagattctcc | aagactctag | cctctgctgc | aaaaacacat | acaaatacct | 120 |
| actactactg | ctgctgtgat | gatgatgatg | acagcaatag | tgagaatatt | ttaaatatgc | 180 |
| caggcacggt | ggcaactgct | ttccaaatat | tatcatattt | aatctgatca | ttgccctatg | 240 |
| aggtagggag | tattctgatt | cccattttat | aaataaggaa | cccgaggctt | agagagcatc | 300 |
| rgtgacttgt | tcaaggtcac | ccacagctgt | caagtgacag | aacttcgata | aaaatccaga | 360 |
| ctcctttaat | ggagtatgga | gggaggtcag | aaaacatagg | aagtaaggga | ttgtgattga | 420 |
| caatgtgtcc | ttgcaaaggg | acaggttaag | agacacaagg | gcagctgtct | gaggtgtgcc | 480 |
| attcaccagc | ttcaggagag | aagtggcagg | ctacctccag | ctatccagcc | ctatccagcc | 540 |
| aaggaagctt | gggagacatg | ttagttcccg | ccttcatttc | catcagcaac | ctcaaagcca | 600 |
| c | | | | | | 601 |

<210> SEQ ID NO 416
<211> LENGTH: 5823
<212> TYPE: DNA
<213> ORGANISM: Homo sapiens

<400> SEQUENCE: 416

| | | | | | |
|---|---|---|---|---|---|
| tatttcaggc | tttcttctttt | ctatggataa | gaaagctcct | caggtggcaa | caaaggccat | 60 |
| ttctttggaa | gcaggcatgg | catgtgacga | aaaaaagaca | tctcagaaaa | gagccaagaa | 120 |
| taagactgga | gagccactgt | cagagaacag | aaactgggct | taatcaagga | acatctcttg | 180 |
| ttcccagagt | aggaggctgg | caatattttc | tcactgaaat | tcagaattg | ttatggacca | 240 |
| gtgactgctc | tatgtgttca | atttgttccc | ttttcaaatg | gaagcattta | ttgcagacga | 300 |
| cctgcctctg | tcccaccatt | gtgtattagg | tttgtagagy | gtagacaact | tgccttttta | 360 |

-continued

```
gtttgtaggt ttctgtatca agagaagatg tgtgtgggcc taacctagat tacaggatcc    420
tggacttcaa gtctgatata atgactggat gagactttga ctgtcctaga attgggatga    480
acatattttg ccggtgggag ggcgtgagta attgcggtta gagggcagac tgtccctcac    540
acctattcct tttcatggtg ccttcccaaa ctgcctctgg aggtggccac acaaatggct    600
ttggccattg tgaccatggg aaacttgatg cagaggctgg aaaaagcact tgcatgtttc    660
tgtctcctct cttgttcctc tacaatcaca agaaatgtct aggcaggtct gagcaggccc    720
aggctcatct gccatggaag aagaatggca catggaagag ggtcacattg tcccaaccaa    780
gacgatccta gaccagccag gccccagttc atggttcaag acacatgaac atagttgcac    840
gaaccaagat tagttgtgta tggcccagac tagcagcagc acccatccaa cctacagact    900
ctgagaaata atactagtt gtcttaagct tccaagtttc agtgtgagca ttaggtagta    960
acagttaatg aataagacag ataatcattt tatctgtctg gatacttata caatgatttc   1020 tatttttat tgatacataa tattttacat attgctgggg tacatgtgac attttgctac   1080
atacatagaa tgtgtaatga tccagtcagg atatctgagg tgtccatcac tttgagaatt   1140
tctcacttct gtgtgttggg aacaattcaa gtcgtctctt ctagttattt taaaatatac   1200
aatacattgt taactgtagt cttttttatt gaatgacagg acttgtacct tttatctaac   1260
tgtatgtttg tatctattaa gctagttctc tttatccctg cccctccta cccactcact   1320 cttcccaacc tctaacatgt atcatcctat tctatatctc catgagatca acttcttag   1380 ctcccacata tgagcaaaaa catatgatgt tgtctttct gtgcccggtt tatttcactt   1440
atgacctcca tttccatcca tgttactata aatgacagga tttcattctt tttgtggcca   1500
aacagtattt cattgtgtat atatactaca ttttcttat ccattcatcc attgatgaac   1560
acttacgttg attccatatc tttgctattg tgaatggtgc tgcaataaac atgcacgtgc   1620
agttatccct ttgatacact gatttatttt cctttggata aatacccagt agtgagattg   1680
ctggatcata cggtagttct acttttagtt tttgagacat ttccatactt ttccagtgtt   1740
tgtattaatt tacattccca tcaacaatgt ataagatttc cctttcctcc acatcctcac   1800
cagcatctgc tatttttgt cttttaata atagtcattc taactggggt gagaggatat   1860
ctcgctatgg ttttgatttg catttccctg atatttaatg atattgagca tttcttcata   1920
taacctattg gccatttgtg tgtctttttt tttttttttt tttttttga gaattgtcta   1980 ctcatttttg gctttttaaa agatttattt tttgttgttg ttgagtttag tgcatatcct   2040
ggatattagt ctcttatctg atgaagagtt tgccaatatt ttctcccatt caacaggttg   2100
tctcttcatt ctgttgactg tttcctttgc tgtgcagaag cactttatat acagtcccat   2160
ttgtctattt tttagtagtc tatgcattta aggtctcagc cacaaaatct ttgcctagac   2220
cagtcctaaa gtgtttcccc tatatttct tctagtagtt ttattgtttc atgtcttata   2280
tttaagtcta taatccattg tgagttgatt tttgtatatg gtgagatagg ggccttgttt   2340
cattcctctg catatagata tttaattttc tcagcaccat ttattgaagg tgtccttccc   2400
tattgtatgt tcttggtgcc tttgtcaaaa ttcagttggc tataaatatg tgaatttatt   2460
tctgggttct ctatgtggtt ccattagtct atgtgtctat ttttatacca atatcatgct   2520
gttttgatta ccatagcctt gtaatatatt ttgaagtcag gtagtgtgat gcctccagct   2580
ttgttctttt tgctcaggat tgctgtgcat actctggctt tttggttaca tacaaatttc   2640 aggattttt tatttctgtg aaaaatggca ttagtatttt gataggaatt gcactggatc   2700
tgtatattgt cctggacaac atggtcattt taacaatatt aattcttcta atctatgagt   2760
```

-continued

```
atgagacgtc ttcccacttg tttgtgtcct cttcaatttc tttcattggt gtttcataat    2820
ctcccttcta caggcctttc acctccttgg ttaaattaat tcctaggtat ttttttgtag    2880
ctactgtaaa tgggactgcc ttctttctca gctagttcat ttttggtgca tagaaaccct    2940 attttgtat gttcattttc tatcctgcaa cattaccaaa tttgcttatc agctttaagt    3000
gtgtattttg ctttgcttgt agagtcttct ggtttctcta aatgtaagac gatgtcatct    3060
gcaaacgggg acaatttgac ttcctcttaa aaatctgtat gccttttatt cctttctctt    3120
gcctgattgc tctggctcta cctccagtac tatactgaat aaaagtggta aaagtgagca    3180
tccttccttg tcttgctcta gttcttagag gaaatacttt cagttttcc ccactcagta    3240 tgatgttagc tgtgggtcat atatagcctt tattatgtta agatatgttt cttctgtacc    3300
tggtttgttg acagctttt atcataaaag gatgtagaat tttatcaaat gttttttctg    3360
catctgttga gataatcata tggttttgt cattccttct actgttgtga tgtatcatgt    3420
ttattgattt gtgtatgtta aaccatcctt gtgtccttgg tataaattat acttggtcat    3480
ggtgtattat cttttggca tcctgtcgaa ttgtttgcta gcttttgtt ttgttctttt    3540 tgagaattt tatgtctagg ttccttagaa acactggcct gtagttctct ttttgtgtgt    3600
gtgtccttgt ctagtttggt gtcagggaaa tggtggtctt gtagaatgag ttgtttttc    3660 tttgattttt ttgcaagagt ttgaggagaa tgggtattag ttcttcttta tgtggttggt    3720
caaattggca gtgaattcat tcagtcatga gctttctttt tttgggagg ttctcatta    3780 ctgagttaat cacactgctc attactgatc tgttcagatt ttctatttct tctggaatct    3840
cagtagttgt atgtttccag caatttatcc atttcctcta ggttttctag tttggtagta    3900
tatagctatt cataatagtc tctgatgatc ttttgtattt ctgtgatatc agttgtaatg    3960 tcttttcat ttcctatttt atttgggtct tttcttgttt agtctagcaa ggggtttatc    4020
tattttatct ttttgaagaa ccaacttttt gtttcattga ccctttctac gtctttagtc    4080
tttatttcat ttagatttgc tctgaacttt actatgtctt tccttctaat tttgggtttg    4140
gtttgttctt ttctagttcc ttgaggtgca tcattgaatt gtttctttga tatctatcta    4200
ctcatttgat gtaggtgttt attgctatac actctcccct cctagagctc cttttgttgt    4260
gtcccatagg tcttggtatg ttgttctat tttcatttgt ttcaaacatt ttatttccat    4320
attaattttt atcattcagg aggagcatat tatttaattc ccatgtattt gtatagtttc    4380
caaagttcct cttatttcta ttttactcc attgtggtct gagaagatac ttcatatgat    4440
ttcaattttt aaaaatttgt caagacttgt ttttgtcct aacatatggt ctatcctgga    4500
gaatgttcca tgtgctgatg agaaaaatgt gtactcagca gttgttgagt aacatgttct    4560
acaaatatct gttagatcca tttggtctaa agtctagttt aaatccaatg agtttttgtt    4620 aatttgtct agatgatcat gatctgagac tgaggtgaag tccccaacaa ttatcgtgtt    4680
ggagtctacc tctcttttta aatctagaaa tatttgcttt ataaatccgg gtggtctagt    4740
gttgggtgca tatatttagt tgttatttcc tcattagatt gatctcttta ctattatata    4800
ataactgttt actgcttctg gcataaagtc tgttttatgt aagtacagcc attcctgctt    4860
gagtttagta ccatgttgac aaagggatgc atagagagtt ggtaaagcat gatttctggg    4920
tgtctgtgtg aaggtgtttt gagaagagtt tagcatgagt ctgtggagtg agtgggaaga    4980 ttctcctca atgtcagcag gaaccatcca tccactgggg gcccaggtag aaaaagatga    5040
agaaatggtg aattctctct ctctcctgga gctgggtcac ccttcttctg cccttgaaca    5100
```

| | |
|---|---:|
| ggacatcaca actccaggct ctccagcctt tggactccaa gactgacacc agtgcccctc | 5160 |
| cccaattacc ccaggccctc aggcctttgg cctaggattg agacttacac catcagcttc | 5220 |
| cctggttctg aggcttctgg acttgcactg ggccatacta ccagcatccc agggtctcca | 5280 |
| gcttgcagag agcctgttgt gggactttc agcctccata atcaagtaag ccaatttccc | 5340 |
| tggtatctat atagatatac aatcatgttt tgcttaccag cctgaaaaat gtatcgctag | 5400 |
| atgagtctgt cattgcataa acatcatagt gtacttacac aaacctagat tctatagcct | 5460 |
| actacacacc tagtctataa acatgtacag catgttactg tactgaatat tgtaggcaac | 5520 |
| tgtaacacaa tggtgaatat ttgcatattt aaacatatct tatcattaaa agatacagt | 5580 |
| aaacataagg tataaaagac aaaaaccggc acacctatat agggcactta ccataaatgc | 5640 |
| agcttgcagg actagaagtc actcagggtg agtcagtgag cgaacgtgaa ggcctaggtt | 5700 |
| attactgtcc actacggtag actttatcaa cactgtacac aggctacact aaatttattt | 5760 |
| tttaaaaatt tgctctccaa taataaatta atcttcgcat ccttttttg ttgttcactg | 5820 |
| tgg | 5823 |

<210> SEQ ID NO 417
<211> LENGTH: 5823
<212> TYPE: DNA
<213> ORGANISM: Homo sapiens

<400> SEQUENCE: 417

| | |
|---|---:|
| tatttcaggc tttcttcttt ctatggataa gaaagctcct caggtggcaa caaaggccat | 60 |
| ttctttggaa gcaggcatgg catgtgacga aaaaaagaca tctcagaaaa gagccaagaa | 120 |
| taagactgga gagccactgt cagagaacag aaactgggct taatcaagga acatctcttg | 180 |
| ttcccagagt aggaggctgg caatattttc tcactgaaat ttcagaattg ttatggacca | 240 |
| gtgactgctc tatgtgttca atttgttccc ttttcaaatg gaagcattta ttgcagacga | 300 |
| cctgcctctg tcccaccatt gtgtattagg tttgtagagt gtagacaact tgcctttta | 360 |
| gtttgtaggt ttctgtatca agagaagatg tgtgtrggcc taacctagat tacaggatcc | 420 |
| tggacttcaa gtctgatata atgactggat gagactttga ctgtcctaga attgggatga | 480 |
| acatattttg ccggtgggag ggcgtgagta attgcggtta gagggcagac tgtccctcac | 540 |
| acctattcct tttcatggtg ccttcccaaa ctgcctctgg aggtggccac acaaatggct | 600 |
| ttggccattg tgaccatggg aaacttgatg cagaggctgg aaaaagcact tgcatgtttc | 660 |
| tgtctcctct cttgttcctc tacaatcaca agaaatgtct aggcaggtct gagcaggccc | 720 |
| aggctcatct gccatggaag aagaatggca catggaagag ggtcacattg tcccaaccaa | 780 |
| gacgatccta gaccagccag gccccagttc atggttcaag acacatgaac atagttgcac | 840 |
| gaaccaagat tagttgtgta tggcccagac tagcagcagc acccatccaa cctacagact | 900 |
| ctgagaaata aatactagtt gtcttaagct tccaagtttc agtgtgagca ttaggtagta | 960 |
| acagttaatg aataagacag ataatcattt tatctgtctg gatacttata caatgatttc | 1020 |
| tatttttat tgatacataa tatttacat attgctgggg tacatgtgac attttgctac | 1080 |
| atacatagaa tgtgtaatga tccagtcagg atatctgagg tgtccatcac tttgagaatt | 1140 |
| tctcacttct gtgtgttggg aacaattcaa gtcgtctctt ctagttattt taaaatatac | 1200 |
| aatacattgt taactgtagt cttttttatt gaatgacagg acttgtacct tttatctaac | 1260 |
| tgtatgtttg tatctattaa gctagttctc tttatccctg cccctccta cccactcact | 1320 |
| cttcccaacc tctaacatgt atcatcctat tctatatctc catgagatca acttctttag | 1380 |

```
ctcccacata tgagcaaaaa catatgatgt ttgtctttct gtgcccggtt tatttcactt    1440
atgacctcca tttccatcca tgttactata aatgacagga tttcattctt tttgtggcca    1500
aacagtattt cattgtgtat atatactaca ttttctttat ccattcatcc attgatgaac    1560
acttacgttg attccatatc tttgctattg tgaatggtgc tgcaataaac atgcacgtgc    1620
agttatccct ttgatacact gatttatttt cctttggata aatacccagt agtgagattg    1680
ctggatcata cggtagttct acttttagtt tttgagacat ttccatactt ttccagtgtt    1740
tgtattaatt tacattccca tcaacaatgt ataagatttc cctttcctcc acatcctcac    1800
cagcatctgc tattttttgt cttttaata atagtcattc taactggggt gagaggatat    1860
ctcgctatgg ttttgatttg catttccctg atatttaatg atattgagca tttcttcata    1920
taacctattg gccatttgtg tgtctttttt tttttttttt ttttttttga gaattgtcta    1980 ctcattttg gctttttaaa agatttatttt tttgttgttg ttgagtttag tgcatatcct    2040
ggatattagt ctcttatctg atgaagagtt tgccaatatt ttctcccatt caacaggttg    2100
tctcttcatt ctgttgactg tttcctttgc tgtgcagaag cactttatat acagtcccat    2160
ttgtctattt tttagtagtc tatgcattta aggtctcagc cacaaaatct ttgcctagac    2220
cagtcctaaa gtgtttcccc tatattttct tctagtagtt ttattgtttc atgtcttata    2280
tttaagtcta taatccattg tgagttgatt tttgtatatg gtgagatagg ggccttgttt    2340
cattcctctg catatagata tttaattttc tcagcaccat ttattgaagg tgtccttccc    2400
tattgtatgt tcttggtgcc tttgtcaaaa ttcagttggc tataaatatg tgaatttatt    2460
tctgggttct ctatgtggtt ccattagtct atgtgtctat ttttatacca atatcatgct    2520
gttttgatta ccatagcctt gtaatatatt ttgaagtcag gtagtgtgat gcctccagct    2580
ttgttctttt tgctcaggat tgctgtgcat actctggctt tttggttaca tacaaatttc    2640 aggattttg tatttctgtg aaaaatggca ttagtatttt gataggaatt gcactggatc    2700
tgtatattgt cctggacaac atggtcattt taacaatatt aattcttcta atctatgagt    2760
atgagacgtc ttcccacttg tttgtgtcct cttcaatttc tttcattggt gtttcataat    2820
ctcccttcta caggcctttc acctccttgg ttaaattaat tcctaggtat tttttgtag    2880 ctactgtaaa tgggactgcc ttcttttctca gctagttcat ttttggtgca tagaaaccct    2940 attttttgtat gttcattttc tatcctgcaa cattaccaaa tttgcttatc agctttaagt    3000
gtgtattttg ctttgcttgt agagtcttct ggtttctcta aatgtaagac gatgtcatct    3060
gcaaacgggg acaatttgac ttcctcttaa aaatctgtat gccttttatt cctttctctt    3120
gcctgattgc tctggctcta cctccagtac tatactgaat aaaagtggta aaagtgagca    3180
tccttccttg tcttgctcta gttcttagag gaaatacttt cagtttttcc ccactcagta    3240
tgatgttagc tgtgggtcat atatagcctt tattatgtta agatatgttt cttctgtacc    3300
tggtttgttg acagcttttt atcataaaag gatgtagaat tttatcaaat gttttttctg    3360
catctgttga gataatcata tggttttgt cattccttct actgttgtga tgtatcatgt    3420
ttattgattt gtgtatgtta aaccatcctt gtgtccttgg tataaattat acttggtcat    3480
ggtgtattat cttttggca tcctgtcgaa ttgtttgcta gctttttgtt ttgttctttt    3540
tgagaatttt tatgtctagg ttccttagaa acactggcct gtagttctct ttttgtgtgt    3600
gtgtccttgt ctagtttggt gtcagggaaa tggtggtctt gtagaatgag ttgttttttc    3660 tttgatttt ttgcaagagt ttgaggagaa tgggtattag ttcttcttta tgtggttggt    3720
```

```
caaattggca gtgaattcat tcagtcatga gcttttcttt ttttgggagg gttctcatta    3780
ctgagttaat cacactgctc attactgatc tgttcagatt ttctatttct tctggaatct    3840
cagtagttgt atgtttccag caatttatcc atttcctcta ggttttctag tttggtagta    3900
tatagctatt cataatagtc tctgatgatc ttttgtattt ctgtgatatc agttgtaatg    3960 tcttttcat ttcctatttt atttgggtct tttcttgttt agtctagcaa ggggtttatc    4020
tattttatct ttttgaagaa ccaactttt gtttcattga ccctttctac gtctttagtc    4080
tttatttcat ttagatttgc tctgaacttt actatgtctt tccttctaat tttgggtttg    4140
gtttgttctt ttctagttcc ttgaggtgca tcattgaatt gtttctttga tatctatcta    4200
ctcatttgat gtaggtgttt attgctatac actctcccct cctagagctc cttttgttgt    4260
gtcccatagg tcttggtatg ttgtttctat tttcatttgt ttcaaacatt ttatttccat    4320
attaattttt atcattcagg aggagcatat tatttaattc ccatgtattt gtatagtttc    4380
caaagttcct cttatttcta tttttactcc attgtggtct gagaagatac ttcatatgat    4440
ttcaattttt aaaaatttgt caagacttgt ttttttgtcct aacatatggt ctatcctgga    4500
gaatgttcca tgtgctgatg agaaaaatgt gtactcagca gttgttgagt aacatgttct    4560
acaaatatct gttagatcca tttggtctaa agtctagttt aaatccaatg agttttttgtt    4620 aattttgtct agatgatcat gatctgagac tgaggtgaag tccccaacaa ttatcgtgtt    4680
ggagtctacc tctcttttta aatctagaaa tatttgcttt ataaatccgg gtggtctagt    4740
gttgggtgca tatatttagt tgttatttcc tcattagatt gatctcttta ctattatata    4800
ataactgttt actgcttctg gcataaagtc tgttttatgt aagtacagcc attcctgctt    4860
gagtttagta ccatgttgac aaagggatgc atagagagtt ggtaaagcat gatttctggg    4920
tgtctgtgtg aaggtgtttt gagaagagtt tagcatgagt ctgtggagtg agtgggaaga    4980
ttctccctca atgtcagcag gaaccatcca tccactgggg gcccaggtag aaaaagatga    5040
agaaatggtg aattctctct ctctcctgga gctgggtcac ccttcttctg cccttgaaca    5100
ggacatcaca actccaggct ctccagcctt tggactccaa gactgacacc agtgcccctc    5160
cccaattacc ccaggccctc aggcctttgg cctaggattg agacttacac catcagcttc    5220
cctggttctg aggcttctgg acttgcactg ggccatacta ccagcatccc agggtctcca    5280
gcttgcagag agcctgttgt gggacttttc agcctccata atcaagtaag ccaatttccc    5340
tggtatctat atagatatac aatcatgttt tgcttaccag cctgaaaaat gtatcgctag    5400
atgagtctgt cattgcataa acatcatagt gtacttacac aaaccctagat tctatagcct    5460 actacacacc tagtctataa acatgtacag catgttactg tactgaatat tgtaggcaac    5520
tgtaacacaa tggtgaatat ttgcatattt aaacatatct tatcattaaa aagatacagt    5580
aaacataagg tataaaagac aaaaaccggc acacctatat agggcactta ccataaatgc    5640
agcttgcagg actagaagtc actcagggtg agtcagtgag cgaacgtgaa ggcctaggtt    5700
attactgtcc actacggtag actttatcaa cactgtacac aggctacact aaatttattt    5760
tttaaaaatt tgctctccaa taataaatta atcttcgcat cctttttttg ttgttcactg    5820
tgg                                                                  5823
```

<210> SEQ ID NO 418
<211> LENGTH: 707
<212> TYPE: DNA
<213> ORGANISM: Homo sapiens

<400> SEQUENCE: 418

```
aacggtgtca gctggagtga actcctgtgt gtgcaaggcc tgggtctcct ggtcagacta    60
ctttctatgg gaaaggcata gtgtatagtc tatatactat acatagggt gctgggagga   120
actggggttt tcacagccag ctttggtttt cattaggttt gtttagtttc cattgcttca   180
ggggtgttag ttttgtgttc mcaactagat tataaactcc tcttgcattc ctgatggcag   240
tgacttgaag gcatttattt gaagaataat agacatacag aaaggggcgc atgtcataaa   300
ggtacagctg gacgactttt cacaaagtga gcacatttgt atgatcgatg ttgagaccaa   360
gagcattcag tggacaactc ctttccagtt actccacccc actcccagtg accatcattc   420
tgacttctaa ctgtgtagac atgttttgct tgttttgtac tttacaaaca tatctactct   480
attttaggtg gctagacaat gtgttttaca atgctggcca tgacagtgtt tgaaagaata   540
aaatggaatc aaatagaatg gcagtatca gagtgtgttg cctgcctaag aaatgttttg    600
tgacattttg gctttgggtc tatttacaca ttaaatctaa gagcaccaga atgtggtgtc   660
aaaatgtgtt tggggatgaa gatattctaa agtcctgtag taagcaa                 707

<210> SEQ ID NO 419
<211> LENGTH: 712
<212> TYPE: DNA
<213> ORGANISM: Homo sapiens

<400> SEQUENCE: 419
cagactactt tctatgggaa aggcatagtg tatagtctat atactataca tagggtgct     60
gggaggaact ggggttttca gccagcttt ggttttcat taggtttgtt tagtttccat    120
tgcttcaggg gtgttagttt tgtgttccca actagattat aaactcctct tgcattcctg   180
atggcagtga cttgaaggca tttatttgaa gaataataga catacagaaa ggggcrcatg   240
tcataaaggt acagctggac gacttttcac aaagtgagca catttgtatg atcgatgttg   300
agaccaagag cattcagtgg acaactcctt ccagttact ccaccccact cccagtgacc    360
atcattctga cttctaactg tgtagacatg ttttgcttgt tttgtacttt acaaacatat   420
ctactctatt ttaggtggct agacaatgtg ttttacaatg ctggccatga cagtgtttga   480
aagaataaaa tggaatcaaa tagaatgggc agtatcagag tgtgttgcct gcctaagaaa   540
tgttttgtga cattttggct ttgggtctat ttacacatta aatctaagag caccagaatg   600
tggtgtcaaa atgtgtttgg ggatgaagat attctaaagt cctgtagtaa gcaatgcaaa   660
acgttctgga ggtgtttatt aaacatttgt ttgtagaatg gagaggaaga ca           712

<210> SEQ ID NO 420
<211> LENGTH: 1210
<212> TYPE: DNA
<213> ORGANISM: Homo sapiens

<400> SEQUENCE: 420
aaagcagcac tgctctgcat tcagccttgc tacgtctcct tcagatgggc gcactagata     60
ctgagtgatg atcatgcctt gtctaggatc tcaccaagac agttcatgaa agagacagtg    120
cagctcatgg aggagatggt gcagctcaca gagaggatgg tgccatcatg gaaagcatgg    180
ggcagtcatg gagatgacgg rgtagctcat ggagaatata atgccatcat ggaaggcata    240
gtgcagtcat ggagatgatg gtgcagctca tggagaagat ggtgccatca tggaaggcat    300
ggtgcaatca tggagtagac agtgcagctg gccaagatt ctccctgact aagctcttct     360
caggcacctc tgagccgtcg tcttaactag gcctccagct tggcttgtga aaactgcaga    420
```

```
ctctcagcac aaatgatttg cctcctacat taagagactt aaataaacac ttgcatggct      480
gtgtttattt aaacagctca aggctgtgtc cctgggatga caatgactcc agcccctaaa      540
attcctgctt gtgaaagctc attgctgaca gaaggatcta ccatttgttc cagccaacac      600
ctggtggcag gcagataggc cctgagcccc atttaagagc agttccttta gaaagcttgc      660
aattgtaaat cttttctctg cccatttgag atgtaaatct tctaccacct agaactgtct      720
tctcaaggac ctgtgagctg actcactgaa atgcaaacat tcagggagat aactccactc      780
ctgtccccat gcgacggcga ggccctgact ttggtgggca ccttgctctt atttgcacca      840
ccacctcctg tcctaaagac atgagacgtt tgtctctcct ctggataagt gcctattaac      900
caacccaggt gtcctggtca catgaaccag tccagcctag cacctggcac tgcctttccc      960
tcagcacact ccagtctgta aaagtctcct tatggttgtt ttggcaaagt tgagcttagt     1020
taatgctaga ccccttctct actgcaatag ttactgctga ataaagtcta tccttaccac     1080
tttaactagt gttgggcttt gtttctcttt cataagctca tggagaagac aatgcagttc     1140
catcaagttt ctggctctta cactgctaac agtcagctct ggggtccctg agagggacag     1200
actcacacca                                                             1210
```

<210> SEQ ID NO 421
<211> LENGTH: 1194
<212> TYPE: DNA
<213> ORGANISM: Homo sapiens

<400> SEQUENCE: 421

```
gcattcagcc ttgctacgtc tccttcagat gggcgcacta gatactgagt gatgatcatg       60
ccttgtctag gatctcacca agacagttca tgaaagagac agtgcagctc atggaggaga      120
tggtgcagct cacagagagg atggtgccat catggaaagc atgggcagt catggagatg       180 acggagtagc tcatggagaa kataatgcca tcatggaagg catagtgcag tcatggagat      240
gatggtgcag ctcatggaga agatggtgcc atcatggaag gcatggtgca atcatggagt      300
agacagtgca gctgggccaa gattctccct gactaagctc ttctcaggca cctctgagcc      360
gtcgtcttaa ctaggcctcc agcttggctt gtgaaaactg cagactctca gcacaaatga      420
tttgcctcct acattaagag acttaaataa acacttgcat ggctgtgttt atttaaacag      480
ctcaaggctg tgtccctggg atgacaatga ctccagcccc taaaattcct gcttgtgaaa      540
gctcattgct gacagaagga tctaccattt gttccagcca cacctggtg gcaggcagat       600 aggccctgag ccccatttaa gagcagttcc tttagaaagc ttgcaattgt aaatcttttc      660
tctgcccatt tgagatgtaa atcttctacc acctagaact gtcttctcaa ggacctgtga      720
gctgactcac tgaaatgcaa acattcaggg agataactcc actcctgtcc ccatgcgacg      780
gcgaggccct gactttggtg ggcaccttgc tcttatttgc accaccacct cctgtcctaa      840
agacatgaga cgtttgtctc tcctctggat aagtgcctat taaccaaccc aggtgtcctg      900
gtcacatgaa ccagtccagc ctagcacctg gcactgcctt tccctcagca cactccagtc      960
tgtaaaagtc tccttatggt tgttttggca aagttgagct tagttaatgc tagacccctt     1020
ctctactgca atagttactg ctgaataaag tctatcctta ccactttaac tagtgttggg     1080
ctttgtttct ctttcataag ctcatggaga agacaatgca gttccatcaa gtttctggct     1140
cttacactgc taacagtcag ctctggggtc cctgagaggg acagactcac acca           1194
```

<210> SEQ ID NO 422
<211> LENGTH: 1194

<212> TYPE: DNA
<213> ORGANISM: Homo sapiens

<400> SEQUENCE: 422

```
gcattcagcc ttgctacgtc tccttcagat gggcgcacta gatactgagt gatgatcatg    60
ccttgtctag gatctcacca agacagttca tgaaagagac agtgcagctc atggaggaga   120
tggtgcagct cacagagagg atggtgccat catggaaagc atggggcagt catggagatg   180
acggagtagc tcatggagaa kataatgcca tcatggaagg catagtgcag tcatggagat   240
gatggtgcag ctcatggaga agatggtgcc atcatggaag gcatggtgca atcatggagt   300
agacagtgca gctgggccaa gattctccct gactaagctc ttctcaggca cctctgagcc   360
gtcgtcttaa ctaggcctcc agcttggctt gtgaaaactg cagactctca gcacaaatga   420
tttgcctcct acattaagag acttaaataa acacttgcat ggctgtgttt atttaaacag   480
ctcaaggctg tgtccctggg atgacaatga ctccagcccc taaaattcct gcttgtgaaa   540
gctcattgct gacagaagga tctaccattt gttccagcca acacctggtg gcaggcagat   600
aggccctgag ccccatttaa gagcagttcc tttagaaagc ttgcaattgt aaatcttttc   660
tctgcccatt tgagatgtaa atcttctacc acctagaact gtcttctcaa ggacctgtga   720
gctgactcac tgaaatgcaa acattcaggg ataactcc actcctgtcc ccatgcgacg   780
gcgaggccct gactttggtg ggcaccttgc tcttatttgc accaccacct cctgtcctaa   840
agacatgaga cgtttgtctc tcctctggat aagtgcctat taaccaaccc aggtgtcctg   900
gtcacatgaa ccagtccagc ctagcacctg gcactgcctt tccctcagca cactccagtc   960
tgtaaaagtc tccttatggt tgtttggca aagttgagct tagttaatgc tagacccctt  1020
ctctactgca atagttactg ctgaataaag tctatcctta ccactttaac tagtgttggg  1080
cttttgtttct ctttcataag ctcatggaga agacaatgca gttccatcaa gtttctggct  1140
cttacactgc taacagtcag ctctggggtc cctgagaggg acagactcac acca         1194
```

<210> SEQ ID NO 423
<211> LENGTH: 1118
<212> TYPE: DNA
<213> ORGANISM: Homo sapiens

<400> SEQUENCE: 423

```
accaagacag ttcatgaaag agacagtgca gctcatggag gagatggtgc agctcacaga    60
gaggatggtg ccatcatgga aagcatgggg cagtcatgga gatgacggag tagctcatgg   120
agaagataat gccatcatgg aaggcatagt gcagtcatgg agatgatggt gcagctcatg   180
agaagatgg tgccatcatg raaggcatgg tgcaatcatg gagtagacag tgcagctggg   240
ccaagattct ccctgactaa gctcttctca ggcacctctg agccgtcgtc ttaactaggc   300
ctccagcttg gcttgtgaaa actgcagact ctcagcacaa atgatttgcc tcctacatta   360
agagacttaa ataaacactt gcatggctgt gtttatttaa acagctcaag gctgtgtccc   420
tgggatgaca atgactccag cccctaaaat tcctgcttgt gaaagctcat tgctgacaga   480
aggatctacc atttgttcca gccaacacct ggtggcaggc agataggccc tgagccccat   540
ttaagagcag ttcctttaga aagcttgcaa ttgtaaatct tttctctgcc catttgagat   600
gtaaatcttc taccacctag aactgtcttc tcaaggacct gtgagctgac tcactgaaat   660
gcaaacattc agggagataa ctccactcct gtccccatgc gacggcgagg ccctgacttt   720
ggtgggcacc ttgctcttat ttgcaccacc acctcctgtc ctaaagacat gagacgtttg   780
```

```
tctctcctct ggataagtgc ctattaacca acccaggtgt cctggtcaca tgaaccagtc    840
cagcctagca cctggcactg cctttccctc agcacactcc agtctgtaaa agtctcctta    900
tggttgtttt ggcaaagttg agcttagtta atgctagacc ccttctctac tgcaatagtt    960
actgctgaat aaagtctatc cttaccactt taactagtgt tgggctttgt ttctctttca   1020
taagctcatg gagaagacaa tgcagttcca tcaagtttct ggctcttaca ctgctaacag   1080
tcagctctgg ggtccctgag agggacagac tcacacca                           1118
```

<210> SEQ ID NO 424
<211> LENGTH: 601
<212> TYPE: DNA
<213> ORGANISM: Homo sapiens

<400> SEQUENCE: 424

```
gtaggggcac tgtctatact ggctgcactc tggccagtgc tgtcccaacg ctgacccctc     60
tggaagctaa tctggcttat aatgaggatg ctttctttag agggactct ccatgcacag    120 cagaaaatcc caatggagtg gttcttccct atgtccccaa gggactggga atattctttc    180
agtaacaatg gcccattggg ggaagaagga tgaaagtggg gtgagagacg tgaaatttgg    240
agaggtccct caaagattgt gatgtgcctc tcttgttcca atcacaggac aggggtataa    300
yggctttcct ttgaaacacg gggatgaatt taactattca cttcccaggt agattcatca    360
gggtctagag cttcagctaa cagcatgagg aagattccaa atgtgcccc atcagcatag    420 gaactgggta tgttgagtct atggtctcat aaaaccagaa aaggacaag ggattgtggc     480 tccaggcttg ggagcacctt ttccttacca tgggctacag tatttattta gggtaaagga    540
aggaaactcc tgaggtgcta tggggtgcca gcaatttgga gcatcagtaa ttcaatgtcc    600
c                                                                   601
```

<210> SEQ ID NO 425
<211> LENGTH: 601
<212> TYPE: DNA
<213> ORGANISM: Homo sapiens

<400> SEQUENCE: 425

```
acgctgaccc ctctggaagc taatctggct tataatgagg atgctttctt tagaggggac     60
tctccatgca cagcagaaaa tcccaatgga gtggttcttc cctatgtccc caagggactg    120
ggaatattct ttcagtaaca atggcccatt ggggggaagaa ggatgaaagt ggggtgagag    180
acgtgaaatt tggagaggtc cctcaaagat tgtgatgtgc ctctcttgtt ccaatcacag    240
gacaggggta taacggcttt cctttgaaac acggggatga atttaactat tcacttccca    300
rgtagattca tcagggtcta gagcttcagc taacagcatg aggaagattc caaatgtgcc    360
cccatcagca taggaactgg gtatgttgag tctatggtct cataaaacca agaagggac    420 aagggattgt ggctccaggc ttgggagcac cttttcctta ccatgggcta cagtatttat    480
ttagggtaaa ggaaggaaac tcctgaggtg ctatggggtg ccagcaattt ggagcatcag    540
taattcaatg tcccttcagc catgtgtatt caactcctgc tgtgggtgtg gacttggtgc    600
a                                                                   601
```

<210> SEQ ID NO 426
<211> LENGTH: 701
<212> TYPE: DNA
<213> ORGANISM: Homo sapiens

<400> SEQUENCE: 426

-continued

```
ttcctgggca tcgtcatatt ctgtaaaaca aggaagctca gcccagtgtg ttctaacatg      60
acctcctttc tacatcctta ggtgttgtta tgcgtgaatc acgtcccccc aaaagacatg     120
ttcatgtcct aaccccagg acctcagaat gtgtgatctg gtttggaaat aaggtcatca     180
cagatgaaat tagctaagac aaggtcatat tggaataggg ttggcccttta atccactgtg   240 actggtgtcc ttttaagaag aggacacaga cacaggaggg gagagggcca tgggatgatg    300
caggtggaga ctggagtgct acagctgcaa gcaaatacat ttctgtgctg tgaagccacc    360
catttggtgg tactacgtta aaacagctct aggaaattaa tacagatgtt gcctgtattt    420
ttgtttctca tattactact cattgtttta atgatgactg ttttattcat taagttgaaa    480
gctcctaaag cagagggacc rtatttttat gtcccaactc tccttaaggc cttgcctatg    540
atagcacatc tcttcaatag aattgtccta actttaacag agacaacttg ggttatttaa    600
tatggagaac aaagggttaa gctggtgcca gatgggtttc attttctcta aatctggaac    660
caaaggcagc aagtctatgg ggtggacgga gttcttagct c                         701
```

<210> SEQ ID NO 427
<211> LENGTH: 701
<212> TYPE: DNA
<213> ORGANISM: Homo sapiens

<400> SEQUENCE: 427

```
caaggaagct cagcccagtg tgttctaaca tgacctcctt tctacatcct taggtgttgt     60
tatgcgtgaa tcacgtcccc ccaaaagaca tgttcatgtc ctaaccccca ggacctcaga   120
atgtgtgatc tggtttggaa ataaggtcat cacagatgaa attagctaag acaaggtcat   180
attggaatag ggttggccct taatccactg tgactggtgt ccttttaaga agaggacaca    240
gacacaggag gggagagggc catgggatga tgcaggtgga gactggagtg ctacagctgc    300
aagcaaatac atttctgtgc tgtgaagcca cccatttggt ggtactacgt taaaacagct    360
ctaggaaatt aatacagatg ttgcctgtat ttttgtttct catattacta ctcattgttt    420
taatgatgac tgttttattc attaagttga agctcctaa agcagaggga ccatatttttt   480 atgtcccaac tctccttaag sccttgccta tgatagcaca tctcttcaat agaattgtcc    540
taactttaac agagacaact tgggttattt aatatggaga acaaagggtt aagctggtgc    600
cagatgggtt tcattttctc taaatctgga accaaaggca gcaagtctat ggggtggacg    660
gagttcttag ctcaacccctt tggtgaggta agaagaagga t                       701
```